(12) United States Patent
Jin et al.

(10) Patent No.: US 11,840,696 B2
(45) Date of Patent: Dec. 12, 2023

(54) METHODS OF INTRODUCING MULTIPLE EXPRESSION CONSTRUCTS INTO A EUKARYOTIC CELL

(71) Applicant: Novozymes A/S, Bagsvaerd (DK)

(72) Inventors: Qiming Jin, Sacramento, CA (US); Jeffrey Shasky, Davis, CA (US); Donna Moyer, Davis, CA (US); Abigail Jang, Roseville, CA (US); Gloria Muzzi-Erichsen, Vacaville, CA (US); Cara Kleindienst, Dixon, CA (US)

(73) Assignee: Novozymes A/S, Bagsvaerd (DK)

( * ) Notice: Subject to any disclaimer, the term of this patent is extended or adjusted under 35 U.S.C. 154(b) by 1173 days.

(21) Appl. No.: 16/506,201

(22) Filed: Jul. 9, 2019

(65) Prior Publication Data

US 2019/0330644 A1  Oct. 31, 2019

Related U.S. Application Data

(62) Division of application No. 15/556,439, filed as application No. PCT/US2016/021568 on Mar. 9, 2016, now Pat. No. 10,385,352.

(60) Provisional application No. 62/207,650, filed on Aug. 20, 2015, provisional application No. 62/130,455, filed on Mar. 9, 2015.

(51) Int. Cl.
*C12N 15/79* (2006.01)
*C12N 15/90* (2006.01)

(52) U.S. Cl.
CPC ........... *C12N 15/79* (2013.01); *C12N 15/902* (2013.01); *C12N 2800/30* (2013.01)

(58) Field of Classification Search
None
See application file for complete search history.

(56) References Cited

U.S. PATENT DOCUMENTS 10,385,352 B2 * 8/2019 Jin ....................... C12N 15/902

FOREIGN PATENT DOCUMENTS

| EP | 2527448 A1 | 5/2011 |
| WO | 2010039889 A2 | 4/2010 |
| WO | 2013028912 A2 | 2/2013 |

OTHER PUBLICATIONS

Catlett et al. "Split-Marker Recombination for Effiecient Targeted Deletion of Fungal Genes" 50 Fungal Genetics Newsletter 9-11 (Year: 2003).*
Lubertozzi et al., 2009, Biotechnol Adv, 27(1), 53-75.

* cited by examiner

*Primary Examiner* — Nancy J Leith
(74) *Attorney, Agent, or Firm* — Eric J Fechter

(57) ABSTRACT

The present invention relates to methods of introducing multiple expression constructs into a eukaryotic cell, methods of constructing a eukaryotic cell having multiple target loci for expressing multiple heterologous proteins of interest, eukaryotic cells for expressing multiple heterologous proteins of interest, and methods of production of multiple heterologous proteins of interest.

17 Claims, 15 Drawing Sheets

Specification includes a Sequence Listing.

METHODS OF INTRODUCING MULTIPLE EXPRESSION CONSTRUCTS INTO A EUKARYOTIC CELL

CROSS-REFERENCE TO RELATED APPLICATIONS

This application is a divisional application of U.S. application Ser. No. 15/556,439, now U.S. Pat. No. 10,385,352, which is a 35 U.S.C. § 371 national application of PCT/US2016/021568 filed Mar. 9, 2016, which claims priority or the benefit under 35 U.S.C. § 119 of U.S. Provisional Application No. 62/207,650 filed Aug. 20, 2015 and U.S. Provisional Application No. 62/130,455 filed Mar. 9, 2015, the contents of which are fully incorporated herein by reference.

REFERENCE TO A SEQUENCE LISTING

This application contains a Sequence Listing that was submitted as an ASCII text file named SQ_ST25.txt (created on Jul. 9, 2019, containing 111,211 bytes), which is incorporated herein by reference.

BACKGROUND OF THE INVENTION

Field of the Invention

The present invention relates to methods of introducing multiple expression constructs into a eukaryotic cell, methods of constructing a eukaryotic cell having multiple target loci for expressing multiple heterologous proteins of interest, eukaryotic cells for expressing multiple heterologous proteins of interest, and methods of production of multiple heterologous proteins of interest.

Description of the Related Art

Recombinant production of a protein in a eukaryotic host cell, e.g., fungal cell, may provide for a more desirable vehicle for producing the protein in commercially relevant quantities. The recombinant production of a protein is generally accomplished by constructing an expression cassette in which the DNA coding for the protein is placed under the expression control of a promoter from a regulated gene. The expression cassette is introduced into the host cell, usually by plasmid-mediated transformation. Production of the protein is then achieved by culturing the transformed host cell under inducing conditions necessary for the proper functioning of the promoter contained on the expression cassette.

Fungal cells may be transformed with a vector by a process involving protoplast formation, transformation of the protoplasts, and regeneration of the cell wall in a manner known per se. Transformation of a fungal host cell with two or more vectors, alone or together (co-transformation) is very inefficient and limited by the availability of useful selectable markers.

There is a need in the art for methods of constructing eukaryotic strains capable of expressing multiple recombinant proteins by targeting expression constructs to two or more (e.g., several) specific genomic loci to achieve desired expression levels of multiple heterologous proteins of interest.

The present invention provides improved methods for producing multiple recombinant proteins in a eukaryotic cell.

SUMMARY OF THE INVENTION

The present invention relates to methods of introducing multiple expression constructs into two or more target loci of a eukaryotic cell, said method comprising.
(a) transforming a population of the eukaryotic cell with one or more first constructs and one or more second constructs,
wherein the eukaryotic cell comprises (1) one or more first target loci (e.g., 1, 2, 3, 4, 5, 6, 7, 8, etc.) each comprising a pair of a first recombination recognition site and a second recombination recognition site, and (2) one or more second target loci (e.g., 1, 2, 3, 4, 5, 6, 7, 8, etc.) each comprising a first fragment of a first selectable marker lacking a selectable function;
wherein the one or more first constructs (e.g., 1, 2, 3, 4, 5, 6, 7, 8, etc.) each comprises one or more first expression cassettes each comprising a first polynucleotide encoding a first protein of interest, wherein in each of the first constructs the one or more first expression cassettes are flanked on one side by the first recombination recognition site and on the other side by the second recombination recognition site corresponding to the same recombination recognition sites of the first target loci; and
wherein the one or more second constructs (e.g., 1, 2, 3, 4, 5, 6, 7, 8, etc.) each comprises one or more second expression cassettes each comprising a second polynucleotide encoding a second protein of interest, and wherein in each of the second constructs the one or more second expression cassettes are flanked on one side by a homologous region of the corresponding second target locus and on the other side by a second fragment of the first selectable marker that lacks the selectable function, wherein the second fragment comprises a sequence overlapping homologously the corresponding sequence of the first fragment of the first selectable marker of the second target loci; and
(b) selecting a transformant using each of the first selectable markers wherein the first fragment and the second fragment of each of the first selectable markers undergo recombination (e.g., homologous recombination or recombinase-mediated recombination) to become functional and the homologous region of the second constructs undergo homologous recombination with the same corresponding region of the second target loci, wherein each of the second expression cassettes are integrated at the corresponding second target loci, and wherein the first and second recombination recognition sites of the first constructs undergo recombination at the corresponding first and second recombination recognition sites of the first target loci driven by at least one recombinase integrating each of the first expression cassettes at the corresponding first target loci.

The present invention also relates to methods of constructing a eukaryotic cell having multiple target loci for expressing multiple heterologous proteins of interest, comprising:
(a) transforming a population of the eukaryotic cell with a first construct comprising (1) a 5' homologous region of a first target locus, (2) a first recombination recognition site, (3) a first selectable marker conferring a first selectable function, (4) a second recombination recognition site, and (5) a 3' homologous region of the first target locus;
(b) selecting a first transformant having the first construct integrated at the first target locus using the first selectable marker for selection of the first transformant, wherein the 5' homologous region and the 3' homologous region of the first construct undergo homologous recombination with the corresponding regions of the first target locus integrating the first construct at the first target locus, and wherein the first recombination recognition site and the second recombination recognition site are integrated at the first target locus;

(c) transforming a population of the first transformant with a second construct comprising (1) a 5' homologous region of a second target locus, (2) a first fragment of a second selectable marker that lacks a second selectable function, (3) a third selectable marker conferring a third selectable function, and (4) a 3' homologous region of the second target locus;

(d) selecting a second transformant having the second construct integrated at the second target locus using the third selectable marker for selection of the second transformant, wherein the 5' homologous region and the 3' homologous region of the second construct undergo homologous recombination with the corresponding regions of the second target locus integrating the second construct at the second target locus, and wherein the first fragment of the second selectable marker that lacks a second selectable function is integrated at the second target locus;

(e) co-transforming a population of the second transformant with (i) a third construct comprising (1) the first recombination recognition site, (2) one or more first expression cassettes each comprising a first polynucleotide encoding a first protein of interest, and (3) the second recombination recognition site, and (ii) a fourth construct comprising (1) the 5' homologous region of the second target locus, (2) one or more second expression cassettes each comprising a second polynucleotide encoding a second protein of interest, and (3) a second fragment of the second selectable marker that lacks the second selectable function wherein the second fragment comprises a sequence overlapping homologously the corresponding sequence of the first fragment of the first selectable marker; and (f) selecting a third transformant using the second selectable marker wherein the first integrated fragment and the second fragment of the second selectable marker become functional upon recombination (e.g., homologous recombination or recombinase-mediated recombination), wherein the 5' homologous region of the fourth construct undergoes homologous recombination with the same corresponding region of the second target locus, wherein the one or more second expression cassettes are integrated at the second target locus, and wherein the first recombination recognition site and the second recombination recognition site undergo recombination at the first target locus driven by at least one recombinase integrating the one or more first expression cassettes at the first target locus.

The present invention also relates to eukaryotic cells for expressing multiple heterologous proteins of interest, comprising:

(a) one or more first target loci (e.g., 1, 2, 3, 4, 5, 6, 7, 8, etc.) each comprising a pair of a first recombination recognition site and a second recombination recognition site; and (b) one or more second target loci (e.g., 1, 2, 3, 4, 5, 6, 7, 8, etc.) each comprising a first fragment of a first selectable marker lacking a selectable function.

The present invention also relates to eukaryotic cells comprising (1) one or more first target loci each comprising one or more first expression cassettes each comprising a first polynucleotide encoding a first protein of interest, wherein the one or more first expression cassettes are each flanked 5' by a first recombination recognition site and 3' by a second recombination recognition site, and (2) one or more second target loci each comprising one or more second expression cassettes each comprising a second polynucleotide encoding a second protein of interest, wherein each of the one or more second expression cassettes are flanked on one side by a region of the second target locus and on the other side by a first fragment of a first selectable marker that lacks selectable function, wherein each of the pairs of the first and second recombination recognition sites at the first loci are able to undergo recombination with a first construct comprising one or more third expression cassettes each comprising a third polynucleotide encoding a third protein of interest, wherein each of the one or more third expression cassettes are flanked on one side by the first recombination recognition site and on the other side by the second recombination recognition site of the corresponding first target locus, and wherein each of the target loci regions and the first fragment of the first selectable marker that lacks selectable function at the second loci are able to undergo recombination (e.g., homologous recombination or recombinase-mediated recombination) with a second construct comprising one or more fourth expression cassettes each comprising a fourth polynucleotide encoding a fourth protein of interest, wherein each of the one or more fourth expression cassettes are flanked on one side by a homologous region of the corresponding second target locus and on the other side by a second fragment of the first selectable marker that lacks the selectable function wherein the second fragment comprises a sequence overlapping homologously the corresponding sequence of the first fragment of the first selectable marker.

The present invention also relates to methods for producing proteins of interest, comprising cultivating a eukaryotic cell of the present invention under conditions conducive for production of the proteins.

The present invention also relates to nucleic acid constructs selected from the group consisting of:

(a) a first nucleic acid construct comprising (i) a 5' homologous region of a first target locus of a eukaryotic cell, (ii) a first recombination recognition site, (iii) a first repeat sequence, (iv) a first selectable marker conferring a first selectable function, (v) a second repeat sequence, (vi) a second recombination recognition site, and (vii) a 3' homologous region of the first target locus of the eukaryotic cell;

(b) a second nucleic acid construct comprising: (1) a 5' homologous region of a second target locus of a eukaryotic cell, (2) a first fragment of a second selectable marker that lacks a second selectable function, (3) a third repeat sequence, (4) a third selectable marker conferring a third selectable function, (5) a fourth repeat sequence, and (6) a 3' homologous region of the second target locus of the eukaryotic cell;

(c) a third nucleic acid construct comprising: (1) a first recombination recognition site, (2) one or more first expression cassettes each comprising a first polynucleotide encoding a first protein of interest, and (3) a second recombination recognition site; and (d) a fourth nucleic acid construct comprising: (1) a 5' homologous region of the second target locus, (2) one or more second expression cassettes each comprising a second polynucleotide encoding a second protein of interest, and (3) a second fragment of a second selectable marker that lacks a second selectable function.

The present invention also relates to methods of introducing multiple expression constructs into a eukaryotic cell, said method comprising.

(a) transforming a population of the eukaryotic cell with one or more first constructs and one or more second constructs, wherein the eukaryotic cell comprises (1) one or more first target loci (e.g., 1, 2, 3, 4, 5, 6, 7, 8, etc.) each comprising a pair of a first recombination recognition site and a second recombination recognition site, wherein the first recombination recognition site and a second recombination recognition site are TP901-1 sites of the Xis-att system, and (2) one or more second target loci (e.g., 1, 2, 3, 4, 5, 6, 7, 8, etc.) each comprising a pair of a third recombination recognition site and a fourth recombination recognition site, wherein the third recombination recognition site and the fourth recombination recognition site are flippase recognition sites of the FLP-FRT system;

wherein the one or more first constructs (e.g., 1, 2, 3, 4, 5, 6, 7, 8, etc.) each comprises one or more first expression cassettes each comprising a first polynucleotide encoding a first protein of interest, wherein in each of the first constructs the one or more first expression cassettes are flanked on one side by the first recombination recognition site and on the other side by the second recombination recognition site corresponding to the same recombination recognition sites of the first target loci;

wherein the one or more second constructs (e.g., 1, 2, 3, 4, 5, 6, 7, 8, etc.) each comprises one or more second expression cassettes each comprising a second polynucleotide encoding a second protein of interest, and wherein in each of the second constructs the one or more second expression cassettes are flanked on one side by the third recombination recognition site and on the other side by the fourth recombination recognition site corresponding to the same recombination recognition sites of the second target loci; and wherein one or more of the first constructs and second constructs comprise one or more first selectable markers;

(b) selecting a transformant using the one or more first selectable markers, wherein each of the second expression cassettes are integrated at the corresponding second target loci, and wherein the first and second recombination recognition sites of the first constructs undergo recombination at the corresponding first and second recombination recognition sites of the first target loci driven by at least one recombinase integrating each of the first expression cassettes at the corresponding first target loci.

DEFINITIONS

Figure 1:
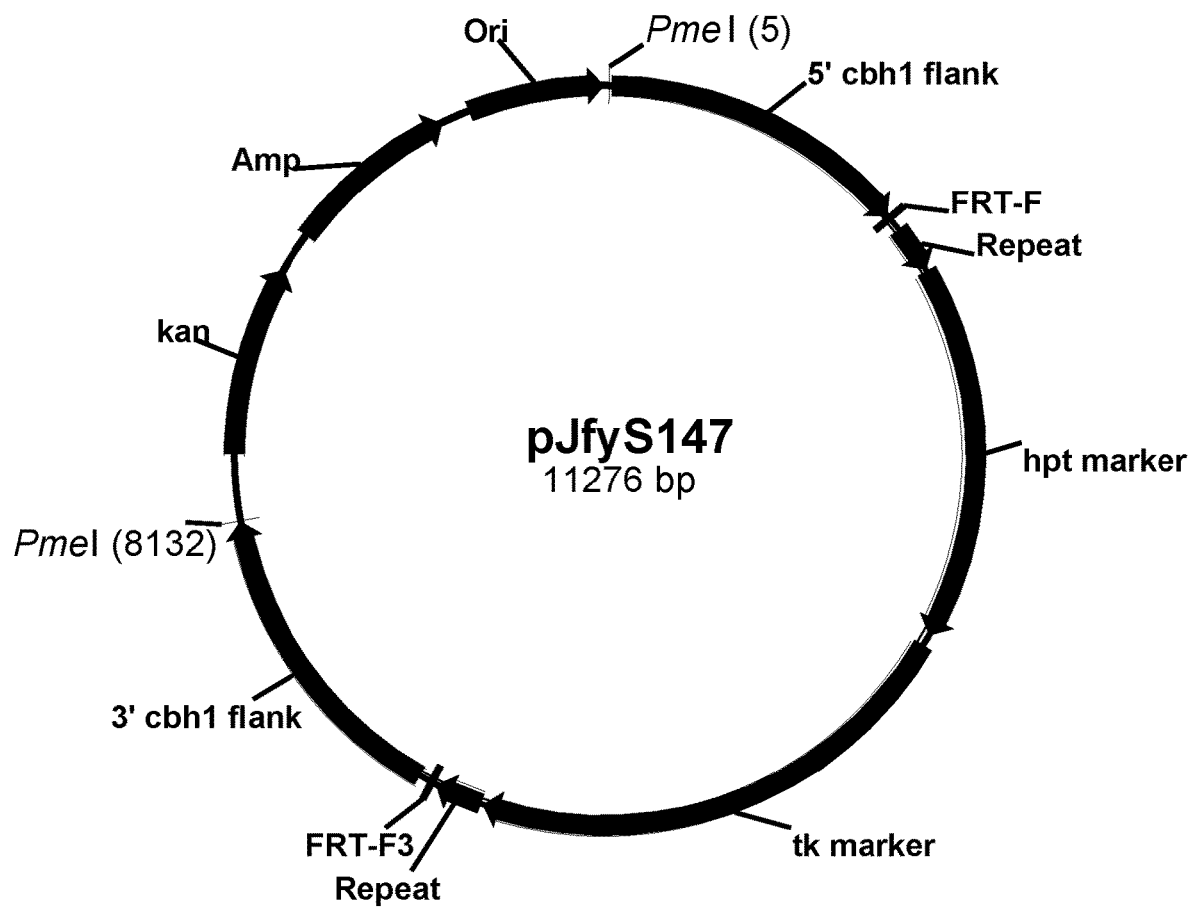
FIG. 1 shows a restriction map of plasmid pJfyS147.

Aspartic protease: The term "aspartic protease" means a protease that uses an aspartate residue(s) for catalyzing the hydrolysis of peptide bonds in peptides, polypeptides, and proteins. Aspartic proteases are a family of protease enzymes that use an aspartate residue for catalytic hydrolysis of their peptide substrates. In general, they have two highly-conserved aspartates in the active site and are optimally active at acidic pH (Szecsi, 1992, *Scand. J. Clin. Lab. In vest.* Suppl. 210: 5-22). For purposes of the present invention, aspartic protease activity is determined according to the procedure described by Aikawa et al., 2001, *J. Biochem.* 129: 791-794.

Auxiliary Activity 9 polypeptide: The term "Auxiliary Activity 9 polypeptide" or "AA9 polypeptide" means a polypeptide classified as a lytic polysaccharide monooxygenase (Quinlan et al., 2011, *Proc. Natl. Acad. Sci. USA* 208: 15079-15084; Phillips et al., 2011, *ACS Chem. Biol.* 6: 1399-1406; Lin et al., 2012, *Structure* 20: 1051-1061). AA9 polypeptides were formerly classified into the glycoside hydrolase Family 61 (GH61) according to Henrissat, 1991, *Biochem. J.* 280: 309-316, and Henrissat and Bairoch, 1996, *Biochem. J.* 316: 695-696.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. For purposes of the present invention, beta-glucosidase activity is determined using p-nitrophenyl-beta-D-glucopyranoside as substrate according to the procedure of Venturi et al., 2002, Extracellular beta-D-glucosidase from *Chaetomium thermophilum* var. *coprophilum*: production, purification and some biochemical properties, *J. Basic Microbiol.* 42: 55-66. One unit of beta-glucosidase is defined as 1.0 μmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellobiohydrolase: The term "cellobiohydrolase" means a 1,4-beta-D-glucan cellobiohydrolase (E.C. 3.2.1.91 and E.C. 3.2.1.176) that catalyzes the hydrolysis of 1,4-beta-D-glucosidic linkages in cellulose, cellooligosaccharides, or any beta-1,4-linked glucose containing polymer, releasing cellobiose from the reducing end (cellobiohydrolase I) or non-reducing end (cellobiohydrolase II) of the chain (Teeri, 1997, *Trends in Biotechnology* 15: 160-167; Teeri et al., 1998, *Biochem. Soc. Trans.* 26: 173-178). Cellobiohydrolase activity is determined according to the procedures described by Lever et al., 1972, *Anal. Biochem.* 47: 273-279; van Tilbeurgh et al., 1982, *FEBS Letters,* 149: 152-156; van Tilbeurgh and Claeyssens, 1985, *FEBS Letters,* 187: 283-288; and Tomme et al., 1988, *Eur. J. Biochem.* 170: 575-581. In the present invention, the Tomme et al. method can be used to determine cellobiohydrolase activity.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic enzyme activity include: (1) measuring the total cellulolytic enzyme activity, and (2) measuring the individual cellulolytic enzyme activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic enzyme activity can be measured using insoluble substrates, including Whatman No1 filter paper, microcrystalline cellulose, bacterial cellulose, algal cellulose, cotton, pretreated lignocellulose, etc. The most common total cellulolytic activity assay is the filter paper assay using Whatman No1 filter paper as the substrate. The assay was established by the International Union of Pure and Applied Chemistry (IUPAC) (Ghose, 1987, Measurement of cellulase activities, *Pure Appl. Chem.* 59: 257-68).

For purposes of the present invention, cellulolytic enzyme activity is determined by measuring the increase in production/release of sugars during hydrolysis of a cellulosic material by cellulolytic enzyme(s) under the following conditions: 1-50 mg of cellulolytic enzyme protein/g of cellulose in pretreated corn stover (PCS) (or other pretreated cellulosic material) for 3-7 days at a suitable temperature such as 40° C.-80° C., e.g., 40° C., 45° C., 50° C., 55° C., 60° C., 65° C., 70° C., 75° C., or 80° C., and a suitable pH, such as 4-9, e.g., 4.0, 4.5, 5.0, 5.5, 6.0, 6.5, 7.0, 7.5, 8.0, 8.5, or 9.0, compared to a control hydrolysis without addition of cellulolytic enzyme protein. Typical conditions are 1 ml reactions, washed or unwashed PCS, 5% insoluble solids (dry weight), 50 mM sodium acetate pH 5, 1 mM $MnSO_4$, 50° C., 55° C., or 60° C., 72 hours, sugar analysis by AMINEX® HPX-87H column chromatography (Bio-Rad Laboratories, Inc., Hercules, CA, USA).

Coding sequence: The term "coding sequence" means a polynucleotide, which directly specifies the amino acid sequence of a protein. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a protein. Each control sequence may be native (i.e., from the same gene) or foreign (i.e., from a different gene) to the polynucleotide encoding the protein or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a protein.

Ectopic integration: The term "ectopic integration" means the insertion of a nucleic acid into the genome of a microorganism at a non-targeted site or at a site other than its usual chromosomal locus, i.e., random integration.

Endoglucanase: The term "endoglucanase" means a 4-(1, 3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3-1,4 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

Expression: The term "expression" includes any step involved in the production of a protein including, but not limited to, transcription, post-transcriptional modification, translation, post-translational modification, and secretion.

Expression vector: The term "expression vector" means a linear or circular DNA molecule that comprises a polynucleotide encoding a protein and is operably linked to control sequences that provide for its expression.

Flanking sequence or region: The term "flanking sequence or region" means DNA sequences extending on either side of a specific DNA sequence, locus, or gene. The flanking DNA is immediately adjacent to another DNA sequence, locus, or gene that is to be integrated into the genome of a filamentous fungal cell.

Fragment: The term "fragment" means a polypeptide having one or more (e.g., several) amino acids absent from the amino and/or carboxyl terminus of a mature polypeptide, wherein the fragment has enzyme activity. In one aspect, a fragment contains at least 85%, e.g., at least 90% or at least 95% of the amino acid residues of the mature polypeptide of an enzyme.

Heterologous protein: The term "heterologous protein" means a protein which is not native to a eukaryotic cell, a native protein in which modifications have been made to alter the native sequence, or a native protein whose expression is quantitatively altered as a result of a manipulation of the eukaryotic cell by recombinant DNA techniques. For example, a native protein may be recombinantly produced by, e.g., placing a gene encoding the protein under the control of a promoter foreign to the gene.

Homolog: The term "homolog" means a polynucleotide related to a second polynucleotide by descent from a common ancestral DNA sequence. The term "homolog" may apply to the relationship between genes separated by the event of speciation or to the relationship between genes separated by the event of genetic duplication. In one aspect, a homolog of a polynucleotide of interest has a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to the polynucleotide. In another aspect, a homolog of a polynucleotide of interest hybridizes under very low stringency conditions, low stringency conditions, medium stringency conditions, medium-high stringency conditions, high stringency conditions, or very high stringency conditions with the polynucleotide.

Homologous 3' or 5' region: The term "homologous 3' region" means a fragment of DNA that is identical in sequence or has a sequence identity of at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to a region in the genome and when combined with a homologous 5' region can target integration of a piece of DNA to a specific site in the genome by homologous recombination. The term "homologous 5' region" means a fragment of DNA that is identical in sequence or has a sequence identity of at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to a region in the genome and when combined with a homologous 3' region can target integration of a piece of DNA to a specific site in the genome by homologous recombination. The homologous 5' and 3' regions must be linked in the genome which means they are on the same chromosome and within at least 200 kb of one another. The homologous regions contain a sufficient number of nucleic acids, such as 20 to 10,000 base pairs, 50 to 10,000 base pairs, 100 to 10,000 base pairs, 400 to 10,000 base pairs, and 800 to 10,000 base pairs.

Homologous flanking sequence or region: The term "homologous flanking sequence or region" means a fragment of DNA that is identical or has a sequence identity of at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to a region in the genome and is located immediately upstream or downstream of a specific site in the genome into which extracellular DNA is targeted for integration.

Host cell: The term "host cell" means any cell type that is susceptible to transformation, transfection, transduction, or the like with a nucleic acid construct or expression vector comprising a polynucleotide encoding a protein. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Mature polypeptide: The term "mature polypeptide" means a polypeptide in its final form following translation and any post-translational modifications, such as N-terminal processing, C-terminal truncation, glycosylation, phosphorylation, etc. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having enzyme activity.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more (e.g., several) control sequences.

Operably linked: The term "operably linked" means a configuration in which a control sequence is placed at an appropriate position relative to the coding sequence of a polynucleotide such that the control sequence directs expression of the coding sequence.

Recombinase: The term "recombinase" is an enzyme that catalyzes directionally sensitive exchange DNA reactions between short target site sequences that are specific to each recombinase.

Recombinase-mediated recombination: The term "recombinase-mediated recombination" means recombination between two recognition sites of identical sequences catalyzed by a recombinase.

Repeat: The term "repeat" means a fragment of DNA that is repeated at least twice in the recombinant DNA introduced into a host cell and which can facilitate the loss of the DNA, i.e., selectable marker that is inserted between two repeats, by homologous recombination. A repeat is also known as a direct repeat or a homologous repeat. In a preferred aspect, the two repeats are identical in sequence. However, two repeats may have a sequence identity to each other of at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%.

Repeat sequences: The term "repeat sequences" means a set of two sequences, one of which is positioned 5' to a polynucleotide of interest and the other is positioned 3' to the polynucleotide sequence of interest, such that the repeat sequences undergo homologous recombination to remove the polynucleotide. A repeat sequence can be at least 20 nucleotides, at least 30 nucleotides, at least 40 nucleotides, at least 50 nucleotides, at least 100 nucleotides, at least 150 nucleotides, at least 200 nucleotides, at least 300 nucleotides, at least 400 nucleotides, or at least 500 nucleotides.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are a gap open penalty of 10, a gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment– Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are a gap open penalty of 10, a gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of Alignment−Total Number of Gaps in Alignment)

Stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 0.2×SSC, 0.2% SDS at 45° C.

The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 0.2×SSC, 0.2% SDS at 50° C.

The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.2×SSC, 0.2% SDS at 55° C.

The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.2×SSC, 0.2% SDS at 60° C.

The term "high stringency conditions" means for probes of at least 100 nucleotides in length, prehybridization and hybridization at 42° C. in 5×SSPE, 0.3% SDS, 200 micrograms/mi sheared and denatured salmon sperm DNA, and 50% formamide, following standard Southern blotting procedures for 12 to 24 hours. The carrier material is finally washed three times each for 15 minutes using 0.2×SSC, 0.2% SDS at 65° C.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 70° C.

Subsequence: The term "subsequence" means a polynucleotide having one or more (e.g., several) nucleotides absent from the 5' and/or 3' end of a mature polypeptide coding sequence, wherein the subsequence encodes a fragment having enzyme activity. In one aspect, a subsequence contains at least 85%, e.g., at least 90% or at least 95% of the nucleotides of the mature polypeptide coding sequence of an enzyme.

Subtilisin-like serine protease: The term "subtilisin-like serine protease" means a protease with a substrate specificity similar to subtilisin that uses a serine residue for catalyzing the hydrolysis of peptide bonds in peptides and proteins. Subtilisin-like proteases (subtilases) are serine proteases characterized by a catalytic triad of the three amino acids aspartate, histidine, and serine. The arrangement of these catalytic residues is shared with the prototypical subtilisin from *Bacillus licheniformis* (Siezen and Leunissen, 1997, *Protein Science* 6: 501-523). Subtilisin-like serine protease activity can be determined using a synthetic substrate, N-succinyl-L-Ala-L-Ala-L-Pro-L-Phe-p-nitroanilide (AAPF) (Bachem A G, Bubendorf, Switzerland) in 100 mM NaCl-100 mM MOPS pH 7.0 at 50° C. for 3 hours and then the absorbance at 405 nm is measured.

Targeted integration: The term "targeted integration" means the stable integration of extracellular DNA at a defined genomic locus.

Transformant: The term "transformant" means a cell which has taken up extracellular DNA (foreign, artificial or modified) and expresses the gene(s) contained therein.

Transformation: The term "transformation" means the introduction of extracellular DNA into a cell, i.e., the genetic alteration of a cell resulting from the direct uptake, incorporation and expression of exogenous genetic material (exogenous DNA) from its surroundings and taken up through the cell membrane(s).

Transformation efficiency: The term "transformation efficiency" means the efficiency by which cells can take up the extracellular DNA and express the gene(s) contained therein, which is calculated by dividing the number of positive transformants expressing the gene(s) by the amount of DNA used during a transformation procedure.

Trypsin-like serine protease: The term "trypsin-like serine protease" means a protease with a substrate specificity similar to trypsin that uses a serine residue for catalyzing the hydrolysis of peptide bonds in peptides and proteins. For purposes of the present invention, trypsin-like serine protease activity is determined according to the procedure described by Dienes et al., 2007, *Enzyme and Microbial Technology* 40: 1087-1094.

Variant: The term "variant" means a polypeptide having enzyme activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined with 0.2% AZCL-arabinoxylan as substrate in 0.01% TRITON® X-100 and 200 mM sodium phosphate buffer pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6.

DETAILED DESCRIPTION OF THE INVENTION

The present invention relates to methods of introducing multiple expression constructs into a eukaryotic cell, methods of constructing a eukaryotic cell having multiple target loci for expressing multiple heterologous proteins of interest, eukaryotic cells for expressing multiple heterologous proteins of interest, and methods of production of multiple heterologous proteins of interest.

The methods of introducing multiple expression constructs into a eukaryotic cell have several advantages. One advantage is the ability to introduce multiple protein expression constructs at two or more specific target loci in the genome of the eukaryotic cell to achieve desirable expression levels of all the proteins of interest. Another advantage is the efficiency of the method for constructing the eukaryotic cell by reducing the steps and time compared to methods known in the art. Another advantage is the flexibility of the method to easily delete one or more of the introduced expression constructs. Another advantage is the flexibility of the method to easily replace one or more of the introduced expression constructs with different expression constructs.

Methods of Constructing a Eukaryotic Cell Having Multiple Target Loci for Expressing Multiple Heterologous Proteins of Interest In an embodiment, the present invention relates to methods of constructing a eukaryotic cell having multiple target loci for expressing multiple heterologous proteins of interest, comprising:

(a) transforming a population of the eukaryotic cell with a first construct comprising (1) a 5' homologous region of a first target locus, (2) a first recombination recognition site, (3) a first selectable marker conferring a first selectable function, (4) a second recombination recognition site, and (5) a 3' homologous region of the first target locus;

(b) selecting a first transformant having the first construct integrated at the first target locus using the first selectable marker for selection of the first transformant, wherein the 5' homologous region and the 3' homologous region of the first construct undergo homologous recombination with the corresponding regions of the first target locus integrating the first construct at the first target locus, and wherein the first recombination recognition site and the second recombination recognition site are integrated at the first target locus;

(c) transforming a population of the first transformant with a second construct comprising (1) a 5' homologous region of a second target locus, (2) a first fragment of a second selectable marker that lacks a second selectable function, (3) a third selectable marker conferring a third selectable function, and (4) a 3' homologous region of the second target locus;

(d) selecting a second transformant having the second construct integrated at the second target locus using the third selectable marker for selection of the second transformant, wherein the 5' homologous region and the 3' homologous region of the second construct undergo homologous recombination with the corresponding regions of the second target locus integrating the second construct at the second target locus, and wherein the first fragment of the second selectable marker that lacks a second selectable function is integrated at the second target locus;

(e) co-transforming a population of the second transformant with (i) a third construct comprising (1) the first recombination recognition site, (2) one or more first expression cassettes each comprising a first polynucleotide encoding a first protein of interest, and (3) the second recombination recognition site, and (ii) a fourth construct comprising (1) the 5' homologous region of the second target locus, (2) one or more second expression cassettes each comprising a second polynucleotide encoding a second protein of interest, and (3) a second fragment of the second selectable marker that lacks the second selectable function wherein the second fragment comprises a sequence overlapping homologously the corresponding sequence of the first fragment of the first selectable marker; and (f) selecting a third transformant using the second selectable marker wherein the first integrated fragment and the second fragment of the second selectable marker become functional upon recombination (e.g., homologous recombination or recombinase-mediated recombination), wherein the 5' homologous region of the fourth construct undergoes homologous recombination with the same corresponding region of the second target locus, wherein the one or more second expression cassettes are integrated at the second target locus, and wherein the first recombination recognition site and the second recombination recognition site undergo recombination at the first target locus driven by at least one recombinase integrating the one or more first expression cassettes at the first target locus.

In step (a), a population of a eukaryotic cell is transformed with a first construct comprising (1) a 5' homologous region of a first target locus, (2) a first recombination recognition site, (3) a first selectable marker conferring a first selectable function, (4) a second recombination recognition site, and (5) a 3' homologous region of the first target locus. Step (a) introduces recombination recognition sites for integration of the third construct at the first locus. The 5' and 3' homologous regions direct the construct to integrate at the first locus. The first selectable marker is used for selection of the first construct integrated at the first locus.

In step (b), a first transformant is selected having the first construct integrated at the first target locus using the first selectable marker for selection. The 5' homologous region and the 3' homologous region of the first construct undergo homologous recombination with the corresponding regions of the first target locus integrating the first construct at the first target locus. Thus, the first recombination recognition site and the second recombination recognition site are integrated at the first target locus.

In step (c), a population of the first transformant is transformed with a second construct comprising (1) a 5' homologous region of a second target locus, (2) a first fragment of a second selectable marker that lacks a second selectable function, (3) a third selectable marker conferring a third selectable function, and (4) a 3' homologous region of the second target locus. Step (c) introduces a first fragment of a second selectable marker that lacks a second selectable function for integration at the second locus. The first fragment of the second selectable marker will recombine by recombination (e.g., homologous recombination or recombinase-mediated recombination) with a second fragment of the second selectable marker to become functional for use as a selectable marker in step (f) below. The 5' and 3' homologous regions direct the construct to integrate at the second locus. The third selectable marker is used for selection of the second construct integrated at the second locus.

In step (d), a second transformant is selected having the second construct integrated at the second target locus using the third selectable marker for selection. The 5' homologous region and the 3' homologous region of the second construct undergo homologous recombination with the corresponding regions of the second target locus integrating the second construct at the second target locus. The first fragment of the second selectable marker that lacks a second selectable function is integrated at the second target locus.

In step (e), a population of the second transformant is co-transformed with (i) a third construct comprising (1) the first recombination recognition site, (2) one or more first expression cassettes each comprising a first polynucleotide encoding a first protein of interest, and (3) the second recombination recognition site, and (ii) a fourth construct comprising (1) the 5' homologous region of the second target locus, (2) one or more second expression cassettes each comprising a second polynucleotide encoding a second protein of interest, and (3) a second fragment of the second selectable marker that lacks the second selectable function. The second fragment comprises a sequence overlapping homologously the corresponding sequence of the first fragment of the first selectable marker. The overlapping homologous sequence contains a sufficient number of nucleic acids, such as 20 to 10,000 base pairs, 50 to 10,000 base pairs, 100 to 10,000 base pairs, 400 to 10,000 base pairs, and 800 to 10,000 base pairs, which have a high degree of sequence identity to the corresponding target sequence to enhance recombination.

In step (f), a third transformant is selected using the second selectable marker where (1) the first integrated fragment and the second fragment of the second selectable marker become functional upon recombination (e.g., homologous recombination or recombinase-mediated recombination), (2) the 5' homologous region of the fourth construct undergoes homologous recombination with the same corresponding region of the second target locus, (3) the one or more second expression cassettes are integrated at the second target locus, and (4) the first recombination recognition site and the second recombination recognition site undergo recombination at the first target locus driven by at least one recombinase integrating the one or more first expression cassettes at the first target locus.

In one aspect, steps (a) and (b) are performed before steps (c) and (d). In another aspect, steps (c) and (d) are performed before steps (a) and (b).

The target loci can be any region of the genome of the eukaryotic cell. In one aspect, the target loci are genes. In another aspect, the target loci are non-genes. In another aspect, the target loci are genes and non-genes. The loci can be targets for introducing a heterologous gene encoding a protein of interest. The loci can also be targets for replacing a native gene with a heterologous gene that encodes a protein with the same function but with superior properties, e.g., thermostability, thermal activity, specific activity, pH optimum, substrate specificity, etc. In one preferred embodiment, the target locus is a *Trichoderma reesei* CBHI gene. In another preferred embodiment, the target locus is a *Trichoderma reesei* CBHII gene. In another preferred embodiment, the target locus is a *Trichoderma reesei* EGI gene. In another preferred embodiment, the target locus is a *Trichoderma reesei* EGII gene. In another preferred embodiment, the target locus is a *Trichoderma reesei* EGIII gene. In another preferred embodiment, the target locus is a *Trichoderma reesei* beta-glucosidase gene. In another preferred embodiment, the target locus is a *Trichoderma reesei* AA9A (GH61A) polypeptide gene. In another preferred embodiment, the target locus is a *Trichoderma reesei* AA9B (GH61B) polypeptide gene. In another preferred embodiment, the target locus is a *Trichoderma reesei* aspartic protease gene. In another preferred embodiment, the target locus is a *Trichoderma reesei* subtilisin-like serine protease gene. In another preferred embodiment, the target locus is a *Trichoderma reesei* trypsin-like serine protease gene. In another preferred embodiment, the target locus is a *Trichoderma reesei* xylanase gene. In another preferred embodiment, the target locus is a *Trichoderma reesei* dihydroflavonal-4-reductase gene. In another preferred embodiment, the target locus is a *Trichoderma reesei* paracelsin synthetase gene.

The first and second recombination recognition sites at each of the first target loci can be the same recombination recognition sites, different recombination recognition sites, or a combination of the same and different recombination recognition sites. In one aspect, the first and second recombination recognition sites at each of the first target loci are the same recombination recognition site. In another aspect, the first and second recombination recognition sites at each of the first target loci are a different recombination recognition site. In another aspect, the first and second recombination recognition sites at each of the first target loci are a combination of the same and different recombination recognition sites. In a preferred embodiment, the first and second recombination recognition sites at each of the first target loci are a different recombination recognition site. In an alternative preferred embodiment, the first and second recombination recognition sites at each of the first target loci are the same recombination recognition site.

The recombination recognition sites can be any recombination recognition sites useful in the methods of the present invention. In one aspect, the recombination recognition sites are selected from the group consisting of a B2 system from *Zygosaccharomyces bailii*, B3 system from *Zygosaccharomyces bisporus*, beta-recombinase-six system from a 25 *Bacillus subtilis* plasmid, Bxb1 from phage Bxb1, Cre-lox system of bacteriophase P1, Dre from Bacteriophage D6, FLP-FRT of *Saccharomyces cerevisiae*, Delta-gamma-es system from bacterial transposon Tn1000, Gin-gix system from bacteriophase Mu, HK022 from phage HK022, KD system from *Kluyveromyces drosophilarum*, Mx9 phage transformation system, *Streptomyces* phage 1C31, R-RS system of *Zygosaccharomyces rouxii*, Tn3 from *E. coli*, Vika recombinase from *Vibrio coralliilyticus*, and Xis-att system of temperate lactococcal bacteriophage TP901-1; and combinations thereof. It is understood herein that the enumerated recombination recognition sites encompass homologs and variants thereof. In one embodiment, one of the recombination recognition sites is a B2 system from *Zygosaccharomyces bailii*. In another embodiment, one of the recombination recognition sites is a B3 system from *Zygosaccharomyces bisporus*. In another embodiment, one of the recombination recognition sites is a beta-recombinase-six system from a 25 *Bacillus subtilis* plasmid. In another embodiment, one of the recombination recognition sites is a Bxb1 from phage Bxb1. In another embodiment, one of the recombination recognition sites is a Cre-lox system of bacteriophase P1. In another embodiment, one of the recombination recognition sites is a Dre from Bacteriophage D6. In another embodiment, one of the recombination recognition sites is a FLP-FRT of *Saccharomyces cerevisiae*. In another embodiment, one of the recombination recognition sites is a Delta-gamma-es system from bacterial transposon Tn1000. In another embodiment, one of the recombination recognition sites is a Gin-gix system from bacteriophase Mu. In another embodiment, one of the recombination recognition sites is a HK022 from phage HK022. In another embodiment, one of the recombination recognition sites is a KD system from *Kluyveromyces drosophilarum*. In another embodiment, one of the recombination recognition sites is a Mx9 phage transformation system. In another embodiment, one of the recombination recognition sites is a *Streptomyces* phage lC31. In another embodiment, one of the recombination recognition sites is a R-RS system of *Zygosaccharomyces rouxii*. In another embodiment, one of the recombination recognition sites is a Tn3 from *E. coli*. In another embodiment, one of the recombination recognition sites is a Vika recombinase from *Vibrio coralliilyticus*. In another embodiment, one of the recombination recognition sites is a Xis-att system of temperate lactococcal bacteriophage TP901-1.

In one aspect, the flippase recognition sites of the FLP-FRT system are selected from the group consisting F, F3, F10, F13, F14, F15, Fa, and F3a, and combinations thereof. It is understood herein that the enumerated flippase recognition sites encompass homologs and variants thereof. In one embodiment, the flippase recognition site is F. In another embodiment, the flippase recognition site is F3. In another embodiment, the flippase recognition site is F10. In another embodiment, the flippase recognition site is F13. In another embodiment, the flippase recognition site is F14. In another embodiment, the flippase recognition site is F15. In another embodiment, the flippase recognition site is Fa. In another embodiment, the flippase recognition site is F3a. See Turan et al., 2010, *J. Mol. Biol.* 402: 52-69, which is incorporated herein in its entirety.

In another aspect, the TP901-1 sites of the Xis-att system are selected from the group consisting of attB and attP, and combinations thereof. It is understood herein that the enumerated TP901-1 sites encompass homologs and variants thereof. In one embodiment, the TP901-1 site is attB. In another embodiment, the TP901-1 site is attP.

In another aspect, the Lox sites of the Cre-lox system are selected from the group consisting of LoxP, Lox71, Lox66, Lox511, Lox5171, Lox2272, M2, M3, M7, and M11, and combinations thereof. It is understood herein that the enumerated Lox sites encompass homologs and variants thereof. In one embodiment, the Lox site is LoxP. In another embodiment, the Lox site is Lox71. In another embodiment, the Lox site is Lox66. In another embodiment, the Lox site is Lox511. In another embodiment, the Lox site is Lox5171. In another embodiment, the Lox site is M2. In another embodiment, the Lox site is M3. In another embodiment, the Lox site is M7. In another embodiment, the Lox site is M11.

In the methods of the present invention, the eukaryotic cell requires one or more recombinases to catalyze the recombination between a specific set of recombination recognition sites. The one or more recombinases can be permanent or transient in the eukaryotic cell. The term "permanent" means the gene encoding the recombinase is already present in the genome of the eukaryotic cell. The term "transient" means the gene encoding the recombinase is introduced into the eukaryotic cell when the recombinase encoded by the gene is needed to catalyze the recombination between a specific set of recombination recognition sites and is removed thereafter.

The one or more recombinases can be any recombinase useful in the methods of the present invention. In one aspect, the one or more recombinases are native to the eukaryotic cell. In another aspect, the one or more recombinases are heterologous to the eukaryotic cell. In another aspect, the recombinases are a combination of native and heterologous recombinases. In another aspect, the one or more recombinases are selected from the group consisting of a Bxb1 recombinase, a Cre recombinase, a CinH recombinase, a Flp flippase, a HK022 integrase, a ParA recombinase, a Tn1721 recombinase, a Tn5053 recombinase, a TP901-1 integrase, an U153 recombinase, a λ integrase, and a φC31 recombinase. It is understood herein that the enumerated recombinases encompass homologs and variants thereof. In one embodiment, one of the recombinases is a Bxb1 recombinase. In another embodiment, one of the recombinases is a Cre recombinase. In another embodiment, one of the recombinases is a CinH recombinase. In another embodiment, one of the recombinases is a Flp flippase. In another embodiment, one of the recombinases is a HK022 integrase. In another embodiment, one of the recombinases is a ParA recombinase. In another embodiment, one of the recombinases is a Tn1721 recombinase. In another embodiment, one of the recombinases is a Tn5053 recombinase. In another embodiment, one of the recombinases is a TP901-1 integrase. In another embodiment, one of the recombinases is an U153 recombinase. In another embodiment, one of the recombinases is a λ integrase. In another embodiment, one of the recombinases is a φC31 recombinase.

The selectable markers can be any selectable markers useful in the methods of the present invention. In one aspect, the selectable markers are selected from the group consisting of ADE2, ARO4-OFP, FLD1, HIS3, LEU2, LYS2, MET3, TRP1, URA3, adeA, adeB, amdS, argB, bar, bleR, bsd, fcy1, hpt, hpt-tk, nat1, niaD, ptr1, pyrG, sC, tk, Tn903kan$^r$, trpC, and beta-tubulin.

The first selectable marker can be a dual selectable marker system. The dual selectable marker can be useful to facilitate the removal the first selectable marker and/or to improve screening strength for selecting the third transformant in step (f). The dual selectable marker system can be any useful combination of a negative screenable marker and a positive screenable marker. For example, the screenable marker can be a screenable morphological phenotype. In one aspect, the dual selectable marker system is hpt-tk. In another aspect, the dual selectable marker system is hpt-fcy1. In another aspect, the dual selectable marker system is hpt-laccase.

The first selectable marker can also be a counter selectable marker for negative selection.

The first selectable marker can further comprise a first repeat 5' of the first selectable marker and a second repeat 3' of the first selectable marker. The first and second repeat sequences of the integrated first construct can undergo homologous recombination to remove the first selectable marker.

The third selectable marker can further comprise a third repeat 5' of the third selectable marker and a fourth repeat 3' of the third selectable marker. The third and fourth repeat sequences of the second construct undergo homologous recombination to remove the third selectable marker.

The third selectable marker can be the same as the first selectable marker or different than the first selectable marker. In one aspect, the third selectable marker is the same as the first selectable marker when the third selectable marker is introduced after the first selectable marker is removed. In another aspect, the third selectable marker is different than the first selectable marker when the first selectable marker is present in the genome of the eukaryotic cell.

The second selectable marker can be the same as or different than the first and third selectable markers. In one aspect, the second selectable marker is the same as the first selectable marker when the first selectable marker is removed before step (c). In another aspect, the second selectable marker is the same as the third selectable marker when the third selectable marker is removed before step (e). In another aspect, the second selectable marker is the same as the third selectable marker when a portion of the third selectable marker is removed leaving a non-functional selectable marker in the genome. In another aspect, the second selectable marker is different than the first and third selectable markers.

The first and second non-functional fragments of the second selectable marker may each further comprise a recombination recognition site in an intron of the second selectable marker. In one aspect, each recombination recognition site in the first and second non-functional fragments is the same, which can undergo recombinase-mediated recombination. In another aspect, each recombination recognition site in the first and second non-functional fragments are different but can undergo recombinase-mediated recombination.

The first construct can further comprise a third counter selectable marker for negative selection between the first and the second recombination recognition sites to improve screening strength for selecting the third transformant in step (f).

The second construct can further comprise a third counter selectable marker for negative selection before or after the non-functional first fragment of the second selectable marker. In one embodiment, the second construct further comprises a third counter selectable marker for negative selection before the non-functional first fragment of the second selectable marker. In another embodiment, the second construct further comprises a third counter selectable marker for negative selection after the non-functional first fragment of the second selectable marker In one aspect, the second transformant comprises a third counter selectable marker at both the first and the second target loci to improve screening strength for selecting the third transformant in step (f). In another aspect, the third transformant comprises no counter selectable marker at both the first and second target loci and is selected using only the selection function of the second selectable marker.

The counter selectable marker for negative selection can be any useful counter selectable marker. In one aspect, the counter selectable marker is selected from the group consisting of URA3, amdS, fcy1, pyrG, tk, and beta-tubulin. In one embodiment, the counter selectable marker is URA3. In another embodiment, the counter selectable marker is amdS. In another embodiment, the counter selectable marker is fcy1. In another embodiment, the counter selectable marker is pyrG. In another embodiment, the counter selectable marker is tk. In another embodiment, the counter selectable marker is beta-tubulin.

In one embodiment of the above method, steps (a)-(f) are repeated at two or more additional target loci with different recombination recognition sites, different polynucleotides encoding proteins of interest, and the same or a different second selectable marker.

In another embodiment of the above method, steps (a)-(b) or (c)-(d) are repeated at one additional target locus with different recombination recognition sites, different polynucleotides encoding proteins of interest, and the same or a different selectable marker.

Methods of Introducing Multiple Expression Constructs into a Eukaryotic Cell

In one embodiment, the present invention relates to methods of introducing multiple expression constructs into two or more target loci of a eukaryotic cell, comprising.

(a) transforming a population of the eukaryotic cell with one or more first constructs and one or more second constructs, wherein the eukaryotic cell comprises (1) one or more first target loci (e.g., 1, 2, 3, 4, 5, 6, 7, 8, etc.) each comprising a pair of a first recombination recognition site and a second recombination recognition site, and (2) one or more second target loci (e.g., 1, 2, 3, 4, 5, 6, 7, 8, etc.) each comprising a first fragment of a first selectable marker lacking a selectable function;

wherein the one or more first constructs (e.g., 1, 2, 3, 4, 5, 6, 7, 8, etc.) each comprises one or more first expression cassettes each comprising a first polynucleotide encoding a first protein of interest, wherein in each of the first constructs the one or more first expression cassettes are flanked on one side by the first recombination recognition site and on the other side by the second recombination recognition site corresponding to the same recombination recognition sites of the first target loci; and wherein the one or more second constructs (e.g., 1, 2, 3, 4, 5, 6, 7, 8, etc.) each comprises one or more second expression cassettes each comprising a second polynucleotide encoding a second protein of interest, and wherein in each of the second constructs the one or more second expression cassettes are flanked on one side by a homologous region of the corresponding second target locus and on the other side by a second fragment of the first selectable marker that lacks the selectable function, wherein the second fragment comprises a sequence overlapping homologously the corresponding sequence of the first fragment of the first selectable marker of the second target loci; and (b) selecting a transformant using each of the first selectable markers wherein the first fragment and the second fragment of each of the first selectable markers undergo recombination (e.g., homologous recombination or recombinase-mediated recombination) to become functional and the homologous region of the second constructs undergo homologous recombination with the same corresponding region of the second target loci, wherein each of the second expression cassettes are integrated at the corresponding second target loci, and wherein the first and second recombination recognition sites of the first constructs undergo recombination at the corresponding first and second recombination recognition sites of the first target loci driven by at least one recombinase integrating each of the first expression cassettes at the corresponding first target loci.

The transformation of the population of the eukaryotic cell can be performed sequentially in any order with the one or more first constructs and the one or more second constructs. Alternatively, the transformation of the population of the eukaryotic cell can be performed as a co-transformation with the one or more first constructs and the one or more second constructs.

The selectable markers can be any selectable markers useful in the methods of the present invention. In one aspect, the selectable markers can be selected from the group consisting of ADE2, ARO4-OFP, FLD1, HIS3, LEU2, LYS2, MET3, TRP1, URA3, adeA, adeB, amdS, argB, bar, bleR, bsd, fcy1, hpt, hpt-tk, nat1, niaD, ptr1, pyrG, sC, tk, Tn903kan$^r$, trpC, and beta-tubulin.

The one or more first target loci can each further comprise a second selectable marker between the recombination recognition sites. In one aspect, the second selectable marker at each of the first target loci is a counter selectable marker for negative selection. The counter selectable marker for negative selection can be any useful counter selectable marker. In one aspect, the counter selectable marker is selected from the group consisting of URA3, amdS, fcy1, pyrG, tk, and beta-tubulin. In one embodiment, the counter selectable marker is URA3. In another embodiment, the counter selectable marker is amdS. In another embodiment, the counter selectable marker is fcy1. In another embodiment, the counter selectable marker is pyrG. In another embodiment, the counter selectable marker is tk. In another embodiment, the counter selectable marker is beta-tubulin.

The one or more second target loci can each further comprise a third selectable marker before or after the non-functional first fragment of the first selectable marker. In one aspect, the third selectable marker is before the non-functional first fragment of the first selectable marker. In another aspect, the third selectable marker is after the non-functional first fragment of the first selectable marker.

In one aspect, the third selectable marker at each of the second target loci is a counter selectable marker for negative selection. The counter selectable marker for negative selection can be any useful counter selectable marker. In one aspect, the counter selectable marker is selected from the group consisting of URA3, amdS, fcy1, pyrG, tk, and beta-tubulin. In one embodiment, the counter selectable marker is URA3. In another embodiment, the counter selectable marker is amdS. In another embodiment, the counter selectable marker is fcy1. In another embodiment, the counter selectable marker is pyrG. In another embodiment, the counter selectable marker is tk. In another embodiment, the counter selectable marker is beta-tubulin.

The first selectable marker can be the same selectable marker, a different selectable marker, or a combination of the same and different selectable markers at each of the second target loci. In one aspect, the first selectable marker is the same selectable marker at each of the second target loci. In another aspect, the first selectable marker is a different selectable marker at each of the second target loci. In another aspect, the first selectable marker is a combination of the same and different selectable markers at each of the second target loci.

The first and second fragments of the first selectable markers can each further comprise a repeat sequence 5' of the first fragment and a repeat sequence 3' of the second fragment. The repeat sequences undergo homologous recombination to remove the selectable markers.

The first and second fragments of the first selectable markers can each further comprise repeat sequences allowing removal of a portion of each of the selectable markers by homologous recombination resulting in selectable markers lacking a selectable function, which can undergo recombination (e.g., homologous recombination or recombinase-mediated recombination) with the second fragment of a first selectable marker lacking a selectable function. This allows reuse of the eukaryotic cell for expressing different multiple heterologous proteins of interest.

In one aspect, one of the repeat sequences can be located within an intron of the first selectable markers and the other of the repeat sequences can be located 5' or 3' of the first selectable markers, wherein the repeat sequences undergo homologous recombination to remove a portion of the first selectable markers.

In another aspect, one of the repeat sequences is located 5' or 3' of the first selectable markers and the other of the repeat sequences is a homologous region of the first selectable markers, wherein the repeat sequences undergo homologous recombination to remove a portion of the first selectable markers.

The one or more first constructs can each further comprise a fourth selectable marker between the recombination recognition sites.

Each of the fourth selectable markers can be the same selectable marker, a different selectable marker, or a combination of the same and different selectable markers. In one aspect, each of the fourth selectable markers is the same selectable marker. In another aspect, each of the fourth selectable markers is a different selectable marker. In another aspect, each of the fourth selectable markers is a combination of the same and different selectable markers.

Each of the fourth selectable markers can be the same as the first selectable markers of the second constructs, different from the first selectable markers of the second constructs, or a combination of the same and different selectable markers from the first selectable markers of the second constructs. In one aspect, each of the fourth selectable markers is the same as the first selectable markers of the second constructs. In another aspect, each of the fourth selectable markers is different from the first selectable markers of the second constructs. In another aspect, each of the fourth selectable markers is a combination of the same and different selectable markers from the first selectable markers of the second constructs.

In one aspect, each of the fourth selectable markers of the one or more first constructs is a counter selectable marker for negative selection. The counter selectable marker for negative selection can be any useful counter selectable marker. In one aspect, the counter selectable marker is selected from the group consisting of URA3, amdS, fcy1, pyrG, tk, and beta-tubulin. In one embodiment, the counter selectable marker is URA3. In another embodiment, the counter selectable marker is amdS. In another embodiment, the counter selectable marker is fcy1. In another embodiment, the counter selectable marker is pyrG. In another embodiment, the counter selectable marker is tk. In another embodiment, the counter selectable marker is beta-tubulin.

Each of the fourth selectable markers can comprise a repeat sequence 5' and a repeat sequence 3' of each of the selectable markers, wherein the repeat sequences undergo homologous recombination to remove the selectable markers.

The first and second recombination recognition sites at each of the first target loci can be the same recombination recognition sites, different recombination recognition sites, or a combination of the same and different recombination recognition sites. In one embodiment, the first and second recombination recognition sites at each of the first target loci are the same recombination recognition site. In another embodiment, the first and second recombination recognition sites at each of the first target loci are a different recombination recognition site. In another embodiment, the first and second recombination recognition sites at each of the first target loci are a combination of the same and different recombination recognition sites.

The recombination recognition sites can be any recombination recognition sites useful in the methods of the present invention. In one aspect, the recombination recognition sites are selected from the group consisting of a B2 system from *Zygosaccharomyces bailii*, B3 system from *Zygosaccharomyces bisporus*, beta-recombinase-six system from a *Bacillus subtilis* plasmid, Bxb1 from phage Bxb1, Cre-lox system of bacteriophase P1, Dre from Bacteriophage D6, FLP-FRT of *Saccharomyces cerevisiae*, Delta-gamma-es system from bacterial transposon Tn1000, Gin-gix system from bacteriophage Mu, HK022 from phage HK022, KD system from *Kluyveromyces drosophilarum*, Mx9 phage transformation system, *Streptomyces* phage lC31, R-RS system of *Zygosaccharomyces rouxii*, Tn3 from *E. coli*, Vika recombinase from *Vibrio coralliilyticus*, and Xis-att system of temperate lactococcal bacteriophage TP901-1; and combinations thereof. It is understood herein that the enumerated recombination recognition sites encompass homologs and variants thereof. In one embodiment, one of the recombination recognition sites is a B2 system from *Zygosaccharomyces bailii*. In another embodiment, one of the recombination recognition sites is a B3 system from *Zygosaccharomyces bisporus*. In another embodiment, one of the recombination recognition sites is a beta-recombinase-six system from a 25 *Bacillus subtilis* plasmid. In another embodiment, one of the recombination recognition sites is a Bxb1 from phage Bxb1. In another embodiment, one of the recombination recognition sites is a Cre-lox system of bacteriophase P1. In another embodiment, one of the recombination recognition sites is a Dre from Bacteriophage D6. In another embodiment, one of the recombination recognition sites is a FLP-FRT of *Saccharomyces cerevisiae*. In another embodiment, one of the recombination recognition sites is a Delta-gamma-es system from bacterial transposon Tn1000. In another embodiment, one of the recombination recognition sites is a Gin-gix system from bacteriophage Mu. In another embodiment, one of the recombination recognition sites is a HK022 from phage HK022. In another embodiment, one of the recombination recognition sites is a KD system from *Kluyveromyces drosophilarum*. In another embodiment, one of the recombination recognition sites is a Mx9 phage transformation system. In another embodiment, one of the recombination recognition sites is a *Streptomyces* phage lC31. In another embodiment, one of the recombination recognition sites is a R-RS system of *Zygosaccharomyces rouxii*. In another embodiment, one of the recombination recognition sites is a Tn3 from *E. coli*. In another embodiment, one of the recombination recognition sites is a Vika recombinase from *Vibrio coralliilyticus*. In another embodiment, one of the recombination recognition sites is a Xis-att system of temperate lactococcal bacteriophage TP901-1.

In one aspect, the flippase recognition sites of the FLP-FRT system are selected from the group consisting F, F3, F10, F13, F14, F15, Fa, and F3a; and combinations thereof. It is understood herein that the enumerated Lox sites encompass homologs and variants thereof. In one embodiment, the flippase recognition site is F. In another embodiment, the flippase recognition site is F3. In another embodiment, the flippase recognition site is F10. In another embodiment, the flippase recognition site is F13. In another embodiment, the flippase recognition site is F14. In another embodiment, the flippase recognition site is F15. In another embodiment, the flippase recognition site is Fa. In another embodiment, the flippase recognition site is F3a.

In another aspect, the TP901-1 sites of the Xis-att system are selected from the group consisting attB and attP, and combinations thereof. It is understood herein that the enumerated TP901-1 sites encompass homologs and variants thereof. In one embodiment, the TP901-1 site is attB. In another embodiment, the TP901-1 site is attP.

In another aspect, the Lox sites of the Cre-lox system are selected from the group consisting of LoxP, Lox71, Lox66, Lox511, Lox5171, Lox2272, M2, M3, M7, and M11, and combinations thereof. It is understood herein that the enumerated Lox sites encompass homologs and variants thereof. In one embodiment, the Lox site is LoxP. In another embodiment, the Lox site is Lox71. In another embodiment, the Lox site is Lox66. In another embodiment, the Lox site is Lox511. In another embodiment, the Lox site is Lox5171. In another embodiment, the Lox site is M2. In another embodiment, the Lox site is M3. In another embodiment, the Lox site is M7. In another embodiment, the Lox site is M11.

In a preferred embodiment, the first and second recombination recognition sites at each of the first target loci are the same recombination recognition sites. In another preferred embodiment, the first and second recombination recognition sites at each of the first target loci are different recombination recognition sites. In another preferred embodiment, the first and second recombination recognition sites at each of the first target loci are a combination of the same and different recombination recognition sites.

In another preferred embodiment, the first and second recombination recognition sites at one of the first target loci are flippase recognition sites of the FLP-FRT system and at another of the first target loci are TP901-1 sites of the Xis-att system.

In the methods of the present invention, the eukaryotic cell requires one or more recombinases to catalyze the recombination between a specific set of recombination recognition sites. The one or more recombinases can be permanent or transient in the eukaryotic cell. The term "permanent" means the gene encoding the recombinase is already present in the genome of the eukaryotic cell. The term "transient" means the gene encoding the recombinase is introduced into the eukaryotic cell when the recombinase encoded by the gene is needed to catalyze the recombination between a specific set of recombination recognition sites and is removed thereafter.

The one or more recombinases can be any recombinase useful in the methods of the present invention. In one aspect, the one or more recombinases are native to the eukaryotic cell. In another aspect, the one or more recombinases are heterologous to the eukaryotic cell. In another aspect, the recombinases are a combination of native and heterologous recombinases. In one aspect, the one or more recombinases are selected from the group consisting of a Bxb1 recombinase, a Cre recombinase, a CinH recombinase, a Flp flippase, a HK022 integrase, a ParA recombinase, a Tn1721 recombinase, a Tn5053 recombinase, a TP901-1 integrase, an U153 recombinase, a λ integrase, and a φC31 recombinase. It is understood herein that the enumerated recombinases encompass homologs and variants thereof. In one embodiment, one of the recombinases is a Bxb1 recombinase. In another embodiment, one of the recombinases is a Cre recombinase. In another embodiment, one of the recombinases is a CinH recombinase. In another embodiment, one of the recombinases is a Flp flippase. In another embodiment, one of the recombinases is a HK022 integrase. In another embodiment, one of the recombinases is a ParA recombinase. In another embodiment, one of the recombinases is a Tn1721 recombinase. In another embodiment, one of the recombinases is a Tn5053 recombinase. In another embodiment, one of the recombinases is a TP901-1 integrase. In another embodiment, one of the recombinases is an U153 recombinase. In another embodiment, one of the recombinases is a λ integrase. In another embodiment, one of the recombinases is a φC31 recombinase.

Each of the first polynucleotides can be the same polynucleotide, a different polynucleotide, or a combination of the same and different polynucleotides. In one aspect, each of the first polynucleotides is the same polynucleotide. In another aspect, each of the first polynucleotides is a different polynucleotide. In another aspect, each of the first polynucleotides is a combination of the same and different polynucleotides.

Each of the second polynucleotides can be the same polynucleotide, a different polynucleotide, or a combination of the same and different polynucleotides. In one aspect, each of the second polynucleotides is the same polynucleotide. In another aspect, each of the second polynucleotides is a different polynucleotide. In another aspect, each of the second polynucleotides is a combination of the same and different polynucleotides.

Each of the first polynucleotides and second polynucleotides can be the same polynucleotide, a different polynucleotide, or a combination of the same and different polynucleotides. In one aspect, each of the first polynucleotides and second polynucleotides is the same polynucleotide. In another aspect, each of the first polynucleotides and second polynucleotides is a different polynucleotide. In another aspect, each of the first polynucleotides and second polynucleotides is a combination of the same and different polynucleotides.

In the above methods of the present invention, the eukaryotic cell is reusable by repeating steps (a) and (b) with one or more different first constructs, second constructs, or first and second constructs each comprising an expression cassette comprising a polynucleotide encoding a different protein of interest. The repeat sequences described above can undergo homologous recombination to remove a selectable marker or a portion thereof.

The present invention also relates to methods of introducing multiple expression constructs into a eukaryotic cell, said method comprising.

(a) transforming a population of the eukaryotic cell with one or more first constructs and one or more second constructs,
wherein the eukaryotic cell comprises (1) one or more first target loci (e.g., 1, 2, 3, 4, 5, 6, 7, 8, etc.) each comprising a pair of a first recombination recognition site and a second recombination recognition site, wherein the first recombination recognition site and a second recombination recognition site are TP901-1 sites of the Xis-att system, and (2) one or more second target loci (e.g., 1, 2, 3, 4, 5, 6, 7, 8, etc.) each comprising a pair of a third recombination recognition site and a fourth recombination recognition site, wherein the third recombination recognition site and a fourth recombination recognition site are flippase recognition sites of the FLP-FRT system;
wherein the one or more first constructs (e.g., 1, 2, 3, 4, 5, 6, 7, 8, etc.) each comprises one or more first expression cassettes each comprising a first polynucleotide encoding a first protein of interest, wherein in each of the first constructs the one or more first expression cassettes are flanked on one side by the first recombination recognition site and on the other side by the second recombination recognition site corresponding to the same recombination recognition sites of the first target loci;
wherein the one or more second constructs (e.g., 1, 2, 3, 4, 5, 6, 7, 8, etc.) each comprises one or more second expression cassettes each comprising a second polynucleotide encoding a second protein of interest, and wherein in each of the second constructs the one or more second expression cassettes are flanked on one side by the third recombination recognition site and on the other side by the fourth recombination recognition site corresponding to the same recombination recognition sites of the second target loci; and
wherein one or more of the first constructs and second constructs comprise one or more first selectable markers;
(b) selecting a transformant using the one or more first selectable markers, wherein each of the second expression cassettes are integrated at the corresponding second target loci, and wherein the first and second recombination recognition sites of the first constructs undergo recombination at the corresponding first and second recombination recognition sites of the first target loci driven by at least one recombinase integrating each of the first expression cassettes at the corresponding first target loci.

In one aspect, the TP901-1 sites of the Xis-att system are selected from the group consisting of attB and attP, and combinations thereof.

In another aspect, the flippase recognition sites of the FLP-FRT system are selected from the group consisting F, F3, F10, F13, F14, F15, Fa, and F3a; and combinations thereof.

The selectable markers can be any selectable markers useful in the methods of the present invention. In one aspect, the selectable markers can be selected from the group consisting of ADE2, ARO4-OFP, FLD1, HIS3, LEU2, LYS2, MET3, TRP1, URA3, adeA, adeB, amdS, argB, bar, bleR, bsd, fcy1, hpt, hpt-tk, nat1, niaD, ptr1, pyrG, sC, tk, Tn903kan$^r$, trpC, and beta-tubulin.

In one aspect, the one or more first selectable markers are the same selectable markers.

In another aspect, the one or more first selectable markers are different selectable markers.

The one or more first target loci can each further comprise a second selectable marker between the recombination recognition sites. In one aspect, the second selectable marker at each of the first target loci is a counter selectable marker for negative selection. The counter selectable marker for negative selection can be any useful counter selectable marker. In one aspect, the counter selectable marker is selected from the group consisting of URA3, amdS, fcy1, pyrG, tk, and beta-tubulin. In one embodiment, the counter selectable marker is URA3. In another embodiment, the counter selectable marker is amdS. In another embodiment, the counter selectable marker is fcy1. In another embodiment, the counter selectable marker is pyrG. In another embodiment, the counter selectable marker is tk. In another embodiment, the counter selectable marker is beta-tubulin.

The one or more second target loci can each further comprise a third selectable marker between the recombination recognition sites.

In one aspect, the third selectable marker at each of the second target loci is a counter selectable marker for negative selection. The counter selectable marker for negative selection can be any useful counter selectable marker. In one aspect, the counter selectable marker is selected from the group consisting of URA3, amdS, fcy1, pyrG, tk, and beta-tubulin. In one embodiment, the counter selectable marker is URA3. In another embodiment, the counter selectable marker is amdS. In another embodiment, the counter selectable marker is fcy1. In another embodiment, the counter selectable marker is pyrG. In another embodiment, the counter selectable marker is tk. In another embodiment, the counter selectable marker is beta-tubulin.

The first selectable marker can be the same selectable marker, a different selectable marker, or a combination of the same and different selectable markers at each of the second target loci. In one aspect, the first selectable marker is the same selectable marker at each of the second target loci. In another aspect, the first selectable marker is a different selectable marker at each of the second target loci. In another aspect, the first selectable marker is a combination of the same and different selectable markers at each of the second target loci.

The one or more first constructs, the one or more second constructs, or the one or more first constructs and the second constructs can each further comprise a fourth selectable marker between the recombination recognition sites.

Each of the fourth selectable markers can be the same selectable marker, a different selectable marker, or a combination of the same and different selectable markers. In one aspect, each of the fourth selectable markers is the same selectable marker. In another aspect, each of the fourth selectable markers is a different selectable marker. In another aspect, each of the fourth selectable markers is a combination of the same and different selectable markers.

Each of the fourth selectable markers can be the same as the first selectable markers of the second constructs, different from the first selectable markers of the second constructs, or a combination of the same and different selectable markers from the first selectable markers of the second constructs. In one aspect, each of the fourth selectable markers is the same as the first selectable markers of the second constructs. In another aspect, each of the fourth selectable markers is different from the first selectable markers of the second constructs. In another aspect, each of the fourth selectable markers is a combination of the same and different selectable markers from the first selectable markers of the second constructs.

In one aspect, each of the fourth selectable markers of the one or more first constructs is a counter selectable marker for negative selection. The counter selectable marker for negative selection can be any useful counter selectable marker. In one aspect, the counter selectable marker is selected from the group consisting of URA3, amdS, fcy1, pyrG, tk, and beta-tubulin. In one embodiment, the counter selectable marker is URA3. In another embodiment, the counter selectable marker is amdS. In another embodiment, the counter selectable marker is fcy1. In another embodiment, the counter selectable marker is pyrG. In another embodiment, the counter selectable marker is tk. In another embodiment, the counter selectable marker is beta-tubulin.

Each of the fourth selectable markers can comprise a repeat sequence 5' and a repeat sequence 3' of each of the selectable markers, wherein the repeat sequences undergo homologous recombination to remove the selectable markers.

All other aspects for this method are described above.

Expression Constructs

The present invention also relates to expression constructs comprising a polynucleotide encoding a protein of interest, wherein the polynucleotide is operably linked to one or more control sequences that direct the expression of the coding sequence in a suitable host cell under conditions compatible with the control sequences.

The polynucleotide may be manipulated in a variety of ways to provide for expression of the protein. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a protein. The promoter contains transcriptional control sequences that mediate the expression of the protein. The promoter may be any polynucleotide that shows transcriptional activity in the host cell including mutant, truncated, and hybrid promoters, and may be obtained from genes encoding extracellular or intracellular proteins either homologous or heterologous to the host cell.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dania (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the protein. Any terminator that is functional in the host cell may be used in the present invention.

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a leader, a nontranslated region of an mRNA that is important for translation by the host cell. The leader is operably linked to the 5'-terminus of the polynucleotide encoding the protein. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the protein. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

In one embodiment, a first nucleic acid construct comprises (i) a 5' homologous region of a first target locus of a eukaryotic cell, (ii) a first recombination recognition site, (iii) a first repeat sequence, (iv) a first selectable marker conferring a first selectable function, (v) a second repeat sequence, (vi) a second recombination recognition site, and (vii) a 3' homologous region of the first target locus of the eukaryotic cell. In a preferred embodiment, the second recombination recognition site is before the first repeat sequence. In another preferred embodiment, the second recombination recognition site is after the second repeat sequence.

In another embodiment, a second nucleic acid construct comprises (1) a 5' homologous region of a second target locus of a eukaryotic cell, (2) a first fragment of a second selectable marker that lacks a second selectable function, (3) a third repeat sequence, (4) a third selectable marker conferring a third selectable function, (5) a fourth repeat sequence, and (6) a 3' homologous region of the second target locus of the eukaryotic cell. In a preferred embodiment, the first fragment of the second selectable marker is before the third repeat sequence. In another preferred embodiment, the first fragment of the second selectable marker is after the fourth repeat sequence.

In another embodiment, a third nucleic acid construct comprises (1) a first recombination recognition site, (2) one or more first expression cassettes each comprising a first polynucleotide encoding a first protein of interest, and (3) a second recombination recognition site.

In another embodiment, a fourth nucleic acid construct comprises (1) a 5' homologous region of the second target locus, (2) one or more second expression cassettes each comprising a second polynucleotide encoding a second protein of interest, and (3) a second fragment of a second selectable marker that lacks a second selectable function.

Proteins of Interest

The proteins of interest may be any protein having a biological activity of interest. The term "protein" is not meant herein to refer to a specific length of the encoded product and, therefore, encompasses peptides, oligopeptides, and polypeptides. The term "protein" also encompasses two or more (e.g., several) proteins combined to form the encoded product. The proteins also include fusion proteins, which comprise a combination of partial or complete polypeptide sequences obtained from at least two different proteins wherein one or more (e.g., several) may be heterologous to the eukaryotic cell. The proteins can further include naturally occurring allelic and engineered variations of the below-mentioned proteins and hybrid proteins.

The techniques used to isolate or clone a polynucleotide encoding a protein of interest are known in the art and include isolation from genomic DNA or cDNA, or a combination thereof. The cloning of the polynucleotides from genomic DNA can be effected, e.g., by using the well-known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from any suitable source.

In one aspect, the proteins are selected from the group consisting of an antibody, an antigen, an antimicrobial peptide, an enzyme, a growth factor, a hormone, an immunodilator, a neurotransmitter, a receptor, a reporter protein, a structural protein, or a transcription factor.

In one embodiment, the enzyme is selected from the group consisting of an oxidoreductase, a transferase, a hydrolase, a lyase, an isomerase, and a ligase. In another embodiment, the enzyme is selected from the group consisting of an acetylmannan esterase, acetyxylan esterase, aminopeptidase, alpha-amylase, alpha-galactosidase, alpha-glucosidase, alpha-1,6-transglucosidase, arabinanase, arabinofuranosidase, beta-galactosidase, beta-glucosidase, beta-xylosidase, carbohydrase, carboxypeptidase, catalase, cellobiohydrolase, cellulase, chitinase, coumaric acid esterase, cyclodextrin glycosyltransferase, cutinase, deoxyribonuclease, endoglucanase, esterase, feruloyl esterase, AA9 polypeptide having cellulolytic enhancing activity, glucocerebrosidase, glucose oxidase, glucuronidase, glucuronoyl esterase, haloperoxidase, hemicellulase, invertase, isomerase, laccase, ligase, lipase, mannanase, mannosidase, mutanase, oxidase, pectinolytic enzyme, peroxidase, phospholipase, phytase, phenoloxidase, polyphenoloxidase, proteolytic enzyme, ribonuclease, transglutaminase, urokinase, and xylanase.

In another aspect, the proteins are selected from the group consisting of an albumin, a collagen, a tropoelastin, an elastin, and a gelatin.

In another aspect, the proteins having biological activity may be different proteins. In another aspect, two or more (e.g., several) of the proteins having biological activity are the same protein.

In another aspect, the proteins comprise one or more enzymes selected from the group consisting of a cellulase, a cip1 protein, a AA9 polypeptide having cellulolytic enhancing activity, a hemicellulase, an esterase, an expansin, a laccase, a ligninolytic enzyme, a pectinase, a peroxidase, a protease, and a swollenin. In another aspect, the cellulase is one or more enzymes selected from the group consisting of an endoglucanase, a cellobiohydrolase, and a beta-glucosidase. In another aspect, the hemicellulase is one or more enzymes selected from the group consisting of a xylanase, an acetylxylan esterase, a feruloyl esterase, an arabinofuranosidase, a xylosidase, and a glucuronidase.

In one embodiment, one of the proteins is a cellulase. In another embodiment, one of the proteins is an endoglucanase. In another embodiment, one of the proteins is a cellobiohydrolase. In another embodiment, one of the proteins is a beta-glucosidase. In another embodiment, one of the proteins is a AA9 protein having cellulolytic enhancing activity. In another embodiment, one of the proteins is a swollenin protein. In another embodiment, one of the proteins is a cip1 protein. In another embodiment, one of the proteins is an esterase. In another embodiment, one of the proteins is an expansin. In another embodiment, one of the proteins is a laccase. In another embodiment, one of the proteins is a ligninolytic enzyme. In another embodiment, one of the proteins is a pectinase, In another embodiment, one of the proteins is a peroxidase. In another embodiment, one of the proteins is a protease. In another embodiment, one of the proteins is a swollenin.

In another embodiment, one of the proteins is a hemicellulase. In another embodiment, one of the proteins is a xylanase. In another embodiment, one of the proteins is a beta-xylosidase. In another embodiment, one of the proteins is an acetyxylan esterase. In another embodiment, one of the proteins is a feruloyl esterase. In another embodiment, one of the proteins is an arabinofuranosidase. In another embodiment, one of the proteins is a glucuronidase. In another embodiment, one of the proteins is an acetylmannan esterase. In another embodiment, one of the proteins is an arabinanase. In another embodiment, one of the proteins is a coumaric acid esterase. In another embodiment, one of the proteins is a galactosidase. In another embodiment, one of the proteins is a glucuronoyl esterase. In another embodiment, one of the proteins is a mannanase. In another embodiment, one of the proteins is a mannosidase.

Eukaryotic Cells

The present invention also relates to a eukaryotic cell obtained by the methods of the present invention.

In one embodiment, the eukaryotic cell for expressing multiple heterologous proteins of interest, comprises:
 (a) one or more first target loci (e.g., 1, 2, 3, 4, 5, 6, 7, 8, etc.) each comprising a pair of a first recombination recognition site and a second recombination recognition site; and
 (b) one or more second target loci (e.g., 1, 2, 3, 4, 5, 6, 7, 8, etc.) each comprising a first fragment of a first selectable marker lacking a selectable function.

In one aspect, the eukaryotic cell further comprises one or more first expression cassettes each comprising a first polynucleotide encoding a first protein of interest at each of the first target loci, wherein each of the one or more first expression cassettes are flanked on one side by the first recombination recognition site and on the other side by the second recombination recognition site of the corresponding first target locus.

In another aspect, the eukaryotic cell further or even further comprises one or more second expression cassettes each comprising a second polynucleotide encoding a second protein of interest at each of the second target loci, wherein each of the one or more second expression cassettes are flanked on one side by the first fragment of the selectable marker lacking a selectable function.

In another embodiment, the eukaryotic cell comprises (1) one or more first target loci each comprising one or more first expression cassettes each comprising a first polynucleotide encoding a first protein of interest, wherein the one or more first expression cassettes are each flanked 5' by a first recombination recognition site and 3' by a second recombination recognition site, and (2) one or more second target loci each comprising one or more second expression cassettes each comprising a second polynucleotide encoding a second protein of interest, wherein each of the one or more second expression cassettes are flanked on one side by a region of the second target locus and on the other side by a first fragment of a first selectable marker that lacks selectable function, wherein each of the pairs of the first and second recombination recognition sites at the first loci are able to undergo recombination with a first construct comprising one or more third expression cassettes each comprising a third polynucleotide encoding a third protein of interest, wherein each of the one or more third expression cassettes are flanked on one side by the first recombination recognition site and on the other side by the second recombination recognition site of the corresponding first target locus, and wherein each of the target loci regions and the first fragment of the first selectable marker that lacks selectable function at the second loci are able to undergo recombination (e.g., homologous recombination or recombinase-mediated recombination) with a second construct comprising one or more fourth expression cassettes each comprising a fourth polynucleotide encoding a fourth protein of interest, wherein each of the one or more fourth expression cassettes are flanked on one side by a homologous region of the corresponding second target locus and on the other side by a second fragment of the first selectable marker that lacks the selectable function wherein the second fragment comprises a sequence overlapping homologously the corresponding sequence of the first fragment of the first selectable marker.

The eukaryotic cell can be any eukaryotic cell useful in the methods of the present invention. The eukaryotic cell can be a mammalian, insect, plant, or fungal cell.

The eukaryotic cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, Ainsworth and Bisby's Dictionary of The Fungi, 8th edition, 1995, CAB International, University Press, Cambridge, UK).

The fungal cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, Soc. App. Bacteriol. Symposium Series No. 9, 1980).

The yeast cell may be a *Candida*, *Hansenula*, *Kluyveromyces*, *Pichia*, *Saccharomyces*, *Schizosaccharomyces*, or *Yarrowia* cell, such as a *Kluyveromyces lactis*, *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, *Saccharomyces oviformis*, or *Yarrowia lipolytica* cell.

The fungal cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal cell may be an *Acremonium*, *Aspergillus*, *Aureobasidium*, *Bjerkandera*, *Ceriporiopsis*, *Chrysosporium*, *Coprinus*, *Coriolus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Schizophyllum*, *Talaromyces*, *Thermoascus*, *Thielavia*, *Tolypocladium*, *Trametes*, or *Trichoderma* cell.

For example, the filamentous fungal cell may be an *Aspergillus awamori*, *Aspergillus foetidus*, *Aspergillus fumigatus*, *Aspergillus japonicus*, *Aspergillus nidulans*, *Aspergillus niger*, *Aspergillus oryzae*, *Bjerkandera adusta*, *Ceriporiopsis aneirina*, *Ceriporiopsis caregiea*, *Ceriporiopsis gilvescens*, *Ceriporiopsis pannocinta*, *Ceriporiopsis rivulosa*, *Ceriporiopsis subrufa*, *Ceriporiopsis subvermispora*, *Chrysosporium inops*, *Chrysosporium keratinophilum*, *Chrysosporium lucknowense*, *Chrysosporium merdarium*, *Chrysosporium pannicola*, *Chrysosporium queenslandicum*, *Chrysosporium tropicum*, *Chrysosporium zonatum*, *Coprinus cinereus*, *Coriolus hirsutus*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium suiphureum*, *Fusarium torulosum*, *Fusarium trichothecioides*, *Fusarium venenatum*, *Humicola insolens*, *Humicola lanuginosa*, *Mucor miehei*, *Myceliophthora thermophila*, *Neurospora crassa*, *Penicillium purpurogenum*, *Phanerochaete chrysosporium*, *Phiebia radiata*, *Pleurotus eryngii*, *Talaromyces emersonii*, *Talaromyces leycettanus*, *Thielavia terrestris*, *Trametes villosa*, *Trametes versicolor*, *Trichoderma harzianum*, *Trichoderma koningii*, *Trichoderma longibrachiatum*, *Trichoderma reesei*, or *Trichoderma viride* cell.

In one aspect, the filamentous fungal cell is an *Aspergillus* cell. In another aspect, the filamentous fungal cell is *Aspergillus nidulans*. In another aspect, the filamentous fungal cell is *Aspergillus niger*. In another aspect, the filamentous fungal cell is *Aspergillus oryzae*.

In another aspect, the filamentous fungal cell is a *Fusarium* cell. In another aspect, the filamentous fungal cell is *Fusarium venenatum*.

In another aspect, the filamentous fungal cell is a *Myceliophthora* cell. In another aspect, the filamentous fungal cell is *Myceliophthora thermophila*.

In another aspect, the filamentous fungal cell is a *Talaromyces* cell. In another aspect, the filamentous fungal cell is *Talaromyces emersonii*.

In another aspect, the filamentous fungal cell is a *Trichoderma* cell. In another aspect, the filamentous fungal cell is *Trichoderma reesei*.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

In one aspect, the filamentous fungal cell is an *Aspergillus* cell. In another aspect, the filamentous fungal cell is *Aspergillus nidulans*. In another aspect, the filamentous fungal cell is *Aspergillus niger*. In another aspect, the filamentous fungal cell is *Aspergillus oryzae*.

In another aspect, the filamentous fungal cell is a *Fusarium* cell. In another aspect, the filamentous fungal cell is *Fusarium venenatum*.

In another aspect, the filamentous fungal cell is a *Myceliophthora* cell. In another aspect, the filamentous fungal cell is *Myceliophthora thermophila*.

In another aspect, the filamentous fungal cell is a *Talaromyces* cell. In another aspect, the filamentous fungal cell is *Talaromyces emersonii*.

In another aspect, the filamentous fungal cell is a *Trichoderma* cell. In another aspect, the filamentous fungal cell is *Trichoderma reesei*.

Methods of Production

The present invention also relates to methods of producing a protein of interest, comprising (a) cultivating a eukaryotic cell of the present invention under conditions conducive for production of the protein; and optionally, (b) recovering the protein.

The eukaryotic cell is cultivated in a nutrient medium suitable for production of the protein using methods known in the art. For example, the eukaryotic cell may be cultivated by shake flask cultivation, or small-scale or large-scale fermentation (including continuous, batch, fed-batch, or solid state fermentations) in laboratory or industrial fermentors in a suitable medium and under conditions allowing the protein to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the protein is secreted into the nutrient medium, the protein can be recovered directly from the medium. If the protein is not secreted, it can be recovered from cell lysates.

The protein may be detected using methods known in the art that are specific for the protein. These detection methods include, but are not limited to, use of specific antibodies, formation of an enzyme product, or disappearance of an enzyme substrate. For example, an enzyme assay may be used to determine the activity of the protein.

The protein may be recovered using methods known in the art. For example, the protein may be recovered from the nutrient medium by conventional procedures including, but not limited to, collection, centrifugation, filtration, extraction, spray-drying, evaporation, or precipitation. In one aspect, a whole fermentation broth comprising the protein is recovered.

The protein may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure proteins.

EXAMPLES

Strains

*T. reesei* RutC30 (ATCC 56765) is described by Montenecourt and Eveleigh, 1979, *Adv. Chem. Ser.* 181: 289-301.

*Trichoderma reesei* strain 981-O-8 (D4) is a mutagenized strain of *T. reesei* RutC30.

*Trichoderma reesei* strain AgJg115-104-7B1 (WO 2011/075677) is a ku70-derivative of *T. reesei* strain 981-O-8 (D4).

Media and Buffer Solutions

Cellulase-inducing medium (CIM) was composed of 20 g of cellulose, 10 g of corn steep solids, 1.45 g of $(NH_4)_2SO_4$, 2.08 g of $KH_2PO_4$, 0.28 g of $CaCl_2$, 0.42 g of $MgSO_4 \cdot 7H_2O$, 0.42 ml of *Trichoderma* trace metals solution, 1-2 drops of antifoam, and deionized water to 1 liter; pH adjusted to 6.0.

COVE plates were composed of 342.3 g of sucrose, 20 ml of COVE salt solution, 10 ml of 1 M acetamide, 10 ml of 1.5 M CsCl, 25 g of Noble agar (Difco), and deionized water to 1 liter.

COVE+2% beta-lactose plates were composed of 342.3 g of sucrose, 20 g of beta-lactose, 20 ml of COVE salt solution, 10 ml of 1 M acetamide, 10 ml of 1.5 M CsCl, 25 g of Noble agar (Difco), and deionized water to 1 liter.

COVE+2% beta-lactose overlay was composed of 20 g of beta-lactose, 20 ml of COVE salt solution, 10 ml of 1 M acetamide, 10 ml of 1.5 M CsCl, 25 g of Noble agar (Difco), and deionized water to 1 liter. The autoclaved medium was melted in a microwave and then tempered to 55° C. before use.

COVE+2% glucose transformation plates were composed of 342 g of sucrose, 20 ml of COVE salts solution, 10 ml of 1 M acetamide, 10 ml of 1.5 M CsCl, 20 g of glucose, 25 g of Noble agar, and deionized water to 1 liter.

COVE+2% glucose overlay was composed of 20 ml of COVE salts solution, 10 ml of 1 M acetamide, 10 ml of 1.5 M CsCl, 20 g of glucose, 25 g of Noble agar, and deionized water to 1 liter. The autoclaved medium was melted in a microwave and then tempered to 55° C. before use.

COVE+2% glucose plates were composed of 20 ml of COVE salts solution, 10 ml of 1 M acetamide, 20 g of glucose, 25 g of Noble agar, and deionized water to 1 liter.

COVE glycerol plates were composed of 40 ml of 75% glycerol, 20 ml of COVE salt solution, 10 ml of 1 M acetamide, 25 g of Noble agar (Difco), and deionized water to 1 liter.

COVE 2 plates were composed of 30 g of sucrose, 20 ml of COVE salt solution, 10 ml of 1 M acetamide, 25 g of Noble agar (Difco), and deionized water to 1 liter.

COVE salt solution was composed of 26 g of KCl, 26 g of $MgSO_4 \cdot 7H_2O$, 76 g of $KH_2PO_4$, 50 ml of COVE trace metals solution, and deionized water to 1 liter.

COVE trace metals solution was composed of 0.04 g of $NaB_4O_7 \cdot 10H_2O$, 0.4 g of $CuSO_4 \cdot 5H_2O$, 1.2 g of FeSO$_4$·7H$_2$O, 0.7 g of MnSO$_4$·H$_2$O, 0.8 g of Na$_2$MoO$_2$·2H$_2$O, 10 g of ZnSO$_4$·7H$_2$O, and deionized water to 1 liter.

Denaturing Solution was composed of 0.5 M NaOH and 1.5 M NaCl.

FdU plates were composed of 20 ml of COVE salts solution, 0.6 g/L CaCl$_2$·2H$_2$O, 25 g of Noble agar, and deionized water to 967 ml. After the solution was autoclaved and cooled to 55° C., 20 ml filter sterilized 50% glucose, 12.5 ml filter sterilized 1 M urea, and 12.4 µl 40.6 µM FdU (5-fluoro-2'-deoxyuridine) were added.

LB plus ampicillin medium was composed of 10 g of tryptone, 5 g of yeast extract, 5 g of NaCl, and deionized water to 1 liter. After autoclaving 1 ml of a 100 mg/ml solution of ampicillin in water was added.

LB plates were composed of 10 g of tryptone, 5 g of yeast extract, 5 g of NaCl, 15 g of Bacto agar, and deionized water to 1 liter.

Neutralization Solution was composed of 1 M Tris pH 8.0 and 1.5 M NaCl.

NZY+ medium was composed of 5 g of NaCl, 3 g of MgSO$_4$·7H$_2$O, 5 g of yeast extract, 10 g of NZ amine, 1.2 g of MgCl$_2$, 4 g of glucose, and deionized water to 1 liter.

PDA plates were composed of 39 g of Potato Dextrose Agar (Difco) and deionized water to 1 liter.

PDA overlay medium was composed of 39 g of Potato Dextrose Agar (Difco), 2.44 g uridine, and deionized water to 1 liter. The autoclaved medium was melted in a microwave and then tempered to 55° C. before use.

PEG buffer was composed of 500 g of polyethylene glycol 4000 (PEG 4000), 10 mM CaCl$_2$, 10 mM Tris-HCl pH 7.5, and deionized water to 1 liter; filter sterilized.

SOC medium was composed of 0.5 g of NaCl, 5 g of yeast extract, 20 g of tryptone, 10 ml of 250 mM KCl, and deionized water to 1 liter.

20×SSC was composed of 175.3 g of NaCl, 88.2 g of sodium citrate, and deionized water to 1 liter.

STC was composed of 1 M sorbitol, 10 mM CaCl$_2$, and 10 mM Tris-HCl, pH 7.5; filter sterilized.

TAE buffer was composed of 4.84 g of Tris Base, 1.14 ml of Glacial acetic acid, 2 ml of 0.5 M EDTA pH 8, and deionized water to 1 liter.

TBE buffer was composed of 10.8 g of Tris Base, 5 g of boric acid, 4 ml of 0.5 M EDTA pH 8, and deionized water to 1 liter.

TE Buffer was composed of 1 M Tris pH 8.0 and 0.5 M EDTA pH 8.0.

*Trichoderma* Minimal Medium (TrMM) plates (for transformation) were composed of 342.3 g of sucrose, 20 ml of COVE salt solution, 0.6 g CaCl$_2$·2H$_2$O, 6 g (NH$_4$)$_2$SO$_4$, 25 g Noble agar, and deionized water to 1 liter.

*Trichoderma* Minimal Medium (TrMM) plates (for sub-culturing) were composed of 30 g sucrose, 20 ml COVE salt solution, 0.6 g of CaCl$_2$·2H$_2$O, 6 g of (NH$_4$)$_2$SO$_4$, 25 g of Noble agar, and deionized water to 1 liter.

TrMM medium was composed of 20 ml of COVE salt solution, 6 g of (NH$_4$)$_2$SO$_4$, 0.6 g of CaCl$_2$, 25 g of Noble agar (Difco), 30 g of sucrose, and deionized water to 1 liter.

TrMM-G medium was composed of 20 ml of COVE salt solution, 6 g of (NH$_4$)$_2$SO$_4$, 0.6 g of CaCl$_2$, 25 g of Nobel agar (Difco), 20 g of glucose, and deionized water to 1 liter.

*Trichoderma* trace metals solution was composed of 216 g of FeCl$_3$·6H$_2$O, 58 g of ZnSO$_4$·7H$_2$O, 27 g of MnSO$_4$·H$_2$O, 10 g of CuSO$_4$·5H$_2$O, 2.4 g of H$_3$BO$_3$, 336 g of citric acid, and deionized water to 1 liter.

YP medium was composed of 10 g of yeast extract, 20 g of Bacto peptone, and deionized water to 1 liter.

YPG medium was composed of 4 g of yeast extract, 1 g of K$_2$HPO$_4$, 0.5 g of MgSO$_4$, 15.0 g of glucose, and deionized water to 1 liter (pH 6.0).

2XYT plus ampicillin plates were composed of 16 g of tryptone, 10 g of yeast extract, 5 g of sodium chloride, 15 g of Bacto agar, and deionized water to 1 liter. One ml of a 100 mg/ml solution of ampicillin was added after the autoclaved medium was tempered to 55° C.

DNA Sequencing

DNA sequencing was performed with a Model 377 XL Automated DNA Sequencer (Applied Biosystems Inc.) using dye-terminator chemistry (Giesecke et al., 1992, *J. Viral, Methods* 38: 47-60).

Example 1: *Trichoderma reesei* Protoplast Generation and Transformation

Protoplast preparation and transformation were performed using the following protocol based on Penttila et al., 1987, *Gene* 61: 155-164. A *Trichoderma reesei* strain was cultivated in 25 ml of YP medium supplemented with 2% (w/v) glucose and 10 mM uridine at 27° C. for 17 hours with gentle agitation at 90 rpm. Mycelia were collected by filtration using a Vacuum Driven Disposable Filtration System (Millipore) and washed twice with deionized water and twice with 1.2 M sorbitol. Protoplasts were generated by suspending the washed mycelia in 20 ml of 1.2 M sorbitol containing 15 mg of GLUCANEX® 200 G (Novozymes A/S, Bagsvaerd, Denmark) per ml and 0.36 units of chitinase (Sigma Chemical Co.) per ml for 15-25 minutes at 34° C. with gentle shaking at 90 rpm. Protoplasts were collected by centrifuging for 7 minutes at 400×g and washed twice with cold 1.2 M sorbitol. The protoplasts were counted using a haemacytometer and resuspended to a final concentration of 1×10$^8$ protoplasts/ml in STC.

Approximately 1-10 µg of DNA were added to 100 µl of the protoplast solution and mixed gently. PEG buffer (250 µl) was then added, and the transformation reaction was mixed and incubated at 34° C. for 30 minutes. STC (3 ml) was then added to the transformation reaction and mixed. The transformation reaction was then spread onto COVE plates for amdS selection. The plates were incubated at 28° C. for 6-11 days.

For transformation requiring hygromycin selection, the reaction mix in STC was spread onto PDA plates supplemented with 1 M sucrose. After incubation at 28° C. for 16 hours, 20 ml of overlay PDA medium supplemented with 35 µg of hygromycin B per ml were added to each plate. The plates were incubated at 28° C. for 4-7 days.

Example 2: Genomic DNA Extraction from *Trichoderma reesei* Strains

A *Trichoderma reesei* strain was grown in 50 ml of YP medium supplemented with 2% glucose (w/v) in a 250 ml baffled shake flask at 28° C. for 2 days with agitation at 200 rpm. Mycelia from each cultivation were collected using a MIRACLOTH® (EMD Chemicals Inc.) lined funnel, squeeze-dried, and frozen under liquid nitrogen. The frozen mycelia were transferred to a pre-chilled mortar and pestle. Each mycelia preparation was ground into a fine powder and kept frozen with liquid nitrogen. A total of 1-2 g of powder was transferred to a 50 ml tube and genomic DNA was extracted from the ground mycelial powder using a DNEASY® Plant Maxi Kit (QIAGEN Inc.). Five ml of Buffer AP1 (QIAGEN Inc.) pre-heated to 65° C. were added to the 50 ml tube followed by 10 µl of a RNase A 100 mg/ml stock solution (QIAGEN Inc.), and incubated for 2-3 hours at 65° C. A total of 1.8 ml of AP2 Buffer (QIAGEN Inc.) was added and the tube was incubated on ice for 5 minutes followed by centrifugation at 3000-5000×g for 5 minutes in a LEGEND™ RT swinging bucket centrifuge (Thermo Fisher Scientific Inc.). The supernatant was transferred to a QIAShredder™ Maxi Spin Column (QIAGEN Inc.) placed in a 50 ml collection tube, and centrifuged at 3000-5000×g at room temperature for 5 minutes (15-25° C.) in a swing-out rotor. The flow-through in the collection tube was transferred, without disturbing the pellet, into a new 50 ml tube. A 1.5 ml volume of Buffer AP3/E (QIAGEN Inc.) was added to the cleared lysate, and mixed immediately by vortexing. The sample (maximum 15 ml), including any precipitate that may have formed, was pipetted into a DNEASY® Maxi Spin Column (QIAGEN Inc.) placed in a 50 ml collection tube and centrifuged at 3000-5000×g for 5 minutes at room temperature (15-20° C.) in a swing-out rotor. The flow-through was discarded. Twelve ml of Buffer AW (QIAGEN Inc.) were added to the DNEASY® Maxi Spin Column, and centrifuged at 3000-5000×g for 10 minutes to dry the membrane. The flow-through and collection tube were discarded. The DNEASY® Maxi Spin Column was transferred to a new 50 ml tube. The DNA was eluted by adding 1-1.5 ml of Kit-supplied buffer AE, pre-heated to 65° C., directly onto the DNEASY® Maxi Spin Column membrane, incubating at room temperature for 5 minutes (15-25° C.), and then centrifuging at 3000-5000×g for 5 minutes. The concentration and purity of the genomic DNA was determined by measuring the absorbance at 260 nm and 280 nm.

Example 3: Southern Blot Analysis of Transformants

Two μg of genomic DNA from each transformant were digested with selected restriction enzyme(s). The digestions were submitted to 0.7-0.8% agarose gel electrophoresis in TAE buffer and blotted onto a HYBOND® N+ blotting membrane (GE Healthcare Life Sciences) or a NYTRAN® SuperCharge membrane (Schleicher & Schuell BioScience) using a TURBOBLOTTER® (GE Healthcare Life Sciences) for approximately 1-2 hours. The membrane was hybridized with a digoxigenin-labeled gene-specific or site-specific probe, which was synthesized by PCR using a PCR DIG Probe Synthesis Kit (Roche Applied Science Corp.).

The probe was boiled for 5 minutes, chilled on ice for 2 minutes, and added to 10 ml of DIG Easy Hyb to produce the hybridization solution. Hybridization was performed in DIG Easy Hyb buffer at 42° C. for 15-17 hours. The membrane was then washed in 2×SSC plus 0.1% SDS at room temperature for 5 minutes followed by two washes in 0.5×SSC plus 0.1% SDS each at 65° C. for 15 minutes. After one wash in 1× Blocking Solution (Roche Applied Science Corp.) for a minimum of one hour, the membrane was incubated with 50 ml of 1× Blocking Solution containing 3.75 U of anti-digoxigenin-AP Fab fragments (Roche Applied Science Corp.) for 10 minutes, followed by two washes in 1× Washing Solution (Roche Applied Science Corp.). The CDP-STAR® ready-to-use reagent (disodium 2-chloro-5-(4-methoxyspiro (1,2-dioxetane-3,2'-(5'-chloro) tricyclo[3.3.1.1$^{3.7}$]decan}-4-yl)-1-phenyl phosphate; Roche Applied Science Corp.) was then applied to the membrane and the probe-target hybrids were detected by autoradiography.

Example 4: Construction of Plasmid pJfyS147 to Insert FRT-F and FRT-F3 Sites at the cbh1 Locus of *Trichoderma reesei*

A FRT site integration plasmid pJfyS147 was constructed so that the *T. reesei* cbh1 gene and 1 kb of the upstream region thereof is deleted when the plasmid integrates. The promoter region and desired gene could then be introduced back with a FLP/FRT expression construct. To construct the FRT site integration plasmid the FRT-F site (SEQ ID NO: 1) was inserted downstream of the 5' cbh1 flanking region using splicing by overlap extension (SOE) PCR. First the FRT-F site and 5' cbh1 flanking region were amplified separately and then combined by overlapping PCR.

The 5' cbh1 flanking region was amplified from *T. reesei* RutC30 genomic DNA using the primers shown below. *T. reesei* RutC30 genomic DNA was prepared as described in Example 1.

Forward primer:
(SEQ ID NO: 2)
5'-TCACATGGTTTAAACGGCGCGCCGGTGAAACACCGCCCCCTTC-3'

Reverse primer:
(SEQ ID NO: 3)
5'-TTCGAACAGCCCCAGTCGGT-3'

The PCR was composed of 150 ng of *T. reesei* RutC30 genomic DNA, 200 μM dNTPs, 0.4 μM primers, 1×PHUSION® Reaction Buffer (Thermo Fisher Scientific, Inc.), and 2 units of PHUSION® High Fidelity DNA polymerase (Thermo Fisher Scientific, Inc.) in a final volume of 50 μl. The reaction was performed in a thermocycler programmed for 1 cycle at 95° C. for 2 minutes; 30 cycles each at 95° C. for 25 seconds, 57° C. for 25 seconds, and 72° C. for 1.5 minutes; and 1 cycle at 72° C. for 7 minutes.

The FRT-F site was amplified from plasmid pRika147 (WO 2012/120093) using the primers shown below.

Forward primer:
(SEQ ID NO: 4)
5'-ACCGACTGGGGCTGTTCGAACGGCCGCGAATTCATCTTGA-3'

Reverse primer:
(SEQ ID NO: 5)
5'-AGCCTTGTTTTGTCGGGCGCGCCGCTGCTCTCGGCTAGCGAAG-3'

The PCR was composed of 20 ng of pRika147, 200 μM dNTPs, 0.4 μM primers, 1× PHUSION® Reaction Buffer, and 2 units of PHUSION® High Fidelity DNA polymerase in a final volume of 50 μl. The reaction was performed in a thermocycler programmed for 1 cycle at 95° C. for 2 minutes; 30 cycles each at 95° C. for 25 seconds, 51° C. for 25 seconds, and 72° C. for 40 seconds; and 1 cycle at 72° C. for 7 minutes.

The completed PCRs were submitted to either 2% agarose (FRT-F PCR) or 1% agarose (5' cbh1 flanking region) gel electrophoresis in TAE buffer where a 0.1 kb band (FRT-F PCR) and 1.5 kb band (5' cbh1 flanking region), respectively, were excised from the gels and agarose was extracted using a MINELUTE® Gel Extraction Kit (QIAGEN Inc.). Briefly, 3 volumes of Kit-supplied buffer QG were added to the gel slice and dissolved at 50° C. for approximately 10 minutes. The dissolved gel slice was applied to a Kit-supplied spin column and centrifuging at 13,000 rpm for 1 minute. The column was washed with 750 μl of Kit-supplied buffer PE and then re-centrifuged. DNA was eluted with 10 μl of Kit-supplied buffer EB.

A single fragment was generated from the above individual PCR products by SOE PCR using PHUSION® High Fidelity DNA polymerase and the fragment-specific forward and reverse primers shown below. The region in italics corresponds to sequence homologous to the site of insertion into target vector pJfyS1579-41-11 (WO 2011/075677).

Forward primer:
(SEQ ID NO: 6)
5'-*tcacatggtttaaacggcgcgcc*GGTGAAACACCGCCCCCTTC-3'

Reverse primer:
(SEQ ID NO: 7)
5'-*agccttgttttgtcgggcgcgcc*GCTGCTCTCGGCTAGCGAAG-3'

The SOE PCR was composed of 1 µl of each gel-purified PCR product above, 200 µM dNTPs, 1×PHUSION® Reaction Buffer, and 2 units of PHUSION® High Fidelity DNA polymerase in a final volume of 50 µl. The reaction was performed in a thermocycler programmed for 1 cycle at 95° C. for 2 minutes; and 5 cycles each at 95° C. for 25 seconds, 51° C. for 25 seconds, and 72° C. for 1.5 minutes. Following the above cycling parameters, primers were added to a final concentration of 0.4 µM and subjected to 1 cycle at 95° C. for 2 minutes; 30 cycles each at 95° C. for 25 seconds, 51° C. for 25 seconds, and 72° C. for 40 seconds; and 1 cycle at 72° C. for 7 minutes. The completed PCR was submitted to 1% agarose gel electrophoresis in TAE buffer where a 1.5 kb band containing both sequences was excised from the gel and agarose was extracted using a MINELUTE® Gel Extraction Kit as above.

To generate more PCR product the above gel purified fragment was re-amplified using the forward and reverse primers listed above. The PCR was composed of 1 µl of the gel purified fragment, 200 µM dNTPs, 0.4 µM of primers, 1×PHUSION® Reaction Buffer, and 2 units of PHUSION® High Fidelity DNA polymerase in a final volume of 50 µl. The reaction was performed in a thermocycler programmed for 1 cycle at 98° C. for 2 minutes; 30 cycles each at 95° C. for 25 seconds, 58° C. for 25 seconds, and 72° C. for 1.5 minutes; and 1 cycle at 72° C. for 7 minutes. The completed PCR was submitted to 1% agarose gel electrophoresis in TAE buffer where the 1.5 kb band was excised from the gel and agarose was extracted using a MINELUTE® Gel Extraction Kit as above.

The 1.5 kb fragment was inserted into Asc I-digested pJfyS1579-41-11 (WO 2011/075677) using an IN-FUSION® Advantage PCR Cloning Kit (Clontech Laboratories, Inc.). The reaction was composed of 1× IN-FUSION® Reaction Buffer (Clontech Laboratories, Inc.), 120 ng of pJfyS1579-41-11, 120 ng of the SOE PCR product, and 1 µl of IN-FUSION® Enzyme (Clontech Laboratories, Inc.) in a 10 µl reaction volume. The reaction was incubated at 50° C. for 15 minutes. Then 40 µl of TE were added to the reaction and 2 µl were transformed into ONE SHOT® TOP10 *E. coli* chemically competent cells (Invitrogen Corp.) by addition to a single use tube containing the competent cells and incubating the cells on ice for 5 minutes. The tube was incubated at 42° C. for 30 seconds after which 250 µl of SOC medium were added. The tube was then incubated at 37° C. with agitation at 200 rpm for 1 hour and 250 µl were transferred to a 150 mm 2XYT plus ampicillin plate and incubated overnight at 37° C. *E. coli* transformants were inoculated into 3 ml of LB plus ampicillin medium in 14 ml tubes and incubated overnight at 37° C. with agitation at 200 rpm. Plasmid DNA was isolated using a BIOROBOT® 9600 (QIAGEN Inc.). The insert was confirmed by DNA sequencing. One transformant was identified as containing the insert with no PCR errors and the plasmid was designated pJfyS147A.

The FRT-F3 (SEQ ID NO: 8) site was inserted upstream of the 3' cbh1 flanking region using SOE PCR. First the FRT-F3 site and 3' cbh1 flanking region were amplified separately and then combined by SOE PCR.

The 3' cbh1 flanking region was amplified from *T. reesei* RutC30 genomic DNA using the primers shown below.

Forward primer:
(SEQ ID NO: 9)
5'-GATAACGGAATAGAAGAAAGAG-3'

Reverse primer:
(SEQ ID NO: 10)
5'-GCCATATTTAAATCCGTTTAAACAGTCAACACGTCTCCTATGTCT-3'

The PCR was composed of 150 ng of *T. reesei* RutC30 genomic DNA, 200 µM dNTPs, 0.4 µM primers, 1×PHUSION® Reaction Buffer, and 2 units of PHUSION® High Fidelity DNA polymerase in a final volume of 50 µl. The reaction was performed in a thermocycler programmed for 1 cycle at 95° C. for 2 minutes; 30 cycles each at 95° C. for 25 seconds, 54° C. for 25 seconds, and 72° C. for 1.5 minutes; and 1 cycle at 72° C. for 7 minutes.

The FRT site was amplified from pRika147 using the primers shown below.

Forward primer:
(SEQ ID NO: 11)
5'-CCTAGTTGGAGTATTCCTGCAGGTCAACTCTCTCCTCTAGGTTGAAGTTCCTATTCCGAGTTC-3'

Reverse primer:
(SEQ ID NO: 12)
5'-CTCTTTCTTCTATTCCGTTATCGCATGCACTAGCTAGTTGAAGTTCCTATAC-3'

The PCR was composed of 20 ng of pRika147, 200 µM dNTPs, 0.4 µM primers, 1× PHUSION® Reaction Buffer, and 2 units of PHUSION® High Fidelity DNA polymerase in a final volume of 50 µl. The reaction was performed in a thermocycler programmed for 1 cycle at 95° C. for 2 minutes; 30 cycles each at 95° C. for 25 seconds, 50° C. for 25 seconds, and 72° C. for 40 seconds; and 1 cycle at 72° C. for 7 minutes.

The completed PCRs were submitted to either 2% agarose (FRT-F3 PCR) or 1% agarose (3' cbh1 flank) gel electrophoresis in TAE buffer where a 0.1 kb band (FRT-F3 PCR) and 1.5 kb band (3' cbh1 flanking region), respectively, were excised from the gels and agarose was extracted using a MINELUTE® Gel Extraction Kit as above.

A single fragment was generated from the above individual PCRs by SOE PCR using the primers shown below. The region in italics corresponds to sequence homologous to the desired site of insertion into pJfyS147A (described above).

Forward primer:
(SEQ ID NO: 13)
5'-*CCTAGTTGGAGTATTCCTGCAGGTCAACTCTCTCCTCTAGGTTGAAG*TTCCTATTCCGAGTTC-3'

Reverse primer:
(SEQ ID NO: 14)
5'-*GCCATATTTAAATCCGTTTAAACAGTCAACACGTCTCCTATGTCT*-3'

The PCR was composed of 1 µl of each gel-purified PCR product above, 200 µM dNTPs, 1×PHUSION® Reaction Buffer, and 2 units of PHUSION® High Fidelity DNA polymerase in a final volume of 50 µl. The reaction was performed in a thermocycler programmed for 1 cycle at 95° C. for 2 minutes; and 5 cycles each at 95° C. for 25 seconds, 51° C. for 25 seconds, and 72° C. for 1.5 minutes. Following the above cycling parameters, primers were added to a final concentration of 0.4 µM and subjected to 1 cycle at 95° C. for 2 minutes; 30 cycles each at 95° C. for 25 seconds, 51° C. for 25 seconds, and 72° C. for 40 seconds; and 1 cycle at 72° C. for 7 minutes. The completed PCR was submitted to 1% agarose gel electrophoresis in TAE buffer where a 1.5 kb band containing both sequences was excised from the gel and agarose was extracted using a MINELUTE® Gel Extraction Kit as above.

To generate more PCR product the above gel-purified fragment was re-amplified using the forward and reverse primers used in the preceding step. The PCR was composed of 1 µl of the gel purified 1.5 kb fragment, 200 µM dNTPs, 0.4 µM of primers, 1×PHUSION® Reaction Buffer, and 2 units of PHUSION® High Fidelity DNA polymerase in a final volume of 50 µl. The reaction was performed in a thermocycler programmed for 1 cycle at 98° C. for 2 minutes; 30 cycles each at 95° C. for 25 seconds, 58° C. for 25 seconds, and 72° C. for 1.5 minutes; and 1 cycle at 72° C. for 7 minutes. The completed PCR was submitted to 1% agarose gel electrophoresis in TAE buffer where the 1.5 kb band was excised from the gel and agarose was extracted using a MINELUTE® Gel Extraction Kit as above.

The 1.5 kb fragment was inserted into Sbf I-digested pJfyS147A using an IN-FUSION® Advantage PCR Cloning Kit. The reaction was composed of 1× IN-FUSION® Reaction Buffer, 120 ng of pJfyS147A, 60 ng of the 1.5 kb PCR product, and 1 µl of IN-FUSION® Enzyme in a 10 µl reaction volume. The reaction was incubated at 50° C. for 15 minutes. Then 40 µl of TE were added to the reaction and 2 µl were transformed into ONE SHOT® TOP10 E. coli chemically competent cells as described above. Transformants were screened by sequencing. E. coli transformants were inoculated into 3 ml of LB plus ampicillin medium in 14 ml tubes and incubated overnight at 37° C. with agitation at 200 rpm. Plasmid DNA was isolated using a BIORO-BOT® 9600. The insert was confirmed by DNA sequencing. One transformant was identified as containing the insert with no PCR errors and the plasmid was designated pJfyS147 (FIG. 1). Plasmid pJfyS147 was used to integrate the FRT-F and FRT-F3 sites at the cbh1 locus of T. reesei 981-O-8.

Example 5: Insertion of FRT-F and FRT-F3 Sequences at the cbh1 Locus of Trichoderma reesei 981-O-8 (D4)

Protoplast preparation and transformation of Trichoderma reesei 981-O-8 were performed according to Example 1. In order to insert the FRT-F and FRT-F3 sequences at the cbh1 locus of T. reesei 981-O-8, the strain was transformed with 6×2.5 µg of Pme I-linearized pJfyS147 (Example 4). One hundred and thirty-one transformants were obtained and each one was picked and transferred to a 25 mm PDA plate and incubated for 7 days at 28° C. Transformants were each analyzed by transferring a small amount of spores with a sterile 10 µl inoculation loop into 25 ml of CIM in a 125 ml polycarbonate shake flask and incubating at 28° C. for 5 days with agitation at 200 rpm. Supernatant from each culture was subjected to SDS-PAGE using a CRITERION® 8-16% SDS-PAGE gel (Bio-Rad Laboratories, Inc.) and PRECISION PLUS® Protein Standards (Bio-Rad Laboratories, Inc.). Since successful targeted integration of the FRT-F/FRT-F3 construct at the cbh1 locus effectively removes the cbh1 gene, SDS-PAGE gels were visually analyzed for loss of the CBH1 protein from the proteome. Two transformants, T. reesei JfyS147-20 and T. reesei JfyS147-74, were identified, which produced no CBHI protein. T. reesei JfyS147-20 and T. reesei JfyS147-74 were grown on PDA plates at 28° C. for 7 days. Spores were collected from the plates using 0.01% TWEEN® 20 and diluted to $10^6$ spores/ml using a hemocytometer. One ml and 0.1 ml of each spore suspension were spread onto TrMM-G plates supplemented with 1 µM 5-flurodeoxyuridine (FDU) and incubated at 28° C. for 6 days. Eight spore isolates were picked for T. reesei JfyS147-20 and 1 spore isolate for T. reesei JfyS147-74, which were each transferred to a new 75 mm PDA plate. The plates were incubated at 28° C. for 7 days. Genomic DNA was isolated from T. reesei JfyS147-20 and T. reesei JfyS147-74 as described in Example 1 and analyzed by Southern blotting to insure correct integration of the original FRT integration construct in the primary transformant as well as to insure correct excision of the markers in the resulting FdU-resistant spore progeny.

A probe hybridizing to the 3' flanking region of the cbh1 gene was generated using a PCR DIG Probe Synthesis Kit and the forward and reverse primers shown below. The PCR was composed of 1×HERCULASE® Reaction Buffer (Stratagene Corp.), 400 nM each primer, 200 µM DIG-labeled dUTP-containing dNTPs, 20 ng of pJfyS139 (WO 2013/028927), and 1.5 units of HERCULASE® DNA polymerase (Stratagene Corp.). The reaction was incubated in a thermocycler programmed for 1 cycle at 95° C. for 2 minute; 25 cycles each at 95° C. for 30 seconds, 55° C. for 30 seconds, and 72° C. for 40 seconds; and 1 cycle at 72° C. for 7 minutes.

```
Forward primer:
                                      (SEQ ID NO: 15)
5'-AAAAAACAAACATCCCGTTCATAAC-3'

Reverse primer:
                                      (SEQ ID NO: 16)
5'-AACAAGGTTTACCGGTTTCGAAAAG-3'
```

The probe was purified by 1% agarose gel electrophoresis in TAE buffer where a band corresponding to the probe was excised from the gel and agarose was extracted using a MINELUTE® Gel Extraction Kit (Example 4).

For Southern blot analysis, 2 µg of each genomic DNA was digested with Nde I in a 50 µl reaction volume. The digested DNA was subjected to 1% agarose gel electrophoresis in TAE buffer and transferred to a NYTRAN® Super-Charge membrane as described to Example 3 using the probe hybridizing to the 3' flanking region of the cbh1 gene. Southern blot analysis identified primary transformant T. reesei JfyS147-20 as having correctly integrated the FRT site construct at the cbh1 locus and the resulting hpt/tk-spore isolate JfyS147-20B as having correctly excised the markers leaving the FRT-F and FRT-F3 sites at the cbh1 locus, with a single copy of the 262 bp repeat DNA used for marker excision, separating the FRT-F and FRT-F3 sites.

Example 6: Construction of FLP/FRT Integration Plasmid pJfyS150

Expression plasmid pJfyS150 was constructed for integrating a desired gene at the T. reesei cbh1 locus using the

*Saccharomyces cerevisiae* flippase (FLP) and flippase recognition sequences FRT-F and FRT-F3. The FRT-F3 site was first inserted into plasmid pSMai155 (WO 05/074647) using a QUICKCHANGE® II XL Site-Directed Mutagenesis Kit (Agilent Technologies) with the mutagenic insertion primers shown below.

```
Forward primer:
                                        (SEQ ID NO: 17)
5'-CGAATTCTGCATTGAAGTTCCTATTCCGAGTTCCTATTCTTCAAATA

GTATAGGAACTTCAGATATCCATCACACTGGCG-3'

Reverse primer:
                                        (SEQ ID NO: 18)
5'-GCCAGTGTGATGGATATCTGAAGTTCCTATACTATTTGAAGAATAGG

AACTCGGAATAGGAACTTCAATGCAGAATTCGC-3'
```

The mutagenic PCR contained 10 ng of pSMai155, 200 µM dNTPs, 125 ng of each primer, 1×QUICKCHANGE® Reaction Buffer, 3 µl of QUIKSOLUTION® reagent (Agilent Technologies), and 2.5 units of Pfu Ultra High Fidelity DNA polymerase (Agilent Technologies) in a final volume of 50 µl. The PCR was performed in a thermocycler programmed for 1 cycle at 95° C. for 1 minute; 18 cycles each at 95° C. for 50 seconds, 60° C. for 50 seconds, and 68° C. for 40 seconds; and 1 cycle at 68° C. for 7 minutes. One µl of Kit-supplied Dpn I was added and the reaction was incubated at 37° C. for 1 hour. Two µl of the Dpn I-treated reaction were added to 45 µl of Kit-supplied XL10-Gold Ultracompetent *E. coli* cells (Agilent Technologies) in a 14 ml tube and incubated on ice for 30 minutes. The tube was incubated at 42° C. for 30 seconds after which 0.5 ml of SOC medium was added. The tube was then incubated at 37° C. with agitation at 200 rpm for 1 hour after which 250 µl each were plated onto 2×150 mm 2XYT plus ampicillin plates and incubated at 37° C. overnight. *E. coli* transformants were inoculated into 3 ml of LB plus ampicillin medium in 14 ml tubes and incubated overnight at 37° C. with agitation at 200 rpm. Plasmid DNA was isolated using a BIOROBOT® 9600. The insert was confirmed by DNA sequencing. One transformant was identified as containing the desired sequence insertion corresponding to the FRT-F3 site and the plasmid was designated pJfyS148A.

The FRT-F sequence was then inserted into plasmid pJfyS148A using an IN-FUSION® Advantage PCR Cloning Kit. The FRT-F site was first amplified by PCR from plasmid pRika147 using the primers shown below.

```
Forward primer:
                                        (SEQ ID NO: 19)
5'-ATATCCATCACACTGGCGGCCGCTCAACTCTCTCCTCTAGGTTGAAG

TTCCTATTCCGAGTTC-3'

Reverse primer:
                                        (SEQ ID NO: 20)
5'-AGGATGCATGCTCGAGCATGCACTAGCTAGTTGAAGTTCCTATA

C-3'
```

The PCR was composed of 20 ng of pRika147, 200 µM dNTPs, 0.4 µM primers, 1× PHUSION® Reaction Buffer, and 2 units of PHUSION® High Fidelity DNA polymerase in a final volume of 50 µl. The reaction was performed in a thermocycler programmed for 1 cycle at 95° C. for 2 minutes; 30 cycles each at 95° C. for 25 seconds, 50° C. for 25 seconds, and 72° C. for 40 seconds; and 1 cycle at 72° C. for 7 minutes. The completed PCR was submitted to 2% agarose gel electrophoresis in TAE buffer where a 0.1 kb fragment was excised from the gel and agarose was extracted using a MINELUTE® Gel Extraction Kit (Example 4).

The 0.1 kb PCR product was inserted into Sal I-digested pJfyS148A using an IN-FUSION® Advantage PCR Cloning Kit. The reaction was composed of 1× IN-FUSION® Reaction Buffer, 125 ng of pJfyS147A, 20 ng of FRT-F PCR product, and 1 µl of IN-FUSION® Enzyme in a 10 µl reaction volume. The reaction was incubated at 50° C. for 15 minutes. Then 40 µl of TE were added to the reaction and 2 µl were transformed into ONE SHOT® TOP10 *E. coli* chemically competent cells according to Example 4. Plasmid DNA from *E. coli* transformants was isolated as described in Example 4. The insert was confirmed by DNA sequencing. One transformant was identified as containing the insert with no PCR errors and the plasmid was designated pJfyS148B. Plasmid pJfyS148B was used to insert the *Saccharomyces cerevisiae* flippase (FLP) gene.

A *S. cerevisiae* flippase cassette (WO 2012/120093) was amplified from plasmid pRika147 using the primers shown below.

```
Forward primer:
                                        (SEQ ID NO: 21)
5'-ATCTACGCGTACTAGTTAATTAAGGCTTTCGTGACCGGGCTTCAA

ACA-3'

Reverse primer:
                                        (SEQ ID NO: 22)
5'-GCGGCCGTTACTAGTGGATCCACTCGGAGTTGTTATACGCTA

CTCG-3'
```

The PCR was composed of 20 ng of pRika147, 200 µM dNTPs, 0.4 µM primers, 1× PHUSION® Reaction Buffer, and 2 units of PHUSION® High Fidelity DNA polymerase in a final volume of 50 µl. The reaction was performed in a thermocycler programmed for 1 cycle at 95° C. for 2 minutes; 25 cycles each at 95° C. for 30 seconds, 57° C. for 30 seconds, and 72° C. for 2 minutes; and 1 cycle at 72° C. for 7 minutes. The completed PCR was submitted to 1% agarose gel electrophoresis in TAE buffer where a 2.4 kb fragment was excised from the gel and agarose was extracted using a MINELUTE® Gel Extraction Kit (Example 4).

The 2.4 kb PCR product was inserted into Bam HI-digested pJfyS148B using an IN-FUSION® Advantage PCR Cloning Kit. The reaction was composed of 1× IN-FUSION® Reaction Buffer, 150 ng of pJfyS142-A, 150 ng of the 2.4 kb PCR product, and 1 µl of IN-FUSION® Enzyme in a 10 µl reaction volume. The reaction was incubated at 50° C. for 15 minutes. Then 40 µl of TE were added to the reaction and 2 µl were transformed into ONE SHOT® TOP10 *E. coli* chemically competent cells according to Example 4. Plasmid DNA from *E. coli* transformants was isolated as described in Example 4. The insert was confirmed by DNA sequencing. One transformant was identified as containing the insert with no PCR errors and the plasmid was designated pJfyS148. Plasmid pJfyS148 was used to insert an *Aspergillus fumigatus* beta-glucosidase gene.

The *A. fumigatus* beta-glucosidase gene was amplified by PCR from pEJG107 (WO 05/047499) using the primers shown below.

```
Forward primer:
                                   (SEQ ID NO: 23)
5'-ACCGCGGACTGCGCACCATGAGATTCGGTTGGCTCGAGG-3'

Reverse primer:
                                   (SEQ ID NO: 24)
5'-TTCGCCACGGAGCTTACTAGTAGACACGGGGCAGAGGC-3'
```

The PCR was composed of 20 ng of pEJG107, 200 µM dNTPs, 0.4 µM primers, 1× PHUSION® Reaction Buffer, and 2 units of PHUSION® High Fidelity DNA polymerase in a final volume of 50 µl. The reaction was performed in a thermocycler programmed for 1 cycle at 95° C. for 2 minutes; 25 cycles each at 95° C. for 30 seconds, 57° C. for 30 seconds, and 72° C. for 2 minutes; and 1 cycle at 72° C. for 7 minutes. The completed PCR was submitted to 1% agarose gel electrophoresis in TAE buffer where a 3 kb band was excised from the gel and agarose was extracted using a MINELUTE® Gel Extraction Kit (Example 4).

The *A. fumigatus* beta-glucosidase gene was inserted into Nco I/Pac I-linearized pJfyS148 using an IN-FUSION® Advantage PCR Cloning Kit. The reaction was composed of 1× IN-FUSION® Reaction Buffer, 150 ng of Nco I/Pac I-linearized pJfyS148, 80 ng of the 3 kb PCR product, and 1 µl of IN-FUSION® Enzyme in a 10 µl reaction volume. The reaction was incubated at 50° C. for 15 minutes. Then 40 µl of TE were added to the reaction and 2 µl were transformed into ONE SHOT® TOP10 *E. coli* chemically competent cells according to Example 4. Plasmid DNA from *E. coli* transformants was isolated as described in Example 4. The insert was confirmed by DNA sequencing. One transformant was identified as containing the insert with no PCR errors and the plasmid was designated pJfyS150.

Example 7: Integration of FLP/FRT Construct pJfyS150 at the cbh1 Locus of *Trichoderma reesei* Strain JfyS147-20B In order to integrate the FLP/FRT expression construct at the cbh1 locus using the FLP/FRT system, protoplasts of *Trichoderma reesei* strain JfyS147-20B were generated and transformed according to Example 1 except that xylose was added to a final concentration of 1% to STC. Xylose was included to properly induce transcription of the *Saccharomyces cerevisiae* flippase gene as its expression in pJfyS150 is controlled by the *Aspergillus nidulans* xlnA promoter which is induced by xylose (WO 2012/120093). Protoplasts were transferred to nine 14 ml round-bottom polypropylene tubes and transformed with 2 µg of the Pme I-linearized and gel purified pJfyS150 (Example 6). The transformations were divided into 3 parts and spread onto 150 mm PDA plates supplemented with 1 M sucrose and 1% xylose and incubated overnight at 28° C. After approximately 16 hours of incubation 20 ml of PDA medium supplemented with 10 mM uridine, 1% xylose, and 35 µg of hygromycin B per ml were added to each plate and the plates incubated for 6 days at 28° C. Nineteen transformants were obtained and each was transferred to a 25 mm PDA plate and incubated for 7 days at 28° C. A fungal spore PCR method using a modified protocol by Suzuki et al., 2006, *J. Bioscience and Bioengineering* 102: 572-574 was used to screen for transformants bearing site-specific integration.

The spore PCR was accomplished by collecting spores with a sterile 1 µl inoculation loop and transferring them to 25 µl of TE buffer in a 0.6 ml EPPENDORF® tube. Spores were microwaved on high for 1 minute and 1 µl of the microwaved spore solution was immediately added to ADVANTAGE® GC Genomic LA Polymerase Mix (Clontech Laboratories Inc.) containing the following components: 1× Reaction Buffer (Clontech Laboratories Inc.), 200 µM dNTPs, 400 nM each primer (3 primers for each PCR), and 1.25 units of ADVANTAGE® GC Genomic LA Polymerase (Clontech Laboratories Inc.) in a 25 µl volume. The PCR products were amplified using the forward and reverse primers shown below for either 5' recombination or 3' recombination.

```
5' Recombination:
Forward primer:
                                   (SEQ ID NO: 25)
5'-TTCCCTTCCTCTAGTGTTGAAT-3'

Reverse No integration:
                                   (SEQ ID NO: 26)
5'-TCGTCGAATACTAACATCTTGC-3'

Reverse Integration:
                                   (SEQ ID NO: 27)
5'-CACGGACCTCGAACCTTTATAT-3'

3' Recombination:
Forward primer:
                                   (SEQ ID NO: 28)
5'-CAGCGAGAGCCTGACCTATTGCATC-3'

Reverse No integration:
                                   (SEQ ID NO: 29)
5'-AACAAGGTTTACCGGTTTCGAAAAG-3'

Reverse Integration:
                                   (SEQ ID NO: 30)
5'-GTGGCTGCCGAGGTGTGTATACCA-3'
```

The reaction was performed in a thermocycler programmed for 1 cycle at 95° C. for 10 minutes; 35 cycles each at 95° C. for 30 seconds, 56° C. for 30 seconds, and 72° C. for 1 minute and 40 seconds; 1 cycle at 72° C. for 7 minutes; and a 4° C. hold. The completed PCRs were analyzed by 1% agarose gel electrophoresis in TAE buffer.

The primers were designed such that depending on whether or not the cassette had targeted to the locus two different sized PCR amplicons would be produced. A successful targeted integration at the 5' end produces a 1.8 kb band while an ectopic integration produces a 1 kb band. At the 3' end a successful integration produces a 1.8 kb band while integration elsewhere results in a 0.7 kb band. The results of the spore PCR indicated that three of the nineteen transformants had undergone a successful integration at both 5' and 3' ends corresponding to the FRT-F and FRT-F3 sites, respectively.

Example 8: Construction of FLP Integration Plasmid pJfyS156 Containing the *Saccharomyces cerevisiae* Flippase Controlled by the *Trichoderma reesei* cbh2 Promoter In an attempt to increase the frequency of flippase-mediated targeted integration a new construct was constructed in which the promoter driving the *Saccharomyces cerevisiae* flippase gene was replaced with the *Trichoderma reesei* cbh2 promoter. To construct the plasmid the cbh2 gene promoter and flippase gene were PCR amplified using gene-specific primers shown below and inserted into plasmid pJfyS148B (Example 6).
Flippase

```
Forward primer:
                                   (SEQ ID NO: 31)
5'-CACCCTCTGTGTATTGCACCATGCCCCAGTTCGATATCCTCTGCA-3'

Reverse primer:
                                   (SEQ ID NO: 32)
5'-AAACTCTAGGATGCATGCAAGTGAGGCTATTGCCTATCAGCTC-3'
```

-continued cbh2 gene promoter
Forward primer:
(SEQ ID NO: 33)
5'-CATCACACTGGCGGCCGCGAATTCTAGGCTAGGTATGC-3'

Reverse primer:
(SEQ ID NO: 34)
5'-GGTGCAATACACAGAGGGTG-3'

The PCR was composed of 20 ng of template pRiKa147 for the flippase PCR or 150 ng of *T. reesei* 981-O-8 genomic DNA for the cbh2 promoter PCR, 200 µM dNTPs, 0.4 µM primers, 1×PHUSION® Reaction Buffer, and 2 units of PHUSION® High Fidelity DNA polymerase in a final volume of 50 µl. The reactions were performed in a thermocycler programmed for 1 cycle at 95° C. for 2 minutes; 30 cycles each at 95° C. for 30 seconds, 57° C. for 30 seconds, and 72° C. for 2 minutes; and 1 cycle at 72° C. for 7 minutes. The completed PCRs were submitted to 1% agarose gel electrophoresis in TAE buffer where 1.2 and 0.6 kb bands, corresponding to the coding region for the *S. cerevisiae* flippase gene and the niaD terminator and cbh2 gene promoter, respectively, were excised from the gels and agarose was extracted using a Nucleospin® Extract II Kit (Macherey Nagel, Bethlehem, PA, USA). Three volumes of Kit-supplied NT buffer were added to the gel slice and the sample was heated at 50° C. for 10 minutes. The entire solution was transferred to a Kit-supplied centrifugal column. The column was centrifuged at 13,000 rpm for 1 minute, and washed with Kit-supplied wash buffer NT3 and re-centrifuged. DNA was eluted with 30 µl of Kit-supplied elution buffer NE and centrifuged at 13,000 rpm for 1 minute.

The cbh2 gene promoter and flippase coding sequence were inserted in a single step into Xho I-linearized pJfyS148B using an IN-FUSION® Advantage PCR Cloning Kit. The reaction was composed of 1× IN-FUSION® Reaction Buffer, 180 ng of Xho I-linearized pJfyS148B, 100 ng of the 0.6 kb cbh2 promoter PCR product, 240 ng of the 1.2 kb flippase PCR product, and 1 µl of IN-FUSION® Enzyme in a 10 µl reaction volume. The reaction was incubated for 15 minutes at 37° C. and then 15 minutes at 50° C. Then 40 µl of TE were added to the reaction and 2 µl were transformed into ONE SHOT® TOP10 *E. coli* chemically competent cells according to Example 4. *E. coli* transformants were inoculated into 3 ml of LB plus ampicillin medium in 14 ml tubes and incubated overnight at 37° C. with agitation at 200 rpm. Plasmid DNA was isolated using a BIOROBOT® 9600. The insert was confirmed by DNA sequencing. One transformant was identified as containing the inserts with no PCR errors and the plasmid was designated pJfyS155.

Figure 2:
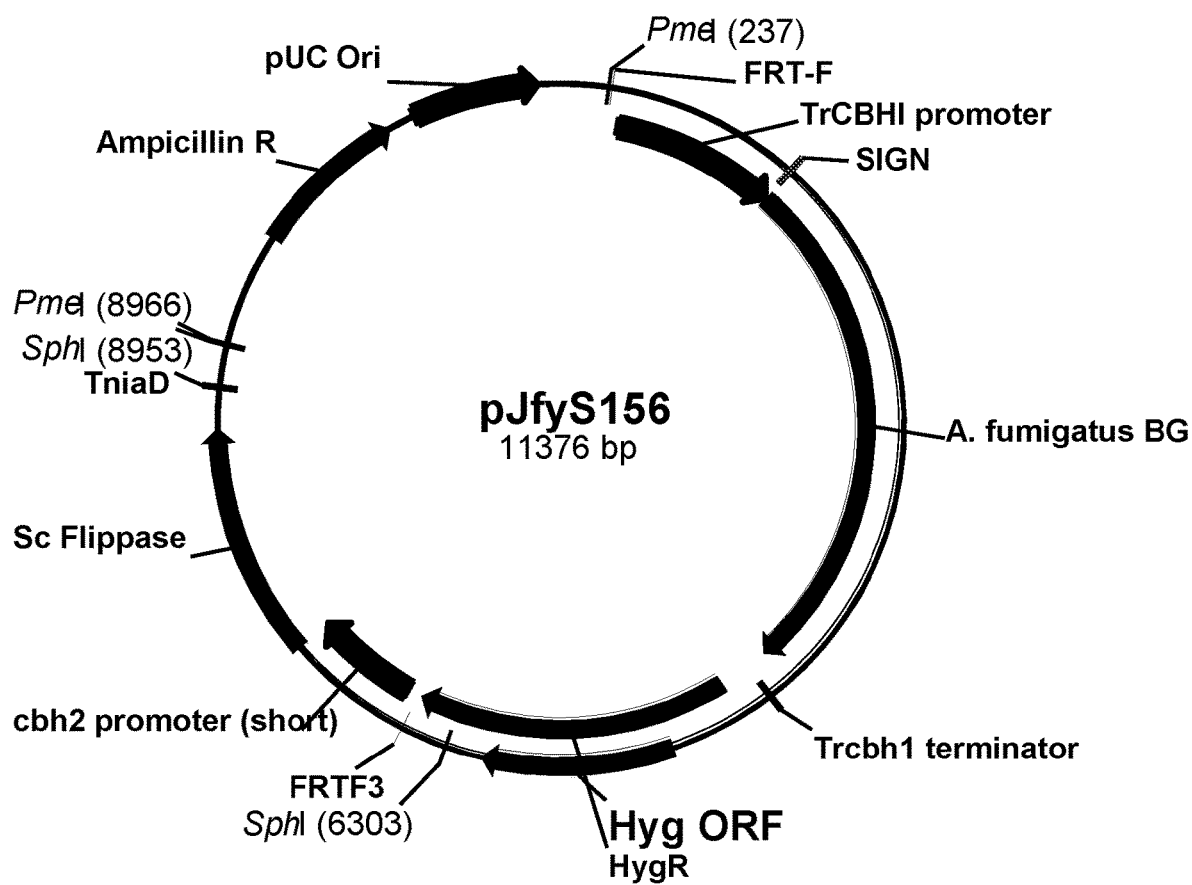
FIG. 2 shows a restriction map of plasmid pJfyS156.

The *A. fumigatus* beta-glucosidase PCR product (Example 6) was inserted into Nco I/Pac I-digested pJfyS155 using an IN-FUSION® Advantage PCR Cloning Kit. The reaction was composed of 150 ng of Nco I/Pac I-digested pJfyS155, 100 ng of the *A. fumigatus* beta-glucosidase PCR product (Example 6), 1× IN-FUSION® Advantage Buffer, and 1 µl of IN-FUSION® Enzyme in a 10 µl reaction volume. The reaction was incubated for 15 minutes at 37° C. and then 15 minutes at 50° C. Then 40 µl of TE were added to the reaction and 2 µl were transformed into ONE SHOT® TOP10 *E. coli* chemically competent cells according to Example 4. Plasmid DNA from *E. coli* transformants was isolated as described in Example 4. The insert was confirmed by DNA sequencing. One transformant was identified as containing the inserts with no PCR errors and the plasmid was designated pJfyS156 (FIG. 2).

Example 9: Protoplast Generation and Transformation of *Trichoderma reesei* Strain AgJg115-104-7B1 to Delete the *Trichoderma reesei* 42 kDa Aspartic Protease to Create *Trichoderma reesei* AgJg115-118-1H1

Protoplast preparation and transformation of *Trichoderma reesei* strain AgJg115-104-7B1 were performed as described in Example 1.

Ninety-six µg of the transforming plasmid pAgJg118 (WO 2011/075677) was digested with Pme I and purified by 1% agarose gel electrophoresis in TAE buffer where a DNA band was excised from the gel and extracted using a QIA-QUICK® Gel Extraction Kit (QIAGEN Inc.). Briefly 3 volumes of Kit-supplied Buffer QG were added to the gel slice and dissolved at 50° C. for approximately 10 minutes. The dissolved gel slice was transferred to a spin column and centrifuged at 13,000 rpm for 1 minute. The column was washed with 750 µl of Kit-supplied Buffer PE and then the centrifugation was repeated. DNA was eluted with 25 µl of Kit-supplied Buffer EB. Approximately 1 µg of the resulting purified DNA fragment was added to 100 µl of the protoplast solution for hygromycin selection transformation as described in Example 1. Seven transformants were subcultured onto new PDA plates to generate spores.

The transformants of *T. reesei* strain AgJg115-104-7B1 were screened by Fungal Spore PCR for the presence of the pAgJg118 deletion vector at the 42 kDa aspartic protease locus. A small amount of spores from each transformant was suspended in 20 µl of Dilution buffer (PHIRE® Plant Direct PCR Kit, Thermo Fisher Scientific Inc.). The spore suspensions were used as templates in the PCRs to screen for the aspartic protease gene deletion. Each reaction was composed of 0.5 µl of the spore suspension, 50 pmol of primer 069134 (shown below), 50 pmol of primer 067947 (shown below), 10 µl of 2×PHIRE® Plant PCR Buffer (PHIRE® Plant Direct PCR Kit), and 0.4 µl of PHIRE® Hot Start II DNA Polymerase (PHIRE® Plant Direct PCR Kit) in a 20 µl reaction. The reactions were performed in a thermocycler programmed for 1 cycle at 98° C. for 5 minutes; 40 cycles each at 98° C. for 5 seconds, 58° C. for 5 seconds, and 72° C. for 2 minutes and 20 seconds; 1 cycle at 72° C. for 2 minutes; and a 10° C. hold. Primer 069134 is located upstream of the 5' flanking region and primer 067947 is located at the beginning of the *E. coli* hygromycin phosphotransferase (hpt) gene coding region. If the deletion vector integrates into the aspartic protease locus, the amplified PCR fragment will be 2.4 kb in length. One transformant designated *T. reesei* AgJg115-118-1 was identified as having the aspartic protease gene deleted.

Primer 069134 (forward):
(SEQ ID NO: 35)
5'-CGCAATCTATCGAATAGCAG-3'

Primer 067947 (reverse):
(SEQ ID NO: 36)
5'-CTACATCGAAGCTGAAAGCACGAGA-3'

The deletion construct pAgJg118 contains the *E. coli* hygromycin phosphotransferase (hpt) gene and the *Herpes simplex* virus thymidine kinase (tk) gene flanked by direct repeats. The direct repeats were inserted to facilitate the curing out of the hpt and tk selectable markers and generate a clean deletion of the 42 kDa aspartic protease.

Spores from *T. reesei* AgJg115-118-1 were spread onto *Trichoderma* Minimal medium plates containing 1 µM 5-fluoro-2'-deoxyuridine (FdU) and incubated at 28° C. Nine isolates were sub-cultured onto PDA plates and incubated at 28° C. The isolates were then screened for the absence of the hpt and tk markers by Fungal Spore PCR in a similar manner described above. The PCR screen was composed of 0.5 µl of the spore suspension, 50 pmol of primer 069134, 50 pmol of primer 1200593, 10 µl of 2×PHIRE® Plant PCR Buffer, and 0.4 µl of PHIRE® Hot Start II DNA Polymerase in a 20 µl reaction. The reaction was performed in a thermocycler programmed for 1 cycle at 98° C. for 5 minutes; 40 cycles each at 98° C. for 5 seconds, 58° C. for 5 seconds, and 72° C. for 1 minute and 45 seconds; 1 cycle at 72° C. for 1 minute; and a 10° C. hold. Primer 069134 is located upstream of the 5' flanking region and primer 067947 is located at the downstream of the 3' flanking region. If the aspartic protease coding sequence is deleted and the hpt and tk markers are looped out, the amplified PCR fragment will be 3.6 kb in length.

Genomic DNA of the *T. reesei* AgJg115-118-1 isolates was prepared as described in Example 2 and analyzed by Southern blot analysis as described in Example 3 to confirm the deletion of the 42 kDa aspartic protease.

For Southern blot analysis, 2 µg of each genomic DNA was digested with 10 units of Nco I in a 30 µl reaction volume and subjected to 0.7% agarose gel electrophoresis in TAE buffer and transferred to a NYTRAN® SuperCharge membrane as described in Example 3.

The membrane was hybridized with a 500 bp digoxigenin-labeled *T. reesei* 42 kDa aspartic protease probe, which was synthesized by incorporation of digoxigenin-11-dUTP by PCR using the primers shown below.

```
Primer 069860 (sense):
                                  (SEQ ID NO: 37)
5'-CTTCTATCTTGGGATGCTTCACGATACGTGA-3'

Primer 069861 (antisense):
                                  (SEQ ID NO: 38)
5'-CGCGCCCTTGAATATCGGAGAAGGT-3'
```

The PCR was composed of 5 µl of 10× Taq Buffer (New England Biolabs, Inc.), 2.5 µl of PCR DIG Labeling Mix (Roche Applied Science Corp.), 5 ng of pAgJg118, 10 pmol of each primer, 2.5 µl of 10 mM dNTPs, 5 units of Taq DNA polymerase (New England Biolabs, Inc.), and 36.5 µl of water. The reaction was performed in a thermocycler programmed for 1 cycle at 95° C. for 2 minutes; 30 cycles each at 95° C. for 30 seconds, 56° C. for 30 seconds, and 72° C. for 40 seconds; 1 cycle at 72° C. for 15 minutes; and a 4° C. hold. The probe was purified by 1% agarose gel electrophoresis in TAE buffer, excised from the gel, and extracted using a QIAQUICK® Gel Extraction Kit as above.

Southern blot analysis identified primary transformant *T. reesei* AgJg115-118-1H1 as containing the replacement and being void of the hpt/tk markers.

Example 10: Protoplast Generation and Transformation of *Trichoderma reesei* Strain AgJg115-118-1H1 to Insert the FRT-F and FRT-F3 Sequences at the cbh1 Locus Protoplast preparation and transformation of *Trichoderma reesei* strain AgJg115-118-1H1 were performed as described in Example 1.

Eighty-five µg of the transforming plasmid pJfyS147 (Example 4) was digested with Pme I. The digestion reaction was purified by 1% agarose gel electrophoresis in TAE buffer where a DNA band of approximately 8.1 kb was excised from the gel, and extracted using a QIAQUICK® Gel Extraction Kit (Example 9). Approximately 3 µg of the resulting purified DNA fragment was used for each transformation according to the procedure described in Example 1. Seven transformants were sub-cultured onto PDA plates to generate spores.

The transformants of *T. reesei* strain AgJg115-104-7B1 were screened by Fungal Spore PCR according to Example 9 for the presence of the pJfyS147 FRT site integration vector at the cbh1 locus, thereby deleting the promoter region and coding sequence of cbh1. The spore suspensions were used as templates in the PCRs to screen for the cbh1 deletion. Each reaction was composed of 1 µl of spore suspension, 25 pmol of primer 1205412, 25 pmol of primer 1204415, 25 pmol of primer 1201430, 10 µl of 2×PHIRE® Plant PCR Buffer, and 0.4 µl of PHIRE® Hot Start II DNA Polymerase in a 20 µl reaction. The reactions were performed in a thermocycler programmed for 1 cycle at 98° C. for 5 minutes; 40 cycles each at 98° C. for 5 seconds, 55° C. for 5 seconds, and 72° C. for 1 minute and 20 seconds; 1 cycle at 72° C. for 1 minute; and a 10° C. hold. Primer 1205412 is located within the cbh1 coding sequence, primer 12054415 is located upstream of the cbh1 5' flanking region, and primer 1201430 is located at the beginning of the *E. coli* hygromycin phosphotransferase (hpt) gene coding region. If the integration vector integrates at the cbh1 locus, the amplified PCR fragment will be 2.7 kb in length. But if integration of the FRT sites did not occur and the cbh1 locus is intact, a 3.8 kb fragment will be produced. *T. reesei* AgJg-FRT1-2 was identified as a strain in which the FRT sites had been successfully integrated at the cbh1 locus of *T. reesei* AgJg115-118-1H1.

```
Reverse primer 1205412:
                                  (SEQ ID NO: 39)
5'-ACTGAGTCAGGCCGCCCTTGTCTGA-3'

Forward primer 1204415:
                                  (SEQ ID NO: 40)
5'-GTACAAACAACTACCTGGTG-3'

Reverse primer 1201430:
                                  (SEQ ID NO: 41)
5'-GTTTCAGGCAGGTCTTGCAACG-3'
```

The integration construct pJfyS147 contains the *E. coli* hygromycin phosphotransferase (hpt) gene and the *Herpes simplex* virus thymidine kinase (tk) gene flanked by direct repeats. The direct repeats were inserted to facilitate the curing out of the hpt and tk selectable markers to generate a clean integration of the FRT sites.

Spores from *T. reesei* AgJg-FRT1-2 were spread onto *Trichoderma* Minimal medium plates containing 1 µM 5-fluoro-2'-deoxyuridine (FdU) and incubated at 28° C. Nine isolates were sub-cultured onto PDA plates and incubated at 28° C. for 6 days. The isolates were then screened for the absence of the hpt and tk markers by Fungal Spore PCR according to Example 9. Each reaction was composed of 1 µl of spore suspension, 25 pmol of primer 1205412, 25 pmol of primer 1205537, 10 µl of 2×PHIRE® Plant PCR Buffer, 0.4 µl of PHIRE® Hot Start II DNA Polymerase in a 20 µl reaction. The reactions were performed in a thermocycler programmed for 1 cycle at 98° C. for 5 minutes; 40 cycles each at 98° C. for 5 seconds, 65° C. for 5 seconds, and 72°

C. for 2 minute and 50 seconds; 1 cycle at 72° C. for 1 minute; and a 10° C. hold. If the cbh1 promoter region and coding sequence are deleted, and the hpt and tk markers are looped out, the amplified PCR fragment will be 3.6 kb in length.

Genomic DNA was prepared according to Example 2 and analyzed by Southern blot analysis according to Example 3 to confirm replacement of the cbh1 promoter region and coding sequence with the FRT sites.

For Southern blot analysis, 2 µg of each genomic DNA was digested with 20 units of Nde I in a 20 µl reaction volume. The digested DNA was subjected to 0.7% agarose gel electrophoresis in TAE buffer as described in Example 3.

The membrane was hybridized with a 500 bp digoxigenin-labeled *T. reesei* cbh1 probe (SEQ ID NO: 42), which was synthesized by incorporation of digoxigenin-11-dUTP by PCR.

Southern blot analysis identified transformant *T. reesei* AgJg-FRT1-2B1A as a strain in which the hpt/tk markers were deleted and the cbh1 coding sequence was deleted and replaced with FRT sites.

Example 11: Construction of Plasmid pAgJg137 to Insert FRT-F and FRT-F3 Sites at the cbh2 Locus of *Trichoderma reesei*

A FRT site integration plasmid pAgJg137 was constructed so that the *T. reesei* cbh2 gene and 1 kb of the upstream region thereof is deleted when the fragment integrates incorporating the FRT-F site (SEQ ID NO: 1) and FRT-F3 site (SEQ ID NO: 8).

The promoter region and a gene of interest could then be introduced with a FLP/FRT expression construct. To construct the FRT site integration plasmid the FRT-F site was inserted downstream of the 5' cbh2 flanking region by SOE PCR. First the FRT-F site and 5' cbh2 flanking region were amplified separately and then combined by overlapping PCR.

The 5' cbh2 flanking region was amplified from *T. reesei* RutC30 genomic DNA using the primers shown below. *T. reesei* RutC30 genomic DNA was prepared as described in Example 2. Bold letters represent sequence from the cbh2 locus and the remaining sequence is homologous to the cloning sites of pJfyS1579-49-11 (WO 2011/075677).

Forward primer:
(SEQ ID NO: 43)
5'-TCACATGGTTTAAACGGCGCGCCACACTTACTCTTCTACACAG-3'

Reverse primer:
(SEQ ID NO: 44)
5'-TTCGAACAGCCCCAGTCGGT-3'

The PCR was composed of 180 ng of *T. reesei* RutC30 genomic DNA, 1 µl of 10 mM dNTPs, 50 pmol of each forward and reverse primer, 1×PHUSION® GC Buffer (Thermo Scientific), and 2 units of PHUSION® Hot Start DNA polymerase (Thermo Fisher Scientific, Inc.) in a final volume of 50 µl. The PCR was performed in a thermocycler programmed for 1 cycle at 98° C. for 30 seconds; 30 cycles each at 98° C. for 10 seconds, 55° C. for 10 seconds, and 72° C. for 1.5 minutes; and 1 cycle at 72° C. for 10 minutes. The PCR products were separated by 1% agarose gel electrophoresis in TAE buffer where a 1.5 kb fragment was excised form the gel and agarose was extracted using a MINELUTE® Gel Extraction Kit (Example 4).

The FRT-F site was amplified from plasmid pJfyS147 using the primers shown below. The sequence in italics denotes sequence that is homologous to the vector pJfyS1579-49-11. The sequence in bold is sequence homologous to the cbh2 locus.

Forward primer:
(SEQ ID NO: 45)
5'-GGAAATACAGGATAGACACTCGGCCGCGAATTCATCTTGA-3'

Reverse primer:
(SEQ ID NO: 46)
5'-*AGCCTTGTTTTGTCGGGCGCGCC*GCTGCTCTCGGCTAGCGAAG-3'

The PCR was composed of 84 ng of pJfyS147 DNA, 1 µl of 10 mM dNTPs, 50 pmol of each forward and reverse primer, 1×PHUSION® GC Buffer, and 2 units of PHUSION® Hot Start DNA polymerase in a final volume of 50 µl. The PCR was performed in a thermocycler programmed for 1 cycle at 98° C. for 30 seconds; 30 cycles each at 98° C. for 10 seconds, 68° C. for 10 seconds, and 72° C. for 30 seconds; and 1 cycle at 72° C. for 10 minutes. The PCR products were separated by 3% agarose gel electrophoresis in TAE buffer where a 0.1 kb fragment was excised from the gel and agarose was extracted using a MINELUTE® Gel Extraction Kit (Example 4).

A single fragment was generated from the above individual PCR products by SOE PCR using the primers shown below. The region in italics corresponds to sequence homologous to the site of insertion into vector pJfyS1579-41-11 (WO 2011/075677).

Forward primer:
(SEQ ID NO: 47)
5'-*TCACATGGTTTAAACGGCGCGCC*ACACTTACTCTTCTACACAG-3'

Reverse primer:
(SEQ ID NO: 48)
5'-*AGCCTTGTTTTGTCGGGCGCGCC*GCTGCTCTCGGCTAGCGAAG-3'

The PCR was composed of 1 µl of each gel-purified PCR product above, 1 µl of 10 mM dNTPs, 50 pmol of each forward and reverse primer, 1×PHUSION® GC Buffer, and 2 units of PHUSION® Hot Start DNA polymerase in a final volume of 50 µl. The PCR was performed in a thermocycler programmed for 1 cycle at 98° C. for 30 seconds; 30 cycles each at 98° C. for 10 seconds, 55° C. for 10 seconds, and 72° C. for 1 minute; and 1 cycle at 72° C. for 10 minutes. The PCR products were separated by 1% agarose gel electrophoresis in TAE buffer where a 1.5 kb fragment was excised form the gel and agarose was extracted using a MINELUTE® Gel Extraction Kit (Example 4).

The 1.5 kb fragment was inserted into Asc I-digested pJfyS1579-41-11 (WO 2011/075677) using an IN-FUSION® Advantage PCR Cloning Kit. The reaction was composed of 1× IN-FUSION® Reaction Buffer, 190 ng of pJfyS1579-41-11, 94 ng of the 1.5 kb fragment, and 2 µl of IN-FUSION® HD Premix Enzyme (Clontech Laboratories, Inc.) in a 10 µl reaction volume. The reaction was incubated at 50° C. for 15 minutes. Then 2.5 µl of the reaction was transformed into ONE SHOT® TOP10 *E. coli* chemically competent cells according to Example 4. Plasmid DNA was isolated using a Mini-prep Kit (QIAGEN Inc.). The plasmid was confirmed by DNA sequencing. The resulting plasmid was designated pAgJg137A.

The FRT-F3 site was inserted upstream of the 3' cbh2 flanking region using SOE PCR. First the FRT-F3 site and 3' cbh2 flanking region were amplified separately and then combined by SOE PCR.

The 3' cbh2 flanking region was amplified from *T. reesei* RutC30 genomic DNA using the primers shown below. Bold letters represent sequence from the cbh2 locus and the remaining sequence is homologous to the cloning sites of pJfyS1579-49-11

```
Forward primer:
                                        (SEQ ID NO: 49)
5'-CACAATGTCGAGTGTCTATT-3'

Reverse primer:
                                        (SEQ ID NO: 50)
5'-GCCATATTTAAATCCGTTTAAACGTTTATAAAATGTTCCTGCC-3'
```

The PCR was composed of 180 ng of *T. reesei* RutC30 genomic DNA, 1 µl of 10 mM dNTPs, 50 pmol of each forward and reverse primer, 1×PHUSION® GC Buffer, and 2 units of PHUSION® Hot Start DNA polymerase in a final volume of 50 µl. The PCR was performed in a thermocycler programmed for 1 cycle at 98° C. for 30 seconds; 30 cycles each at 98° C. for 10 seconds, 55° C. for 10 seconds, and 72° C. for 1.5 minutes; and 1 cycle at 72° C. for 10 minutes. The PCR products were separated by 1% agarose gel electrophoresis in TAE buffer where a 1.5 kb fragment was excised from the gel and agarose was extracted using a MINELUTE® Gel Extraction Kit (Example 4).

The FRT-F3 site was amplified from pJfyS147 using the primers shown below. The sequence in italics denotes sequence that is homologous to the vector pJfyS1579-49-11. The sequence in bold is sequence homologous to the cbh2 locus.

```
Forward primer:
                                        (SEQ ID NO: 51)
5'-cctagttggagtattcctgcaggTCAACTCTCTCCTCTAGGTTGAAG

TTCCTATTCCGAGTTC-3'

Reverse primer:
                                        (SEQ ID NO: 52)
5'-aatagacactcgacattgtgGCATGCACTAGCTAGTTGAAGTTCC

TATAC-3'
```

The PCR was composed of 84 ng of pJfyS147, 1 µl of 10 mM dNTPs, 50 pmol of each forward and reverse primer, 1×PHUSION® GC Buffer, and 2 units of PHUSION® Hot Start DNA polymerase in a final volume of 50 µl. The PCR was performed in a thermocycler programmed for 1 cycle at 98° C. for 30 seconds; 30 cycles each at 98° C. for 10 seconds, 68° C. for 10 seconds, and 72° C. for 30 seconds; and 1 cycle at 72° C. for 10 minutes. The PCR products were separated by 3% agarose gel electrophoresis in TAE buffer where a 0.1 kb fragment was excised from the gel and agarose was extracted using a MINELUTE® Gel Extraction Kit (Example 4).

A single fragment was generated from the above individual PCR products by SOE PCR using the primers shown below. The region in italics corresponds to sequence homologous to the desired site of insertion into pAgJg137A (described above).

```
Forward primer:
                                        (SEQ ID NO: 53)
5'-cctagttggagtattcctgcaggTCAACTCTCTCCTCTAGGTTGAAG

TTCCTATTCCGAGTTC-3'

Reverse primer:
                                        (SEQ ID NO: 54)
5'-gccatatttaaatccgtttaaacGTTTATAAAATGTTCCTGCC-3'
```

The PCR was composed of 1 µl of the cbh2 3' flanking PCR product, 3 µl of the FRT-F3 PCR product, 1 µl of 10 mM dNTPs, 50 pmol of each forward and reverse primer, 1× PHUSION® GC Buffer, and 2 units of PHUSION® Hot Start DNA polymerase in a final volume of 50 µl. The PCR was performed in a thermocycler programmed for 1 cycle at 98° C. for 30 seconds; 30 cycles each at 98° C. for 10 seconds, 55° C. for 10 seconds, and 72° C. for 1 minute; and 1 cycle at 72° C. for 10 minutes. The PCR products were separated by 1% agarose gel electrophoresis in TAE buffer where a 1.5 kb fragment was excised from the gel and agarose was extracted using a MINELUTE® Gel Extraction Kit (Example 4).

The 1.5 kb fragment was inserted into Sbf I-digested pAgJg137A using an IN-FUSION® Advantage PCR Cloning Kit. The reaction was composed of 1× IN-FUSION® Reaction Buffer, 242 ng of the Sbf I-digested pAgJg137A, 140 ng of the 1.5 kb fragment, and 2 µl of IN-FUSION® HD Premix Enzyme in a 10 µl reaction volume. The reaction was incubated at 50° C. for 15 minutes. Then 3.5 µl of the reaction were transformed into ONE SHOT® TOP10 *E. coli* chemically competent cells according to Example 4. One transformant was identified as containing the insert with no PCR errors and the plasmid was designated pAgJg137. Plasmid pAgJg137 was used to integrate the FRT-F and FRT-F3 sites at the cbh2 locus of *T. reesei*.

Example 12: Protoplast Generation and Transformation of *Trichoderma reesei* Strain AgJg-FRT1-2B1A to Insert the FRT-F and FRT-F3 Sequences at the cbh2 Locus Protoplast preparation and transformation of *T. reesei* AgJg-FRT1-2B1A were performed according to Example 1.

A total of 140 µg of the transforming plasmid pAgJg137 (Example 11) was digested with Pme I. The digestion reaction was purified by 1% agarose gel electrophoresis in TAE buffer where a DNA band was excised from the gel, and extracted using a MINELUTE® Gel Extraction Kit (Example 4). Approximately 3 µg of the resulting purified DNA fragment was added to 100 µl of the protoplast solution for hygromycin selection transformation as described in Example 1. Seven transformants were sub-cultured onto PDA plates to generate spores.

The transformants of *Trichoderma reesei* AgJg-FRT1-2B1 were screened by Fungal Spore PCR according to Example 9 for the presence of the pAgJg137 FRT site integration vector at the cbh2 locus, thereby deleting the promoter region and coding sequence of cbh2. Each spore suspension was used as a template in a PCR to screen for the cbh2 deletion. Each reaction was composed of 1 µl of the spore suspension, 25 pmol of primer 1201430, 25 pmol of primer 1206098, 25 pmol of primer 1206099, 10 µl of 2×PHIRE® Plant PCR Buffer, and 0.4 µl of PHIRE® Hot Start II DNA Polymerase in a 20 µl reaction. The reactions were performed in a thermocycler programmed for 1 cycle at 98° C. for 5 minutes; 40 cycles each at 98° C. for 30 seconds, 55° C. for 30 seconds, and 72° C. for 2 minute and 10 seconds; 1 cycle at 72° C. for 1 minute; and a 10° C. hold. Primer 1206099 is located within the cbh2 coding sequence, primer 1206098 is located upstream of the cbh2 5' flanking region, and primer 1201430 is located at the beginning of the *E. coli* hygromycin phosphotransferase (hpt) gene coding region. If the integration vector integrates at the cbh2 locus thereby deleting the coding sequence, the amplified PCR fragment produced will be 2.6 kb in length. But if integration of the FRT sites does not occur and the cbh2 locus is intact, a 3.5 kb fragment will be produced. *T. reesei* AgJg-FRT2-4 was identified with the FRT sites successfully integrated at the cbh2 locus of *T. reesei* AgJg-FRT1-2B1A.

```
Reverse primer (1201430):
                           (SEQ ID NO: 55)
5'-GTTTCAGGCAGGTCTTGCAACG-3'

Forward primer (1206098):
                           (SEQ ID NO: 56)
5'-GCTGATCGAGAAGATTAGCATG-3'

Reverse primer (1206099):
                           (SEQ ID NO: 57)
5'-GATCAGTGATGAAGAAGGCG-3'
```

The integration construct pAgJg137 contains the *E. coli* hygromycin phosphotransferase (hpt) gene and the *Herpes simplex* virus thymidine kinase (tk) gene flanked by direct repeats. The direct repeats were inserted to facilitate the curing out of the hpt and tk selectable markers to generate clean integration of the FRT sites.

Spores from *T. reesei* AgJg-FRT2-4 were spread onto *Trichoderma* Minimal medium plates containing 1 µM 5-fluoro-2'-deoxyuridine (FdU) and incubated at 28° C. for 5 days. Seventeen isolates were sub-cultured onto PDA plates and incubated at 28° C. for 7 days. The isolates were then screened for the absence of the hpt and tk markers by Fungal Spore PCR according to Example 9. The PCR was composed of 1 µl of each spore suspension, 25 pmol of primer 1205457 shown below, 25 pmol of primer 1206335 shown below, 10 µl of 2× PHIRE® Plant PCR Buffer, and 0.4 µl of PHIRE® Hot Start II DNA Polymerase in a 20 µl reaction. The reactions were performed in a thermocycler programmed for 1 cycle at 98° C. for 5 minutes; 40 cycles each at 98° C. for 10 seconds, 55° C. for 10 seconds, and 72° C. for 2 minute and 15 seconds; 1 cycle at 72° C. for 1 minute; and a 10° C. hold. If the cbh2 promoter region and coding sequence is deleted, and the hpt and tk markers are looped out, the amplified PCR fragment will be 2 kb in length.

```
Forward primer (1205457):
                           (SEQ ID NO: 58)
5'-CTCAGGCCATCGTAGGAAAT-3'

Reverse primer (1206335):
                           (SEQ ID NO: 59)
5'-CTAGGTAGGTAGGTAGTATA-3'
```

Genomic DNA of the isolates was prepared according to Example 2 and analyzed by Southern blot analysis according to Example 3 to confirm the replacement of cbh1 with FRT sites.

For Southern blot analysis, 2 µg of each genomic DNA was digested with 20 units of Hind III and 20 units of Bam HI in a 40 µl reaction volume. The digested DNA was subjected to 0.7% agarose gel electrophoresis in TAE buffer and transferred to a NYTRAN® SuperCharge membrane according to Example 3.

The membrane was hybridized with a 500 bp digoxigenin-labeled *T. reesei* cbh2 probe, which was synthesized by incorporation of digoxigenin-11-dUTP by PCR using the primers shown below.

```
Primer 1206366 (sense):
                           (SEQ ID NO: 60)
5'-CCAGTAACAACTTTGCTTGGCC-3'

Primer 1206367 (antisense):
                           (SEQ ID NO: 61)
5'-CACCATGTTACTTTCACCCAAATACA-3'
```

The PCR was composed of 10 µl of 5× HF Buffer, 5 µl of 10×PCR DIG Labeling Mix, 700 ng of pAgJg137, 50 pmol of primer 1206366, 10 pmol of primer 1206367, 1 µl of 10 mM dNTPs, 1 unit of PHUSION® Hot Start II DNA Polymerase (Thermo Fisher Scientific, Inc.), and 31 µl of water. The reaction was performed in a thermocycler programmed for 1 cycle at 98° C. for 30 seconds; 30 cycles each at 98° C. for 10 seconds, 55° C. for 10 seconds, and 72° C. for 30 seconds; 1 cycle at 72° C. for 10 minutes; and a 4° C. hold. The probe was purified by 1% agarose gel electrophoresis in TAE buffer, excised from the gel, and extracted using a QIAQUICK® Gel Extraction Kit.

Southern blot analysis identified transformant *T. reesei* AgJg-FRT2-4B17 as a strain in which the hpt/tk markers were deleted and the cbh2 coding sequence was deleted and replaced with FRT sites.

Example 13: Construction of Plasmid pAgJg136

In order to construct expression plasmid pAgJg136 containing the amdS gene as a selectable marker, the amdS gene was PCR amplified from pMJ09 (U.S. Pat. No. 8,318,458) using the primers shown below.

```
Forward primer:
                           (SEQ ID NO: 62)
5'-CTTGGTACCGAGCTCTGGAAACGCAACCCTGAAGGGA-3'

Reverse primer:
                           (SEQ ID NO: 63)
5'-CAGAATTCGCCCTTGTCTACGCCAGGACCGAGCAAGC-3'
```

The PCR was composed of 10 ng of pMJ09, 200 µM dNTPs, 0.4 µM primers, 1× PHUSION® Reaction Buffer, and 2 units of PHUSION® High Fidelity DNA polymerase in a final volume of 50 µl. The reaction was performed in a thermocycler programmed for 1 cycle at 95° C. for 2 minutes; 30 cycles each at 95° C. for 25 seconds, 57° C. for 25 seconds, and 72° C. for 1.5 minutes; and 1 cycle at 72° C. for 7 minutes.

The completed PCR and Bam HI/Afe I-digested pJfyS148B (Example 6) were submitted to 1% agarose gel electrophoresis in TAE buffer where a 4.1 kb band corresponding to the digested pJfyS148B and a 2.7 kb band corresponding to the amdS gene were both excised from the gels and agarose was extracted using a Nucleospin® Extract II Kit (Example 8).

The amdS gene was inserted into the digested pJfyS148B using an IN-FUSION® HD Cloning Kit (Clontech Laboratories, Inc.). The reaction was composed of 1× IN-FUSION® HD Premix, 120 ng of pJfyS148, and 150 ng of the amdS PCR product in a 10 µl reaction buffer. The reaction was incubated at 50° C. for 15 minutes. Then 40 µl of TE were added to the reaction and 2 µl were transformed into ONE SHOT® TOP10 *E. coli* chemically competent cells according to Example 4. Plasmid DNA was isolated from the transformants according to Example 4. The insert was confirmed by DNA sequencing. One transformant was identified as containing the inserts with no PCR errors and the plasmid was designated pJfyS164. Plasmid pJfyS164 was used to insert the *S. cerevisiae* flippase coding sequence under transcriptional control of the *T. reesei* cbh2 promoter.

The cbh2 promoter and *S. cerevisiae* flippase coding sequence with terminator were amplified using the forward and reverse primers shown below.

cbh2 promoter Forward primer:
(SEQ ID NO: 64)
5'-CATCACACTGGCGGCCGCGAATTCTAGGCTAGGTATGC-3'

Reverse primer:
(SEQ ID NO: 65)
5'-GGTGCAATACACAGAGGGTG-3'

Flippase
Forward primer:
(SEQ ID NO: 66)
5'-CACCCTCTGTGTATTGCACCATGCCCCAGTTCGATATCCTCTGCA-3'

Reverse primer:
(SEQ ID NO: 67)
5'-AAACTCTAGGATGCATGCAAGTGAGGCTATTGCCTATCAGCTC-3'

The PCR was composed of 150 ng *T. reesei* RutC30 genomic DNA for the cbh2 promoter PCR or 10 ng of pRika147 for the flippase PCR, 200 µM dNTPs, 0.4 µM primers, 1× PHUSION® Reaction Buffer, and 2 units of PHUSION® High Fidelity DNA polymerase in a final volume of 50 µl. The reaction was performed in a thermocycler programmed for 1 cycle at 95° C. for 2 minutes; 30 cycles each at 95° C. for 30 seconds, 53° C. (59° C. for flippase PCR) for 30 seconds, and 72° C. for 2 minutes; and 1 cycle at 72° C. for 7 minutes.

The completed PCRs were submitted to 1% agarose gel electrophoresis in TAE buffer where a 0.6 kb band corresponding to the cbh2 promoter and a 2.0 kb band corresponding to the flippase gene were excised from the gels and agarose was extracted using a Nucleospin® Extract II Kit (Example 8).

The cbh2 promoter and flippase coding sequence were inserted into Xho I-digested pJfyS164 using an IN-FUSION® HD Cloning Kit. The reaction was composed of 1× IN-FUSION® HD Premix, 120 ng of the digested pJfyS164, 100 ng of the flippase PCR product, and 50 ng of the cbh2 promoter PCR product in a 10 µl reaction buffer. The reaction was incubated at 50° C. for 15 minutes. Then 40 µl of TE were added to the reaction and 2 µl were transformed into ONE SHOT® TOP10 *E. coli* chemically competent cells according to Example 4. Plasmid DNA was isolated from the transformants according to Example 4. The insert was confirmed by DNA sequencing. One transformant was identified as containing the inserts with no PCR errors and the plasmid was designated pJfyS165. Plasmid pJfyS165 was used to insert an *A. fumigatus* beta-glucosidase 4M variant coding sequence.

Two synthetic oligonucleotide primers shown below were designed to amplify by PCR the *A. fumigatus* beta-glucosidase variant gene from plasmid pDFng133-3 (WO 2013/028912) and introduce flanking regions for insertion into expression vector pJfyS165. Bold letters represent coding sequence and the remaining sequence is homologous to insertion sites of pJfyS165.

Forward primer 1205483:
(SEQ ID NO: 68)
5'-CGCGGACTGCGCACCATGAGATTCGGTTGGCTCGAG-3'

Reverse primer 1205484:
(SEQ ID NO: 69)
5'-TCGCCACGGAGCTTACTAGTAGACACGGGGCAGAGGCG-3'

The PCR was composed of 200 ng of plasmid pDFng133-3, 10 µl of 10 mM dNTPs, 50 pmol of primer 1205483, 50 pmol of primer 1205484, 1×PHUSION® HF buffer (Thermo Fisher Scientific, Inc.), and 2 units of PHUSION® Hot Start DNA polymerase in a final volume of 50 µl. The reaction was performed in a thermocycler programmed for 1 cycle at 98° C. for 30 seconds; 30 cycles each at 98° C. for 10 seconds, 62° C. for 10 seconds, and 72° C. for 1.5 minutes; and 1 cycle at 72° C. for 10 minutes. The PCR products were separated by 1% agarose gel electrophoresis in TAE buffer where a 3 kb fragment was excised from the gel and agarose was extracted using a MINELUTE® Gel Extraction Kit (Example 4).

The 3 kb fragment was then cloned into pJfyS165 using an IN-FUSION™ HD Cloning Kit (Clontech Laboratories, Inc.). The vector was digested with Nco I and Pac I and isolated by 1% agarose gel electrophoresis in TAE buffer where a 9.1 kb fragment was excised from the gel and agarose was extracted using a MINELUTE® Gel Extraction Kit (Example 4). The 3 kb gene fragment of the *A. fumigatus* beta-glucosidase variant coding sequence and the digested vector were ligated together in a reaction resulting in expression plasmid pAgJg136 composed of the *A. fumigatus* beta-glucosidase variant coding sequence under transcriptional control of the *T. reesei* cbh1 promoter, FRT recognition sites for efficient targeting, and *S. cerevisiae* flippase coding sequence under transcriptional control of the *T. reesei* cbh2 promoter. The ligation reaction (10 µl) was composed of 1× IN-FUSION™ HD enzyme mix, 151 ng of pJfyS165 digested with Nco I and Pac I, and 201 ng of the *A. fumigatus* beta-glucosidase variant purified PCR product. The reaction was incubated at 50° C. for 15 minutes. A 2.5 µl volume of the cloning reaction was transformed into ONE SHOT® TOP10 competent cells according to Example 4. Plasmid DNA was isolated using a Mini-prep Kit (QIAGEN Inc.). The insert was confirmed by DNA sequencing. The resulting plasmid was designated pAgJg136.

Example 14: Construction of Plasmid pDM313

A 0.38 kb PCR fragment containing a portion of the hpt marker, the FRT-F3 site, and a portion of the *T. reesei* gpdA promoter was amplified from pJfyS156 (Example 8) using the primers shown below.

Forward primer:
(SEQ ID NO: 70)
5'-CGTGTTTCTTCCCATTCGCATGCGACCTCGTGGTCATTGAC-3'

Reverse primer:
(SEQ ID NO: 71)
5'-GCTTTGACGTTACATTGACGTACTTATAAGCGGCCGCCAGTGTGATGGA-3'

The PCR was composed of 50 picomoles of each of the primers, 100 ng of pJfyS156 DNA, 1×PHUSION™ High-Fidelity Hot Start DNA Polymerase buffer (Thermo Fisher Scientific, Inc.), 1 µl of a 10 mM blend of dNTPs, and 1 unit of PHUSION™ High-Fidelity Hot Start DNA Polymerase (Thermo Fisher Scientific, Inc.) in a final volume of 50 µl. The reaction was performed in a thermocycler programmed for 1 cycle at 98° C. for 2 minutes; 34 cycles each at 98° C. for 15 seconds, 59° C. for 30 seconds, and 72° C. for 1 minute; and 1 cycle at 72° C. for 10 minutes.

A 1.0 kb PCR fragment containing the *T. reesei* gpdA promoter was amplified from *T. reesei* RutC30 genomic DNA using the primers shown below.

```
Forward primer:
                                    (SEQ ID NO: 72)
5'-TCCATCACACTGGCGGCCGCTTATAAGTACGTCAATGTAACGTCAA

AGC-3'

Reverse primer:
                                    (SEQ ID NO: 73)
5'-TGCAGAGGATATCGAACTGGGGCATTTTGTATCTGCGAATTGAGC

TTG-3'
```

The PCR was composed of 50 picomoles of each of the primers, 100 ng of *T. reesei* RutC30 genomic DNA, 1×PHUSION™ High-Fidelity Hot Start DNA Polymerase buffer, 1 μl of a 10 mM blend of dNTPs, and 1 unit of PHUSION™ High-Fidelity Hot Start DNA Polymerase in a final volume of 50 μl. The reaction was performed in a thermocycler programmed for 1 cycle at 98° C. for 2 minutes; 34 cycles each at 98° C. for 15 seconds, 59° C. for 30 seconds, and 72° C. for 1 minute; and 1 cycle at 72° C. for 10 minutes.

A 1.8 kb PCR fragment containing the coding region for the *S. cerevisiae* flippase gene and the niaD terminator was amplified from plasmid pJfyS156 (Example 8) using the primers shown below.

```
Forward primer:
                                    (SEQ ID NO: 74)
5'-CAAGCTCAATTCGCAGATACAAAATGCCCCAGTTCGATATCCTCT

GCA-3'

Reverse primer:
                                    (SEQ ID NO: 75)
5'-GCTGTTTAAACTCTAGGATGCATGCAAGTGAGGCTATTGCC-3'
```

The PCR was composed of 50 picomoles of each of the primers, 100 ng of pJfyS156 DNA, 1×PHUSION™ High-Fidelity Hot Start DNA Polymerase buffer, 1 μl of a 10 mM blend of dNTPs, and 1 unit of PHUSION™ High-Fidelity Hot Start DNA Polymerase in a final volume of 50 μl. The reaction was performed in a thermocycler programmed for 1 cycle at 98° C. for 2 minutes; 34 cycles each at 98° C. for 15 seconds, 59° C. for 30 seconds, and 72° C. for 1 minute; and 1 cycle at 72° C. for 10 minutes.

The three completed PCRs described above were analysed by 0.8% agarose gel electrophoresis in TAE buffer where fragments of 0.38 kb, 1.0 kb, and 1.8 kb were confirmed. The PCR fragments in the original reactions were used as template for a SOE PCR described below.

The 0.38 kb and 1.0 kb PCR fragments were joined by SOE PCR using the primers shown below.

```
Forward primer:
                                    (SEQ ID NO: 76)
5'-CGTGTTTCTTCCCATTCGCATGCGACCTCGTGGTCATTGAC-3'

Reverse primer:
                                    (SEQ ID NO: 77)
5'-TGCAGAGGATATCGAACTGGGGCATTTTGTATCTGCGAATTGAGC

TTG-3'
```

The PCR was composed of 50 picomoles of each of the primers, 0.3 μl of the 0.38 kb fragment PCR, 0.6 μl of the 1.0 kb fragment PCR, 1×PHUSION™ High-Fidelity Hot Start DNA Polymerase buffer, 1 μl of a 10 mM blend of dNTPs, and 1 unit of PHUSION™ High-Fidelity Hot Start DNA Polymerase in a final volume of 50 μl. The reaction was performed in a thermocycler programmed for 1 cycle at 98° C. for 2 minutes; 34 cycles each at 98° C. for 15 seconds, 60° C. for 30 seconds, and 72° C. for 1.5 minutes, and 1 cycle at 72° C. for 10 minutes. Five SOE PCRs were performed and the reactions were combined. The 1.36 kb SOE PCR fragment and the 1.8 kb PCR fragment containing the flippase coding sequence and niaD terminator were separated by 0.8% agarose gel electrophoresis in TAE buffer where a 1.36 kb fragment and a 1.8 kb fragment were excised from the gel and extracted using a Nucleospin® Extract II Kit (Example 8).

Seventeen μg of pJfyS156 DNA were digested with Sph I and purified by 0.8% agarose gel electrophoresis in TAE buffer where an approximately 8.7 kb fragment was excised from the gel and extracted using a Nucleospin® Extract II Kit (Example 8).

The 1.36 kb SOE PCR fragment and the 1.8 kb PCR fragment, containing the flippase coding sequence and niaD terminator, were inserted into Sph I digested pJfyS156 using an IN-FUSION® HD Cloning Kit. The reaction was composed of 116 ng of Sph I digested pJfyS156, 57 ng of the 1.36 kb SOE PCR fragment, 69 ng of the 1.8 kb PCR fragment, and 2 μl of IN-FUSION® buffer with Enzyme in a 10 μl reaction volume. The reaction was incubated at 50° C. for 15 minutes and then chilled on ice. A 40 μl aliquot of TE was added. Two μl of the reaction transformed into ONE SHOT® TOP10 *E. coli* chemically competent cells according to Example 4. Plasmid DNA was isolated from the transformants according to Example 4. Transformants were screened by restriction digestion with Nsi I which produced 2.1 kb, 2.6 kb, and 7 kb fragments. DNA sequencing of one clone verified that the construct contained the correct inserts with no PCR errors. The construct was designated pDM313.

Example 15: Multiple Site Specific Integrations at *Trichoderma reesei* cbh1 and cbh2 Loci with pJfyS156 Using FLP/FRT System

*T. reesei* strain AgJg-FRT2-4B17 containing FRT sites inserted at the cbh1 and cbh2 loci (Example 12) was transformed with plasmid pJfyS156 (Example 8) to achieve targeting of one construct to the FRT sites at two different loci. Plasmid pJfyS156 contains an *A. fumigatus* beta-glucosidase expression cassette and the hpt marker for hygromycin resistance flanked by FRT sites, and the *S. cerevisiae* flippase gene under transcriptional control of the *T. reesei* cbh2 promoter. Approximately 50 μg of plasmid pJfyS156 were digested with Pme I. The digested pJfyS156 DNA was recovered using a Nucleospin® Extract II Kit (Example 8).

Protoplasts of *T. reesei* strain AgJg-FRT2-4B17 were prepared as described in Example 1 except that media and solutions were supplemented with 2% (w/v) beta-lactose to induce the *T. reesei* cbh2 promoter driving the flippase gene. The strain was cultivated in 25 ml of YP medium supplemented with 2% (w/v) beta-lactose at 27° C. for 17 hours with gentle agitation at 90 rpm. Approximately 3 μg of Pme I digested pJfyS156 DNA were added to 100 μl of the protoplast solution and mixed gently. PEG buffer+2% beta-lactose (250 μl) was added, and the transformation reaction was mixed and incubated at 34° C. for 30 minutes. STC+2% beta-lactose (3 ml) was then added, and the transformation reaction was mixed and then spread onto two PDA plates supplemented with 1 M sucrose and 2% beta-lactose. Eight transformation reactions were prepared and plated. After incubation at 30° C. for 16 hours, 20 ml of overlay PDA medium supplemented with 2% beta-lactose and 35 µg of hygromycin B per ml were added to each plate.

The transformation plates were incubated at 30° C. for 4 days and at room temperature for 5 days. Forty-four transformants were transferred to PDA plates and incubated for 4 days at 30° C. Fungal Spore PCR was utilized according to Example 9 to identify transformants that had integrated the *A. fumigatus* beta-glucosidase expression cassette and hpt marker at both the cbh1 and cbh2 loci. The spore PCR was composed of 1×PHIRE® Plant Direct PCR buffer (contains dNTPs and Mg), 10 pmol each of the forward and reverse primers shown below, 0.4 µl of PHIRE® II Hot Start DNA Polymerase, and 1 µl of supernatant from the spore suspension in a final volume of 20 µl.

PCR Screen for pJfyS156 Targeting: 5' End of cbh1 and cbh2 Loci

```
Forward primer (homology to 5' flanking
region of cbh1, upstream of FRT-F site):
                                     (SEQ ID NO: 78)
5'-TTCCCTTCCTCTAGTGTTGAAT-3'

Forward primer (homology to 5' flanking region
of cbh2, upstream of FRT-F site):
                                     (SEQ ID NO: 79)
5'-GTTGGTATAGAGCAGCGTTC-3'

Reverse primer (homology to A. fumigatus
beta-glucosidase gene):
                                     (SEQ ID NO: 80)
5'-CTATATCCGAAACAATGACG-3'
```

The reaction was performed in a thermocycler programmed for 1 cycle at 98° C. for 5 minutes; 40 cycles each at 98° C. for 15 seconds, 61° C. for 15 seconds, and 72° C. for 1 minute and 10 seconds; and 1 cycle at 72° C. for 15 minutes.

The completed PCRs were subjected to 0.8% agarose gel electrophoresis in TBE buffer. Transformants having correct targeting of pJfyS156 DNA to the cbh1 locus produced a 2.0 kb fragment. Transformants having correct targeting of pJfyS156 DNA to the cbh2 locus produced a 1.3 kb fragment. Transformants having correct targeting to both the cbh1 and cbh2 loci produced both the 2.0 kb and 1.3 kb fragments.

PCR Screen for pJfyS156 Targeting: 3' End of cbh1 and cbh2 Loci

```
Forward primer (homology to hpt marker):
                                     (SEQ ID NO: 81)
5'-CGTGTTTCTTCCCATTCGCATGCGACCTCGTGGTCATTGAC-3'

Reverse primer (homology to 3' flanking region
of cbh1, downstream of FRT-F3 site):
                                     (SEQ ID NO: 82)
5'-AAAGACAGGCCAGCGACGAAG-3'

Reverse primer (homology to 3' flanking region
of cbh2, downstream of FRT-F3 site):
                                     (SEQ ID NO: 83)
5'-GCATTGCAACCGCGGCTTTC-3'
```

The PCRs were performed as described above. Transformants having correct targeting of pJfyS156 DNA to the cbh1 locus produced a 1.4 kb fragment. Transformants having correct targeting of pJfyS156 DNA to the cbh2 locus produced a 0.75 kb fragment. Transformants having correct targeting to both the cbh1 and cbh2 loci produced both the 1.4 kb and 0.75 kb fragments.

Transformants that produced PCR fragments indicating correct targeting to both the cbh1 and cbh2 loci were chosen for spore isolation. Spores from a 6 day old PDA plate were collected in 4 ml of 0.01% TWEEN® 20 and the spore concentration was determined using a hemocytometer. Spores were diluted appropriately to a concentration of $10^3$ spores per ml using sterile water and 100 spores were spread onto PDA plates supplemented with 10 µg of hygromycin per ml. The plates were incubated for 4 days at room temperature. Isolated colonies from each transformant were transferred with a sterile 10 µl inoculation loop to PDA plates and incubated at 30° C. Fungal Spore PCR was utilized according to Example 9 to identify spore isolates with correct targeting at both loci.

Genomic DNA from the spore isolates was prepared as described below and subjected to Southern blot analysis. *T. reesei* strains were grown in 25 ml of YP medium supplemented with 2% glucose (w/v) in a 125 ml baffled shake flask at 28° C. for 2 days with agitation at 200 rpm. Mycelia were harvested by vacuum filtration through Whatman 1 filter paper in a Buchner funnel. The mycelia were washed twice in deionized water, dried under vacuum, and then transferred to 2 ml microfuge tubes. The mycelia were then dried approximately 16 hours in a Savant ISS110 SpeedVac concentrator (Thermo Scientific). The dried mycelia were ground to fine powders and total DNA was isolated using a MasterPure™ Yeast DNA Purification Kit (Epicentre). Ground mycelia equivalent to approximately a 50 µl volume were transferred to 2 ml microfuge tubes. Yeast Cell Lysis Solution (300 µl) was added to each mycelia sample and vortexed. The samples were incubated at 65° C. for 20 minutes and then placed on ice for 5 minutes. MPC Protein Precipitation Reagent (150 µl) was added to each sample and briefly vortexed. The samples were centrifuged in a microcentrifuge at 0,000 rpm for 10 minutes. The supernatants were transferred to 1.7 ml microcentrifuge tubes and 500 µl of isopropanol were added to each tube. The samples were mixed thoroughly by inversion. The DNA was pelleted by centrifugation in a microcentrifuge for 10 minutes at 10,000 rpm. The supernatants were discarded. The pellets containing the DNA were washed with 0.5 ml of 70% ethanol. The samples were centrifuged in a microcentrifuge for 4 minutes at 0,000 rpm. The ethanol was removed with a pipette and the pellets were air dried for 7 minutes at room temperature. The DNA pellets were resuspended in 60 µl of TE. A 1.5 µl aliquot of 5 µg/µl RNase A was added to each tube and the samples were incubated at 37° C. for 30 minutes.

For Southern blot analysis approximately 1 µg of each genomic DNA was digested with 20 units of Nsi I and Sac I. The digested DNA was subjected to 0.8% agarose gel electrophoresis in TAE buffer and transferred to a NYTRAN® SuperCharge membrane as described in Example 3.

A probe hybridizing to the *A. fumigatus* beta-glucosidase coding sequence was generated using a PCR DIG Probe Synthesis Kit with the primers shown below.

```
Primer 0615057:
                                     (SEQ ID NO: 84)
5'-ATGAGATTCGGTTGGCTCGAG-3'

Primer 068911:
                                     (SEQ ID NO: 85)
5'-CCGTGATGTTGTAACCATAT-3'
```

The PCR was composed of 100 ng of pDM313, 1 µl of 10 mM dNTPs, 1 µM primers, 1×PHUSION® High-Fidelity Reaction Buffer, and 1 unit of PHUSION® Hot Start High-Fidelity DNA Polymerase in a final volume of 50 µl. The PCR was performed in a thermocycler programmed for 1 cycle at 98° C. for 2 minutes; and 35 cycles each at 98° C. for 15 seconds, 60° C. for 30 seconds, and 72° C. for 40 seconds; and 1 cycle at 72° C. for 10 minutes. The PCR product was separated by 0.7% agarose gel electrophoresis in TAE buffer where an approximately 800 bp fragment was excised from the gel and extracted using a Nucleospin® Extract II Kit (Example 8).

The DIG Probe Synthesis PCR was composed of approximately 10 ng of the purified PCR fragment described above as template, 1 µM primers, 5 µl of PCR DIG Synthesis Mix (Roche Applied Science Corp.), 1×PCR buffer with $MgCl_2$ (Roche Applied Science Corp.), and 0.75 µl of Enzyme Mix (Roche Applied Science Corp.) in a final volume of 50 µl. The reaction was performed in a thermocycler programmed for 1 cycle at 95° C. for 2 minutes; 10 cycles each at 95° C. for 30 seconds, 60° C. for 30 seconds, and 72° C. for 40 seconds; 20 cycles each at 95° C. for 30 seconds, 60° C. for 30 seconds, and 72° C. for 40 seconds plus an additional 20 seconds for each successive cycle; and 1 cycle at 72° C. for 7 minutes. The PCR product (the *A. fumigatus* BG probe) was purified using a Nucleospin® Extract II Kit (Example 8).

Southern blot analysis verified that the predicted 6.0 kb fragment characteristic of the correct FLP/FRT recombination at the cbh1 locus and the predicted 4.4 kb fragment characteristic of the correct FLP/FRT recombination at the cbh2 locus were both produced from the same transformant.

Example 16: Multiple Site Specific Integrations at *Trichoderma reesei* cbh1 and cbh2 Loci with pDM313 Using FLP/FRT System

*T. reesei* strain AgJg-FRT2-4B17 with FRT sites inserted at the cbh1 and cbh2 loci (Example 12) was transformed with plasmid pDM313 (Example 14) to achieve targeting of one construct to the FRT sites at two different loci. Plasmid pDM313 contains an *A. fumigatus* beta-glucosidase expression cassette and the hpt marker for hygromycin resistance flanked by FRT sites, and the *S. cerevisiae* flippase gene under transcriptional control of the *T. reesei* gpdA promoter. Approximately 50 µg of plasmid pDM313 were digested with Pme I and recovered using a Nucleospin® Extract II Kit (Example 8). Protoplasts of *T. reesei* strain AgJg-FRT2-4B17 were prepared as described in Example 1. Approximately 3 µg of the Pme I digested pDM313 DNA were added to 100 µl of the protoplast solution and mixed gently. PEG buffer (250 µl) was added, and the reaction was mixed and incubated at 34° C. for 30 minutes. STC (3 ml) was then added, and the reaction was mixed and then spread onto two PDA plates supplemented with 1 M sucrose. Eight transformation reactions were prepared and plated. After incubation at 30° C. for 16 hours, 20 ml of overlay PDA medium supplemented with 35 µg of hygromycin B per ml were added to each plate.

The transformation plates were incubated at 30° C. for 3 days and at room temperature for 5 days. Forty-eight transformants were transferred to PDA plates and incubated for 4 days at 30° C. Fungal Spore PCR was utilized according to Example 9 to identify transformants with the *A. fumigatus* beta-glucosidase expression cassette and hpt marker integrated at the cbh1 and cbh2 loci. The Spore PCR was composed of 1×PHIRE® Plant Direct PCR buffer (contains dNTPs and Mg), 10 pmol each of the primers shown below, 0.4 µl of PHIRE® Hot Start DNA Polymerase, and 1 µl of supernatant from each spore suspension in a final volume of 20 µl.

PCR Screen for pDM313 Targeting: 5' End of cbh1 and cbh2 Loci

Forward primer (homology to 5' flanking region of cbh1, upstream of FRT-F site):
(SEQ ID NO: 86)
5'-TTCCCTTCCTCTAGTGTTGAAT-3'

Forward primer (homology to 5' flanking region of cbh2, upstream of FRT-F site):
(SEQ ID NO: 87)
5'-GTTGGTATAGAGCAGCGTTC-3'

Reverse primer (homology to A. fumigatus beta-glucosidase gene):
(SEQ ID NO: 88)
5'-CTATATCCGAAACAATGACG-3'

The reaction was performed in a thermocycler programmed for 1 cycle at 98° C. for 5 minutes; 40 cycles each at 98° C. for 15 seconds, 61° C. for 15 seconds, and 72° C. for 1 minute and 10 seconds; and 1 cycle at 72° C. for 15 minutes.

The completed PCRs were subjected to 0.8% agarose gel electrophoresis in TBE buffer. Transformants with correct targeting of pDM313 DNA to the cbh1 locus produced a 2.0 kb fragment. Transformants with correct targeting of pDM313 DNA to the cbh2 locus produced a 1.3 kb fragment. Transformants with correct targeting to both the cbh1 and cbh2 loci produced both the 2.0 kb and 1.3 kb fragments.

PCR Screen for pDM313 Targeting: 3' End of cbh1 and cbh2 Loci

Forward primer (homology to hpt marker):
(SEQ ID NO: 89)
5'-CGTGTTTCTTCCCATTCGCATGCGACCTCGTGGTCATTGAC-3'

Reverse primer (homology to 3' flanking region of cbh1, downstream of FRT-F3 site):
(SEQ ID NO: 90)
5'-AAAGACAGGCCAGCGACGAAG-3'

Reverse primer (homology to 3' flanking region of cbh2, downstream of FRT-F3 site):
(SEQ ID NO: 91)
5'-GCATTGCAACCGCGGCTTTC-3'

The PCRs were performed as described above. Transformants with correct targeting of pDM313 DNA to the cbh1 locus produced a 1.4 kb fragment. Transformants with correct targeting of pDM313 DNA to the cbh2 locus produced a 0.75 kb fragment. Transformants with correct targeting to both the cbh1 and cbh2 loci produced both the 1.4 kb and 0.75 kb fragments.

Transformants that produced PCR fragments indicating correct targeting to both the cbh1 and cbh2 loci were chosen for spore isolation as described in Example 15. Fungal Spore PCR was utilized according to Example 9 to identify spore isolates with correct targeting at both loci.

Genomic DNA was isolated from the spore isolates according to Example 15 and subjected to Southern blot analysis according to Example 15 using the *A. fumigatus* beta-glucosidase gene probe.

Southern blot analysis verified that the predicted 6.0 kb fragment characteristic of correct FLP/FRT recombination at the cbh1 locus and the predicted 4.4 kb fragment characteristic of correct FLP/FRT recombination at the cbh2 locus were both produced from the same transformant.

Example 17: Construction of Plasmid pDM296

Plasmid pDM296 was constructed to insert the hpt (hygromycin resistance) marker between the cbh1 flanking regions. A 0.28 kb fragment containing a portion of the cbh1 5' flanking region was PCR amplified from plasmid pSMai155 (U.S. Pat. No. 7,361,495) using the primers shown below.

```
Forward primer
                                      (SEQ ID NO: 92)
5'-AATAGAAAGAGAAGCTTAGCCAAG-3'

Reverse primer
                                      (SEQ ID NO: 93)
5'-GCCGTTTAAATGAATTCGAACCCTTAATTAACTAGTACGCGTA

GATC-3'
```

The PCR was composed of 100 picomoles of each primer, 133 ng of pSMai155 DNA, 1×PHUSION™ High-Fidelity Hot Start DNA Polymerase buffer, 1 μl of a 10 mM blend of dNTPs, and 1 unit of PHUSION™ High-Fidelity Hot Start DNA Polymerase in a final volume of 50 μl. The reaction was performed in a thermocycler programmed for 1 cycle at 98° C. for 2 minutes; 34 cycles each at 98° C. for 15 seconds, 59° C. for 30 seconds, and 72° C. for 1 minute; and 1 cycle at 72° C. for 10 minutes. The PCR product was separated by 0.8% agarose gel electrophoresis in TAE buffer where an approximately 0.28 kb fragment was excised from the gel and extracted using a Nucleospin® Extract II Kit (Example 8).

A 0.85 kb fragment containing a portion of the hpt marker was amplified by PCR from plasmid pSMai155 using the primers shown below.

```
Forward primer:
                                      (SEQ ID NO: 94)
5'-GATCTACGCGTACTAGTTAATTAAGGGTTCGAATTCATTTAAAC

GGC-3'

Reverse primer:
                                      (SEQ ID NO: 95)
5'-GACCGATTCCTTGCGGTCCGAAT-3'
```

The PCR was composed of 100 picomoles of each primer, 133 ng of pSMai155 DNA, 1×PHUSION™ High-Fidelity Hot Start DNA Polymerase buffer, 1 μl of a 10 mM blend of dNTPs, and 1 unit of PHUSION™ High-Fidelity Hot Start DNA Polymerase (New England Biolabs, Inc.) in a final volume of 50 μl. The reaction was performed in a thermocycler programmed for 1 cycle at 98° C. for 2 minutes; 34 cycles each at 98° C. for 15 seconds, 59° C. for 30 seconds, and 72° C. for 1 minute; and 1 cycle at 72° C. for 10 minutes. The PCR product was separated by 0.8% agarose gel electrophoresis in TAE buffer where an approximately 0.85 kb fragment was excised from the gel and extracted using a Nucleospin® Extract II Kit (Example 8).

Approximately 11 μg of pJfyS139 (WO 20131028928) DNA was digested with Hind III and Rsr II. The digested DNA was separated by 0.8% agarose gel electrophoresis in TAE buffer where an approximately 5.8 kb fragment was excised from the gel and extracted using a Nucleospin® Extract II Kit (Example 8).

The 0.28 and 0.85 kb PCR products were inserted into Hind III/Rsr II digested pJfyS139 using an IN-FUSION™ Advantage PCR Cloning Kit. The reaction was composed of 1× IN-FUSION™ Reaction buffer, 100 ng of the Hind III/Rsr II digested pJfyS139, 44.5 ng of the 0.28 kb PCR product, 111 ng of the 0.85 kb PCR product, and 1 μl of IN-FUSION™ enzyme in a 10 μl reaction volume. The reaction was incubated for 15 minutes at 37° C. and 15 minutes at 50° C. After the incubation period the reaction was chilled on ice and then 40 μl of TE were added to the reaction. *E. coli* XL10 Gold Ultracompetent cells were transformed with the reaction. A 100 μl aliquot of cells was transferred to a tube on ice and 4 μl of beta-mercaptoethanol were added. A 2 μl aliquot of the reaction was added to the cells and the reaction was chilled on ice for 30 minutes. The reaction was heat shocked at 42° C. for 30 seconds and then chilled on ice for 2 minutes. A 900 μl aliquot of NZY+ medium was added. The reaction was then incubated at 37° C. with agitation at 200 rpm for 1 hour. The *E. coli* transformation reaction was transferred to a microfuge tube and centrifuged for 10 seconds at 13,000 rpm. Approximately 850 μl of supernatant were discarded and the cells were resuspended in approximately 150 μl of supernatant. The cells were spread onto a 150 mm 2XYT plus ampicillin plate. Plasmid DNA was isolated from the transformants according to Example 4. Plasmid DNA from the transformants was screened by restriction digestion with Pac I and Rsr II, which produced 0.8 and 6.1 kb fragments, respectively. DNA sequencing of one clone verified that a construct contained the correct inserts with no PCR errors. The construct was designated pDM296.

Example 18: Construction of Plasmid pDM297

Plasmid pDM297 was constructed to insert the amdS marker between the cbh1 flanking regions. A 2.8 kb fragment containing the *A. nidulans* amdS marker was amplified by PCR from plasmid pMJ09 (U.S. Pat. No. 7,361,495) using the primers shown below.

```
Forward primer:
                                      (SEQ ID NO: 96)
5'-CCGCGGACTGCGCACCATGGATGCATCTGGAAACGCAACC-3'

Reverse primer:
                                      (SEQ ID NO: 97)
5'-GGTGCGTCAGGCTTTCGCCACATTTAAATCATGCATTCTACGCCAG

GACC-3'
```

The PCR was composed of 100 picomoles of each primer, 100 ng of pMJ09 DNA, 1× PHUSION™ High-Fidelity Hot Start DNA Polymerase buffer, 1 μl of a 10 mM blend of dNTPs, and 1 unit of PHUSION™ High-Fidelity Hot Start DNA Polymerase in a final volume of 50 μl. The reaction was performed in a thermocycler programmed for 1 cycle at 98° C. for 2 minutes; 34 cycles each at 98° C. for 15 seconds, 59° C. for 30 seconds, and 72° C. for 1.5 minutes; and 1 cycle at 72° C. for 10 minutes. The PCR product was separated by 0.8% agarose gel electrophoresis in TAE buffer where an approximately 2.8 kb fragment was excised from the gel and extracted using a Nucleospin® Extract II Kit (Example 8).

A 1.3 kb 3' cbh1 flanking DNA sequence was amplified by PCR from plasmid pJfyS139 (WO 2013/028928) using the primers shown below.

```
Forward primer:
                                       (SEQ ID NO: 98)
5'-TGGCGTAGAATGCATGATTTAAATGTGGCG

AAAGCCTGACGCACC-3'

Reverse primer:
                                       (SEQ ID NO: 99)
5'-ATGCATGCTCGAGCGGCCGCACGGCACGG-3'
```

The PCR was composed of 100 picomoles of each primer, 100 ng of pJfyS139 DNA, 1×PHUSION™ High-Fidelity Hot Start DNA Polymerase buffer, 1 µl of a 10 mM blend of dNTPs, and 1 unit of PHUSION™ High-Fidelity Hot Start DNA Polymerase in a final volume of 50 µl. The reaction was performed in a thermocycler programmed for 1 cycle at 98° C. for 2 minutes; 34 cycles each at 98° C. for 15 seconds, 59° C. for 30 seconds, and 72° C. for 1.5 minutes, and 1 cycle at 72° C. for 10 minutes. The PCR product was separated by 0.8% agarose gel electrophoresis in TAE buffer where an approximately 1.3 kb fragment was excised from the gel and extracted using a Nucleospin® Extract II Kit (Example 8).

Fifteen µg of pSMai155 (U.S. Pat. No. 7,361,495) were digested with Nco I HF and Not I. The digested DNA was separated by 0.8% agarose gel electrophoresis in TAE buffer where an approximately 3.7 kb fragment was excised from the gel and extracted using a Nucleospin® Extract II Kit (Example 8).

The 2.8 kb and 1.3 kb PCR products were inserted into Nco I/Not I digested pSMai155 using an IN-FUSION™ Advantage PCR Cloning Kit. The reaction was composed of 1× IN-FUSION™ Reaction buffer, 100 ng of the Nco I/Not I digested pSMai155, 145 ng of the 2.8 kb PCR product, 67 ng of the 1.3 kb PCR product, 1 µl of IN-FUSION™ enzyme, and 2.4 µl of water in a 10 µl reaction volume. The reaction was incubated at 37° C. for 15 minutes and at 50° C. for 15 minutes. After the incubation period the reaction was chilled on ice and then 40 µl of TE were added to the reaction. *E. coli* XL10 Gold Ultracompetent cells were transformed with a 2 µl aliquot of the reaction according to Example 17. Plasmid DNA was isolated from the transformants according to Example 4 and screened by restriction digestion with Nco I HF and Bam HI, which produced 2.0 and 5.8 kb fragments, respectively. DNA sequencing of one clone verified that a construct contained the correct inserts with no PCR errors. The construct was designated pDM297.

Example 19: Multiple Site Specific Integrations at *Trichoderma reesei* cbh1 and cbh2 Loci with pJfyS156 and pAgJg136 Using FLP/FRT System

*T. reesei* strain AgJg-FRT2-4B17 containing FRT sites inserted at the cbh1 and cbh2 loci (Example 12) was transformed with plasmids pJfyS156 (Example 8) and pAgJg136 (Example 13) to achieve targeting of two constructs to the FRT sites at two different loci. Plasmid pJfyS156 comprises an *A. fumigatus* beta-glucosidase expression cassette and the hpt marker for hygromycin resistance flanked by FRT sites, and the *S. cerevisiae* flippase gene under transcriptional control of the *T. reesei* cbh2 promoter. Plasmid pAgJg136 comprises an *A. fumigatus* beta-glucosidase 4M variant (WO 2013/028912) expression cassette and the amdS marker flanked by FRT sites, and the *S. cerevisiae* flippase gene under transcriptional control of the *T. reesei* cbh2 promoter. Approximately 50 µg of plasmid pJfyS156 and approximately 80 µg of plasmid pAgJg136 were digested with Pme I. The digested DNA was heated for 20 minutes at 65° C. to inactivate the restriction enzyme and then was ethanol precipitated. The pJfyS156 DNA and pAgJg136 DNA were resuspended in 30 µl and 50 µl of TE, respectively. Protoplasts of *T. reesei* strain AgJg-FRT2-4B17 were prepared as described in Example 1 except that 2% beta-lactose (w/v) was added to growth media and protoplast solutions. Approximately 2 µg of Pme I digested pJfyS156 DNA and approximately 2 µg of Pme I digested pAgJg136 DNA were added to 100 µl of the protoplast solution and mixed gently. PEG buffer (250 µl) supplemented with 2% beta-lactose was added, and the reaction was mixed and incubated at 34° C. for 30 minutes. STC (3 ml) supplemented with 2% beta-lactose was then added and the reaction was mixed and then spread onto two COVE+2% beta-lactose plates. Seven transformation reactions were prepared and plated. After incubation at 28° C. for 16 hours, 20 ml of COVE+2% beta-lactose overlay supplemented with 35 µg of hygromycin B per ml were added to each plate.

The transformation plates were incubated at 28° C. for 9 days. Forty transformants were transferred to COVE2 plates and incubated at 30° C. for 5 days. Fungal Spore PCR was utilized according to Example 9 to identify transformants with the two different plasmids integrated at the cbh1 and cbh2 loci. The Spore PCR was composed of 1×PHIRE® Plant Direct PCR buffer (contains dNTPs and Mg), 10 pmol each of the forward and reverse primers shown below, 0.4 µl of PHIRE® II Hot Start DNA Polymerase, and 1 µl of supernatant from the spore suspension in a final volume of 20 µl.

PCR Screen of 5' End of Both cbh1 and cbh2 Loci

```
Forward primer (homology to 5' flanking region of
cbh1 upstream of FRT-F site):
                                      (SEQ ID NO: 100)
5'-TTCCCTTCCTCTAGTGTTGAAT-3'

Forward primer (homology to 5' flanking region of
cbh2, upstream of FRT-F site):
                                      (SEQ ID NO: 101)
5'-GTTGGTATAGAGCAGCGTTC-3'

Reverse Primer (homology to A. fumigatus beta-
glucosidase gene):
                                      (SEQ ID NO: 102)
5'-CTATATCCGAAACAATGACG-3'
```

The reactions were performed in a thermocycler programmed for 1 cycle at 98° C. for 5 minutes; 40 cycles each at 98° C. for 15 seconds, 61° C. for 15 seconds, and 72° C. for 1 minute and 10 seconds; and 1 cycle at 72° C. for 15 minutes.

The completed PCRs were subjected to 0.8% agarose gel electrophoresis in TBE buffer. Transformants having correct targeting of plasmid DNA to the cbh1 locus produced a 2.0 kb fragment. Transformants having correct targeting of plasmid DNA to the cbh2 locus produced a 1.3 kb fragment. Transformants having correct targeting to both the cbh1 and cbh2 loci produced both the 2.0 kb and 1.3 kb fragments.

Fungal Spore PCR was utilized as described above to identify the exact locus of integration for each of the two plasmids. Transformants identified as having integration at both the cbh1 and cbh2 loci by the 5' end PCR screen described above were screened with the primers shown below.

Screen for Site of Integration of pJfyS156

```
Forward primer (homology to hpt marker):
                                      (SEQ ID NO: 103)
5'-CGTGTTTCTTCCCATTCGCATGCGACCTCGTGGTCATTGAC-3'

Reverse primer (homology to 3' flanking region of
cbh1, downstream of FRT-F3 site):
                                      (SEQ ID NO: 104)
5'-AAAGACAGGCCAGCGACGAAG-3'

Reverse primer (homology to 3' flanking region of
cbh2, downstream of FRT-F3 site):
                                      (SEQ ID NO: 105)
5'-GCATTGCAACCGCGGCTTTC-3'
```

Screen for Site of Integration of pAgJg136

```
Forward primer (homology to the amdS marker):
                                      (SEQ ID NO: 106)
5'-ACCTGCCGTGTCAGCCTCTACGGTTGTTA-3'

Reverse primer (homology to 3' flanking region of
cbh1, downstream of FRT-F3 site):
                                      (SEQ ID NO: 107)
5'-AAAGACAGGCCAGCGACGAAG-3'

Reverse primer (homology to 3' flanking region of
cbh2, downstream of FRT-F3 site):
                                      (SEQ ID NO: 108)
5'-GCATTGCAACCGCGGCTTTC-3'
```

The reactions were performed in a thermocycler programmed for 1 cycle at 98° C. for 5 minutes; 40 cycles each at 98° C. for 10 seconds, 61° C. for 10 seconds, and 72° C. for 30 seconds; and 1 cycle at 72° C. for 1 minute.

The completed PCRs were subjected to 0.8% agarose gel electrophoresis in TBE buffer. Transformants having correct targeting of pJfyS156 DNA to the cbh1 locus produced a 1.4 kb fragment. Transformants having correct targeting of pJfyS156 DNA to the cbh2 locus produced a 0.75 kb fragment. Transformants having correct targeting of pAgJg136 DNA to the cbh1 locus produced a 1.35 kb fragment. Transformants having correct targeting of pAgJg136 DNA to the cbh2 locus produced a 0.67 kb fragment.

Transformants that produced the correct PCR fragments were chosen for spore isolation according to Example 15 except that the spores were collected from a COVE2 plate and 100 spores were spread onto COVE plates and incubated at 30° C. for 4 days. Isolated colonies from each transformant were transferred with a sterile 10 µl inoculation loop to COVE glycerol plates and incubated at 30° C. for 5 days. Spore PCR using a PHIRE® Plant Direct PCR Kit and the primers and PCR conditions shown above for the PCR screen of the 5' end of both loci was used to screen the spore isolates.

The completed PCRs were subjected to 0.8% agarose gel electrophoresis in TBE buffer. Transformants having correct targeting of plasmid DNA to the cbh1 locus produced a 2.0 kb fragment. Transformants having correct targeting of plasmid DNA to the cbh2 locus produced a 1.3 kb fragment. Transformants having correct targeting to both the cbh1 and cbh2 loci produced both the 2.0 kb and 1.3 kb fragments.

Genomic DNA from the spore isolates was prepared according to Example 15. For Southern blot analysis approximately 1 µg of each genomic DNA was digested with 20 units of Mfe I and subjected to Southern blot analysis according to Example 15. Two blots were prepared for separate hybridizations with hpt and amdS probes.

The hpt gene probe was prepared according to the following protocol. Twelve µg of pDM296 (Example 17) were digested with Nco I and Not I and separated by 0.8% agarose gel electrophoresis in TAE buffer where an approximately 1.9 kb fragment was excised from the gel and extracted using a Nucleospin® Extract II Kit (Example 8). A 0.5 kb PCR fragment was generated from the 1.9 kb Nco I/Not I hpt fragment using the primers shown below.

```
Forward primer:
                                      (SEQ ID NO: 109)
5'-ATGAAAAAGCCTGAACTCACC-3'

Reverse primer:
                                      (SEQ ID NO: 110)
5'-TCCATCACAGTTTGCCAGTGA-3'
```

The PCR was composed of 50 picomoles of each of the primers, 25 ng of the 1.9 kb Nco I/Not I hpt fragment, 1×PHUSION™ High-Fidelity Hot Start DNA Polymerase buffer, 1 µl of a 10 mM blend of dNTPs, and 1 unit of PHUSION™ High-Fidelity Hot Start DNA Polymerase in a final volume of 50 µl. The reaction was performed in a thermocycler programmed for 1 cycle at 98° C. for 2 minutes; 34 cycles each at 98° C. for 15 seconds, 60° C. for 30 seconds, and 72° C. for 30 seconds, and 1 cycle at 72° C. for 10 minutes. The PCR product was separated by 0.8% agarose gel electrophoresis in TAE buffer where an approximately 0.5 kb fragment was excised from the gel and extracted using a Nucleospin® Extract II Kit (Example 8).

The hpt probe was generated using a PCR DIG Probe Synthesis Kit with the forward and reverse primers shown directly above. The PCR was composed of 1×PCR DIG Probe Synthesis mix, 50 pmol of each primer, 1×PCR buffer with $MgCl_2$, 45 ng purified 0.5 kb hpt PCR fragment (described above), and 2.6 units of EXPAND® High Fidelity DNA polymerase (Roche Applied Science Corp.) in a final volume of 50 µl. The reaction was performed in a thermocycler programmed for 1 cycle at 95° C. for 2 minutes; 30 cycles each at 95° C. for 30 seconds, 59° C. for 30 seconds, and 72° C. for 45 seconds; and 1 cycle at 72° C. for 7 minutes.

The amdS gene probe was prepared according to the following protocol. Ten µg of pDM297 (Example 18) was digested with Nco I and Bam HI. The digested DNA was separated by 0.8% agarose gel electrophoresis in TAE buffer where an approximately 2.0 kb fragment was excised from the gel and extracted using a Nucleospin® Extract II Kit (Example 8). A 0.59 kb PCR fragment was generated from the 2.0 kb Nco I/Bam HI amdS fragment using the primers shown below.

```
Forward primer:
                                      (SEQ ID NO: 111)
5'-ACATTGCCGTCGAAGTTGTA-3'

Reverse primer:
                                      (SEQ ID NO: 112)
5'-AAGACCTCTGTCCCGCAGAC-3'
```

The PCR was composed of 50 picomoles of each of the primers, 18 ng of the 2.0 kb Nco I/Bam HI amdS fragment, 1×PHUSION™ High-Fidelity Hot Start DNA Polymerase buffer, 1 µl of a 10 mM blend of dNTPs, and 1 unit of PHUSION™ High-Fidelity Hot Start DNA Polymerase in a final volume of 50 µl. The reaction was performed in a thermocycler programmed for 1 cycle at 98° C. for 2 minutes; 34 cycles each at 98° C. for 15 seconds, 59° C. for 30 seconds, and 72° C. for 1 minute; and 1 cycle at 72° C. for 10 minutes. The PCR product was separated by 0.8% agarose gel electrophoresis in TAE buffer where an approximately 0.59 kb fragment was excised from the gel and extracted using a Nucleospin® Extract II Kit (Example 8). The amdS probe was generated using a PCR DIG Probe Synthesis Kit with the forward and reverse primers shown directly above.

The PCR was composed of 1×PCR DIG Probe Synthesis mix, 50 pmol of each primer, 1×PCR buffer with $MgCl_2$, 14 ng of the purified 0.59 kb amdS PCR fragment (described above), and 2.6 units of EXPAND® High Fidelity DNA polymerase in a final volume of 50 µl. The reaction was performed in a thermocycler programmed for 1 cycle at 95° C. for 2 minute; 30 cycles each at 95° C. for 30 seconds, 59° C. for 30 seconds, and 72° C. for 45 seconds; and 1 cycle at 72° C. for 7 minutes.

Each probe was boiled for 5 minutes, chilled on ice for 2 minutes, and added to 10 ml of DIG Easy Hyb to produce the hybridization solution. One blot was probed with the hpt probe and the other blot was probed with the amdS probe.

Transformants having correct integration of pJfyS156 at the cbh1 locus produced a 2.6 kb hpt hybridizing fragment. Transformants having correct integration of pJfyS156 at the cbh2 locus produced a 3.0 kb hpt hybridizing fragment. Transformants having correct integration of pAgJg136 at the cbh1 locus produced a 3.4 kb amdS hybridizing fragment. Transformants having correct integration of pAgJg136 at the cbh2 locus produced a 3.8 kb amdS hybridizing fragment. Southern blot analysis verified that transformants having one copy of pJfyS156 plus one copy of pAgJg136 were obtained and that the plasmid DNAs were correctly integrated at the cbh1 and cbh2 loci.

Example 20: Construction of Plasmid pQM41 for Targeting a Non-Functional amdS Marker to *Trichoderma reesei* cbh2 Locus Plasmid pQM41 was constructed by inserting an approximately 1.9 kb fragment of a non-functional amdS fragment 1 into an approximately 10.3 kb vector backbone from pJfyS142 (WO 2013/028912) digested with Nco I and Pac I. The non-functional amdS fragment 1 was amplified from pAllo1 (WO 04/111228) using the primers shown below.

```
Forward primer 1208222:
                                    (SEQ ID NO: 113)
5'-ATCACCCTCTGTGTATTGCACCAGGGCATGGGGATGACCTTG-3'

Reverse primer 1207436:
                                    (SEQ ID NO: 114)
5'-CCGGTCACGAAAGCCTTAATTAATCTACGCCAGGACCGAGCAAG-3'
```

The PCR was composed of 100 ng of pAllo1, 1 µl of 10 mM dNTPs, 1 µM primers, 1× PHUSION® High-Fidelity Reaction Buffer, and 1 unit of PHUSION® Hot Start High-Fidelity DNA Polymerase in a final volume of 50 µl. The reaction was performed in a thermocycler programmed for 1 cycle at 95° C. for 2 minutes; 35 cycles each at 95° C. for 15 seconds, 60° C. for 30 seconds, and 72° C. for 1 minute 15 seconds; and 1 cycle at 72° C. for 10 minutes. The PCR product was separated by 0.7% agarose gel electrophoresis in TAE buffer where an approximately 1.9 kb fragment was excised from the gel and extracted using a Nucleospin® Extract II Kit (Example 8).

Figure 3:
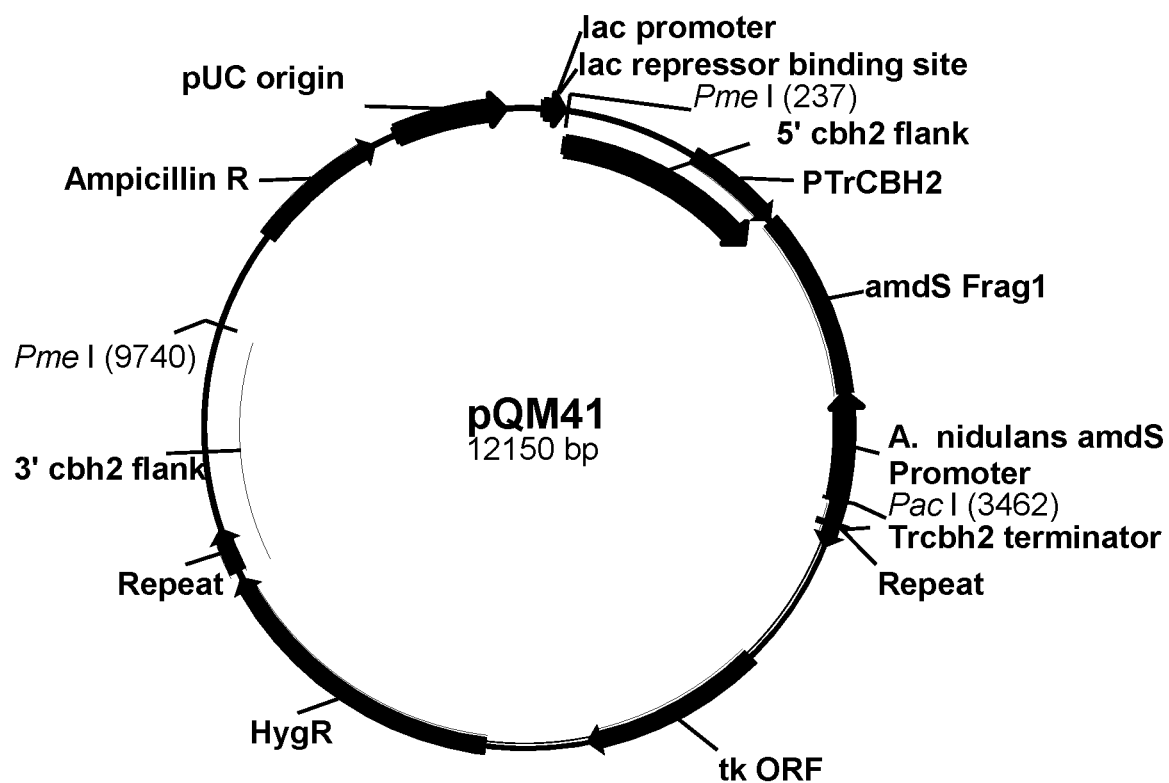
FIG. 3 shows a restriction map of plasmid pQM41.

The 1.9 kb PCR product was inserted into Nco I and Pac I digested pJfyS142 using an IN-FUSION™ HD Cloning Kit. The IN-FUSION™ reaction was composed of 1× IN-FUSION™ HD Enzyme Premix, 300 ng of Nco I and Pac I digested pJfyS142, and 109 ng of the 1.9 kb PCR product in a 10 µl reaction volume. The reaction was incubated at 50° C. for 15 minutes. After the incubation period, a 1 µl aliquot was transformed into ONE SHOT® TOP10 Chemically Competent cells according to Example 4. Plasmid DNA was isolated from the transformants according to Example 4. The insert was confirmed by DNA sequencing. One transformant was identified as containing the insert with no PCR errors and the plasmid was designated pQM41 (FIG. 3).

Example 21: Insertion of a Non-Functional amdS Marker at the cbh2 Locus in *Trichoderma reesei* AgJg-FRT1-2B1A

*Trichoderma reesei* AgJg-FRT1-2B1A (Example 10) was transformed with 1-5 µg of Pme I-linearized pQM41 using hygromycin selection (Example 1) in order to insert the non-functional amdS fragment 1 at the cbh2 locus. Thirty-four transformants were obtained and each one was picked and transferred to a PDA plate and incubated for 7 days at 28° C. The transformants were cultured in 2 ml of CIM at 30° C. for 3 days with agitation at 250 rpm. Supernatant from each culture was subjected to SDS-PAGE using a CRITERION® 8-16% TGX Stain-Free gel (Bio-Rad Laboratories, Inc.) and PRECISION PLUS® Protein Unstained Standards (Bio-Rad Laboratories, Inc.). Since successful targeted integration of pQM41 at the cbh2 locus effectively disrupts the cbh2 gene, SDS-PAGE gels were visually analyzed for loss of the CBH2 protein from the proteome. One strain designated *T. reesei* QMJi056-8, which produced no CBH2 protein, was identified and selected for genomic DNA extraction and Southern blot analysis to confirm the integration of the non-functional amdS fragment 1 at the *T. reesei* cbh2 locus. Genomic DNA was isolated from *T. reesei* QMJi056-8 according to Example 2.

Plasmid pQM41 contains the *Herpes simplex* virus thymidine kinase (tk) gene and the *E. coli* hygromycin phosphotransferase (hpt/hygR) selection marker flanked by direct repeats. The direct repeats were inserted to facilitate the curing out of the tk and hpt selection markers. Spores from *T. reesei* QMJi056-8 were plated onto *Trichoderma* minimal media plates containing 1 µM 5-fluoro-2'-deoxyuridine (FdU) and incubated at 28° C. for 5-7 days. Four Fdu-resistant isolates were sub-cultured onto PDA plates and incubated at 28° C. for 5-7 days. Genomic DNA of those isolates were prepared as described in Example 2 and used for Southern blot analysis to confirm the absence of the hpt and tk markers.

A digoxigenin-labeled *T. reesei* cbh2 probe hybridizing to the 3' flanking region of the cbh2 locus was synthesized by PCR using a PCR DIG Probe Synthesis Kit and the primers shown below.

```
Primer 069773:
                                    (SEQ ID NO: 115)
5'-CAACCAAAATTTCTGTTTATAGATC-3'

Primer 069774:
                                    (SEQ ID NO: 116)
5'-GATGATATAATGGAGCAAATAAGGG-3'
```

The DIG Probe Synthesis PCR was composed of approximately 10 ng of pQM22 (WO 2013/028912) as template, 1 µM primers, 5 µl of PCR DIG Synthesis Mix, 1×PCR buffer with $MgCl_2$, and 0.75 µl of Enzyme Mix in a final volume of 50 µl. The reaction was performed in a thermocycler programmed for 1 cycle at 95° C. for 2 minutes; 10 cycles each at 95° C. for 30 seconds, 60° C. for 30 seconds, and 72°

C. for 40 seconds; 20 cycles each at 95° C. for 30 seconds, 60° C. for 30 seconds, and 72° C. for 40 seconds plus an additional 20 seconds for each successive cycle; and 1 cycle at 72° C. for 7 minutes. The PCR product was separated by 1% agarose gel electrophoresis in TAE buffer where the fragment was excised from the gel and extracted using a Nucleospin® Extract II Kit (Example 8).

The correct integration at the cbh2 locus was confirmed by Southern blot analysis as described in Example 3 using the *T. reesei* cbh2 probe. Integration of the non-functional amdS fragment 1 with the tk/hpt marker at the cbh2 locus generated a hybridization signal at approximately 7.3 kb in Nhe I and Psi I digest. Successful removal of the tk/hpt marker at the cbh2 locus generated a hybridization signal at approximately 2.7 kb in the Bam HI digestion.

Two µg of genomic DNA of the Fdu-resistant isolates were digested with and submitted to Southern blot analysis according to Example 3 using the *T. reesei* cbh2 probe. Isolates that result in a hybridized signal at recognized by the *T. reesei* cbh2 probe, indicating the successful removal of the tk/hpt marker at the cbh2 locus. Southern blot analysis confirmed the correct integration at the cbh2 locus.

Example 22: Construction of Plasmid pJfyS145

An empty expression vector was constructed containing the cbh2 promoter and amdS marker. The amdS marker was PCR amplified from pMJ09 (U.S. Pat. No. 7,361,495) using the primers shown below.

```
Forward primer:
                                    (SEQ ID NO: 117)
5'-ATAACAACTCCGAGTGGATCCTGGAAACGCAACCCTGA

AGGGATTCTTCCTT-3'

Reverse primer:
                                    (SEQ ID NO: 118)
5'-TGTTTAAACTCTAGGATGCATTCTACGCCAGGACCGA

GCAAGCCCA-3'
```

The PCR was composed of 20 ng of pMJ09 DNA, 200 µM dNTPs, 0.4 µM primers, 1× HERCULASE® Reaction Buffer, and 2.5 units of HERCULASE® High Fidelity DNA polymerase (Stratagene Corp.) in a final volume of 50 µl. The reaction was performed in a thermocycler programmed for 1 cycle at 95° C. for 2 minutes; 30 cycles each at 95° C. for 30 seconds, 60° C. for 30 seconds, and 72° C. for 3 minutes; and 1 cycle at 72° C. for 7 minutes. The completed PCR was submitted to 1% agarose gel electrophoresis in TAE buffer where a 2.7 kb band was excised from the gel and agarose was extracted using a MINELUTE® Gel Extraction Kit (Example 4).

The amdS PCR fragment was inserted into Bam HI/Not I digested pJfyS142-B (WO 2013/028928) using an IN-FUSION® Advantage PCR Cloning Kit. The reaction was composed of 150 ng of Bam HI/Not I digested pJfyS142-B, 100 ng of the amdS PCR fragment, 1× IN-FUSION® Advantage Reaction Buffer, and 1 µl of IN-FUSION® Enzyme in a 10 µl reaction volume. The reaction was incubated at 37° C. for 15 minutes and then at 50° C. for 15 minutes. Then 40 µl of TE were added to the reaction and 2 µl were transformed into ONE SHOT® TOP10 *E. coli* chemically competent cells according to Example 4. Plasmid DNA was isolated from the transformants according to Example 4. The insert was confirmed by DNA sequencing. One transformant was identified as containing the insert with no PCR errors and the plasmid was designated pJfyS143.

The *A. fumigatus* cbh2 coding sequence was amplified from pAlLo33 (US20110111453 A1) using the primers shown below.

```
Forward primer:
                                    (SEQ ID NO: 119)
5'-CTCTGTGTATTGCACCATGAAGCACCTTGCATCTTCCATCG-3'

Reverse primer:
                                    (SEQ ID NO: 120)
5'-CTCTGTGTATTGCACCATGAAGCACCTTGCATCTTCCATCG-3'
```

The PCR was composed of 20 ng of pAlLo33 (US20110111453), 200 µM dNTPs, 0.4 µM primers, 1×HERCULASE® Reaction Buffer, and 2.5 units of HERCULASE® High Fidelity DNA polymerase in a final volume of 50 µl. The reaction was performed in a thermocycler programmed for 1 cycle at 95° C. for 2 minutes; 30 cycles each at 95° C. for 30 seconds, 58° C. for 30 seconds, and 72° C. for 2 minutes; and 1 cycle at 72° C. for 7 minutes. The completed PCR was subjected to 1% agarose gel electrophoresis in TAE buffer where a 2.7 kb band was excised from the gel and agarose was extracted using a MINELUTE® Gel Extraction Kit (Example 4).

Figure 4:
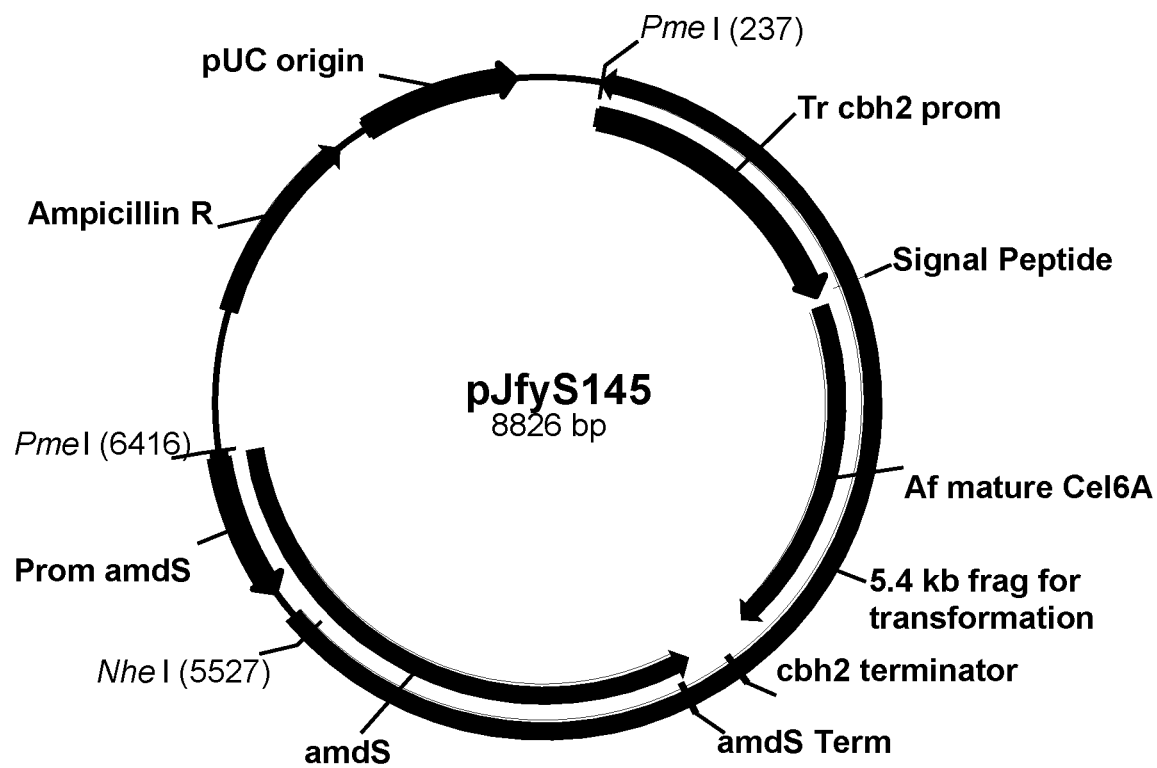
FIG. 4 shows a restriction map of plasmid pJfyS145.

The *A. fumigatus* cbh2 PCR fragment was inserted into Nco I/Pac I-digested pJfyS143 (described above) using an IN-FUSION® Advantage PCR Cloning Kit. The reaction was composed of 112 ng of Nco I/Pac I-digested pJfyS143, 75 ng of the *A. fumigatus* cbh2 PCR, 1× IN-FUSION® Advantage Reaction Buffer, and 1 µl of IN-FUSION® Enzyme in a 10 µl reaction volume. The reaction was incubated at 37° C. for 15 minutes and then at 50° C. for 15 minutes. Then 40 µl of TE were added to the reaction and 2 µl were transformed into ONE SHOT® TOP10 *E. coli* chemically competent according to Example 4. Plasmid DNA was isolated from the transformants according to Example 4. The insert was confirmed by DNA sequencing. One transformant was identified as containing the insert with no PCR errors and the plasmid was designated pJfyS145 (FIG. 4).

Example 23: Multiple Site Specific Integrations at *Trichoderma reesei* cbh1 and cbh2 Loci with pJfyS156 and pJfyS145 Using FLP/FRT System and Split-Marker Technology Plasmid pJfyS145 (Example 22) was digested with Pme I and Nhe I and purified by 0.7% agarose gel electrophoresis in TAE buffer where an approximately 5.3 kb fragment was excised from the gel and extracted using a Nucleospin® Extract II Kit (Example 8). The purified 5.3 kb fragment was used as template in PCRs with the primers shown below to obtain enough DNA for transformation.

```
Primer 068422:
                                    (SEQ ID NO: 121)
5'-ACGAATTGTTTAAACGTCGACCCAAGTATCCAGA

GGTGTATGGAAATATCAGAT-3'

Primer 1201305:
                                    (SEQ ID NO: 122)
5'-GTGCGTCAGGCTTTCGCCACGGATCCTTTCAGA

GGCCGAACTGAAG-3'
```

Each PCR was composed of 10 ng of pJfyS145, 1 μl of 10 mM dNTPs, 1 μM primers, 1×PHUSION® High-Fidelity Reaction Buffer, and 1 unit of PHUSION® Hot Start High-Fidelity DNA Polymerase in a final volume of 50 μl. Forty-eight PCRs were performed in a thermocycler programmed for 1 cycle at 98° C. for 2 minutes; 35 cycles each at 98° C. for 15 seconds, 60° C. for 30 seconds, and 72° C. for 3 minutes, and 1 cycle at 72° C. for 10 minutes. All of the completed PCRs were combined and purified using a Nucleospin® Extract II Kit (Example 8). The resulting purified PCR fragment (approximately 5.3 kb) contains an *Aspergillus fumigatus* CBH2 expression cassette and a non-functional amdS fragment 2.

*T. reesei* strain QMJi056-8 (Example 22) was transformed with pJfyS156 (Example 8) and the 5.3 kb pJfyS145 derived fragment according to the procedure described in Example 1 except that protoplasts of *T. reesei* QMJi056-8 were re-suspended in STC solution supplemented with 2% lactose. Approximately 13 μg of pJfyS156 and approximately 4 μg of the 5.3 kb pJfyS145 derived fragment containing the *Aspergillus fumigatus* CBH2 expression cassette and the non-functional amdS fragment 2 were added to 100 μl of the protoplast solution and mixed gently. PEG buffer+2% beta-lactose (250 μl) was added, and the reaction was mixed and incubated at 34° C. for 30 minutes. STC+2% beta-lactose (3 ml) was then added and the reaction was mixed and spread onto two COVE plates and incubated at 30° C. for 7-14 days. Two transformation reactions were prepared and plated. Thirty transformants were obtained and each one was picked and transferred to a COVE2 plate supplemented with 10 mM uridine and incubated for 7 days at 30° C. The transformants were cultured in 25 ml of CIM and incubated at 28° C. for 4 days with agitation at 200 rpm. Supernatant from each culture was subjected to SDS-PAGE using a CRITERION® 8-16% TGX Stain-Free gel and PRECISION PLUS® Protein Unstained Standards. Three transformants producing both *A. fumigatus* CBH2 and *A. fumigatus* CEL3A beta-glucosidase were selected for spore isolation according to Example 16. Eight spore isolates from each transformant were picked and transferred to COVE2 plates supplemented with 10 mM uridine and incubated for 7 days at 30° C. Spore isolates were cultured in 2 ml of CIM and incubated at 30° C. for 3 days with agitation at 250 rpm. Supernatant from each culture was subjected to SDS-PAGE as described in Example 22. Genomic DNA from isolates producing both *A. fumigatus* CBH2 and *A. fumigatus* CEL3A beta-glucosidase were prepared for Southern blot analysis to evaluate the integration sites. Southern blot analysis results confirmed correct integrations at both the cbh1 locus and the cbh2 locus.

Example 24: Identification of *Trichoderma reesei* adeB Gene

A BLAST search, using the *Aspergillus oryzae* phosphoribosylaminoimidazole carboxylase (AdeB) protein sequence (GenBank Accession Number AB121756) against the *Trichoderma reesei* genome database (Version 2.0) maintained by the Joint Genome Institute was performed. A DNA fragment (on scaffold 6: 149561-151463) was identified that, when translated, was found to share 74% amino acid sequence identity with *Aspergillus oryzae* AdeB.

Example 25: Construction of adeB Deletion Vector pSMai199

The 3' adeB flanking region was amplified from *T. reesei* RutC30 genomic DNA using the primers shown below. Underlined letters represent an added Sbf I site to facilitate the cloning of the amplified fragment.

```
Forward primer:
                                  (SEQ ID NO: 123)
5'-AAAAAACCTGCAGGGGGAGTCTTGATCTGACGCTGC-3'

Reverse primer:
                                  (SEQ ID NO: 124)
5'-AAAAAACCTGCAGGCGGCCGCATATCGAACGGTAGTGACTG-3'
```

The PCR was composed of 300 ng of the *T. reesei* RutC30 genomic DNA template, 300 μM dNTPs, 50 pmol of the forward primer, 50 pmol of the reverse primer, 1× Reaction buffer (Invitrogen Corp.), 1 mM MgSO$_4$, and 2.5 units of PLATINUM® Pfx DNA polymerase (Invitrogen Corp.). The reaction was performed in a thermocycler programmed for 1 cycle at 94° C. for 3 minutes; and 30 cycles each at 94° C. for 30 seconds, 54° C. for 30 seconds, and 72° C. for 1 minute. After the 30 cycles, the reaction was incubated at 72° C. for 15 minutes. The completed PCR was submitted to 1% agarose gel electrophoresis in TAE buffer where a 1035 bp band was excised from the gel and agarose was extracted using a MINELUTE® Gel Extraction Kit (Example 4).

The 1035 bp PCR product was cloned into pCR2.1® TOPO® (Invitrogen Corp.). Briefly 1 μl of the gel-purified PCR was added to 1 μl of Kit-supplied salt solution and 1 μl of pCR2.1® TOPO® in a 6 μl reaction volume and incubated at room temperature for 30 seconds. Following incubation, 2 μl were transformed into ONE SHOT® TOP10 *E. coli* chemically competent cells according to Example 4. Plasmid DNA was isolated from the transformants according to Example 4. The insert was confirmed by DNA sequencing. One transformant was identified as containing the insert with no PCR errors and the plasmid was digested with Sbf I to liberate the adeB 3' flanking region fragment. The digestion was submitted to 1% agarose gel electrophoresis where a 1.0 kb band was excised from the gel and agarose was extracted using a MINELUTE® Gel Extraction Kit (Example 4). The fragment was ligated to Sbf I-digested and CIP dephosphorylated pJfyS1579-41-11 using a QUICK LIGATION™ Kit. The ligation reaction was composed of 1× Quick Ligation buffer, 50 ng of the 3' adeB fragment, and 1 μl of Quick Ligase in a 20 μl reaction volume. The reaction was incubated at room temperature for 5 minutes and 2 μl were transformed into ONE SHOT® TOP10 *E. coli* chemically competent cells according to Example 4. Plasmid DNA was isolated from the transformants according to Example 4. The insert was confirmed by DNA sequencing. One transformant containing the insert with no PCR errors, designated pClone1, was identified and used to insert the 5' adeB flanking region.

The 5' adeB flanking region was amplified from *T. reesei* RutC30 genomic DNA using the primers shown below. Underlined letters represent an added Pme I site to the sense and antisense primers to facilitate the cloning of the amplified fragment.

```
Forward primer:
                                  (SEQ ID NO: 125)
5'-AAAAAAGTTTAAACGCGGCCGCGAGAATGCTTCCTAATGCTA-3'

Reverse primer:
                                  (SEQ ID NO: 126)
5'-AAAAAAGTTTAAACCTTGAACGTCGAGAGAGAGC-3'
```

The PCR was composed of 300 ng of the *T. reesei* RutC30 genomic DNA, 300 μM dNTPs, 50 pmol of the forward primer, 50 pmol of the reverse primer, 1× Reaction buffer (Invitrogen Corp.), 1 mM MgSO$_4$, and 2.5 units of PLATINUM® Pfx DNA polymerase. The reaction was performed in a thermocycler programmed for 1 cycle at 94° C. for 3 minutes; and 30 cycles each at 94° C. for 30 seconds, 54° C. for 30 seconds, and 72° C. for 1 minute. After the 30 cycles, the reaction was incubated at 72° C. for 15 minutes. The completed PCR was submitted to 1% agarose gel electrophoresis in TAE buffer where a 1036 bp band was excised from the gel and agarose was extracted using a MINELUTE® Gel Extraction Kit (Example 4).

The 1036 bp PCR product was cloned into pCR2.1® TOPO® as above. Briefly 1 µl of the gel-purified PCR was added to 1 µl of Kit-supplied salt solution and 1 µl of pCR2.1® TOPO® vector in a 6 µl reaction volume and incubated at room temperature for 30 seconds. Following incubation, 2 µl were transformed into ONE SHOT® TOP10 E. coli chemically competent cells according to Example 4. Plasmid DNA was isolated from the transformants according to Example 4. The insert was confirmed by DNA sequencing. One transformant was identified as containing the insert with no PCR errors and the plasmid was digested with Pme I to liberate the adeB 5' flanking fragment. The digestion was submitted to 1% agarose gel electrophoresis where a 1.0 kb band was excised from the gel and agarose was extracted using a MINELUTE® Gel Extraction Kit (Example 4).

The 1.0 kb fragment was ligated to Pme I digested and CIP dephosphorylated pClone1 using a QUICK LIGATION™ Kit. The ligation reaction was composed of 1× Quick Ligation buffer, 50 ng of the adeB 5' flanking fragment, 100 ng of Pme I digested and CIP dephosphorylated pClone 1, and 1 µl of Quick Ligase in a 20 µl reaction volume. The reaction was incubated at room temperature for 5 minutes and 2 µl were transformed into ONE SHOT® TOP10 E. coli chemically competent cells according to Example 4. Plasmid DNA was isolated from the transformants according to Example 4. The insert was confirmed by DNA sequencing. One transformant was identified as containing the insert with no PCR errors and the plasmid was designated pSMai199. Plasmid pSMai199 was used to delete the *T. reesei* adeB gene in *T. reesei* RutC30.

Example 26: Deletion of the adeB Gene in Trichoderma reesei Strain RutC30

Protoplast preparation and transformation of *Trichoderma reesei* strain RutC30 with Not I-linearized pSMai199 were performed as described in Example 1.

One hundred and fifty transformants were each transferred with a sterile 10 µl inoculation loop to an individual well of a 12-well plate containing PDA medium supplemented with 25 µg of hygromycin B per ml and 0.01% adenine and incubated at 28° C. for 3 days. A small amount of mycelia was scraped from each well using a sterile 1 µl inoculation loop and spotted to unsupplemented TrMM medium in a 12-well plate to identify adenine auxotrophs. Two transformants displayed adenine auxotrophy.

Genomic DNA was isolated from the two transformants according to Example 2 and analyzed by Southern blot analysis as described in Example 3 except that in each case 2 µg of genomic DNA were digested with Eco RI and Xho I. The digested DNA was subjected to 0.7% agarose gel electrophoresis in TAE buffer and transferred to a NYTRAN® SuperCharge membrane according to Example 3. A probe hybridizing to the 5' flanking region of the adeB gene was generated using a PCR DIG Probe Synthesis Kit and the primers shown below.

```
Forward primer:
                            (SEQ ID NO: 127)
5'-CCACACTACAGATGCTGTCG-3'

Reverse primer:
                            (SEQ ID NO: 128)
5'-TCCATGACTCGCAAGATACG-3'
```

The PCR was composed of 1×HERCULASE® Reaction Buffer, 400 nM each primer, 200 µM DIG-labeled dUTP-containing dNTPs, 50 ng of pSMai199 DNA, and 1.5 units of HERCULASE® DNA polymerase. The reaction was performed in a thermocycler programmed for 1 cycle at 94° C. for 3 minutes; 30 cycles each at 94° C. for 30 seconds, 52° C. for 30 seconds, and 72° C. for 30 seconds; and 1 cycle at 72° C. for 5 minutes.

The digoxigenin-labeled *T. reesei* adeB DNA probe was purified by 1% agarose gel electrophoresis in TAE buffer where a 408 bp band corresponding to the probe was excised from the gel and agarose extracted using a MINELUTE® Gel Extraction Kit (Example 4).

The Southern blot analysis indicated that one auxotroph, designated *T. reesei* SMai199-19-3, contained the deletion cassette at a single copy at the adeB locus.

Example 27: Construction of an Expression Plasmid pSMai205

Plasmid pJfyS117 (Example 31) was digested with Spe I and Bam HI and subjected to 1% agarose gel electrophoresis in TAE buffer where a 2753 bp band was excised from the gel and agarose was extracted using a MINELUTE® Gel Extraction Kit (Example 4). The 2753 bp band was then ligated into Spe I and Bam HI digested pEJG107 (WO 05/047499) using a QUICK LIGATION™ Kit. Plasmid pEJG107 contains the *Aspergillus nidulans* amdS gene and the *Aspergillus fumigatus* beta-glucosidase gene under transcriptional control of the *Trichoderma reesei* cellobiohydrolase cel7a gene promoter. The ligation reaction was composed of 1×QUICK LIGATION™ buffer, 50 ng of digested pEJG107, 56 ng of the 2753 bp fragment, and 1 µl of QUICK Ligase in a 20 µl reaction volume. The reaction was incubated at room temperature for 5 minutes and 2 µl were transformed into ONE SHOT® TOP10 E. coli chemically competent cells according to Example 4. Plasmid DNA was isolated from the transformants according to Example 4. The insert was confirmed by DNA sequencing. One transformant was identified as containing the insert with no PCR errors and the plasmid was designated pSMai205.

Example 28: Construction of Trichoderma reesei adeB Based Expression Plasmid pSMai206 and Utilization of adeB as a Selectable Marker The full-length *Trichoderma reesei* adeB gene, including approximately 600 bp of the native promoter, was amplified by PCR from *T. reesei* RutC30 genomic DNA using a PLATINUM® Pfx DNA Polymerase Kit (Invitrogen Corp.) and the primers shown below. Underlined letters represent an added Nsi I site to facilitate cloning of the amplified fragment.

```
Forward primer:
                            (SEQ ID NO: 129)
5'-CCAATGCATAGTCTGAACAGCGATAACAA-3'

Reverse primer:
                            (SEQ ID NO: 130)
5'-CCAATGCATAGGCATTAAGTGGGTTGTAT-3'
```

The PCR was composed of 270 ng of *T. reesei* RutC30 genomic DNA, 300 µM dNTPs, 50 pmol of the forward primer, 50 pmol of the reverse primer, 1× Reaction buffer (Invitrogen Corp.), 1 mM MgSO₄, and 2.5 units of PLATINUM® Pfx DNA polymerase. The reaction was performed in a thermocycler programmed for 1 cycle at 98° C. for 3 minutes; and 30 cycles each at 98° C. for 30 seconds, 58° C. for 30 seconds, and 72° C. for 3 minutes. After the 30 cycles, the reaction was incubated at 72° C. for 15 minutes. The completed PCR was subjected to 1% agarose gel electrophoresis in TAE buffer where a 2877 bp band was excised from the gel and agarose was extracted using a MINELUTE® Gel Extraction Kit (Example 4). The fragment was inserted into pCR2.1® TOPO® using a TOPO® TA Cloning® Kit. Briefly 1 µl of the gel-purified PCR product was added to 1 µl of Kit-supplied salt solution and 1 µl of pCR2.1® TOPO® in a 6 µl reaction volume and incubated at room temperature for 30 seconds. Following incubation 2 µl were transformed into ONE SHOT® TOP10 *E. coli* chemically competent cells according to Example 4. Plasmid DNA was isolated from the transformants according to Example 4. The insert was confirmed by DNA sequencing. One transformant was identified as containing the insert with no PCR errors and the plasmid was digested with Nsi I to liberate the adeB fragment from the plasmid. The digestion was submitted to 1% agarose gel electrophoresis in TAE buffer where a 2877 bp band was excised from the gel and agarose was extracted using a MINELUTE® Gel Extraction Kit (Example 4).

Plasmid pSMai205 (Example 27) was also digested with Nsi I to remove the *Aspergillus nidulans* amdS gene from the plasmid, and subsequently treated with calf intestine phosphatase (CIP) (New England Biolabs, Inc.) to dephosphorylate the ends. The digestion was submitted to 1% agarose gel electrophoresis in TAE buffer where a 7521 bp band was excised from the gel and agarose was extracted using a MINELUTE® Gel Extraction Kit (Example 4).

The 2877 bp Nsi I digested adeB fragment was ligated to the Nsi I-digested and CIP-treated pSMai205 using a QUICK LIGATION™ Kit. The ligation reaction was composed of 1× Quick Ligation buffer, 50 ng of the digested pSMai205, 58 ng of the 2877 bp adeB fragment, and 1 µl of Quick Ligase in a 20 µl reaction volume. The reaction was incubated at room temperature for 5 minutes and 2 µl were transformed into ONE SHOT® TOP10 *E. coli* chemically competent cells according to Example 4. Plasmid DNA was isolated from the transformants according to Example 4. The insert was confirmed by DNA sequencing. One transformant was identified as containing the insert with no PCR errors and the plasmid was designated pSMai206.

Protoplasts of *T. reesei* SMai199-19-3 were prepared as described in Example 1 and transformed with Pme I-linearized pSMai206. The resulting purified DNA was added to 100 µl of the protoplast solution and mixed gently followed by PEG buffer (250 µl) and mixed. The transformation reaction was incubated at 34° C. for 30 minutes. STC (3 ml) was then added and mixed, and then the transformation reaction was spread onto 150 mm TrMM plates supplemented with 1 M sucrose. The transformation plates were incubated for 8 days at 28° C. and 45 transformants were transferred with a sterile 10 µl inoculation loop to a 100 mm PDA plate and grown for 7 days at 28° C. Each transformant was analyzed in a small scale cultivation by transferring a small amount of spores with a sterile 10 µl inoculation loop into 25 ml of CIM in a 125 ml polycarbonate shake flask and incubating at 28° C. for 5 days with agitation at 200 rpm. Supernatant from each culture was subjected to SDS-PAGE using a CRITERION® 8-16% SDS-PAGE gel and PRECISION PLUS® Protein Standards. Since the expression plasmid contained the *Aspergillus fumigatus* beta-glucosidase coding sequence as a reporter the presence of a band at approximately 150 kDa in many of the transformants indicated successful integration of the expression plasmid and utilization of adeB as a selectable marker.

Example 29: Construction of hemA Deletion Vector pJfyS120

The 3' flanking region of the *T. reesei* 5-aminolevulinic acid synthase (hemA) gene was amplified from *T. reesei* RutC30 genomic DNA using the primers shown below.

```
Forward primer:
                                         (SEQ ID NO: 131)
5'-TATAGCGTACCTGCAGGTGTCATGCCCGCGGCTTTGCCTTGA-3'

Reverse primer:
                                         (SEQ ID NO: 132)
5'-ATGCTGTACCTGCAGGCGGCCGCCGCTCCCGATCATCATCCCT

CCGAG-3'
```

The PCR was composed of 150 ng of *T. reesei* RutC30 genomic DNA, 200 µM dNTPs, 0.4 µM primers, 1×HERCULASE® Reaction Buffer, and 2.5 units of HERCULASE® High Fidelity DNA polymerase in a final volume of 50 µl. The reaction was performed in a thermocycler programmed for 1 cycle at 95° C. for 2 minutes; 30 cycles each at 95° C. for 30 seconds, 60° C. for 30 seconds, and 72° C. for 1 minute and 45 seconds; and 1 cycle at 72° C. for 7 minutes. The completed PCR was submitted to 1% agarose gel electrophoresis in TAE buffer where a 1.5 kb band was excised from the gel and agarose was extracted using a MINELUTE® Gel Extraction Kit (Example 4). The hemA 3' flanking region PCR fragment was inserted into pCR2.1® TOPO® using a TOPO® TA Cloning® Kit. Briefly 1 µl of the gel-purified PCR fragment was added to 1 µl of Kit-supplied salt solution and 1 µl of pCR2.1® TOPO® in a 6 µl reaction volume and incubated at room temperature for 30 seconds. Following incubation 2 µl were transformed into ONE SHOT® TOP10 *E. coli* chemically competent cells according to Example 4. Plasmid DNA was isolated from the transformants according to Example 4. The insert was confirmed by DNA sequencing. One transformant was identified as containing the insert with no PCR errors. The plasmid was digested with Sbf I to liberate the hemA 3' flanking region fragment. The digestion was submitted to 1% agarose gel electrophoresis in TAE buffer where a 1.5 kb band was excised from the gel and agarose was extracted using a MINELUTE® Gel Extraction Kit (Example 4).

The fragment was ligated to Sbf I-digested pJfyS1579-41-11 using a QUICK LIGATION™ Kit. The ligation reaction was composed of 1× Quick Ligation buffer, 50 ng of the 3' hemA fragment, 50 ng of Sbf I-digested pJfyS1579-41-11 and 1 µl of Quick Ligase in a 20 µl reaction volume. The reaction was incubated at room temperature for 5 minutes and 2 µl were transformed into ONE SHOT® TOP10 *E. coli* chemically competent cells according to Example 4. Plasmid DNA was isolated from the transformants according to Example 4. The insert was confirmed by DNA sequencing. One transformant was identified as containing the insert with no PCR errors and the plasmid was designated pJfyS120A.

The 5' hemA flanking region sequence was amplified from *T. reesei* RutC30 genomic DNA using the primers shown below.

```
Forward primer:
                                       (SEQ ID NO: 133)
5'-CATGGTTTAAACGGCGGCGCGCCGCGGCCGCAATTCAGAGCATCA

CGGTTGAGGGA-3'

Reverse primer:
                                       (SEQ ID NO: 134)
5'-CCTTGTTTTGTCGGGCGCGCCACATGGCCTTGGATTGACGCAGGA

C-3'
```

The PCR was composed of 150 ng of *T. reesei* RutC30 genomic DNA, 200 µM dNTPs, 0.4 µM primers, 1×HERCULASE® Reaction Buffer, and 2.5 units of HERCULASE® High Fidelity DNA polymerase in a final volume of 50 µl. The reaction was performed in a thermocycler programmed for 1 cycle at 95° C. for 2 minutes; 30 cycles each at 95° C. for 30 seconds, 60° C. for 30 seconds, and 72° C. for 1 minute and 45 seconds; and 1 cycle at 72° C. for 7 minutes. The completed PCR was submitted to 1% agarose gel electrophoresis in TAE buffer where a 1.0 kb band was excised from the gel and agarose was extracted using a MINELUTE® Gel Extraction Kit (Example 4). The PCR fragment was digested with Asc I after and purified by agarose gel electrophoresis as described above.

The hemA 5' flanking region fragment digested with Asc I was ligated to Asc I-digested pJfyS120A using a QUICK LIGATION™ Kit. The ligation reaction was composed of 50 ng of the Asc I-digested pJfyS120A, 1× Quick Ligation buffer, 50 ng of the Asc I-digested 5' hemA fragment, and 1 µl of Quick Ligase in a 20 µl reaction volume. The reaction was incubated at room temperature for 5 minutes and 2 µl were transformed into ONE SHOT® TOP10 *E. coli* chemically competent cells according to Example 4. Plasmid DNA was isolated from the transformants according to Example 4. The insert was confirmed by DNA sequencing. One transformant was identified as containing the insert with no PCR errors and the plasmid was designated pJfyS120. Plasmid pJfyS120 was used to delete the *T. reesei* hemA gene in *T. reesei* RutC30.

Example 30: Deletion of the hemA Gene in *Trichoderma reesei* Strains RutC30

Protoplasts of *T. reesei* RutC30 were prepared as described in Example 1 and transformed with Not I-linearized pJfyS120 (Example 29). The resulting purified DNA was added to 100 µl of the protoplast solution and mixed gently followed by PEG buffer (250 µl) and mixed. The transformation reaction was incubated at 34° C. for 30 minutes. STC (3 ml) was then added and mixed, and then the transformation reaction was spread onto PDA plates supplemented with 1 M sucrose and 5 mM 5-aminolevulinic acid (ALA) (Sigma-Aldrich Chemical Co.). After incubation at 28° C. for 16 hours, 15 ml of overlay PDA medium supplemented with 100 µg of hygromycin B per ml and 5 mM 5-aminolevulinic acid were added to each plate. The plates were incubated at 28° C. for 12 days. Eighty-eight transformants were each transferred with a sterile 10 µl inoculation loop to individual wells of a 12-well plate containing PDA medium supplemented with 25 µg of hygromycin B per ml and 2.5 mM ALA and incubated at 28° C. for 3 days. A small amount of mycelia was scraped from the plate using a sterile 1 µl inoculation loop and spotted onto un-supplemented TrMM in a 12-well plate to identify ALA auxotrophs. Three strains displayed ALA auxotrophy.

Genomic DNA was isolated from the three auxotrophic strains according to Example 2 and analyzed by Southern blot analysis as described in Example 3 except that in each case 2 µg of genomic DNA was digested with 33 units of Nco I. The digested DNA was subjected to 1% agarose gel electrophoresis in TAE buffer and transferred to a NYTRAN® SuperCharge membrane as described in Example 3. A probe hybridizing to the 3' flanking region of the hemA gene was generated using a PCR DIG Probe Synthesis Kit and the primers shown below.

```
Forward primer:
                                       (SEQ ID NO: 135)
5'-GACGCATACAATACAAGCATATGCTGTTGGTGTCT-3'

Reverse primer:
                                       (SEQ ID NO: 136)
5'-AAGGCGTCTGGAAACAGAAGCTGCT-3'
```

The PCR was composed of 1×HERCULASE® Reaction Buffer, 400 nM of each primer, 200 µM DIG-labeled dUTP-containing dNTPs, 150 ng of *T. reesei* RutC30 genomic DNA, and 1.5 units of HERCULASE® DNA polymerase. The reaction was performed in a thermocycler programmed for 1 cycle at 95° C. for 2 minutes; 25 cycles each at 95° C. for 30 seconds, 58° C. for 30 seconds, and 72° C. for 40 seconds; and 1 cycle at 72° C. for 7 minutes.

The probe was purified by 1% agarose gel electrophoresis in TAE buffer where a band corresponding to the probe was excised from the gel and agarose extracted using a MINELUTE® Gel Extraction Kit (Example 4).

The Southern blot analysis indicated that all three auxotrophs contained the deletion cassette as a single copy at the hemA locus. One strain designated *T. reesei* JfyS2010-52-65 was arbitrarily chosen for rescue of auxotrophy with a hemA-based expression plasmid.

Example 31: Construction of hemA-Based Expression Plasmid pJfyS126 and Utilization of hemA as a Selectable Marker To facilitate selectable marker excision from expression plasmid pMJ09 (U.S. Pat. No. 8,318,458) an additional Nsi I site present in the cbh1 terminator was removed using a QUICKCHANGE® II XL Site-Directed Mutagenesis according to Example 6 and the primers shown below.

```
Forward primer:
                                       (SEQ ID NO: 137)
5'-CGATTCCTTAGTAGCCATGCACTTTAAGATAACGGAATAGAAG-3'

Reverse primer:
                                       (SEQ ID NO: 138)
5'-CTTCTATTCCGTTATCTTAAAGTGCATGGCTACTAAGGAATCG-3'
```

Plasmid DNA was isolated from the *E. coli* transformants according to Example 4. The insert was confirmed by DNA sequencing. One transformant was identified as containing the insert with no PCR errors and the fragment was liberated from the plasmid using a Pac I/Asc I digestion. pMJ09 was also digested with Pac I/Asc I and both digestions were submitted to 1% agarose gel electrophoresis in TAE buffer where a 6.7 kb band corresponding to the pMJ09 backbone and a 0.4 kb band corresponding to the mutated region of pMJ09 were excised from the gel and agarose was extracted using a MINELUTE® Gel Extraction Kit (Example 4).

The two fragments were ligated using a QUICK LIGATION™ Kit. The ligation reaction was composed of 1×QUICK LIGATION™ buffer, 50 ng of the digested pMJ09, 20 ng of the mutated fragment, and 1 μl of Quick Ligase in a 20 μl reaction volume. The reaction was incubated at room temperature for 5 minutes and 2 μl were transformed into ONE SHOT® TOP10 *E. coli* chemically competent cells according to Example 4. Plasmid DNA was isolated from the transformants according to Example 4. The insert was confirmed by DNA sequencing. One transformant was identified as containing the insert with no PCR errors and the plasmid was designated pJfyS117. Plasmid pJfyS117 was used to insert the *A. fumigatus* beta-glucosidase gene.

The hemA marker was then inserted into pSMai205 (Example 27). A fragment containing the hemA marker was PCR amplified from *T. reesei* RutC30 genomic DNA using a GC Genomic LA Polymerase Kit (Clontech Laboratories, Inc.) and the primers shown below.

```
Forward primer:
                                  (SEQ ID NO: 139)
5'-TATCACTGTCATTCAATGCATTCTTTGTGTGTGTGTCAGCATTGTA-
3'

Reverse primer:
                                  (SEQ ID NO: 140)
5'-TATCACTGTCATTCAATGCATTCTTTGTGTGTGTGTCAGCATTGTA-
3'
```

The PCR was composed of GC LA Reaction Buffer (Clontech Laboratories, Inc.), 1× GC Melt (Clontech Laboratories, Inc.), 400 nM of each primer, 200 μM dNTPs, 150 ng of *T. reesei* RutC30 genomic DNA, and 1.5 units of Advantage GC LA DNA polymerase (Clontech Laboratories, Inc.). The reaction was performed in a thermocycler programmed for 1 cycle at 95° C. for 2 minute; 16 cycles each at 95° C. for 30 seconds, 60° C. for 30 seconds, and 72° C. for 3 minutes; and 1 cycle at 72° C. for 7 minutes. The completed PCR was subjected to 1% agarose gel electrophoresis in TAE buffer where a 3 kb band was excised from the gel and agarose was extracted using a MINELUTE® Gel Extraction Kit (Example 4).

The 3 kb fragment was inserted into pCR2.1® TOPO® using a TOPO® TA Cloning® Kit. Briefly 1 μl of the gel-purified PCR product was added to 1 μl of Kit-supplied salt solution and 1 μl of pCR2.1® TOPO® in a 6 μl reaction volume and incubated at room temperature for 30 seconds. Following incubation 2 μl were transformed into ONE SHOT® TOP10 *E. coli* chemically competent cells according to Example 4. Plasmid DNA was isolated from the transformants according to Example 4. The insert was confirmed by DNA sequencing. One transformant was identified as containing the insert with no PCR errors and the plasmid was digested with Eco RI to liberate the hemA fragment from the plasmid. The digestion was then treated with Klenow DNA Polymerase to fill in the overhangs generated during digestion after which the digestion was submitted to 1% agarose gel electrophoresis in TAE buffer where a 3.0 kb band was excised from the gel and agarose was extracted using a MINELUTE® Gel Extraction Kit (Example 4).

Plasmid pSMai205 (Example 27) was also digested with Nsi I to liberate the amdS region from the plasmid, and subsequently treated with calf intestine phosphatase (CIP) (to dephosphorylate the ends. The digestion was submitted to 1% agarose gel electrophoresis in TAE buffer where a 7.5 kb band was excised from the gel and agarose was extracted using a MINELUTE® Gel Extraction Kit (Example 4). The Eco RI/Klenow-treated hemA fragment was ligated to the Nsi I-digested/Klenow/CIP-treated pSMai205 using a QUICK LIGATION™ Kit. The ligation reaction was composed of 1× Quick Ligation buffer, 50 ng of the hemA fragment, 50 ng of digested pSMai205, and 1 μl of Quick Ligase in a 20 μl reaction volume. The reaction was incubated at room temperature for 5 minutes and 2 μl transformed into ONE SHOT® TOP10 *E. coli* chemically competent cells according to Example 4. Plasmid DNA was isolated from the transformants according to Example 4. The insert was confirmed by DNA sequencing. One transformant was identified as containing the insert with no PCR errors and the plasmid was designated pJfyS126.

*T. reesei* strain JfyS2010-52-65 protoplasts were prepared and transformed with the Pme I-linearized pJfyS126 as described in Example 1. The transformation reaction was spread onto 150 mm PDA plates supplemented with 1 M sucrose. The transformation plates were incubated for 7 days at 28° C. and transformants were transferred with a sterile 10 μl inoculation loop to a 100 mm PDA plate and grown for 7 days at 28° C. Transformants were each analyzed in small scale cultivations by transferring a small amount of spores with a sterile 10 μl inoculation loop into 25 ml of CIM in 125 ml polycarbonate shake flasks and incubating at 28° C. for 5 days with agitation at 200 rpm. Supernatant from each culture was subjected to SDS-PAGE using a CRITERION® 8-16% SDS-PAGE gel and PRECISION PLUS® Protein Standards. Since the expression plasmid contained the *Aspergillus fumigatus* beta-glucosidase gene as a reporter the presence of a band at approximately 150 kDa in many of the transformants indicated successful integration of the expression plasmid and utilization of hemA as a selectable marker.

Example 32: Construction of an *Aspergillus fumigatus* Beta-Glucosidase Variant Expression Vector Targeted to the *Trichoderma reesei* cbh1 Locus Plasmid pAgJg123 was constructed to comprise an *Aspergillus fumigatus* beta-glucosidase variant under transcriptional control of the *Trichoderma reesei* cellobiohydrolase I gene promoter and terminator, with flanking sequence to target to the *T. reesei* cbh1 locus. Two synthetic oligonucleotide primers shown below were designed to amplify by PCR the 3' flanking region of the *T. reesei* cbh1 promoter from plasmid pJfyS139 (WO 2013/028928) and introduce flanking regions for insertion into expression vector pDFng133-3 (WO 2013/028912), which contains the *T. reesei* cbh1 promoter and *A. fumigatus* beta-glucosidase variant gene. Bold letters represent sequence of the 3' cbh1 flanking region and the remaining sequence is homologous to insertion sites of pDFng133-3.

```
Forward Primer (Primer 0613337):
                                  (SEQ ID NO: 141)
5'-TCTGCCCCGTGTCTAGTGGCGAAAGCCTGACGCACCGGTAGATT-
3'

Reverse Primer (Primer 0613338):
                                  (SEQ ID NO: 142)
5'-CACGGAGCTTACTAGACGGCACGGTTAAGCAGGGTCTTGC-3'
```

The PCR was composed of 0.5 µl of plasmid pJfyS139, 10 µl of 10 mM dNTPs, 50 pmol of the forward primer, 50 pmol of the reverse primer, 1×PHUSION® GC Buffer, and 2 units of PHUSION® Hot Start DNA polymerase in a final volume of 50 µl. The reaction was performed in a thermocycler programmed for 1 cycle at 98° C. for 30 seconds; 35 cycles each at 98° C. for 10 seconds, 60° C. for 10 seconds, and 72° C. for 1 minute; and 1 cycle at 72° C. for 10 minutes. The PCR products were separated by 1% agarose gel electrophoresis in TAE buffer where a 1.3 kb fragment was excised from the gel and agarose was extracted using a MINELUTE® Gel Extraction Kit (Example 4).

The 1.3 kb fragment was then cloned into pDFng133-3 digested with Spe I using an IN-FUSION™ HD Cloning Kit. The digested vector was isolated by 1% agarose gel electrophoresis in TAE buffer where a 10.2 kb fragment was excised from the gel and agarose was extracted using a MINELUTE® Gel Extraction Kit (Example 4). The 1.3 kb 3' flanking region fragment and the digested vector were ligated together in a reaction resulting in the expression plasmid pAgJg123, in which the *A. fumigatus* beta-glucosidase variant could be targeted to the *T. reesei* cbh1 locus, under transcriptional control of the *T. reesei* cbh1 promoter and terminator. The ligation reaction was composed of 1× IN-FUSION™ HD enzyme mix, 98.9 ng of pDFnf133-3 digested with Spe I, and 100.1 ng of the *T. reesei* 3' cbh1 flanking PCR product in a 20 µl reaction. The reaction was incubated at 50° C. for 15 minutes. Then 2.5 µl of the reaction were transformed into XL-1 Blue Subcloning cells (Agilent Technologies). Plasmid DNA was isolated using a Mini-prep Kit (QIAGEN Inc.). The insert was confirmed by DNA sequencing. The resulting plasmid was designated pAgJg123.

Example 33: Targeting the *Aspergillus fumigatus* Beta-Glucosidase Variant Gene into the cbh1 Locus of *Trichoderma reesei* Strain AgJg115-104-7B1

Protoplast preparation and transformation of *T. reesei* AgJg115-104-7B1 was performed as described in Example 1.

Plasmid pAgJg123 (240 µg; Example 32) was digested with Pme I and purified by 1% agarose gel electrophoresis in TAE buffer where a 8.8 kb band was excised from the gel and agarose was extracted using a MINELUTE® Gel Extraction Kit (Example 4). Approximately 3.785 µg of the resulting purified DNA fragment was added to 100 µl of the protoplast solution and spread onto COVE plates as described in Example 1. The plates were incubated at 28° C. for 7-10 days. Transformants were sub-cultured onto COVE2+10 mM uridine plates to generate spores.

The transformants of *T. reesei* strain AgJg115-104-7B1 were screened by Fungal Spore PCR according to Example 9 for the presence of the pAgJg123 replacement vector in the cbh1 locus, thereby deleting the coding sequence of cbh1 and replacing it with an *A. fumigatus* beta-glucosidase variant gene. The Spore PCR was composed of 0.5 µl of spore suspension, 50 pmol of primer 069079, 50 pmol of primer 0614037, 10 µl of 2×PHIRE® Plant PCR Buffer, and 0.4 µl of PHIRE® Hot Start II DNA Polymerase in a 20 µl reaction. The reaction was performed in a thermocycler programmed for 1 cycle at 98° C. for 5 minutes; 40 cycles each at 98° C. for 5 seconds, 68° C. for 5 seconds, and 72° C. for 30 seconds; 1 cycle at 72° C. for 2 minutes; and a 10° C. hold. Primer 069079 is located upstream of the 5' flanking region and primer 0614037 is located at the beginning of the *A. fumigatus* beta-glucosidase variant gene. If the replacement vector integrates into the cbh1 locus, the amplified PCR fragment will be 1.4 kb in length.

```
Primer 069079 (forward):
                                   (SEQ ID NO: 143)
5'-CAAGCAAAGCGTTCCGTCGCAGTAGCAGGC-3'

Primer 0614037 (reverse):
                                   (SEQ ID NO: 144)
5'-GCATCACAAACCTGGGCATTGGCTACAGAA-3'
```

For Southern blot analysis, 2 µg of each genomic DNA were digested with 10 units of Nco I and 20 units of Xba I in a 35 µl reaction volume. The digested DNA was subjected to 0.7% agarose gel electrophoresis in TAE buffer and transferred to a NYTRAN® SuperCharge membrane according to Example 3.

The membrane was hybridized with a 500 bp digoxigenin-labeled *A. fumigatus* beta-glucosidase gene probe, which was synthesized by incorporation of digoxigenin-11-dUTP by PCR using primers 1201134 and 1201135 shown below.

```
Primer 1201134 (forward):
                                   (SEQ ID NO: 145)
5'-ATGAGATTCGGTTGGCTCGAG-3'

Primer 1201135 (reverse):
                                   (SEQ ID NO: 146)
5'-AAAGACTCCGCGGGTATAGCTC-3'
```

The PCR was composed of 5 µl of 10× Taq Buffer, 2.5 µl of PCR DIG Labeling Mix, 20 ng of pAgJg123, 50 pmol of primer 1201134, 50 pmol of primer 1201135, 2.5 µl of 10 mM dNTPs, and 5 units of Taq DNA polymerase in a 50 µl reaction. The reaction was performed in a thermocycler programmed for 1 cycle at 95° C. for 2 minutes; 30 cycles each at 95° C. for 30 seconds, 55° C. for 30 seconds, and 72° C. for 40 seconds; 1 cycle at 72° C. for 15 minutes; and a 10° C. hold. The probe was purified by 1% agarose gel electrophoresis in TAE buffer, excised from the gel, and extracted using a QIAQUICK® Gel Extraction Kit.

Southern blot analysis identified several transformants having the cbh1 coding sequence replaced with a single copy of the coding sequence of the *A. fumigatus* beta-glucosidase variant. One such transformant was designated *T. reesei* AgJg123.

Example 34: Construction of an *Aspergillus fumigatus* Beta-Glucosidase Variant Expression Vector Targeted to a *Trichoderma reesei* Protease Locus Plasmid pAgJg124 was constructed to comprise an *Aspergillus fumigatus* beta-glucosidase variant under transcriptional control of the *Trichoderma reesei* cellobiohydrolase I gene promoter and terminator, with flanking sequence to target a locus encoding a *T. reesei* protease (JGI Protein ID: 70962), a locus that receives a moderate amount of translation signal as found via mRNA analysis. Two synthetic oligonucleotide primers shown below were designed to amplify by PCR the 5' flanking region of the *T. reesei* protease from genomic DNA and introduce flanking regions for insertion into expression vector pMJ05 (U.S. Pat. No. 8,497,115). Bold letters represent sequence of the 5' protease flanking region and the remaining sequence is homologous to insertion sites of pMJ05.

2

Forward Primer (Primer 0613544):
(SEQ ID NO: 147)
5'-CGAATTGTTTAAACGGGCTCCTATGTTCAATCATGGCACA-3'

Reverse Primer (Primer 0613545):
(SEQ ID NO: 148)
5'-CCTACATTCGGTCGACTTGACGATTCAGTGTCTTCTCTTG-3'

The PCR was composed of 118 ng of *T. reesei* genomic DNA, 10 µl of 10 mM dNTPs, 50 pmol of primer 0613544, 50 pmol of primer 0613545, 1×PHUSION® GC Buffer, and 2 units of PHUSION® Hot Start DNA polymerase in a final volume of 50 µl. The reaction was performed in a thermocycler programmed for 1 cycle at 98° C. for 30 seconds; 30 cycles each at 98° C. for 10 seconds, 55° C. for 30 seconds, and 72° C. for 1 minute; and 1 cycle at 72° C. for 10 minutes. The PCR products were separated by 1% agarose gel electrophoresis in TAE buffer where a 1.5 kb fragment was excised from the gel and agarose was extracted using a MINELUTE® Gel Extraction Kit (Example 4).

The 1.5 kb fragment was then cloned into pMJ05 using an IN-FUSION™ HD Cloning Kit. Plasmid pMJ05 was digested with Sal I and isolated by 1% agarose gel electrophoresis in TAE buffer where a 7.9 kb fragment was excised from the gel and agarose was extracted using a MIN-ELUTE® Gel Extraction Kit (Example 4). The 1.5 kb 5' flanking region fragment and the digested vector were ligated together in a reaction resulting in expression plasmid pAgJg124A, in which the 5' flanking region of the *T. reesei* protease gene was cloned upstream of the *T. reesei* cbh1 promoter in pMJ05. The ligation reaction was composed of 1× IN-FUSION™ HD enzyme mix, 100 ng of pMJ05 digested with Sal I, and 150 ng of the *T. reesei* 5' protease flanking region fragment in a 10 µl reaction. The reaction was incubated at 50° C. for 15 minutes. Then 2.5 µl of the reaction were transformed into SoloPack® Gold Supercompetent cells (Stratagene). One aliquot of SoloPack® cells were thawed on ice. Then 2.5 µl of the reaction were added to the competent cells in a tube and incubated on ice for an additional 30 minutes. The tube was incubated at 42° C. for 30 seconds and immediately placed on ice for 2 minutes after which 250 µl of SOC medium were added. The tube was then incubated at 37° C. with agitation at 200 rpm for 1 hour and transferred to 150 mm 2XYT plus ampicillin plates. The plates were incubated at 37° C. overnight. Plasmid DNA was isolated using a Mini-prep Kit (QIAGEN Inc.). The insert was confirmed by DNA sequencing where the resulting plasmid was designated pAgJg124A.

To amplify the 3' flanking region of the *T. reesei* protease, two synthetic oligonucleotide primers shown below were designed for insertion into expression vector pAgJg124A. Bold letters represent sequence of the 3' protease flanking region and the remaining sequence is homologous to insertion sites of pAgJg124A.

Forward Primer (Primer 0613546):
(SEQ ID NO: 149)
5'-AAACGATTCCTTAATAAAACAATGCTTGGACTCCGAAAGT-3'

Reverse Primer (Primer 0613547):
(SEQ ID NO: 150)
5'-CAGTCACCTCTAGTTATGCAATTAAACAAATGCCCACCTAG-3'

The PCR was composed of 118 ng of *T. reesei* genomic DNA, 10 µl of 10 mM dNTPs, 50 pmol of primer 0613546, 50 pmol of primer 0613547, 1×PHUSION® GC Buffer, and 2 units of PHUSION® Hot Start DNA polymerase in a final volume of 50 µl. The reaction was performed in a thermocycler programmed for 1 cycle at 98° C. for 30 seconds; 30 cycles each at 98° C. for 10 seconds, 55° C. for 30 seconds, and 72° C. for 1 minute; and 1 cycle at 72° C. for 10 minutes. The PCR products were separated by 1% agarose gel electrophoresis in TAE buffer where a 1.5 kb fragment was excised from the gel and agarose was extracted using a MINELUTE® Gel Extraction Kit (Example 4).

The 1.5 kb fragment was then cloned into pAgJg124A using an IN-FUSION™ HD Cloning Kit. The vector was digested with Pac I in a reaction consisting of 40 units of Pac I and isolated by 1% agarose gel electrophoresis in TAE buffer where a 9.4 kb fragment was excised from the gel and agarose was extracted using a QIAQUICK® Gel Extraction Kit (Example 9). The 1.5 kb 3' flanking region fragment and the digested vector were ligated together in a reaction resulting in the expression plasmid pAgJg124B, in which the 3' flanking region of the *T. reesei* protease was cloned downstream of the *T. reesei* cbh1 terminator in pAgJg124A. The ligation reaction was composed of 1× IN-FUSION™ HD enzyme mix, 100 ng of pAgJg124A digested with Pac I, and 150 ng of the *T. reesei* 3' protease flanking region fragment in a 20 µl reaction. The reaction was incubated at 50° C. for 15 minutes. Then 2.5 µl of the reaction were transformed into SoloPack® Gold Supercompetent cells as described above. Plasmid DNA was isolated using a Mini-prep Kit (QIAGEN Inc.). The insert was confirmed by DNA sequencing. The resulting plasmid was designated pAgJg124B.

Finally, two synthetic oligonucleotide primers shown below were designed to amplify a portion of the *T. reesei* cbh1 promoter and the entire coding sequence of the *A. fumigatus* beta-glucosidase variant for insertion into expression vector pAgJg124B. Bold letters represent sequence of the *T. reesei* cbh1 promoter and *A. fumigatus* beta-glucosidase fragment, while the remaining sequence is homologous to insertion sites of pAgJg124B.

Forward Primer (Primer 0613727):
(SEQ ID NO: 151)
5'-CTAAGATCTCGGGCCCCTCGGGCCTTCGGCCTTTGGGTGTACATGT-3'

Reverse Primer (Primer 0613728):
(SEQ ID NO: 152)
5'-GCTACTAGTACGCGTCTAGTAGACACGGGGCAGAGGCGCT-3'

The PCR was composed of 200 ng of pDFng133-3 DNA, 10 µl of 10 mM dNTPs, 50 pmol of primer 0613727, 50 pmol of primer 0613728, 1×PHUSION® GC Buffer, and 2 units of PHUSION® Hot Start DNA polymerase in a final volume of 50 µl. The reaction was performed in a thermocycler programmed for 1 cycle at 98° C. for 30 seconds; 30 cycles each at 98° C. for 10 seconds, 60° C. for 30 seconds, and 72° C. for 2 minutes; and 1 cycle at 72° C. for 7 minutes. The PCR products were separated by 1% agarose gel electrophoresis in TAE buffer where a 3.5 kb fragment was excised from the gel and agarose was extracted using a MINELUTE® Gel Extraction Kit (Example 4).

The 3.5 kb fragment was then cloned into pAgJg124B using an IN-FUSION™ HD Cloning Kit. The vector was digested with Apa I and Nu I and isolated by 1% agarose gel electrophoresis in TAE buffer where a 10.9 kb fragment was excised from the gel and agarose was extracted using a MINELUTE® Gel Extraction Kit (Example 4). The 3.5 kb *T. reesei* cbh1 promoter and *A. fumigatus* beta-glucosidase variant fragment and the digested vector were ligated together in a reaction resulting in the expression plasmid pAgJg124, in which the *A. fumigatus* beta-glucosidase variant, under transcriptional control by the *T. reesei* cbh1 promoter and terminator, has 5' and 3' flanking regions for targeting to the *T. reesei* protease locus. The ligation reaction was composed of 1× IN-FUSION™ HD enzyme mix, 100 ng of pAgJg124B digested with Apa I and Nru I, and 150 ng of the *T. reesei* cbh1 promoter and *A. fumigatus* beta-glucosidase variant fragment in a 20 µl reaction. The reaction was incubated at 50° C. for 15 minutes. Then 2.5 µl of the reaction were transformed into SoloPack® Gold Supercompetent cells as described above. Plasmid DNA was isolated using a Mini-prep Kit (QIAGEN Inc.). The insert was confirmed by DNA sequencing. The resulting plasmid was designated pAgJg124.

Example 35: Targeting the *Aspergillus fumigatus* Beta-Glucosidase Variant Gene into a Protease Locus of *Trichoderma reesei* Strain AgJg115-104-7B1

Protoplast preparation and transformation of *Trichoderma reesei* AgJg115-104-7B1 were performed as described in Example 1.

Plasmid pAgJg124 (66 µg; Example 34) was digested with Pme I and purified by 1% agarose gel electrophoresis in TAE buffer where a 10.3 kb band was excised from the gel, and agarose was extracted using a MINELUTE® Gel Extraction Kit (Example 4). Approximately 2.5 µg of the resulting purified DNA fragment were added to 100 µl of the protoplast solution as described in Example 1. The transformation reaction was spread onto COVE plates. The plates were incubated at 28° C. for 7-10 days. The transformants were sub-cultured onto COVE2+10 mM uridine plates to generate spores.

The transformants of *T. reesei* strain AgJg115-104-7B1 were screened by Fungal Spore PCR according to Example 9 for the presence of the pAgJg124 replacement vector at the *T. reesei* protease locus, thereby deleting the coding sequence of the protease and replacing it with the *A. fumigatus* beta-glucosidase variant gene. The Spore PCRs were composed of 0.5 µl of each spore suspension, 50 pmol of primer 0614119, 50 pmol of primer 0614037, 10 µl of 2×PHIRE® Plant PCR Buffer, and 0.4 µl of PHIRE® Hot Start II DNA Polymerase in a 20 µl reaction. The reactions were performed in a thermocycler programmed for 1 cycle at 98° C. for 5 minutes; 40 cycles each at 98° C. for 5 seconds, 65° C. for 5 seconds, and 72° C. for 50 seconds; 1 cycle at 72° C. for 1 minute; and a 10° C. hold. Primer 0614119 is located upstream of the 5' flanking region and primer 0614037 is located at the beginning of the *A. fumigatus* beta-glucosidase variant gene. If the replacement vector integrates into the protease locus, the amplified PCR fragment will be 2.7 kb in length.

```
Primer 0614119 (forward):
                                     (SEQ ID NO: 153)
5'-CTGAGGAAAGGCAGTCTTCACATTC-3'

Primer 0614037 (reverse):
                                     (SEQ ID NO: 154)
5'-GCATCACAAACCTGGGCATTGGCTACAGAA-3'
```

For Southern blot analysis, 2 µg of each genomic DNA were digested with 10 units of Nru I and 20 units of Bam HI in a 35 µl reaction volume. The digested DNA was subjected to 0.7% agarose gel electrophoresis in TAE buffer and transferred to a NYTRAN® SuperCharge membrane according to Example 3. The membrane was hybridized with a 500 bp digoxigenin-labeled *A. fumigatus* beta-glucosidase probe (Example 33).

The Southern blot analysis identified several transformants containing a single copy of the *A. fumigatus* beta-glucosidase variant coding sequence at the *T. reesei* protease locus. One such transformant was designated *T. reesei* AgJg124.

Example 36: Construction of an *Aspergillus fumigatus* Beta-Glucosidase Variant Expression Vector Targeted to a *Trichoderma reesei* Homolog of Dihydroflavonal-4-Reductase Locus Plasmid pAgJg125 was constructed to comprise an *Aspergillus fumigatus* beta-glucosidase variant coding sequence under transcriptional control of the *Trichoderma reesei* cellobiohydrolase I gene promoter and terminator, with flanking sequence to target to a locus encoding a *T. reesei* homolog of dihydroflavonal-4-reductase (DHR) (JGI Protein ID: 111716), a locus that receives no translation signal as found via mRNA analysis. Two synthetic oligonucleotide primers shown below were designed to amplify by PCR the 5' flanking region of the *T. reesei* DHR gene from genomic DNA and introduce flanking regions for insertion into expression vector pMJ05 (U.S. Pat. No. 8,497,115). Bold letters represent sequence of the 5' DHR flanking region and the remaining sequence is homologous to insertion sites of pMJ05.

```
Forward Primer (Primer 0613552):
                                     (SEQ ID NO: 155)
5'-CGAATTGTTTAAACGAAGTCTGCTTCCTTGCAATTATGCA-3'

Reverse Primer (Primer 0613553):
                                     (SEQ ID NO: 156)
5'-CCTACATTCGGTCGAAACGAGAAGTTCTCAACTAAGGGCT-3'
```

The PCR was composed of 118 ng of *T. reesei* genomic DNA, 10 µl of 10 mM dNTPs, 50 pmol of primer 0613552, 50 pmol of primer 0613553, 1×PHUSION® GC Buffer, and 2 units of PHUSION® Hot Start DNA polymerase in a final volume of 50 µl. The reaction was performed in a thermocycler programmed for 1 cycle at 98° C. for 30 seconds; 30 cycles each at 98° C. for 10 seconds, 55° C. for 30 seconds, and 72° C. for 1 minute; and 1 cycle at 72° C. for 10 minutes. The PCR products were separated by 1% agarose gel electrophoresis in TAE buffer where a 1.5 kb fragment was excised from the gel and agarose was extracted using a MINELUTE® Gel Extraction Kit (Example 4).

The 1.5 kb fragment was then cloned into pMJ05 using an IN-FUSION™ HD Cloning Kit. The vector was digested with Sal I and isolated by 1% agarose gel electrophoresis in TAE buffer where a 7.9 kb fragment was excised from the gel and agarose was extracted using a MINELUTE® Gel Extraction Kit (Example 4). The 1.5 kb 5' flanking region fragment and the digested vector were ligated together in a reaction resulting in expression plasmid pAgJg125A, in which the 5' flanking region of the *T. reesei* DHR gene was cloned upstream of the *T. reesei* cbh1 promoter in pMJ05. The ligation reaction was composed of 1× IN-FUSION™ HD enzyme mix, 100 ng of pMJ05 digested with Sal I, and 150 ng of the *T. reesei* 5' DHR flanking region fragment in a 10 µl reaction. The reaction was incubated at 50° C. for 15 minutes. Then 2.5 µl of the reaction were transformed into SoloPack® Gold Supercompetent cells as described in Example 34. Plasmid DNA was isolated using a Mini-prep Kit (QIAGEN Inc.). The insert was confirmed by DNA sequencing. The resulting plasmid was designated pAgJg125A.

To amplify the 3' flanking region of the *T. reesei* DHR gene, two synthetic oligonucleotide primers shown below were designed for insertion into expression vector pAgJg125A. Bold letters represent sequence of the 3' DHR flanking region and the remaining sequence is homologous to insertion sites of pAgJg125A.

Forward Primer (Primer 0613554):
(SEQ ID NO: 157)
5'-AAACGATTCCTTAATGTTATCTGTACGCTCTGATGAGAAG-3'

Reverse Primer (Primer 0613555):
(SEQ ID NO: 158)
5'-CAGTCACCTCTAGTTAGGACAGCTGGCCTAGAGCGCTCAGCAGACT CCTTT-3'

The PCR was composed of 118 ng of *T. reesei* genomic DNA, 10 μl of 10 mM dNTPs, 50 pmol of primer 0613554, 50 pmol of primer 0613555, 1×PHUSION® GC Buffer, and 2 units of PHUSION® Hot Start DNA polymerase in a final volume of 50 μl. The reaction was performed in a thermocycler programmed for 1 cycle at 98° C. for 30 seconds; 30 cycles each at 98° C. for 10 seconds, 55° C. for 30 seconds, and 72° C. for 1 minute; and 1 cycle at 72° C. for 10 minutes. The PCR products were separated by 1% agarose gel electrophoresis in TAE buffer where a 1.5 kb fragment was excised from the gel and agarose was extracted using a MINELUTE® Gel Extraction Kit (Example 4).

The 1.5 kb fragment was then cloned into pAgJg125A using an IN-FUSION™ HD Cloning Kit. The vector was digested with Pac I and isolated by 1% agarose gel electrophoresis in TAE buffer where a 9.4 kb fragment was excised from the gel and agarose was extracted using a MINELUTE® Gel Extraction Kit (Example 4). The 1.5 kb 3' flanking region fragment and the digested vector were ligated together in a reaction resulting in expression plasmid pAgJg125B, in which the 3' flanking region of the *T. reesei* DHR gene was cloned downstream of the *T. reesei* cbh1 terminator in pAgJg125A. The ligation reaction was composed of 1× IN-FUSION™ HD enzyme mix, 100 ng of pAgJg125A digested with Pac I, and 150 ng of the *T. reesei* 3' DHR flanking region fragment in a 20 μl reaction. The reaction was incubated at 50° C. for 15 minutes. A 2.5 μl volume of the cloning reaction was transformed into SoloPack® Gold Supercompetent cells as described in Example 34. Plasmid DNA was isolated using a Mini-prep Kit (QIAGEN Inc.). The insert was confirmed by DNA sequencing. The resulting plasmid was designated pAgJg125B.

Finally, two synthetic oligonucleotide primers shown below were designed to amplify a portion of the *T. reesei* cbh1 promoter and the entire coding sequence of the *A. fumigatus* beta-glucosidase variant for insertion into expression vector pAgJg125B. Bold letters represent sequence of the *T. reesei* cbh1 promoter and *A. fumigatus* beta-glucosidase variant fragment, while the remaining sequence is homologous to insertion sites of pAgJg125B.

Forward Primer (Primer 0613727):
(SEQ ID NO: 159)
5'-CTAAGATCTCGGGCCCTCGGGCCTTCGGCCTTTGGGTGTACATGT-3'

Reverse Primer (Primer 0613728):
(SEQ ID NO: 160)
5'-GCTACTAGTACGCGTCTAGTAGACACGGGGCAGAGGCGCT-3'

The PCR was composed of 200 ng of pDFng133-3 DNA, 10 μl of 10 mM dNTPs, 50 pmol of primer 0613727, 50 pmol of primer 0613728, 1×PHUSION® GC Buffer, and 2 units of PHUSION® Hot Start DNA polymerase in a final volume of 50 μl. The reaction was performed in a thermocycler programmed for 1 cycle at 98° C. for 30 seconds; 30 cycles each at 98° C. for 10 seconds, 60° C. for 30 seconds, and 72° C. for 2 minutes; and 1 cycle at 72° C. for 7 minutes. The PCR products were separated by 1% agarose gel electrophoresis in TAE buffer where a 3.5 kb fragment was excised from the gel and agarose was extracted using a MINELUTE® Gel Extraction Kit (Example 9).

The 3.5 kb fragment was then cloned into pAgJg125B using an IN-FUSION™ HD Cloning Kit. The vector was digested with Apa I and Nu I and isolated by 1% agarose gel electrophoresis in TAE buffer where a 10.9 kb fragment was excised from the gel and agarose was extracted using a MINELUTE® Gel Extraction Kit (Example 4). The 3.5 kb *T. reesei* cbh1 promoter and *A. fumigatus* beta-glucosidase variant fragment and the digested vector were ligated together in a reaction resulting in the expression plasmid pAgJg125, in which the *A. fumigatus* beta-glucosidase variant coding sequence, under transcriptional control of the *T. reesei* cbh1 promoter and terminator, has 5' and 3' flanking regions for targeting to the *T. reesei* DHR gene locus. The ligation reaction was composed of 1× IN-FUSION™ HD enzyme mix, 100 ng of pAgJg125B digested with Apa I and Nu I, and 150 ng of the *T. reesei* cbh1 promoter and *A. fumigatus* beta-glucosidase variant fragment in a 20 μl reaction. The reaction was incubated at 50° C. for 15 minutes. Then 2.5 μl of the reaction were transformed into SoloPack® Gold Supercompetent cells as described in Example 34. Plasmid DNA was isolated using a Mini-prep Kit (QIAGEN Inc.). The insert was confirmed by DNA sequencing. The resulting plasmid was designated pAgJg125.

Example 37: Targeting the *Aspergillus fumigatus* Beta-Glucosidase Variant Gene into a *Trichoderma reesei* Homolog of Dihydroflavonal-4-Reductase Locus of *Trichoderma reesei* Strain AgJg115-104-7B1

Protoplast preparation and transformation of *Trichoderma reesei* AgJg115-104-7B1 were performed as described in Example 1.

A total of 112 μg of the transforming plasmid pAgJg125 (Example 36) was digested with Pme I and purified by 1% agarose gel electrophoresis in TAE buffer where a 10.3 kb band was excised from the gel, and agarose was extracted using a MINELUTE® Gel Extraction Kit (Example 4). Approximately 3.377 μg of the resulting purified DNA fragment were added to 100 μl of the protoplast solution according to Example 1. The transformation reaction was spread onto COVE plates. The plates were incubated at 28° C. for 7-10 days. Transformants were sub-cultured onto COVE2+10 mM uridine plates to generate spores.

The transformants of *T. reesei* strain AgJg115-104-7B1 were screened by Fungal Spore PCR according to Example 9 for the presence of the pAgJg125 replacement vector at the *T. reesei* DHR gene locus, thereby deleting the coding sequence of the DHR gene and replacing it with the *A. fumigatus* beta-glucosidase variant coding sequence. The Spore PCRs were composed of 0.5 μl of spore suspension, 50 pmol of primer 0614118, 50 pmol of primer 0614037, 10 μl of 2×PHIRE® Plant PCR Buffer, and 0.4 μl of PHIRE® Hot Start II DNA Polymerase in a 20 μl reaction. The reactions were performed in a thermocycler programmed for 1 cycle at 98° C. for 5 minutes; 40 cycles each at 98° C. for 5 seconds, 68° C. for 5 seconds, and 72° C. for 50 seconds; 1 cycle at 72° C. for 1 minute; and a 10° C. hold. Primer 0614118 is located upstream of the 5' flanking region and primer 0614037 is located at the beginning of the A. fumigatus beta-glucosidase variant gene. If the replacement vector integrates into the DHR gene locus, the amplified PCR fragment will 2.7 kb in length.

```
Primer 0614118 (forward):
                                    (SEQ ID NO: 161)
5'-ATCTCATCCCACGAGAAGGTTATGC-3'

Primer 0614037 (reverse):
                                    (SEQ ID NO: 162)
5'-GCATCACAAACCTGGGCATTGGCTACAGAA-3'
```

For Southern blot analysis, 2 µg of each genomic DNA was digested with 10 units of Nco I and 10 units of Sca I. The digested DNA was subjected to 0.7% agarose gel electrophoresis in TAE buffer and transferred to a NYTRAN® SuperCharge membrane according to Example 3. The membrane was hybridized with a 500 bp digoxigenin-labeled A. fumigatus beta-glucosidase probe (Example 32).

The Southern blot analysis identified one transformant designated T. reesei AgJg125 as containing a single copy of the A. fumigatus beta-glucosidase variant coding sequence replacing the T. reesei DHR coding sequence.

Example 38: Construction of Plasmid pAgJg133

Plasmid pAgJg133 was constructed to comprise the Trichoderma reesei endoglucanase I (EG1) gene promoter, the T. reesei cellobiohydrolase I gene (cbh1) terminator, and restriction sites to clone in a gene of interest. Two synthetic oligonucleotide primers shown below were designed to amplify by PCR the T. reesei EG1 promoter region (1 kb sequence upstream of the EG1 coding sequence) from genomic DNA and introduce flanking regions for insertion into expression vector pSMai226 (WO 2012/083081). Bold letters represent coding sequence and the remaining sequence is homologous to insertion sites of pSMai226. The reverse primer also includes a Spe I site and Pac I site for cloning in a gene of interest.

```
Forward Primer:
                                    (SEQ ID NO: 163)
5'-GTTTAAACGTCGACGCATGGAAGTGGTATGTACCATCGTGCTCTGT-
3'
Reverse Primer:
                                    (SEQ ID NO: 164)
5'-CTTTCGCCACGGAGCTTAATTAATAGTACGCGTAGATCTGCGGACTA
GTTTGGGACAACAAGAAGGAC-3'
```

The PCR was composed of 90 ng of T. reesei genomic DNA, 1 µl of 10 mM dNTPs, 50 pmol of the forward primer, 50 pmol of the reverse primer, 1×PHUSION® HF buffer, and 2 units of PHUSION® Hot Start DNA polymerase in a final volume of 50 µl. The reaction was performed in a thermocycler programmed for 1 cycle at 98° C. for 30 seconds; 30 cycles each at 98° C. for 10 seconds, 59° C. for 10 seconds, and 72° C. for 30 seconds; and 1 cycle at 72° C. for 10 minutes. The PCR products were separated by 1% agarose gel electrophoresis in TAE buffer where a 1 kb fragment was excised from the gel and agarose was extracted using a MINELUTE® Gel Extraction Kit (Example 4).

The 1 kb fragment was then cloned into pSMai226 using an IN-FUSION™ HD Cloning Kit. The vector was digested with Sph I and Spe I and isolated by 1% agarose gel electrophoresis in TAE buffer where a 6.2 kb fragment was excised from the gel and agarose was extracted using a MINELUTE® Gel Extraction Kit (Example 4). The 1 kb fragment and the digested vector were ligated together in a reaction resulting in expression plasmid pAgJg133. The ligation reaction (20 µl) was composed of 1× IN-FUSION™ HD enzyme mix, 186 ng of pSMai226 digested with Spe I and Sph I, and 190 ng of the T. reesei EG1 promoter purified PCR product. The reaction was incubated at 50° C. for 15 minutes. Four µl of the reaction were transformed into ONE SHOT® TOP10 competent cells according to Example 4. Plasmid DNA was isolated using a Mini-prep Kit (QIAGEN Inc.). The insert was confirmed by DNA sequencing. The resulting plasmid was designated pAgJg133.

Example 39: Construction of Plasmid pGMEr189

Plasmid pGMEr189 is the expression plasmid for the T. reesei codon optimized cDNA for the Talaromyces leycettanus cbh2 gene. Such cDNA for the T. leycettanus cbh2 gene was obtained by designing three 500 bp DNA fragments (G-blocks) with 5' and 3' homology with one another to facilitate the correct assembly of the gene cDNA. The sequence of the three G-blocks used are listed below and the regions highlighted in italics and in underlined characters show the regions of homology between the DNA blocks:

```
G-block 1:
                                    (SEQ ID NO: 165)
TGTAAGATCACCCTCTGTGTATTGCACCATGCGGTCTCTTCTCGCCCTTG

CACCTACTCTACTCGCGCCCGTTGTGCAGGCCCAGCAGACCATGTGGGGC

CAATGTGGCGGCCAAGGCTGGACCGGCCCGACGATCTGTGTTGCCGGCGC

AACATGTAGCACACAGAATCCCTGGTACGCTCAGTGTACCCGGCACCTA

CCGCGCCGACGACTTTGCAAACGACGACGACGACGAGCTCGAAATCGTCC

ACGACCACCAGCTCGAAGTCGTCCACTACCACAGGTGGAAGTGGCGGTGG

TACTACTACATCCACGTCAGCCACCATCACCGCGGCACCATCCGGTAACC

CTTACAGCGGCTACCAGCTGTATGTGAACCAGGAATACTCCTCCGAGGTC

TACGCGTCTGCCATTCCTTCTCTGACCGGCACTCTGGTCGCGAAGGCTAG

TGCTGCGGCTGAAGTGCCCTCATTCCTGTGGCTGGACACTGCCTCCAAGG

G-block 2:
                                    (SEQ ID NO: 166)
GAAGTGCCCTCATTCCTGTGGCTGGACACTGCCTCCAAGGTGCCCCTGAT

GGGAACCTACCTGCAGGACATCCAGGCCAAGAACGCTGCCGGCGCCAACC

CTCCTTACGCTGGTCAATTCGTGGTCTACGACTTGCCGGACCGTGACTGC

GCCGCTCTGGCCAGTAATGGCGAGTACTCAATTGCCAACAACGGTGTGGC

CAACTACAAGGCGTACATTGACTCCATCCGTGCTCTTCTGGTGCAATACT

CTAACGTTCACGTCATCCTCGTCATCGAACCCGACAGCTTGGCCAACCTG

GTGACCAACCTCAACGTCCAGAAATGCGCCAACGCCCAGAGCGCCTACCT

GGAGTGTATCAACTATGCTCTGACTCAGCTCAACCTGAAGAACGTCGCCA
```

-continued
TGTACATCGACGCAGGCCATGCGGGCTGGCTCGGATGGCCCGCCAACTTG

AGCCCCGCCGCACAACTCTT<u>CGCCTCCGTCTACCAGAATGCCAGTTCCCC</u>

G-block 3:
(SEQ ID NO: 167)
<u>CGCCTCCGTCTACCAGAATGCCAGTTCCCC</u>CGCGGCTGTTCGTGGCCTGG

CCACCAACGTCGCCAACTACAACGCCTGGTCGATCGCCACCTGCCCCTCC

TACACCCAGGGAGACCCCAACTGCGACGAGCAGAAGTACATCAACGCCCT

GGCCCCTCTTCTCCAGCAACAGGGCTGGTCATCAGTTCACTTCATCACCG

ATACCGGCCGGAATGGCGTCCAGCCCACGAAGCAAAACGCCTGGGGTGAC

TGGTGCAACGTCATCGGCACCGGCTTCGGTGTTCGCCCCACCACGAACAC

CGGCGATCCGCTCGAGGATGCCTTTGTGTGGGTCAAGCCCGGTGGAGAGA

GTGATGGCACGTCCAACTCGACTTCCCCTCGGTATGACGCCCACTGCGGA

TATAGTGATGCTCTGCAGCCTGCTCCTGAGGCAGGTACTTGGTTCGAGGC

CTACTTTGAGCAGCTTCTGACCAACGCTAACCCGTCCTTTTAATAGTTAA

The sequence highlighted in bold at the beginning of G-block 1 and at the end of G-block 2 indicates the homology with the sense PCR primer 1203972 and the antisense PCR primer 1203973 used in the G-blocks assembly reaction:

Primer 1203972 (sense):
(SEQ ID NO: 168)
5'-GCAGCTCACCTGAAGAGGCTTGTAAGATCACCCTCTGTGTATTGCAC

CAT-3'

Primer 1203973 (antisense):
(SEQ ID NO: 169)
5'-CCGGTCACGAAAGCCTTAATTAACTATTAAAAGGACGGGTTAGCGTT

GG-3'

The three G-blocks were synthetized by Integrated DNA Technologies, Inc. (Coralville, Iowa) and received as dry DNA fragments. The 500 bp G-block 1, the 500 bp G-block 2, and the 500 bp G-block 3 were assembled together by PCR using primer 1203972 (sense) and primer 1203973 (antisense), resulting in a 1469 bp fragment comprising the entire cDNA for the *T. leycettanus* cbh2 gene. The PCR (50 µl) was composed of an equimolecular ratio of all the three G-block fragments for a total amount of DNA of approximately 120 ng, 1× PHUSION® HF buffer, 50 pmol of primer 1203972, 50 pmol of primer 1203973, 200 µM each of dATP, dCTP, dGTP, and dTTP, 1.5 µl of 100% DMSO, and 1 unit of PHUSION® High Fidelity DNA polymerase. The reaction was performed in a thermocycler programmed for 1 cycle at 98° C. for 5 minutes; 35 cycles each at 98° C. for 30 seconds, 60° C. for 30 seconds, and 72° C. for 2 minutes and 30 seconds; and a final extension cycle at 72° C. for 7 minutes. The completed PCR was submitted to 0.8% agarose gel electrophoresis in TBE buffer where an approximately 1469 bp PCR product was excised from the gel and purified using a NUCLEOSPIN® Extract II Gel and PCR Clean-up Kit.

The resulting 1469 bp fragment, comprising the complete *T. leycettanus* cbh2 gene cDNA, was cloned after PCR and gel purification into plasmid pCR®4-blunt TOPO® (Life Technologies Corp.) and transformed into ONE SHOT® TOP10 *E. coli* chemically competent cells according to Example 4. Transformants were spread onto 2XYT plus ampicillin plates and incubated at 37° C. overnight. Several of the resulting transformants were screened for proper insertion of the desired fragment by sequencing analysis. One transformant containing the correct plasmid was identified and the plasmid was designated pGMEr187.

The *T. leycettanus* cbh2 cDNA was PCR cloned out of plasmid pGMEr187 using primer 1203972 (sense) and primer 1203973 (antisense). The PCR (50 µl) was composed of an equimolecular ratio of about 100 ng of plasmid pGMEr187, 1×PHUSION® HF buffer, 50 pmol of primer 1203972, 50 pmol of primer 1203973, 200 µM each of dATP, dCTP, dGTP, and dTTP, 1.5 µl of 100% DMSO, and 1 unit of PHUSION® High Fidelity DNA polymerase. The reaction was performed in a thermocycler programmed for 1 cycle at 98° C. for 5 minutes; 35 cycles each at 98° C. for 30 seconds, 60° C. for 30 seconds, and 72° C. for 50 seconds; and a final extension cycle at 72° C. for 7 minutes. The completed PCR was submitted to 0.8% agarose gel electrophoresis in TBE buffer where an approximately 1469 bp PCR product was excised from the gel and purified using a NUCLEOSPIN® Extract II Gel and PCR Clean-up Kit.

The resulting 1469 bp PCR fragment (*T. leycettanus* cbh2 cDNA) was inserted into Nco I/Pac I-linearized plasmid pJfyS142 (PCT/US2012/052143, WO2013028912 A2) using an IN-FUSION® Advantage PCR Cloning Kit. The reaction was composed of 1× IN-FUSION® Reaction Buffer, 50 ng of Nco I/Pac I-linearized pJfyS142, 100 ng of the *T. leycettanus* cbh2 cDNA fragment (1469 bp), and 1 µl of IN-FUSION® Enzyme in a 10 µl reaction volume. The reaction was incubated for 15 minutes at 50° C. Then 40 µl of TE were added to the reaction and a 2 µl aliquot of the reaction was transformed into ONE SHOT® TOP10 *E. coli* chemically competent cells according to Example 4. Transformants were spread onto 2XYT plus ampicillin plates and incubated at 37° C. overnight. Several of the resulting transformants were screened for proper insertion of the desired insert by Sac I restriction digestion. Plasmid DNA was extracted and purified using a QIAGEN® Plasmid Mini Kit. A transformant containing a plasmid yielding the desired band sizes of 4223 bp, 3912 bp, 2741 bp and 874 by was isolated and the plasmid was designated pGMEr189.

Example 40: Construction of Plasmid pECW1

Plasmid pECW1 was constructed to comprise the 5' and the 3' flanking regions of the *T. reesei* strain AgJg115-104-7B1 (WO 2011/075677) cbh1 locus to facilitate homologous recombination at the cbh1 locus.

The cbh1 locus 5' flanking region was PCR amplified from *T. reesei* strain AgJg115-104-7B1 genomic DNA using the primers shown below. Genomic DNA was prepared according to Example 2.

```
Primer 1205799 (sense):
                                                         (SEQ ID NO: 170)
      Pme I
5'-CGGTTTAAACGGGAGAGCAACAACAATCATTCTGCTGTCG-3'

Primer 1205800 (anti-sense):
                                                         (SEQ ID NO: 171)
         Pac I                      Nco I
5'-TTATTAATTAACTAGTACGCGTAGATCTGCGGCCATGGGCTTCGAACAGCCCCAGTC

GGTCAAGCAGGCA-3'
```

The sense primer added a Pme I restriction site at the 5' end of the fragment while the anti-sense primer added Pac I and Nco I restriction sites at its 3' end.

The PCR (50 µl) was composed of 100 ng of T. reesei strain AgJg115-104-7B1 genomic DNA, 1×PHUSION® HF buffer, 50 pmol of primer 1205799, 50 pmol of primer 1205800, 200 µM each of dATP, dCTP, dGTP, and dTTP, 1.5 µl of 100% DMSO, and 1 unit of PHUSION® High Fidelity DNA polymerase. The reaction was performed in a thermocycler programmed for 1 cycle at 98° C. for 5 minutes; 40 cycles each at 98° C. for 30 seconds, 58° C. for 30 seconds, and 72° C. for 3 minutes; and a final extension cycle at 72° C. for 7 minutes. The completed PCR was submitted to 0.8% agarose gel electrophoresis in TBE buffer where an approximately 1550 bp PCR product was excised from the gel and purified using a NUCLEOSPIN® Extract II Gel and PCR Clean-up Kit (Macherey-Nagel Inc.).

A second PCR fragment containing 5' homology to the PCR product above, including Pac I and the Nco I sites, was generated to amplify the cbh1 locus 3' flanking region from T. reesei AgJg115-104-7B1 genomic DNA using the following primers:

```
Primer 1205801 (sense):
                                                         (SEQ ID NO: 172)
       Nco I                     Pac I
5'-GCCCATGGCCGCAGATCTACGCGTACTAGTTAATTAATAAAGCTCCGTGGCGAAAGC

CTGACGCACCGGT-3'

Primer 1205802 (anti-sense):
                                                         (SEQ ID NO: 173)
      Pme I
5'-CGGTTTAAACGGACTTCGGTGGAGGTGTCGAGTACGAGT-3'
```

The sense primers added Nco I and a Pac I restriction sites at the 5' end of the fragment while the anti-sense primer added a Pme I restriction site at its 3' end.

The PCR (50 µl) was composed of about 100 ng of T. reesei strain AgJg115-104-7B1 genomic DNA, 1×PHUSION® HF buffer, 50 pmol of primer 1205801, 50 pmol of primer 1205802, 200 µM each of dATP, dCTP, dGTP, and dTTP, 1.5 µl of 100% DMSO, and 1 unit of PHUSION® High Fidelity DNA polymerase. The reaction was performed in a thermocycler programmed for 1 cycle at 98° C. for 5 minutes; 40 cycles each at 98° C. for 30 seconds, 58° C. for 30 seconds, and 72° C. for 3 minutes; and a final extension cycle at 72° C. for 7 minutes. The completed PCR was submitted to 0.8% agarose gel electrophoresis in TBE buffer where an approximately 1549 bp PCR product was excised from the gel and purified using a NUCLEOSPIN® Extract II Gel and PCR Clean-up Kit.

The 1550 bp and 1549 bp fragments were fused together by PCR using primer 1205799 (sense) and primer 1205802 (anti-sense), resulting in a 3049 bp fragment in which the cbh1 locus 5' and 3' flanking regions were joined together.

The PCR (50 µl) was composed of about 80 ng of each of the fragments, 1×PHUSION® HF buffer, 50 pmol of primer 1205799, 50 pmol of primer 1205802, 200 µM each of dATP, dCTP, dGTP, and dTTP, 1.5 µl of 100% DMSO, and 1 unit of PHUSION® High Fidelity DNA polymerase. The reaction was performed in a thermocycler programmed for 1 cycle at 98° C. for 3 minutes; 40 cycles each at 98° C. for 30 seconds, 60° C. for 30 seconds, and 72° C. for 3 minutes; and a final extension cycle at 72° C. for 7 minutes. The completed PCR was submitted to 0.8% agarose gel electrophoresis in TBE buffer where an approximately 3049 bp PCR product was excised from the gel and purified using a NUCLEOSPIN® Extract II Gel and PCR Clean-up Kit.

The resulting 3049 bp fragment was digested with Pme I and ligated to the 2647 bp Pme I fragment from plasmid pGMEr189 (Example 39) bearing the ampicillin resistance gene and the E. coli origin of replication. About 20 µg of plasmid pGMEr189 were digested with Pme I at 37° C. for 3 hours. One hour before the end of the digestion, 1 µl of calf intestinal alkaline phosphatase was added to the pGMEr189-Pme I digestion in order to de-phosphorylate the ends and prevent self-ligation. The resulting digestion was submitted to 0.8% agarose gel electrophoresis in TBE buffer where a 2647 bp vector fragment, containing the ampicillin resistance gene and the E. coli origin of replication, was excised from the gel and purified using a NUCLEOSPIN® Extract II Gel and PCR Clean-up Kit.

The ligation reaction was performed using a QUICK LIGATION™ Kit. The ligation reaction was composed of 2 µl of pGMEr189 vector fragment, 3 µl of the cbh1 locus 5' flanking region/3' flanking region insert fragment, 5 µl of sterile deionized water, 10 µl of 2× Quick Ligation Buffer, and 1 µl of Quick T4 Ligase. The ligation reaction was incubated for 1 hour at room temperature. A 5 µl aliquot of the ligation reaction was transformed into ONE SHOT® TOP10 E. coli chemically competent cells according to Example 4. Transformants were spread onto 2XYT plus ampicillin plates and incubated at 37° C. overnight. Several of the resulting transformants were screened for proper insertion of the desired insert by Pme I restriction digestion. Plasmid DNA was extracted and purified using a Plasmid Mini Kit (QIAGEN Inc.). A transformant containing a plasmid yielding the desired band sizes of 2647 bp and of 3047 bp was isolated and the plasmid was designated pECW1.

Plasmid pECW1 comprises the cbh1 locus 5' flanking region/3' flanking region, and restriction sites for Nco I and Pac I in the sequence spacer between the two flanking regions.

Example 41: Construction of Plasmid pSaMe-TsGH10

Plasmid pSaMe-TsGH10 was constructed to comprise the *Trichoderma reesei* cellobiohydrolase I gene promoter and terminator and the *Trichophaea saccata* GH10 xylanase coding sequence. Two synthetic oligonucleotide primers shown below were designed to PCR amplify the *Trichophaea saccata* GH10 xylanase gene from plasmid pDAu81 #5 (WO 2011/057083) and introduce flanking regions for insertion into expression vector pMJ09 (WO 2005/056772). Bold letters represent coding sequence and the remaining sequence is homologous to the insertion sites of pMJ09.

```
Forward Primer:
                                       (SEQ ID NO: 174)
5'-cggactgcgcaccatgcgtaccttctcgtctctt-3'

Reverse Primer:
                                       (SEQ ID NO: 175)
5'-tcgccacggagcttatcaagccgcaagagcagacg-3'
```

Cloning of the *Trichophaea saccata* xylanase followed the overall expression cloning protocol described below.

Fifty picomoles of each of the primers above were used in a PCR composed of 50 ng of plasmid pDAu81 #5 DNA, 1 µl of 10 mM blend of dATP, dTTP, dGTP, and dCTP, 5 µl of 10×PLATINUM® Pfx DNA Polymerase Buffer, and 1 unit of PLATINUM® Pfx DNA Polymerase in a final volume of 50 µl. The reaction was performed in a thermocycler programmed for 1 cycle at 94° C. for 2 minutes; and 30 cycles each at 94° C. for 15 seconds, 55° C. for 30 seconds, and 68° C. for 1 minute. After the 30 cycles, the reaction was incubated at 72° C. for 10 minutes and then cooled to 4° C. until further processing.

The reaction products were isolated by 1.0% agarose gel electrophoresis in TAE buffer where a 1.2 kb product band was excised from the gel and purified using a QIAQUICK® Gel Extraction Kit (Example 9).

The 1.2 kb fragment was then cloned into pMJ09 using an IN-FUSION® Advantage PCR Cloning Kit. The vector was digested with Nco I and Pac I and purified by agarose gel electrophoresis as described above. The gene fragment and the digested vector were ligated together in a reaction resulting in the expression plasmid pSaMe-TsGH10 in which transcription of the xylanase gene was under the control of the *T. reesei* cbh1 gene promoter. The ligation reaction (50 µl) was composed of 1× IN-FUSION® Reaction Buffer, 1×BSA, 1 µl of IN-FUSION® Enzyme (diluted 1:10), 100 ng of pMJ09 digested with Nco I and Pac I, and 100 ng of the *Trichophaea saccata* xylanase purified PCR product. The reaction was incubated at room temperature for 30 minutes. One µl of the reaction was used to transform *E. coli* XL10 SOLOPACK® Gold cells. An *E. coli* transformant containing pSaMe-AfGH10 was detected by restriction enzyme digestion and plasmid DNA was prepared using a BIOROBOT® 9600 (QIAGEN Inc.). DNA sequencing of the *Trichophaea saccata* xylanase gene from pSaMe-TsGH10 confirmed the correct sequence of plasmid pSaMe-TsGH10.

Example 42: Construction of Plasmid pECW2

Plasmid pECW2 was constructed from plasmid pECW1 to comprise the cbh1 locus 5' and 3' flanking regions upstream and downstream, respectively, of the *A. nidulans* amdS gene expression cassette with TP901-1 attP sites added at its 5' and 3' ends.

The TP901-1 attP site is 56 bp long and its sequence is shown below. The portions of the attP sequence in italics and underlined highlight the fragments included in the PCR primers used to add the TP901-1 attP site at each end of the amdS gene expression cassette. attP site (56 bp):

```
                                       (SEQ ID NO: 176)
TCCAACTCGCTTAATTGCGAGTTTTTATTTCGTTTATTTCAATTAAGGTA

ACTAAA
```

The amdS expression cassette was PCR amplified from plasmid pSaMe-TsGH10 using the primers shown below.

```
Primer 1205803 (sense):
                                       (SEQ ID NO: 177)
5'-CGTTTATTTCAATTAAGGTAACTAAATTCTACGCCAGGACCGAGCAA

GCCCAGATGAGAA-3'

Primer 1205804 (anti-sense):
                                       (SEQ ID NO: 178)
5'-ATAAAAACTCGCAATTAAGCGAGTTGGAATGCATCTGGAAACGCAAC

CCTGAAGGGATTC-3'
```

The sense primer added the second half of the TP901-1 attP site at the 5' end of the amdS expression cassette (underlined sequence), while the anti-sense primer added the first half of the attP site at its 3' end (sequence in italics).

The PCR (50 µl) was composed of 25 ng of pSaMe-TsGH10 DNA, 1×PHUSION® HF buffer, 50 pmol of primer 1205803, 50 pmol of primer 1205804, 200 µM each of dATP, dCTP, dGTP, and dTTP, 1.5 µl of 100% DMSO, and 1 unit of PHUSION® High Fidelity DNA polymerase. The reaction was performed in a thermocycler programmed for 1 cycle at 98° C. for 5 minutes; 40 cycles each at 98° C. for 30 seconds, 58° C. for 30 seconds, and 72° C. for 3 minutes; and a final extension cycle at 72° C. for 7 minutes. The completed PCR was submitted to 0.8% agarose gel electrophoresis in TBE buffer where an approximately 2780 bp PCR product was excised from the gel and purified using a NUCLEOSPIN® Extract II Gel and PCR Clean-up Kit.

To complete the TP901-1 attP sites at the 5' and 3' ends of the amdS expression construct a second PCR was performed using the PCR product described above as template DNA and the primers shown below.

```
Primer 1205805 (sense):
                                       (SEQ ID NO: 179)
      Nco I
5'-GCCCATGGTCCAACTCGCTTAATTGCGAGTTTTTATTTCGTTTATTT

CAATTAAGGTAACTAAATTCTACGCCAG-3'

Primer 1205806 (anti-sense):
                                       (SEQ ID NO: 180)
      Pac I
5'-CGTTAATTAATTTAGTTACCTTAATTGAAATAAACGAAATAAAAACT

CGCAATTAAGCGAGTTGGAATGCATCTG-3'
```

The sense and antisense primers completed the TP901-1 attP sites flanking the amdS expression construct and added an Nco I restriction site at the 5' end of the construct and a Pac I site at its 3' end. The bold portion of the sequence in both primers highlights the complete TP901-1 attP site.

The PCR (50 µl) was composed of 25 ng of the 2780 bp PCR product, 1×PHUSION® HF buffer, 50 pmol of primer 1205805, 50 pmol of primer 1205806, 200 µM each of dATP, dCTP, dGTP, and dTTP, 1.5 µl of 100% DMSO, and 1 unit of PHUSION® High Fidelity DNA polymerase. The reaction was performed in a thermocycler programmed for 1 cycle at 98° C. for 5 minutes; 40 cycles each at 98° C. for 30 seconds, 58° C. for 30 seconds, and 72° C. for 3 minutes; and a final extension cycle at 72° C. for 7 minutes. The completed PCR was submitted to 0.8% agarose gel electrophoresis in TBE buffer where an approximately 2856 bp PCR product was excised from the gel and purified using a NUCLEOSPIN® Extract II Gel and PCR Clean-up Kit.

The resulting 2856 bp fragment was digested with Pac I and Nco I and ligated to Pac I/Nco I digested plasmid pECW1. About 20 µg of plasmid pECW1 was double digested with Pac I and Nco I at 37° C. for 4 hours. One hour before the end of the digestion reaction, 1 µl of calf intestinal alkaline phosphatase was added to the pECW1-Pac I/Nco I digestion in order to de-phosphorylate the ends to prevent self-ligation. The resulting digestion was submitted to 0.8% agarose gel electrophoresis in TBE buffer where a 5663 bp vector fragment was excised from the gel and purified using a NUCLEOSPIN® Extract II Gel and PCR Clean-up Kit.

Figure 5:
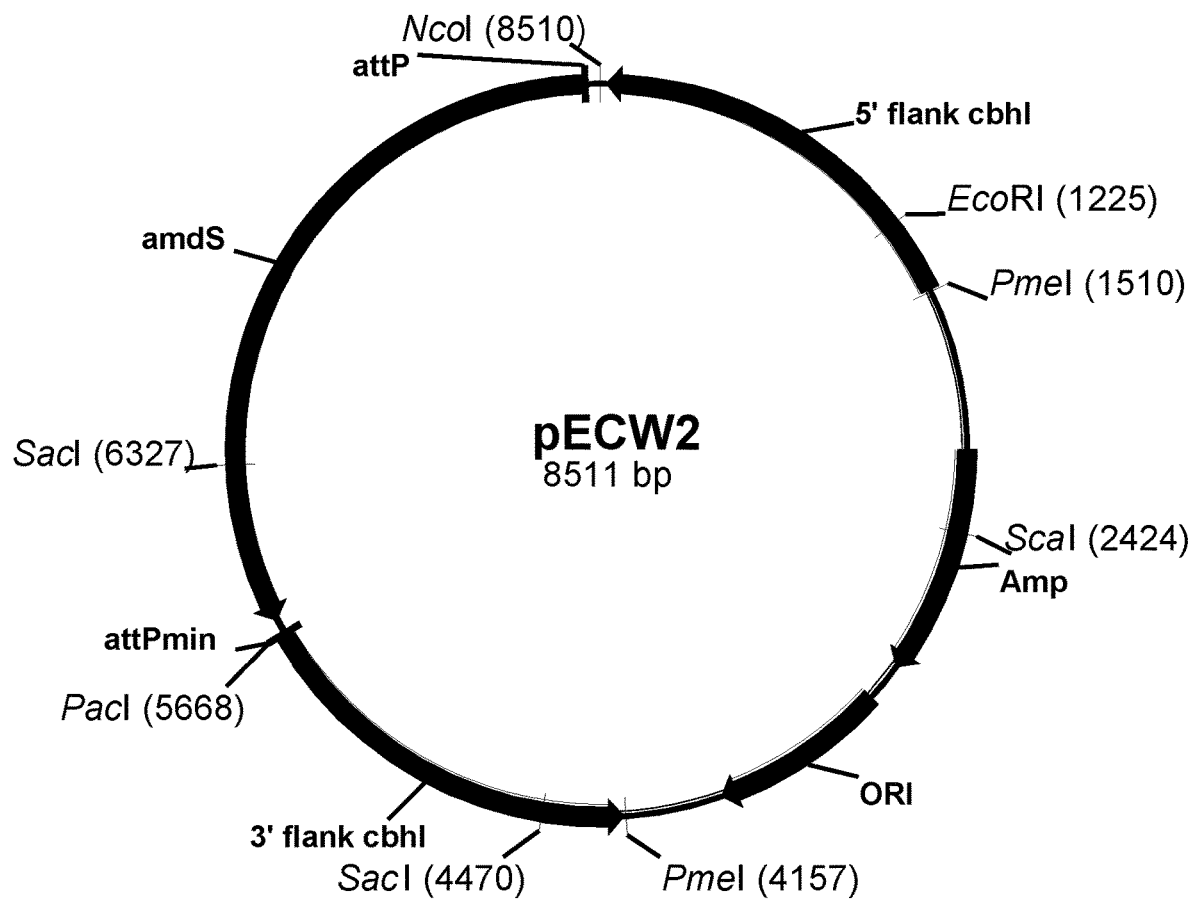
FIG. 5 shows a restriction map of plasmid pECW2.

The ligation reaction was performed using a QUICK LIGATION™ Kit. The ligation reaction was composed of 2 µl of vector fragment, 3 µl of the insert fragment, 5 µl of sterile deionized water, 10 µl of 2× Quick Ligase Buffer, and 1 µl of Quick T4 Ligase. The ligation reaction was incubated for 1 hour at room temperature. A 5 µl aliquot of the ligation reaction was transformed into ONE SHOT® TOP10 *E. coli* chemically competent cells according to Example 4. Transformants were spread onto 2XYT plus ampicillin plates and incubated at 37° C. overnight. Several of the resulting transformants were screened for proper insertion of the desired insert by Nco I and Sca I double digestion. Plasmid DNA was extracted and purified using a QIAGEN® Plasmid Mini Kit. One transformant containing a plasmid yielding restriction fragments of 2425 bp and 6086 bp was identified and the plasmid was designated pECW2 (FIG. 5).

Plasmid pECW2 comprises the amdS expression cassette flanked by the TP901-1 attP sites, the cbh1 locus 5' flanking region upstream, and the cbh1 locus 3' flanking region downstream.

Example 43: Construction of *Trichoderma reesei* Strain ECW1

When inserting the TP901-1 attP sites at the cbh1 locus in a *Trichoderma reesei* host strain, the amdS marker gene was chosen as a reporter gene to track the integration event. In plasmid pECW2, the amdS expression cassette, flanked by the attP sites, was inserted between the cbh1 locus 5' and 3' flanking regions, allowing homologous recombination at the target locus with a gene replacement.

Protoplast preparation and transformation of *T. reesei* AgJg115-104-7B1 were performed according to the protocol described in Example 1.

Approximately 100 µg of plasmid pECW2 were digested with Pme I, which excised a 5864 bp fragment comprising the cbh1 flanking regions, and the amdS selection marker flanked by the attP sites. The 5864 bp fragment was separated by 0.8% agarose gel electrophoresis in TBE buffer, excised from the gel, and purified using a NUCLEOSPIN® Extract II Gel and PCR Clean-up Kit.

Approximately 800 ng of the 5864 bp Pme I digested pECW2 fragment were added to 100 µl of the protoplast solution and mixed gently. PEG buffer (250 µl) was added, and the reaction was mixed and incubated at 34° C. for 30 minutes. STC (3 ml) was then added and mixed and then the reaction was spread onto COVE plates for amdS selection. The plates were incubated at 28° C. for 6-11 days.

Thirty primary transformants were identified and insertion of the attP-amdS-attP construct at the cbh1 locus of *T. reesei* AgJg115-104-7B1 was verified by PCR analysis of the upstream and downstream integration sites. Each putative primary transformant was patched onto COVE2 plates supplemented with 10 mM uridine and incubated at 30° C. for 2-3 days. Transformants were screened using a PHIRE® Plant Direct PCR Kit. Briefly, a small amount of spores from each transformant was resuspended in 30 µl of Dilution Buffer (provided with the Kit) and incubated at room temperature for 10 minutes. The samples were then centrifuged using a table top microcentrifuge and 1 µl of each supernatant was used in the PCRs as template DNA.

The 5' integration site was confirmed using the primers shown below.

```
Primer 1206299 (sense):
                                 (SEQ ID NO: 181)
5'-ACAGCACTCTCTCGCCCAATGATG-3'

Primer 1206000 (anti-sense):
                                 (SEQ ID NO: 182)
5'-GGGCGAACTTGACTGTCGTC-3'
```

The 3' integration site was confirmed using the primers shown below.

```
Primer 1205994 (sense):
                                 (SEQ ID NO: 183)
5'-TTCCATCTCTCAAAGGAAGA-3'

Primer 1206301 (anti-sense):
                                 (SEQ ID NO: 184)
5'-CAGTTTCAGCCCTAGAAGCGCC-3'
```

The total lengths of the resulting PCR fragments were approximately 1906 bp for the 5' integration site and 1672 bp for the 3' integration site.

The PCR (20 µl) was composed of 1 µl of genomic DNA, 1×PHIRE® Plant PCR Buffer, 0.5 µM of primer 1206299 or 1205994, 0.5 µM of primer 1206000 or 1206301, and 0.4 µl of PHIRE® Hot Start II DNA Polymerase. The reaction was performed in a thermocycler programmed for 1 cycle at 98° C. for 3 minutes; 40 cycles each at 98° C. for 30 seconds, 57° C. for 20 seconds, and 72° C. for 1 minute and 15 seconds; and a final extension cycle at 72° C. for 7 minutes. Following thermocycling, the PCR products were visualized by 0.8% agarose gel electrophoresis in TBE buffer.

Transformants showing the correct PCR products by both PCRs were chosen and grown in shake flasks by inoculating 25 ml of CIM in a 125 ml polycarbonate non-baffled shake flask with spores collected using a 10 µl inoculation loop. The flasks were incubated at 28° C. for 5 days with agitation at 200 rpm. The shake flasks were harvested by pouring samples of the cultures into 1.5 ml microcentrifuge tubes and centrifuging the samples for 10 minutes at 13,000 rpm in a SORVALL® Biofuge Pico (Kendro Laboratory Products/Thermo Scientific). Samples were analyzed by SDS-PAGE using a CRITERION® 8-16% Tris-HCl Gel and 10 µl of PRECISION PLUS™ All Blue Protein Standards (Bio-Rad Laboratories, Inc.). Gels were stained with BIO-SAFE® Coomassie Stain (Bio-Rad Laboratories, Inc.). The SDS-PAGE analysis revealed that the positively identified primary transformants had lost the CBH I band, as a consequence of replacement of the cbh1 gene with the amdS gene.

Sixteen positive transformants were spore purified by adding spores collected on a 10 μl inoculation loop to 1.5 ml of 0.01% TWEEN® 20. Spore dilutions of 1:1500 and 1:150 were spread onto 150 mm PDA plates and incubated at 28° C. for 3 days. Two spore isolates per transformant were obtained and transferred to COVE2 plates supplemented with 10 mM uridine and incubated at 30° C. for 2-3 days. Each spore isolate was analyzed again by PCR as described above to confirm the upstream and downstream sites of integration. Of the thirty-two spore isolates, seven were analyzed by Southern blotting to confirm correct integration of the attP-amdS-attP construct at the cbh1 locus with consequent replacement of the cbh1 gene. For Southern analysis genomic DNA was extracted according to Example 2.

Two μg of genomic DNA from each transformant were digested with Nhe I. The digestions were submitted to 0.7-0.8% agarose gel electrophoresis in TAE buffer and blotted onto a HYBOND® N+ blotting membrane using a TURBOBLOTTER® for approximately 1-2 hours. The membrane was hybridized with a digoxigenin-labeled probe specific for the 3' flanking region of the cbh1 locus, which was synthesized using a PCR DIG Probe Synthesis Kit.

A probe hybridizing to the 3' flanking region of the cbh1 gene was generated using a PCR DIG Probe Synthesis Kit with the forward and reverse primers shown below. The PCR (50 μl) was composed of 1× Taq DNA Polymerase Buffer, 50 pmol of each primer, 0.5×PCR DIG Probe Synthesis mix (Kit), 0.5× dNTP stock solution (Kit), 100 ng *T. reesei* RutC30 genomic DNA, and 2.5 units of Taq DNA polymerase. The PCR was incubated in a thermocycler programmed for 1 cycle at 95° C. for 2 minute; 30 cycles each at 95° C. for 30 seconds, 60° C. for 30 seconds, and 72° C. for 40 seconds; and 1 cycle at 72° C. for 15 minutes.

```
Forward primer:
                                  (SEQ ID NO: 185)
5'-AATGACCCATAGGGAGACAAACAGCATAAT-3'

Reverse primer:
                                  (SEQ ID NO: 186)
5'-TGTTGGACGCAGGATTTTGGA-3'
```

The 0.56 kb probe was purified by 1% agarose gel electrophoresis in TAE buffer where a band corresponding to the probe was excised from the gel and extracted using a QIAQUICK® Gel Extraction Kit (Example 9).

Hybridization was performed as described in Example 3.

Transformants with the correct integration of pECW2 DNA produced a 3.5 kb hybridizing fragment. The untransformed strain produced a 6.0 kb hybridizing fragment. One transformant with correct integration of pECW2 was chosen and designated *T. reesei* ECW1.

Example 44: Construction of Plasmid pECW4

Plasmid pECW4 was constructed to comprise the temperate *Lactococcus lactis* bacteriophage TP901-1 integrase expression cassette, where the integrase gene was under transcriptional control of a *T. reesei* glyceraldehyde-3-phosphate dehydrogenase gene (gpd) promoter and terminator and the SV40 virus nuclear localization signal (NLS) (SEQ ID NO: 187) added at the 5' end of the gene just after the ATG codon. To ensure maximum expression and activity in *T. reesei* the TP901-1 integrase coding sequence was codon optimized (SEQ ID NO: 188 [native DNA sequence], SEQ ID NO: 189 [codon-optimized DNA sequence], and SEQ ID NO: 190 [amino acid sequence]) and synthesized by GENEART® Gene Synthesis (Life Technologies).

The *Trichoderma reesei* gpd promoter fragment was PCR amplified from *Trichoderma reesei* strain AgJg115-104-7B1 genomic DNA using the primers shown below.

```
Primer 1205807 (sense):
                                  (SEQ ID NO: 191)
5'-GGTTAATTAAGTACGTCAATGTAACGTCAAAGCCGCCCTC-3'
    Pac I Primer 1205808 (anti-sense):
                                  (SEQ ID NO: 192)
5'-CATTTTGTATCTGCGAATTGAGCTTGCGTGAGTCG-3'
```

The sense primer added a Pac I restriction site at the 5' end of the fragment.

The PCR (50 μl) was composed of 100 ng of *T. reesei* AgJg115-104-7B1 genomic DNA, 1×PHUSION® HF buffer, 50 pmol of primer 1205807, 50 pmol of primer 1205808, 200 μM each of dATP, dCTP, dGTP, and dTTP, 1.5 μl of 100% DMSO, and 1 unit of PHUSION® High Fidelity DNA polymerase. The reaction was performed in a thermocycler programmed for 1 cycle at 98° C. for 3 minutes; 40 cycles each at 98° C. for 30 seconds, 57° C. for 30 seconds, and 72° C. for 1 minute and 30 seconds; and a final extension cycle at 72° C. for 7 minutes. The completed PCR was submitted to 0.8% agarose gel electrophoresis in TBE buffer where an approximately 995 bp PCR product was excised from the gel and purified using a NUCLEOSPIN® Extract II Gel and PCR Clean-up Kit.

The *Trichoderma reesei* gpd terminator fragment was PCR amplified from *Trichoderma reesei* strain AgJg115-104-7B1 genomic DNA using the primers shown below.

```
Primer 1205809 (sense):
                                  (SEQ ID NO: 193)
5'-TAATAAGTGCTGTGTTCCTCAGAATGGGCCCCAGAAGGG-3'

Primer 1205810 (anti-sense):
                                  (SEQ ID NO: 194)
5'-CGCTTAATTAACGGCCTCTTGAGATCATTCTTCTTCTGCTCCTTT
TC-3'
    Pac I
```

The anti-sense primer added a Pac I restriction site at the 3' end of the fragment.

The PCR (50 μl) was composed of 100 ng of *T. reesei* AgJg115-104-7B1 genomic DNA, 1×PHUSION® HF buffer, 50 pmol of primer 1205809, 50 pmol of primer 1205810, 200 μM each of dATP, dCTP, dGTP, and dTTP, 1.5 μl of 100% DMSO, and 1 unit of PHUSION® High Fidelity DNA polymerase. The reaction was performed in a thermocycler programmed for 1 cycle at 98° C. for 3 minutes; 40 cycles each at 98° C. for 30 seconds, 57° C. for 30 seconds, and 72° C. for 1 minute and 30 seconds; and a final extension cycle at 72° C. for 7 minutes. The completed PCR was submitted to 0.8% agarose gel electrophoresis in TBE buffer where an approximately 614 bp PCR product was excised from the gel and purified using a NUCLEOSPIN® Extract II Gel and PCR Clean-up Kit.

The TP901-1 integrase codon optimized CDS plus the SV40 virus NLS was amplified by PCR from the GENEART® vector pMA and the primers shown below.

```
Primer 1205812 (sense):
                                            (SEQ ID NO: 195)
5'-GCTCACGACTCACGCAAGCTCAATTCGCAGATACAAAATGTCGGGTC

TCCGTTCTCGTGCGGACCCCAAGAAGAAGCGCAAGGTC-3'

Primer 1205813 (anti-sense):
                                            (SEQ ID NO: 196)
5'-CCCTTCTGGGGCCCATTCTGAGGAACACAGCACTTATTAAGCGAGCT

GAAACTTGAAGATAATGTCGACGTTGTCGGCAGTCACG-3'
```

The sense primer added 37 bp of homologous sequence to the 3' end of the gpd promoter fragment upstream of the ATG codon of the codon optimized integrase coding sequence, and the anti-sense primer added 36 bp of homologous sequence to the 5' end of the gpd terminator fragment downstream of the stop codon of the integrase coding sequence.

The PCR (50 μl) was composed of 10 ng of the GENEART® vector pMA containing the codon optimized integrase coding sequence, 1×PHUSION® HF buffer, 50 pmol of primer 1205812, 50 pmol of primer 1205813, 200 μM each of dATP, dCTP, dGTP, and dTTP, 1.5 μl of 100% DMSO, and 1 unit of PHUSION® High Fidelity DNA polymerase. The reaction was performed in a thermocycler programmed for 1 cycle at 98° C. for 3 minutes; 40 cycles each at 98° C. for 30 seconds, 57° C. for 30 seconds, and 72° C. for 1 minute and 30 seconds; and a final extension cycle at 72° C. for 7 minutes. The completed PCR was submitted to 0.8% agarose gel electrophoresis in TBE buffer where an approximately 1582 bp PCR product was excised from the gel and purified using a NUCLEOSPIN® Extract II Gel and PCR Clean-up Kit.

The 995 bp gpd promoter fragment and the 1585 bp TP901-1 NLS-integrase fragment were fused together by PCR using primer 1205807 (sense) and primer 1205813 (anti-sense), resulting in a 2540 bp fragment in which the $T.$ reesei gpd promoter was placed upstream of the codon optimized integrase. The PCR (50 μl) was composed of an equimolecular ratio of both fragments for a total amount of DNA of approximately 125 ng, 1×PHUSION® HF buffer, 50 pmol of primer 1205807, 50 pmol of primer 1205813, 200 μM each of dATP, dCTP, dGTP, and dTTP, 1.5 μl of 100% DMSO, and 1 unit of PHUSION® High Fidelity DNA polymerase. The reaction was performed in a thermocycler programmed for 1 cycle at 98° C. for 3 minutes; 40 cycles each at 98° C. for 30 seconds, 60° C. for 30 seconds, and 72° C. for 2 minutes and 30 seconds; and a final extension cycle at 72° C. for 7 minutes. The completed PCR was submitted to 0.8% agarose gel electrophoresis in TBE buffer where an approximately 2540 bp PCR product was excised from the gel and purified using a NUCLEOSPIN® Extract II Gel and PCR Clean-up Kit.

The 2540 bp PCR fragment comprising the gpd promoter fragment and TP901-1 NLS-integrase fragment were fused together by PCR to the 614 bp gpd terminator fragment using primer 1205807 (sense) and primer 1205810 (anti-sense), resulting in a 3115 bp fragment in which the $T.$ reesei gpd terminator was placed downstream of the codon optimized integrase. The PCR (50 μl) was composed of an equimolecular ratio of both fragments for a total amount of DNA of approximately 200 ng, 1×PHUSION® HF buffer, 50 pmol of primer 1205807, 50 pmol of primer 1205810, 200 μM each of dATP, dCTP, dGTP, and dTTP, 1.5 μl of 100% DMSO, and 1 unit of PHUSION® High Fidelity DNA polymerase. The reaction was performed in a thermocycler programmed for 1 cycle at 98° C. for 3 minutes; 40 cycles each at 98° C. for 30 seconds, 60° C. for 30 seconds, and 72° C. for 3 minutes; and a final extension cycle at 72° C. for 7 minutes. The completed PCR was submitted to 0.8% agarose gel electrophoresis in TBE buffer where an approximately 3115 bp PCR product was excised from the gel and purified using a NUCLEOSPIN® Extract II Gel and PCR Clean-up Kit.

The resulting 3115 bp fragment, comprising the complete TP901-1 integrase expression cassette, was cloned after PCR and gel purification into plasmid pCR® 2.1-TOPO® (Life Technologies Corp.) and transformed into ONE SHOT® TOP10 $E.$ $coli$ chemically competent cells according to Example 4. Transformants were spread onto 2XYT plus ampicillin plates and incubated at 37° C. overnight. Several of the resulting transformants were screened for proper insertion of the desired fragment by Eco RI digestion and sequencing analysis. Plasmid DNA was extracted and purified using a QIAGEN® Plasmid Mini Kit. One transformant containing a plasmid yielding Eco RI restriction fragments of 3939 bp and 3133 bp was identified and the plasmid was designated pECW4.

Plasmid pECW4 comprises the TP901-1 integrase expression cassette, in which gene transcription is regulated by the $T.$ reesei gpd promoter and terminator, and the SV40 virus NLS added after the ATG of the codon optimized integrase CDS.

Example 45: Construction of Plasmid pECW5

Plasmid pECW5 was constructed to comprise the hpt-tk dual selectable marker system (WO 2010/039889) flanked by attB sites shown below.

```
                                            (SEQ ID NO: 197)
CTGATAATTGCCAACACAATTAACATCTCAATCAAGGTAAATGCTTT
```

The tk fragment was PCR amplified from plasmid pGMEr189 (Example 39) using the primers shown below. The underlined sequences in the primers highlight the portion of the attB site the primer will add to the 5' end of the tk fragment.

```
Primer 1206177 (sense):
                                            (SEQ ID NO: 198)
5'-TAACATCTCAATCAAGGTAAATGCTTTGAGCTGAACCCGTACTACT

ACCAGTGTTTGTGATTACATTAAGC-3'

Primer 1206331 (anti-sense):
                                            (SEQ ID NO: 199)
5'-GGCCATGGTGCCCGTGAAGCCGTTTAAATGAATTCGAACCC-3'
      Nco I
```

The sense primer added the 3' half of the attB site at the 5' end of the fragment; while the anti-sense primer added an Nco I restriction site at its 3' end.

The PCR (50 μl) was composed of 25 ng of pGMEr189 DNA, 1×PHUSION® HF buffer, 50 pmol of primer 1206177, 50 pmol of primer 1206331, 200 μM each of dATP, dCTP, dGTP, and dTTP, 1.5 μl of 100% DMSO, and 1 unit of PHUSION® High Fidelity DNA polymerase. The reaction was performed in a thermocycler programmed for 1 cycle at 98° C. for 3 minutes; 40 cycles each at 98° C. for 30 seconds, 57° C. for 30 seconds, and 72° C. for 2 minutes; and a final extension cycle at 72° C. for 7 minutes. The completed PCR was submitted to 0.8% agarose gel electrophoresis in TBE buffer where an approximately 2906 bp PCR product was excised from the gel and purified using a NUCLEOSPIN® Extract II Gel and PCR Clean-up Kit.

The resulting gel purified PCR product was used as template DNA in a second PCR to complete the attB site (underlined sequence in primer 1206178) upstream of the tk construct, using the primers shown below.

```
Primer 1206178 (sense):
                                     (SEQ ID NO: 200)
     Pme I                      attB
5'-CGGTTTAAACCTGATAATTGCCAACACAATTAACATCTCAATCAAG

GTAAATGCTTTGAGCTGAAC-3'

Primer 1206331 (anti-sense):
                                     (SEQ ID NO: 201)
     Nco I
5'-GGCCATGGTGCCCGTGAAGCCGTTTAAATGAATTCGAACCC-3'
```

The sense primer completed the attB site upstream of the tk construct and added a Pme I restriction site at the 5' end of the fragment, while the anti-sense primer conserved an Nco I restriction site at its 3' end.

The PCR (50 μl) was composed of 25 ng of the 2906 kb fragment, 1×PHUSION® HF buffer, 50 pmol of primer 1206178, 50 pmol of primer 1206331, 200 μM each of dATP, dCTP, dGTP, and dTTP, 1.5 μl of 100% DMSO, and 1 unit of PHUSION® High Fidelity DNA polymerase. The reaction was performed in a thermocycler programmed for 1 cycle at 98° C. for 3 minutes; 40 cycles each at 98° C. for 30 seconds, 57° C. for 30 seconds, and 72° C. for 2 minutes; and a final extension cycle at 72° C. for 7 minutes. The completed PCR was submitted to 0.8% agarose gel electrophoresis in TBE buffer where an approximately 2936 bp PCR product was excised from the gel and purified using a NUCLEOSPIN® Extract II Gel and PCR Clean-up Kit.

The hpt gene construct was PCR amplified from plasmid pGMEr189 (Example 39) using the following primers:

```
Primer 1206330 (sense):
                                     (SEQ ID NO: 202)
5'-GCCCATGGGTTCGAATTCATTTAAACGGCTTCACGGGCA-3'

Primer 1206180 (anti-sense):
                                     (SEQ ID NO: 203)
     Pme I    Pac I             attB
5'-CGGTTTAAACTTAATTAAAGCATTTACCTTGATTGAGATGTTAATT

GTGTTGGCAATTATCAGGCCGTGGTACTGGG-3'
```

The anti-sense primer added the attB site downstream of the hpt gene (underlined sequence) and Pac I and Pme I restriction sites at the 3' end of the fragment.

The PCR (50 μl) was composed of 25 ng of pGMEr189 DNA, 1×PHUSION® HF buffer, 50 pmol of primer 1206330, 50 pmol of primer 1206180, 200 μM each of dATP, dCTP, dGTP, and dTTP, 1.5 μl of 100% DMSO, and 1 unit of PHUSION® High Fidelity DNA polymerase The reaction was performed in a thermocycler programmed for 1 cycle at 98° C. for 3 minutes; 40 cycles each at 98° C. for 30 seconds, 57° C. for 30 seconds, and 72° C. for 2 minutes; and a final extension cycle at 72° C. for 7 minutes. The completed PCR was submitted to 0.8% agarose gel electrophoresis in TBE buffer where an approximately 2349 bp PCR product was excised from the gel and purified using a NUCLEOSPIN® Extract II Gel and PCR Clean-up Kit.

The resulting 2936 bp fragment (comprising the attB-tk gene construct) and the 2349 bp fragment (comprising the hpt gene-attB construct) were double digested with Pme I and Nco I and ligated to the 2647 bp Pme I fragment from plasmid pGMEr189 bearing the ampicillin resistance gene and the *E. coli* origin of replication. About 20 μg of plasmid pGMEr189 were digested with Pme I at 37° C. for 3 hours. One hour before the end of the digestion, 1 μl of calf intestinal alkaline phosphatase was added to the pGMEr189-Pme I digestion to de-phosphorylate the ends to prevent self-ligation. The resulting digestion was submitted to 0.8% agarose gel electrophoresis in TBE buffer where a 2647 bp vector fragment, containing the ampicillin resistance gene and the *E. coli* origin of replication, was excised from the gel and purified using a NUCLEOSPIN® Extract II Gel and PCR Clean-up Kit.

The ligation reaction was performed using a QUICK LIGATION™ Kit. The ligation reaction was composed of 1.5 μl of the pGMEr189 vector fragment, 2 μl of the attB-tk gene fragment, 2 μl of the hpt gene-attB fragment, 4 μl of sterile deionized water, 10 μl of 2× Quick Ligation Buffer, and 1 μl of Quick T4 Ligase. The ligation reaction was incubated for 1 hour at room temperature. A 5 μl aliquot of the ligation reaction was transformed into ONE SHOT® TOP10 *E. coli* chemically competent cells according to Example 4. Transformants were spread onto 2XYT plus ampicillin plates and incubated at 37° C. overnight. Several of the resulting transformants were screened for proper insertion of the desired inserts by Pme I restriction digestion and sequencing analysis. Plasmid DNA was extracted and purified using a QIAGEN® Plasmid Mini Kit. One transformant containing a plasmid yielding Pme I restriction fragments of approximately 2.6 kb and of 5.2 kb was identified and the plasmid was designated pECW5.

Plasmid pECW5 comprises the hpt-tk dual selectable marker system flanked by the TP901-1 attB sites.

Example 46: Construction of Plasmid pECW7

Plasmid pECW5 and plasmid pECW4 were digested with Pme I. The restriction reaction products were submitted to 0.8% agarose gel electrophoresis in TBE buffer where the 5226 bp pECW5 fragment and the 7072 bp pECW4 fragment were excised from the gels and purified using a NUCLEOSPIN® Extract II Gel and PCR Clean-up Kit. The 5226 bp Pme I fragment from plasmid pECW5, comprising the hpt-tk dual selectable marker system flanked by the TP901-1 attB sites, was ligated to the 7072 bp Pme I linearized pECW4 fragment. The ligation reaction was performed using a 1:3 vector:insert ratio. The reaction was composed of 2 μl of the 7072 bp linearized vector, 5 μl of the 5226 bp insert fragment, 3 μl of sterile deionized water, 9 μl of 2× Reaction Buffer, and 1 μl of Quick T4 DNA ligase. The ligation reaction was incubated for 1 hour at room temperature.

Figure 6:
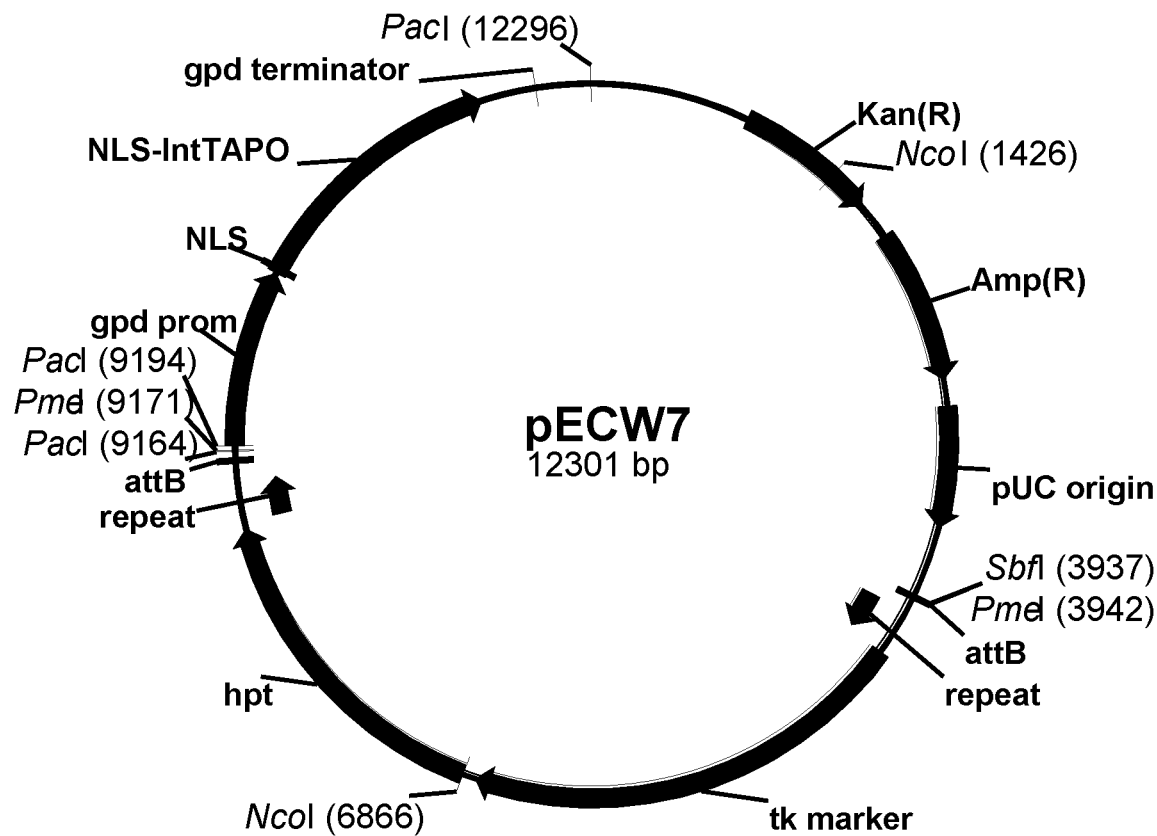
FIG. 6 shows a restriction map of plasmid pECW7.

Five μl of the ligation reaction were transformed into ONE SHOT® TOP10 *E. coli* chemically competent cells according to Example 4. Transformants were spread onto 2XYT plus ampicillin plates and incubated at 37° C. overnight. Several of the resulting transformants were screened for proper insertion of the desired insert by Nco I and Pac I restriction digestions. Plasmid DNA was extracted and purified using a QIAGEN® Plasmid Mini Kit. One transformant containing a plasmid yielding Nco I restriction fragments of approximately 5.4 kb and 6.9 kb and Pac I restriction fragments of approximately 9.2 kb, 3.1 kb, and 0.03 kb was identified and the plasmid was designated pECVV7 (FIG. 6).

Plasmid pECW7 harbors the hpt-tk dual selectable marker system flanked by the
TP901-1 attB sites upstream of the TP901-1 integrase expression cassette.

Example 47: Construction of *Trichoderma reesei* Strain TrGMEr60

Plasmid pECW7 was transformed into *Trichoderma reesei* strain ECW1 (Example 43) to show that the TP901-1 integrase can be expressed, is functional in filamentous fungal host cells, and able to promote a site-specific recombination event between the attP sites present in the recipient host strain and the attB sites in the transforming construct.

Plasmid pECW7 was linearized with Sbf I and transformed into *T. reesei* ECW1. *T. reesei* ECW1 harbors TP901-1 and two attP sites at the cbh1 locus, one upstream and the other one downstream of the amdS marker gene. *T. reesei* ECW1 was able to grow on COVE2 plates supplemented with 10 mM uridine. To track the attP/attB recombination, mediated by the TP901-1 integrase, the transforming construct comprised two attB sites at each ends of the hpt-tk dual selectable marker system fragment.

Protoplast preparation and transformation of *Trichoderma reesei* ECW1 were performed according to the protocol described in Example 1.

Approximately 100 µg of plasmid pECW7 were digested with Sbf I. The linearized pECW7 plasmid was submitted to 0.8% agarose gel electrophoresis in TBE buffer, excised from the gel, and purified using a NUCLEOSPIN® Extract II Gel and PCR Clean-up Kit.

Approximately 2 µg of the Sbf I digested pECW7 were added to 100 µl of the protoplast solution and mixed gently. PEG buffer (250 µl) was added, and the reaction was mixed and incubated at 34° C. for 30 minutes. STC (3 ml) was then added and mixed and then the mixture was spread onto PDA plates for protoplast regeneration selection. The plates were incubated at 28° C. overnight. After overnight incubation the transformation plates were overlaid with PDA medium supplemented with 35 µg of hygromycin B per ml for transformant selection. The plates were incubated at 28° C. for 6-9 days.

Thirty-eight primary transformants were identified and insertion of the amdS gene with the hpt-tk construct at the cbh1 locus was verified by PCR analysis of the upstream and downstream integration sites as described below. In particular each putative primary transformant was patched onto COVE2 plates supplemented with 10 mM uridine selection plates and incubated at 30° C. for 2-3 days. Transformants were screened using a PHIRE® Plant Direct PCR Kit.

The 5' integration site was confirmed using the primers shown below.

```
Primer 1205989 (sense):
                                (SEQ ID NO: 204)
5'-CACCTCTTCTCAACCTTTGG-3'

Primer 1206548 (anti-sense):
                                (SEQ ID NO: 205)
5'-ACGGGGCAAAGCTGCCTACC-3'
```

The 3' integration site was confirmed using the primers shown below.

```
Primer 1206537 (sense):
                                (SEQ ID NO: 206)
5'-GCAGGGTCGATGCGACGCAA-3'

Primer 1202659 (anti-sense):
                                (SEQ ID NO: 207)
5'-TACCATGACTGTCACGATAG-3'
```

The total length of the resulting PCR fragments were approximately 1174 bp and 2422 bp for the 5' integration site and the 3' integration site, respectively.

The PCRs (20 µl) were composed of 1 µl of spore purified genomic DNA, 1×PHIRE® Plant PCR Buffer, 0.5 µM of primer 1205989 or 1206537, 0.5 µM of primer 1206548 or 1202659, and 0.4 µl of PHIRE® Hot Start II DNA Polymerase. The reaction was performed in a thermocycler programmed for 1 cycle at 98° C. for 3 minutes; 40 cycles each at 98° C. for 30 seconds, 57° C. for 20 seconds, and 72° C. for 1 minute and 15 seconds; and a final extension cycle at 72° C. for 7 minutes. Following thermocycling, the PCR products were visualized by 0.8% agarose gel electrophoresis in TBE buffer.

The thirty-eight primary transformants were patched onto COVE2 plates supplemented with 10 mM uridine to test for the amdS minus phenotype. The plates were incubated at 28° C. for 6-9 days.

Five transformants showing the correct PCR products by both PCRs and a negative amdS phenotype were spore purified by adding spores collected on a 10 µl inoculation loop to 1.5 ml of 0.01% TWEEN® 20. Spore dilutions of 1:1500 and 1:150 were spread onto 150 mm PDA plates and cultured for 3 days at 28° C. Four spore isolates per strain were obtained and transferred to COVE2 plates supplemented with 10 mM uridine and cultivated at 30° C. for 2-3 days. Each spore isolate was tested again by PCR to check the upstream and downstream sites of integration as described above. Of the twenty spore isolated transformants, eight were analyzed by Southern blotting according to Example 3 to confirm the correct recombination event between the attP and the attB sites mediated by the TP901-1 integrase. A correct recombination event led to the replacement of the amdS marker with the hpt-tk expression cassettes flanked by the attR (upstream) and the attL (downstream) sites.

Two µg of genomic DNA from each transformant were digested with Nhe I. The digestions were submitted to 0.7-0.8% agarose gel electrophoresis in TAE buffer and blotted onto a HYBOND® N+ blotting membrane using a TURBOBLOTTER® according to Example 3. The membrane was hybridized with a digoxigenin-labeled probe specific for the hpt marker gene, which was synthesized using a PCR DIG Probe Synthesis Kit. Plasmid pJfyS1579-41-11 (WO 2011/075677) was digested with Bsp HI and purified by 0.8% agarose gel electrophoresis in TAE buffer. A 2.7 kb Bsp HI fragment containing the hpt gene was excised and the DNA was recovered using a Nucleospin® Extract II Kit (Example 8). This 2.7 kb fragment was used as the hpt probe template.

A probe hybridizing to the hpt gene was generated using a PCR DIG Probe Synthesis Kit with the forward and reverse primers indicated below. The 50 µl PCR contained 1×PCR DIG Probe Synthesis mix, 50 pmol each primer, 1×PCR buffer with $MgCl_2$, approximately 100 ng of purified 2.7 kb probe template (described above), and 2.6 units of EXPAND® High Fidelity DNA polymerase. The PCR was incubated in a thermocycler programmed for 1 cycle at 95° C. for 2 minutes; 30 cycles each at 95° C. for 30 seconds, 59° C. for 30 seconds, and 72° C. for 45 seconds; and 1 cycle at 72° C. for 7 minutes.

```
Primers for 0.5 kb hpt probe:
Primer 0614123 (sense):
                                (SEQ ID NO: 208)
5'-ATGAAAAAGCCTGAACTCACC-3'

Primer 0614124 (anti-sense):
                                (SEQ ID NO: 209)
5'-TCCATCACAGTTTGCCAGTGA-3'
```

Hybridization was performed as described in Example 3.

One transformant with the correct upstream and downstream sites of integration was chosen and designated *T.* reesei TrGMEr60. Furthermore the presence of a correct attR site (SEQ ID NO: 210 below) and attL site (SEQ ID NO: 211 below), respectively, upstream and downstream of the hpt-tk marker genes were confirmed by sequencing analysis.

```
attR:
                                     (SEQ ID NO: 210)
TCCAACTCGCTTAATTGCGAGTTTTTATTTCGTTTATTTCAATCAAGGTA

AATG attL:
                                     (SEQ ID NO: 211)
CTGATAATTGCCAACACAATTAACATCTCAATTAAGGTAACTAAA
```

The results demonstrated that a site specific recombination event between the attP sites in the recipient strain ECW1 and the attB sites in the transforming construct, mediated by the TP901-1 integrase, led to the replacement of the amdS expression cassette with the hpt-tk dual selectable marker system, resulting in *T. reesei* strain TrGMER60, which is able to grow on medium supplemented with hygromycin B and unable to grow on COVE2 plates supplemented with 10 mM uridine.

Example 48: Construction of Plasmid pGMEr193

Plasmid pGMEr193 was constructed to comprise the hpt-tk dual selectable marker system flanked by the TP901-1 attB sites upstream of the TP901-1 integrase expression cassette. The only difference between plasmid pGMEr193 and pECW7 is that the TP901-1 integrase gene doesn't include the SV40 virus nuclear localization signal (NLS).

The *T. reesei* gpd promoter fragment was PCR amplified from plasmid pECW7 using the primers shown below:

```
Primer 1209171 (sense):
                                     (SEQ ID NO: 212)
                                     Ale I
5'-AGCATGAATGTCGCTCATCCGATGCCGCATCACCGTTGTGTCAG-3'

Primer 1208898 (anti-sense):
                                     (SEQ ID NO: 213)
5'-TAGTATAGATGGCGACCTTCTTGGTCATTTTGTATCTGCGAATTGAG

CTTGCGTGAGTCGTGAGCTTCC-3'
```

The sense primer added an Ale I restriction site at the 5' end of the fragment while the anti-sense primer added the ATG start codon and the first nine amino acids of the TP901-1 CDS without the NLS at the 3' end of the fragment.

The PCR (50 µl) was composed of 50 ng of plasmid pECW7 DNA, 1×PHUSION® HF buffer, 50 pmol of primer 1209171, 50 pmol of primer 1208898, 200 µM each of dATP, dCTP, dGTP, and dTTP, 1.5 µl of 100% DMSO, and 1 unit of PHUSION® High Fidelity DNA polymerase. The reaction was performed in a thermocycler programmed for 1 cycle at 98° C. for 3 minutes; 40 cycles each at 98° C. for 30 seconds, 57° C. for 30 seconds, and 72° C. for 1 minutes; and a final extension cycle at 72° C. for 7 minutes. The completed PCR was submitted to 0.8% agarose gel electrophoresis in TBE buffer where an approximately 551 bp PCR product was excised from the gel and purified using a NUCLEOSPIN® Extract II Gel and PCR Clean-up Kit.

A second PCR fragment, containing 5' homology to the PCR product above, comprising the first 266 amino acids of the TP901-integrase without the SV40 virus NLS sequence was generated using the following primers:

```
Primer 1208899 (sense):
                                     (SEQ ID NO: 214)
5'-TTCGCAGATACAAAATGACCAAGAAGGTCGCCATCTATACTAGAGTC

TCGACGACCAACCAG-3'

Primer 1209170 (anti-sense):
                                     (SEQ ID NO: 215)
                                     AflII
5'-CTGCTGCTGGCGCTCTTCCAATTCCTTTTGGACCTTAAGATAC-3'
```

The sense primer is reverse and complementary to the antisense primer 1208898 used in the PCR described above to create the gpd promoter fragment. The anti-sense primer added an Afl II restriction site at the fragment 3' end.

The PCR (50 µl) was composed of 50 ng of plasmid pECW7 DNA, 1×PHUSION® HF buffer, 50 pmol of primer 1209171, 50 pmol of primer 1208898, 200 µM each of dATP, dCTP, dGTP, and dTTP, 1.5 µl of 100% DMSO, and 1 unit of PHUSION® High Fidelity DNA polymerase. The reaction was performed in a thermocycler programmed for 1 cycle at 98° C. for 3 minutes; 40 cycles each at 98° C. for 30 seconds, 57° C. for 30 seconds, and 72° C. for 1 minutes; and a final extension cycle at 72° C. for 7 minutes. The completed PCR was submitted to 0.8% agarose gel electrophoresis in TBE buffer where an approximately 812 bp PCR product was excised from the gel and purified using a NUCLEOSPIN® Extract II Gel and PCR Clean-up Kit.

Figure 7:
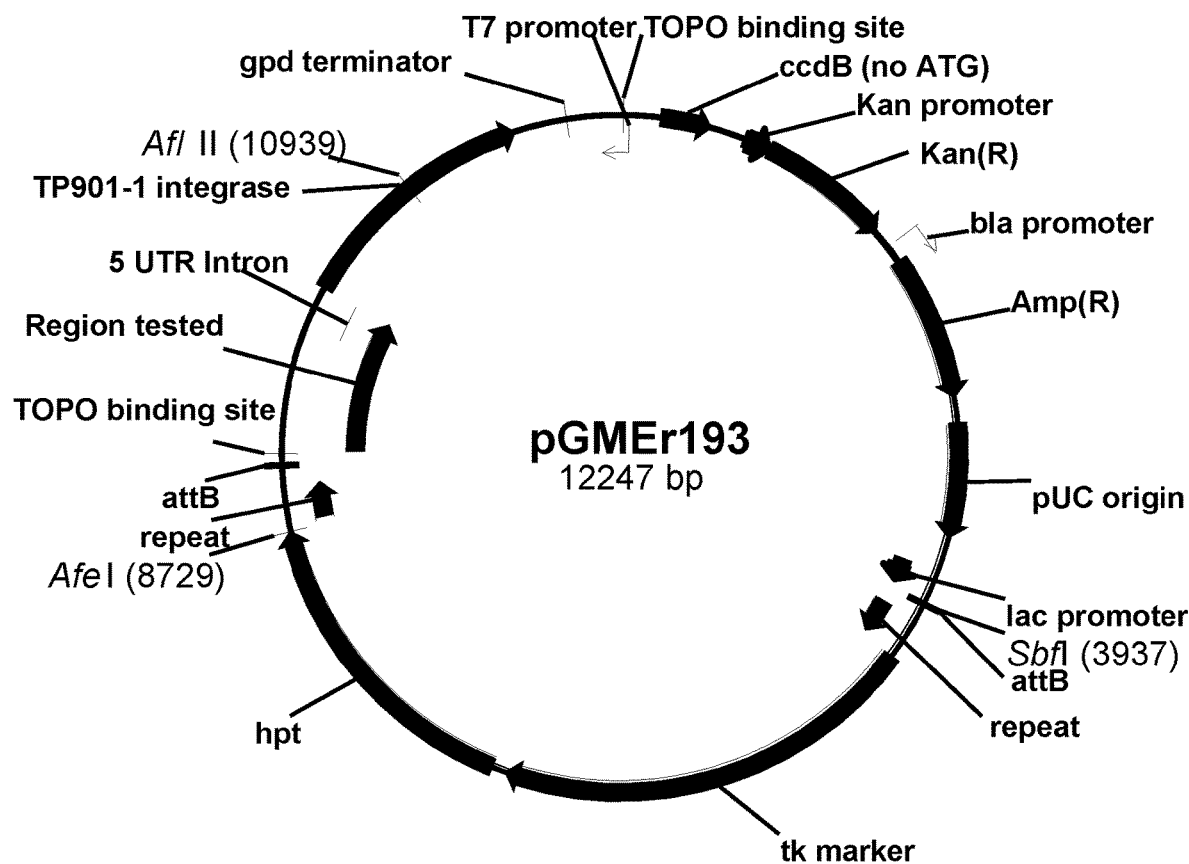
FIG. 7 shows a restriction map of plasmid pGMEr193.

The resulting 551 bp gpd promoter fragment was digested with Ale I and the 812 bp TP901-1 integrase fragment was digested with Afl II for two hours at 37° C. Both digested fragments were then inserted into Ale I/Afl II-linearized pECW7 using an IN-FUSION® Advantage PCR Cloning Kit. The reaction was composed of 1× IN-FUSION® Reaction Buffer, 50 ng of Ale I/Afl II-linearized pECW7, 100 ng of the Ale I-cbh1 promoter fragment (~551 bp), and 100 ng of the TP901-1 integrase Afl II fragment (~812 bp), and 1 µl of IN-FUSION® Enzyme in a 10 µl reaction volume. The reaction was incubated for 15 minutes at 50° C. Then 40 µl of TE were added to the reaction and a 2 µl aliquot of the reaction was transformed into ONE SHOT® TOP10 *E. coli* chemically competent cells according to Example 4. Transformants were spread onto 2XYT plus ampicillin plates and incubated at 37° C. overnight. Several of the resulting transformants were screened for proper insertion of the desired inserts by Ale I and Afl II double restriction digestion. Plasmid DNA was extracted and purified using a QIAGEN® Plasmid Mini Kit. A transformant containing a plasmid yielding the desired band sizes of 10999 bp and 1248 bp was isolated and the plasmid was designated pGMEr193 (FIG. 7).

Plasmid pGMEr193 comprises the hpt-tk dual selectable marker system flanked by the TP901-1 attB sites upstream of the TP901-1 integrase expression cassette without the SV40 virus NLS.

Example 49: Testing the Integration Efficiency of the TP901-1 Integrase with and without the SV40 Virus NLS Comparison Construction of *Trichoderma reesei* Strain TrGMEr60

Plasmid pECW7 and pGMEr193 were transformed into *Trichoderma reesei* strain ECW1 (Example 43) to test whether the TP901-1 integrase needs a nuclear localization signal (NLS) sequence to successfully promote a site-specific recombination event between the attP sites present in the recipient host strain and the attB sites in the transforming construct.

Plasmid pECW7 and pGMEr193 were linearized with Sbf I and transformed into *T. reesei* ECW1. *T. reesei* ECW1 harbors TP901-1 and two attP sites at the cbh1 locus, one upstream and the other one downstream of the amdS marker gene. *T. reesei* ECW1 was able to grow on COVE2 plates supplemented with 10 mM uridine. To track the attP/attB recombination, mediated by the TP901-1 integrase, the transforming construct comprised two attB sites at each end of the hpt-tk dual selectable marker fragment.

Protoplast preparation and transformation of *Trichoderma reesei* ECW1 were performed according to the protocol described in Example 1.

Approximately 100 µg of plasmids pECW7 and pGMEr193 were digested and linearized with Sbf I. The linearized pECW7 and pGMEr193 plasmids were submitted to 0.8% agarose gel electrophoresis in TBE buffer, excised from the gel, and purified using a NUCLEOSPIN® Extract II Gel and PCR Clean-up Kit.

Approximately 2 µg of the Sbf I digested pECW7 and pGMEr193 were added to 100 µl of the protoplast solution, respectively, and mixed gently. PEG buffer (250 µl) were added, and the reaction was mixed and incubated at 34° C. for 30 minutes. STC (3 ml) was then added and mixed and then the mixture was spread onto PDA plates for protoplast regeneration selection. The plates were incubated at 28° C. overnight. After overnight at 28° C. the transformation plates were overlaid with PDA medium supplemented with 35 µg of hygromycin B per ml for transformant selection. The plates were incubated 28° C. for 6-9 days.

Totally 10-11 primary transformants/µg of plasmid DNA were obtained with both linearized plasmid pECVV7 and pGMEr193 confirming that both plasmids had retained the same transformation efficiency. After PCR checking of all the primary transformants it was shown that 46% of the pECW7 transformants integrated at the expected cbh1 locus while only 13% for plasmid pGMEr193.

At the same time, approximately 4 µg of circular pECW7 and pGMEr193 were added to 100 µl of the protoplast solution, respectively, and mixed gently. PEG buffer (250 µl) were added, and the reaction was mixed and incubated at 34° C. for 30 minutes. STC (3 ml) was then added and mixed and the mixture was spread onto PDA plates for protoplast regeneration selection. The plates were incubated at 28° C. overnight. After overnight at 28° C. the transformation plates were overlaid with PDA medium supplemented with 35 µg of hygromycin B per ml for transformant selection. The plates were incubated 28° C. for 6-9 days.

About 11 primary transformants/µg of plasmid DNA were obtained with circular plasmid pGMEr193, and about 4 primary transformants/µg of plasmid DNA were obtained with circular plasmid pECW7, showing that uncut plasmid pGMEr193 has a higher transformation efficiency than uncut plasmid pECW7. Although, PCR checking of all the primary transformants showed that pECW7 retains the best targeting efficiency of the construct at the desired locus, in particular about 60% of the pECW7 (circular) transformants integrated at the expected cbh1 locus while only 40% for plasmid pGMEr193 (circular).

In all the primary transformants the insertion of the hpt-tk construct at the cbh1 locus was verified by PCR analysis of the upstream and downstream integration sites using a PHIRE® Plant Direct PCR Kit as described below.

The 5' integration site was confirmed using the primers shown below.

```
Primer 1203893 (sense):
                                  (SEQ ID NO: 216)
5'-GTAATTTGCCTGCTTGACCG-3'

Primer 1208272 (anti-sense):
                                  (SEQ ID NO: 217)
5'-CACCAGCCTTTCCACTTCGG-3'
```

The 3' integration site was confirmed using the primers shown below.

```
Primer 1208273 (sense):
                                  (SEQ ID NO: 218)
5'-CCTTCTGGCATGACCTTTTG-3'

Primer 1202659 (anti-sense):
                                  (SEQ ID NO: 219)
5'-TACCATGACTGTCACGATAG-3'
```

The total lengths of the resulting PCR fragments were approximately 620 bp and 1959 bp for the 5' integration site and the 3' integration site, respectively.

The PCRs (20 µl) were composed of 1 µl of spore purified genomic DNA, 1×PHIRE® Plant PCR Buffer, 0.5 µM of primer 1203893 or 1208273, 0.5 µM of primer 1208272 or 1202659, and 0.4 µl of PHIRE® Hot Start II DNA Polymerase. The reaction was performed in a thermocycler programmed for 1 cycle at 98° C. for 3 minutes; 40 cycles each at 98° C. for 30 seconds, 57° C. for 20 seconds, and 72° C. for 1 minute and 15 seconds; and a final extension cycle at 72° C. for 7 minutes. Following thermocycling, the PCR products were visualized by 0.8% agarose gel electrophoresis in TBE buffer.

This experiment showed that adding the SV40 virus NLS is not essential for a proper site directed integration mediated by the TP901-1 integrase, but the NLS increases the success rate of the integration event.

Example 50: Generation of *Trichoderma reesei* Strain attP-FRT

This Example describes the introduction of FRT sites at the cbh2 locus of *T. reesei* strain ECW1 (Example 43) to create a strain with TP901-1 attP recognition sites at the cbh1 locus and FRT sites at the cbh2 locus.

Seventy µg of pAgJg137 (Example 11) were digested with Pme I. The digested DNA was ethanol precipitated and the DNA was resuspended in TE buffer. *T. reesei* strain ECW1 protoplasts were prepared as described in Example 1. The protoplasts were transformed with Pme I digested pAgJg137 DNA selecting for the hygromycin resistance marker (hpt) as described in Example 1. Transformation plates were incubated 5 days at 28° C. Transformants were transferred to PDA plates and incubated for 3-5 days at 30° C. A spore PCR using a PHIRE® Plant Direct PCR Kit was utilized to identify transformants which had the correct integration of the pAgJg137 DNA at the cbh2 locus. Briefly, spores from the transformants were collected with a sterile 1 µl inoculation loop and transferred to 15 µl of Kit-supplied dilution buffer in microfuge tubes and incubated for 5 minutes at room temperature. Each spore suspension was centrifuged at 13,000 rpm for 10 seconds and 1 µl of supernatant was used in the spore PCR. The 20 µl spore PCR contained 1×PHIRE® Plant Direct PCR buffer (contains dNTPs and Mg), 10 pmol of the forward primer and 10 pmol of the reverse primer listed below, 0.4 µl of PHIRE® II Hot Start DNA Polymerase and 1 µl of each supernatant from the spore suspensions.

```
Forward primer (homology to 5' cbh2 flank):
                                  (SEQ ID NO: 220)
5'-CTGATCGAGAAGATTAGCATG-3'

Reverse primer (homology to hpt marker):
                                  (SEQ ID NO: 221)
5'-GTTTCAGGCAGGTCTTGCAACG-3'

Reverse primer (homology to cbh2 gene):
                                  (SEQ ID NO: 222)
5'-GATCAGTGATGAAGAAGGCG-3'
```

The PCRs were incubated in a thermocycler programmed for 1 cycle at 98° C. for 5 minutes; 40 cycles each at 98° C. for 5 seconds, 60° C. for 5 seconds, and 72° C. for 1 minute and 15 seconds; and 1 cycle at 72° C. for 1 minute and 15 seconds.

The completed PCRs were subjected to 0.8% agarose gel electrophoresis in TAE buffer. Transformants with correct targeting of plasmid DNA to the cbh2 locus produced a 2.6 kb fragment. Transformants that did not have correct targeting of plasmid DNA to the cbh2 locus produced a 3.5 kb fragment.

Transformants with correct targeting of plasmid DNA to the cbh2 locus were chosen for spore isolation. Spores from a PDA plate culture were collected using a 1 µl inoculation loop and added to 2 ml of 0.01% TWEEN® 20. One µl of each spore suspension and 100 µl 0.01% TWEEN® 20 were spread onto 150 mm PDA plates. The plates were incubated for 2 days at 30° C. Isolated colonies were picked with a sterile 10 µl inoculation loop and transferred to PDA plates and incubated 3-5 days at 30° C. A spore PCR using a PHIRE® Plant Direct PCR Kit and the primers and PCR conditions shown above was performed to identify spore isolates that had the correct integration at the cbh2 locus.

Correct spore isolates were chosen and the hpt/tk markers were looped out using 5-fluorodeoxyuridine (FdU) counterselection as described below. Spores from 6 day old PDA plates were collected in 4 ml of 0.01% TWEEN® 20 and the spore concentration was determined using a hemocytometer. Approximately $10^6$ and $10^5$ spores from each isolate were plated to 150 mm FdU plates. The FdU plates were incubated at 30° C. for 7 days. Eight to nine FdU colonies were selected for each strain and transferred to PDA plates. The plates were incubated at 30° C. for 3 days. Spore PCRs using the PHIRE® Plant Direct PCR Kit were performed as described above using the primers shown below.

```
Forward primer 1 (homology to 5' flanking region
cbh2 locus):
                                  (SEQ ID NO: 223)
5'-CTCAGGCCATCGTAGGAAAT-3'

Reverse primer 1 (homology to 3' flanking region
cbh2 locus):
                                  (SEQ ID NO: 224)
5'-CTAGGTAGGTAGGTAGTATA-3'

Forward primer 2 (homology to hpt marker):
                                  (SEQ ID NO: 225)
5'-CGTGTTTCTTCCCATTCGCATGCGACCTCGTGGTCATTGAC-3'

Reverse primer 2 (homology to 3' flanking region
cbh2 locus):
                                  (SEQ ID NO: 226)
5'-CTCCTGTCACGACGTGCTTTT-3'
```

The PCRs were performed in a thermocycler programmed for 1 cycle at 98° C. for 5 minutes; 40 cycles each at 98° C. for 5 seconds, 55° C. for 5 seconds, and 72° C. for 1 minute 45 seconds; and 1 cycle at 72° C. for 1 minute 15 seconds.

The completed PCRs were subjected to 0.8% agarose gel electrophoresis in TBE buffer. Isolates with correct loopout of the hpt/tk markers produced a 2 kb fragment using the first set of primers and did not produce a 3.2 kb fragment with the second set of primers. Isolates retaining the hpt/tk markers produced a 6.6 kb fragment using the first set of primers and a 3.2 kb fragment using the second set of primers.

An additional round of spore isolation was performed with isolates containing the correct hpt/tk marker loopout. Spores from a 6 day old PDA plate were collected in 4 ml of 0.01% TWEEN® 20 and the spore concentration was determined using a hemocytometer. Spores were diluted appropriately to a concentration of $10^3$ spores per ml using sterile water and approximately 50 spores were spread onto PDA plates. The plates were incubated for 2 days at 30° C. Isolated colonies were picked with a sterile 10 µl inoculation loop, transferred to PDA plates, and incubated at 30° C. A spore PCR using a PHIRE® Plant Direct PCR Kit and forward primer 1 and reverse primer 1 described above was utilized to identify final spore isolates with the correct hpt/tk marker loopout.

Genomic DNA from the final spore isolates was prepared and subjected to Southern blot analysis as described in Example 15.

For Southern blot analysis approximately 1 µg of genomic DNA was digested with 20 units of Eco RI and subjected to 0.8% agarose electrophoresis in TAE buffer. The DNA in the gel was depurinated, denatured, neutralized, and transferred to a NYTRAN® Supercharge membrane according to Example 3. The DNA was UV cross-linked to the membrane using a UV STRATALINKER™ (Stratagene) and prehybridized for 1 hour at 42° C. in 20 ml of DIG Easy Hyb.

A template for a probe hybridizing to the 3' flanking region of the cbh2 gene was generated using PHUSION™ High Fidelity Hot Start DNA Polymerase (New England Biolabs, Inc.) and gene-specific forward and reverse primers shown below.

Fifty picomoles of each of the primers were used in a PCR containing 100 ng of *T. reesei* RutC30 genomic DNA, 1×PHUSION™ High Fidelity Hot Start DNA Polymerase buffer, 1 µl of a 10 mM blend of dATP, dTTP, dGTP, and dCTP, and 1 unit of PHUSION™ High Fidelity Hot Start DNA Polymerase in a final volume of 50 µl. The PCR was performed in a thermocycler programmed for 1 cycle at 98° C. for 2 minutes; 34 cycles each at 98° C. for 15 seconds, 60° C. for 30 seconds, and 72° C. for 1 minute and 30 seconds; and 1 cycle at 72° C. for 10 minutes. The completed PCR was purified by 0.8% agarose gel electrophoresis in TAE buffer where a 0.46 kb DNA band was excised from the gel and the DNA was extracted using a Nucleospin® Extract II Kit (Example 8).

A probe hybridizing to the 3' flanking region of the cbh2 gene was generated using a PCR DIG Probe Synthesis Kit with the forward and reverse primers shown below. The 50 µl PCR contained 1×PCR DIG Probe Synthesis mix, 50 pmol of each primer, 1×PCR buffer with $MgCl_2$, 24 ng of purified probe template (described above), and 2.6 units of EXPAND® High Fidelity DNA polymerase. The PCR was performed in a thermocycler programmed for 1 cycle at 95° C. for 2 minute; 30 cycles each at 95° C. for 30 seconds, 59° C. for 30 seconds, and 72° C. for 45 seconds; and 1 cycle at 72° C. for 7 minutes.

Primers for cbh2 3' Flanking Region Probe

```
Forward primer:
                                    (SEQ ID NO: 227)
5'-TCTTGAGCCGCATCGCATAGA-3'

Reverse primer:
                                    (SEQ ID NO: 228)
5'-TACGGTCAGCGCTCATGCGAA-3'
```

The probe was boiled for 5 minutes, chilled on ice for 2 minutes, and added to 10 ml of DIG Easy Hyb to produce the hybridization solution. Hybridization was performed as described in Example 3.

Southern blot analysis identified several final spore isolates that produced a 2.1 kb hybridizing fragment, verifying the correct integration of FRT sites at the cbh2 locus with loopout of the hpt/tk markers. The native *T. reesei* cbh2 locus produced a 4.1 kb hybridizing fragment. One spore isolate was chosen as the final strain and designated *T. reesei* attP-frt.

Example 51: Construction of Plasmid pCKIe137 for Removal of the amdS Marker from the cbh1 Locus of *Trichoderma reesei* Strain attP-FRT Plasmid pCKIe137 was constructed so that the amdS marker could be removed from the cbh1 locus in *T. reesei* attP-FRT via homologous recombination. Plasmid pCKIe137 contains cbh1 flanking regions, attP sites, and the hpt/tk selectable markers, which can be looped out to generate a marker-free strain. The TP901-1 attP site was inserted downstream of the 5' cbh1 flanking region using PCR. The 5' cbh1 flanking region and attP site were amplified together from pJfyS147 (Example 4) plasmid DNA using PHUSION™ Hot Start II High Fidelity DNA Polymerase (Thermo Scientific).

```
Forward primer:
                                    (SEQ ID NO: 229)
5'-CATGGTTTAAACGGCGCGCCGGTGAAACACCGCCCCTTC-3'

Reverse primer (attP site is underlined):
                                    (SEQ ID NO: 230)
5'-CCTTGTTTTGTCGTTTAGTTACCTTAATTGAAATAAACGAAATAAAA

ACTCGCAATTAAGCGAGTTGGATTCGAACAGCCCC-3'
```

Ten picomoles of each of the primers were used in a PCR composed of 7.4 ng of pJfyS147 DNA, 10 µl of 5×PHUSION™ HF buffer, 1 µl of a 10 mM blend of dATP, dTTP, dGTP, and dCTP, and 1.5 units of PHUSION™ Hot Start II DNA Polymerase in a final volume of 50 µl. The PCR was performed in a thermocycler programmed for 1 cycle at 98° C. for 30 seconds; 30 cycles each at 98° C. for 7 seconds, 55° C. for 15 seconds, and 72° C. for 25 seconds; and 1 cycle at 72° C. for 5 minutes.

The completed PCR was submitted to 0.65% agarose gel electrophoresis in TBE buffer where a 1.58 kb band was excised from the gel and agarose was extracted using a Nucleospin® PCR Cleanup and Gel Extraction Kit (Macherey-Nagel Inc.).

The 1.58 kb purified fragment was inserted into Asc I-digested pJfyS1579-41-11 (WO 2011/075677) using an IN-FUSION® HD PCR Cloning Kit. The reaction was composed of 2 µl of 5× IN-FUSION® HD Enzyme Premix, 100 ng of Asc I-digested pJfyS1579-41-11, and 40 ng of the purified PCR product in a 10 µl reaction volume. The reaction was incubated for 15 minutes at 50° C. Then 1 µl was used to transform 50 µl of Stellar™ *E. coli* chemically competent cells (Clontech Laboratories, Inc.) by addition to a tube containing the competent cells and incubating the cells on ice for 30 minutes. The tube was incubated at 42° C. for 45 seconds after which 450 µl of SOC medium were added. The tube was then incubated at 37° C. with agitation at 250 rpm for 1 hour. Volumes of 50 µl and 150 µl were transferred to two 150 mm 2XYT plus ampicillin plates. The plates were incubated overnight at 37° C. *E. coli* transformants were used to inoculate 3 ml of LB plus ampicillin medium in a 14 ml Falcon round-bottom polypropylene tube and incubated at 37° C. overnight with agitation at 200 rpm. Plasmid DNA was isolated using a QIAprep® Spin Miniprep Kit (QIAGEN Inc.). Plasmid DNA from the transformants was screened by restriction digestion with Stu I FD for production of 1.4 kb, 3.5 kb, and 4.6 kb fragments. Sequencing of one of the plasmids verified that the plasmid contained the correct inserts with no PCR errors. The plasmid was designated pCKIe136.

The 3' cbh1 flanking region and attP site were amplified together from pJfyS147 plasmid DNA using PHUSION™ Hot Start II High Fidelity DNA Polymerase (Thermo Scientific, Pittsburgh, PA, USA).

```
Forward primer (attP site is underlined):
                                    (SEQ ID NO: 231)
5'-GTATTCCTGCAGGTCCAACTCGCTTAATTGCGAGTTTTTATTTCGTT

TATTTCAATTAAGGTAACTAAAGATAACGGAATAG-3'

Reverse primer:
                                    (SEQ ID NO: 232)
5'-TGGCCATATTTAAATAGTCAACACGTCTCCTATGTCT-3'
```

Twenty-five picomoles of each of the primers were used in a PCR composed of 7.4 ng of pJfyS147 DNA, 10 µl of 5×PHUSION™ HF buffer, 1 µl of a 10 mM blend of dATP, dTTP, dGTP, and dCTP, and 1 unit of PHUSION™ Hot Start II DNA Polymerase in a final volume of 50 µl. The PCR was performed in a thermocycler programmed for 1 cycle at 98° C. for 30 seconds; 30 cycles each at 98° C. for 7 seconds, 55° C. for 15 seconds, and 72° C. for 25 seconds, and 1 cycle at 72° C. for 5 minutes.

The completed PCR was submitted to 0.65% agarose gel electrophoresis in TBE buffer where a 1.6 kb band was excised from the gel and agarose was extracted using a Nucleospin® PCR Cleanup and Gel Extraction Kit.

Figure 8:
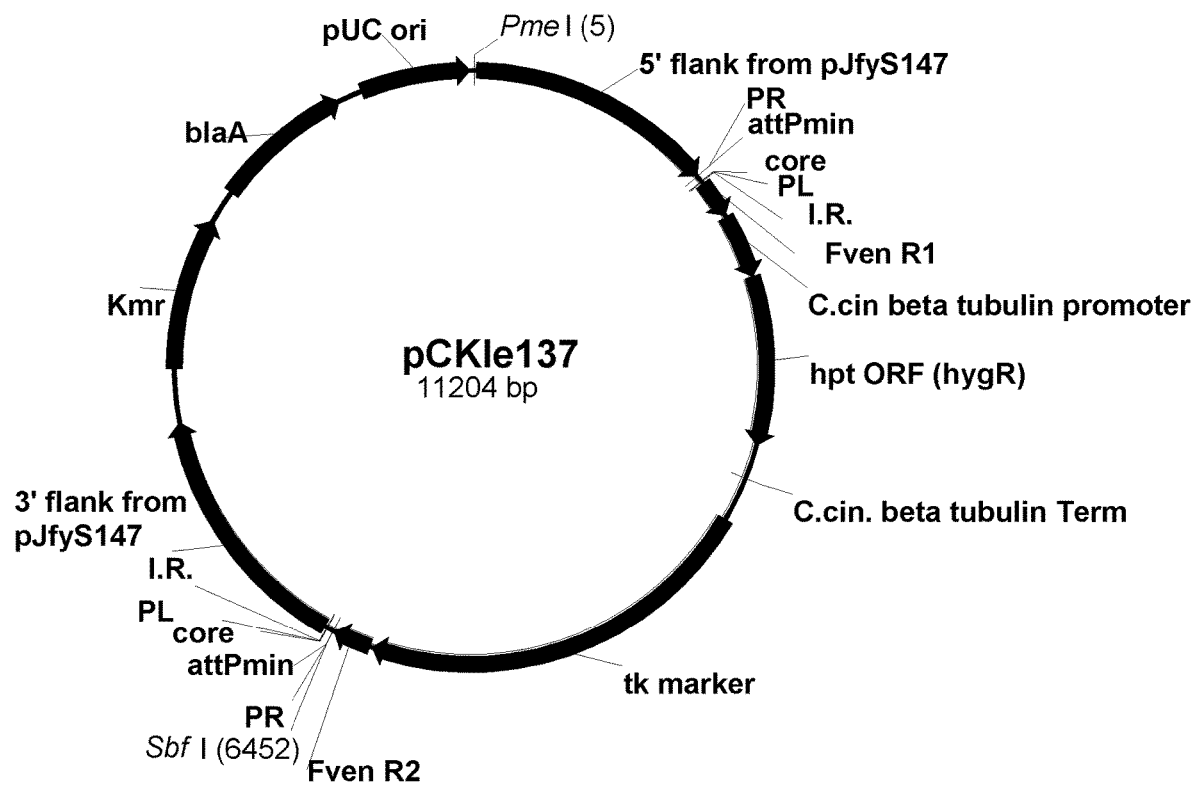
FIG. 8 shows a restriction map of plasmid pCKIe137.

The purified fragment was inserted into Sbf 1-digested pCKIe136 using an IN-FUSION® HD PCR Cloning Kit. The reaction was composed of 2 µl of 5× IN-FUSION® HD Enzyme Premix, 100 ng of Sbf I-digested pCKIe136, and 33.6 ng of the 1.6 kb purified PCR product in a 10 µl reaction volume. The reaction was incubated for 15 minutes at 50° C. Then 1 µl was used to transform 50 µl of Stellar™ *E. coli* chemically competent cells as described above. Plasmid DNA was isolated using a QIAprep® Spin Miniprep Kit. Plasmid DNA from the transformants was screened by restriction digestion with Stu I FD for production of 1.4 kb, 4.6 kb, and 5.1 kb fragments. Sequencing of one of the plasmids verified that the plasmid contained the correct inserts with no PCR errors. The plasmid was designated pCKIe137 (FIG. 8).

Example 52: Removal of the amdS Marker from the cbh1 locus of *Trichoderma reesei* Strain attP-FRT to Generate Strain CKIe215

*Trichoderma reesei* strain attP-FRT (Example 50) was transformed with Pme I-linearized pCKIe137 selecting for hygromycin resistance as described in Example 1. Transformation plates were incubated at 28° C. for 5 days. Fifty transformants were obtained and each one was picked and transferred to a PDA plate and incubated for 6 days at 30° C. Spore PCR using a PHIRE® Plant Direct PCR Kit was utilized to identify transformants which had the correct integration of the pCKIe137 DNA at the 3' end of the cbh1 locus. Briefly, spores from each of the transformants were collected with a sterile 1 µl inoculation loop and transferred to 15 µl of Kit-supplied dilution buffer in microfuge tubes and incubated for 5 minutes at room temperature. The 20 µl spore PCR contained 1×PHIRE® Plant Direct PCR buffer (contains dNTPs and Mg), 10 pmol of forward and reverse primers listed below, 0.4 µl of PHIRE® II Hot Start DNA Polymerase, and 1 µl of supernatant from each spore suspension.

```
Forward primer (homology to tk marker):
                                 (SEQ ID NO: 233)
5'-TACCTCCGGGATGGTCCAGA-3'

Forward primer (homology to amdS marker):
                                 (SEQ ID NO: 234)
5'-TTCCATCTCTCAAAGGAAGA-3'

Reverse primer (homology to
outside 3' cbh1 flank):
                                 (SEQ ID NO: 235)
5'-TTGCTCTTATTGAGACCATGCG-3'
```

The PCRs were incubated in a thermocycler programmed for 1 cycle at 98° C. for 5 minutes; 40 cycles each at 98° C. for 5 seconds, 60° C. for 5 seconds, and 72° C. for 38 seconds; and 1 cycle at 72° C. for 1 minute.

The completed PCRs were subjected to 0.8% agarose gel electrophoresis in TBE buffer. Transformants with correct targeting of plasmid DNA to the cbh1 locus produced a 2.5 kb fragment. Transformants that did not have correct targeting of plasmid DNA to the cbh1 locus produced a 1.9 kb fragment.

Spore PCR was also performed as described above for the 5' end of the cbh1 locus.

```
Forward primer (homology to
outside 5' cbh1 flank):
                                 (SEQ ID NO: 236)
5'-GTACAAACAACTACCTGGTG-3'

Reverse primer (homology to hpt marker):
                                 (SEQ ID NO: 237)
5'-GTCAGCTTCATTTTCCGTGT-3'

Reverse primer (homology to amdS marker):
                                 (SEQ ID NO: 238)
5'-CTCGAATCGAGCCACCGATA-3'
```

The PCRs were incubated in a thermocycler programmed for 1 cycle at 98° C. for 5 minutes; 40 cycles each at 98° C. for 5 seconds, 55° C. for 5 seconds, and 72° C. for 1 minute 5 seconds; and 1 cycle at 72° C. for 1 minute.

The completed PCRs were subjected to 0.8% agarose gel electrophoresis in TBE buffer. Transformants with correct targeting of plasmid DNA to the cbh1 locus produced a 2 kb fragment. Transformants that did not have the correct targeting of plasmid DNA to the cbh1 locus produced a 3.2 kb fragment.

Transformants with correct targeting of plasmid DNA to the cbh1 locus were chosen for spore isolation. Spores from PDA plates were collected using a 1 µl inoculation loop and added to 2 ml of 0.01% TWEEN® 20. One µl of each spore suspension and 200 µl of 0.01% TWEEN® 20 were spread onto 150 mm PDA+1M sucrose plates. The plates were incubated for 2 days at 30° C. Isolated colonies were picked with a sterile metal spear and transferred to PDA plates and incubated at 30° C. for 5 days. Spore PCR using a PHIRE® Plant Direct PCR Kit and the primers and PCR conditions shown above was performed to identify spore isolates with correct integration at the cbh1 locus.

Correct spore isolates were chosen and the hpt/tk markers were looped out using 5-fluorodeoxyuridine (FdU) counterselection as described below. Spores from a 6 day old PDA plate were collected in 3 ml of 0.01% TWEEN® 20 and the spore concentration was determined using a hemocytometer. Approximately $10^5$ spores from each isolate were spread onto 150 mm FdU plates. The FdU plates were incubated at 30° C. for 6-7 days. Two to eight FdU colonies were selected for each strain and transferred to PDA plates. The plates were incubated at 30° C. for 5-6 days. Spore PCRs using a PHIRE® Plant Direct PCR Kit were performed as described above using the primers shown below.

```
Forward primer (homology to tk marker):
                                 (SEQ ID NO: 239)
5'-TACCTCCGGGATGGTCCAGA-3'

Reverse primer (homology to 3' cbh1 flank):
                                 (SEQ ID NO: 240)
5'-ATGGGTCATTACCAATTGGC-3'

Forward primer (homology to 5' cbh1 flank):
                                 (SEQ ID NO: 241)
5'-GTAATTTGCCTGCTTGACCG-3'
```

The PCRs were incubated in a thermocycler programmed for 1 cycle at 98° C. for 5 minutes; 40 cycles each at 98° C. for 5 seconds, 63° C. for 5 seconds, and 72° C. for 25 seconds; and 1 cycle at 72° C. for 1 minute.

The completed PCRs were subjected to 0.8% agarose gel electrophoresis in TBE buffer.

Isolates with loopout of the hpt/tk markers produced a 0.6 kb fragment and isolates that retained the hpt/tk markers produced a 1.2 kb fragment.

An additional round of spore isolation was performed with isolates with the hpt/tk marker looped-out as described above. Plates were incubated for 2 days at 30° C. Isolated colonies were picked with a sterile metal spear, transferred to PDA plates, and incubated at 30° C. Spore PCR using the PHIRE® Plant Direct PCR Kit and forward primers and reverse primers was utilized to identify final spore isolates with the correct hpt/tk marker loopout as described above.

PCRs using the primers and PCR conditions shown below were used to generate a PCR fragment from nine spore isolates for sequencing.

```
Forward primer (homology to 5' cbh1
flank, upstream of attP site):
                                 (SEQ ID NO: 242)
5'-TTTGAGCTACAAGAACCTGTGGGG-3'

Reverse primer (homology to 3' cbh1 flank,
downstream of attP site):
                                 (SEQ ID NO: 243)
5'-CGAAAAGGCCACCTGTTGAGAGGCT-3'
```

Spore PCR was performed using a PHIRE® Plant Direct PCR Kit. The PCRs (20 µl) were composed of 1×PHIRE® Plant Direct PCR buffer (contains dNTPs and Mg), 10 pmol of forward and reverse primers listed above, 0.4 µl of PHIRE® II Hot Start DNA Polymerase, and 1 µl of supernatant from a spore suspension. The PCRs were performed in a thermocycler programmed for 1 cycle at 98° C. for 5 minutes; 40 cycles each at 98° C. for 5 seconds, 72° C. for 28 seconds, and 1 cycle at 72° C. for 1 minute. The 1.37 kb PCR fragments were purified using a USB® ExoSAP-IT® PCR Product Cleanup Kit (Affymetrix). Sequencing of the PCR fragments verified that integration of pCKIe137 at the cbh1 locus had occurred by TP901-1 recombinase-mediated recombination between the host attP sites and plasmid attB sites.

Genomic DNA from the final spore isolates was prepared and subjected to Southern blot analysis. *Trichoderma reesei* strains were grown in 25 ml of YP medium supplemented with 2% glucose (w/v) in a 125 ml baffled shake flask at 28° C. for 2 days with agitation at 200 rpm. The mycelia were harvested by filtration using a MIRACLOTH® lined funnel and frozen in liquid nitrogen. The frozen mycelia were disrupted by quickly smashing with a hammer while wrapped inside the MIRACLOTH®. Approximately 2 g of the disrupted mycelia were then transferred to a 50 ml polypropylene conical centrifuge tube containing 10 ml of 1× lysis buffer (100 mM EDTA, 10 mM Tris pH 8.0, 1% TRITON® X-100, 0.5 M Guanidine-HCl, 200 mM NaCl) and 3 µl of a 100 mg RNase A (QIAGEN Inc.) per ml stock solution. The tube was mixed by gentle vortexing, and then incubated at room temperature for 5 minutes after which was added 150 µl of a Proteinase K (QIAGEN Inc.) stock solution containing 20 mg/ml. The tube was mixed by inversion and incubated at 50° C. for 1 hour. The tube was then centrifuged at 7240×g for 20 minutes. The supernatant was then added to a pre-equilibrated QIAGEN-tip 100 (QIAGEN Inc.) and the remaining DNA extraction steps were performed according to the manufacturer's instructions for a Plasmid Midi Kit. The DNA was re-suspended in 200 µl of TE buffer.

For Southern blot analysis approximately 2 µg of genomic DNA was digested with 1 µl of Nco I and subjected to 0.8% agarose electrophoresis in TBE buffer. The DNA in the gel was depurinated, denatured, neutralized, and transferred to a NYTRAN® Supercharge membrane as described in Example 3. The DNA was UV cross-linked to the membrane using a CL-1000 UV Crosslinker (UVP), LLC) and prehybridized for 1 hour at 42° C. in 20 ml of DIG Easy Hyb.

Templates for probes hybridizing to the 5' and 3' flanks of the cbh1 gene were generated using PHUSION™ Hot Start II High Fidelity DNA Polymerase and gene-specific forward and reverse primers shown below.

Twenty-five picomoles of each of the primers were used in PCRs composed of 100 ng of *T. reesei* 981-0-8 genomic DNA, 10 µl of 5×PHUSION™ HF buffer, 1 µl of a 10 mM blend of dATP, dTTP, dGTP, and dCTP, and 1 unit of PHUSION™ Hot Start II DNA Polymerase in a final volume of 50 µl. The PCRs were performed in a thermocycler programmed for 1 cycle at 98° C. for 2 minutes; 35 cycles each at 98° C. for 10 seconds, 72° C. for 30 seconds, and 1 cycle at 72° C. for 5 minutes. The completed PCRs were purified by 0.65% agarose gel electrophoresis in TBE buffer where a 0.55 kb DNA band (3' flank) and a 0.35 kb band (5' flank) were excised from the gels and the DNA was extracted using a Nucleospin® PCR Cleanup and Gel Extraction Kit.

Probes hybridizing to the 5' and 3' flanks of the cbh1 gene were generated using a PCR DIG Probe Synthesis Kit with the forward and reverse primers indicated below. The 50 µl PCRs were composed of 1×PCR DIG Probe Synthesis mix, 25 pmol of each primer, 1× PCR buffer with MgCl$_2$, 80 ng of purified probe template (described above), and 2.6 units of EXPAND® High Fidelity DNA polymerase. The PCRs were performed in a thermocycler programmed for 1 cycle at 95° C. for 2 minute; 30 cycles each at 95° C. for 30 seconds, 55° C. for 30 seconds, and 72° C. for 40 seconds; and 1 cycle at 72° C. for 7 minutes.

Primers for cbh1 5' Flanking Region Probe

```
Forward primer:
                                        (SEQ ID NO: 244)
    5'-TAGGGTCGGCAACGGCAAAA-3'

Reverse primer:
                                        (SEQ ID NO: 245)
    5'-CCCACATTGCTCCAAACCCC-3'
```

Primers for cbh1 3' Flanking Region Probe

```
Forward primer:
                                        (SEQ ID NO: 246)
    5'-AATGACCCATAGGGAGACAAACAGCATAAT-3'

Reverse primer:
                                        (SEQ ID NO: 247)
    5'-TGTTGGACGCAGGATTTTGGA-3'
```

Hybridization was performed as described in Example 3.

Southern blot analysis identified several final spore isolates that produced a 5.4 kb hybridizing fragment, verifying the correct removal of the amdS marker at the cbh1 locus and loopout of the hpt/tk markers. The parent *T. reesei* (attP-FRT) cbh1 locus produced 1.6 kb and 6.4 kb hybridizing fragments while strains containing the hpt/tk marker produced 2.7 kb and 7.3 kb hybridizing fragments. One spore isolate was chosen as the final strain and designated *T. reesei* CKIe215.

Example 53: Construction of TP901-1 Integration Plasmid pDM315

Expression plasmid pDM315 was constructed to target a *Humicola insolens* endoglucanase V (EGV) (U.S. Pat. No. 8,735,549) expression cassette to TP901-1 recombinase recognition sites at the cbh1 locus in *T. reesei* CKIe215. Plasmid pDM315 has attB sites which can recombine with the attP sites at the cbh1 locus.

A 0.25 kb PCR fragment was generated from pECVV7 (Example 46) using PHUSION™ Hot Start II DNA Polymerase and the forward and reverse primers shown below.

```
Forward primer:
                                        (SEQ ID NO: 248)
5'-GCAATTAATGTGAGTTAGCT-3'

Reverse primer:
                                        (SEQ ID NO: 249)
5'-TAACAATCCTACATTCGGTCGAAAAGCATTTACCTTGATTGAGAT-
3'
```

Fifty picomoles of each of the primers were used in a PCR composed of 700 ng of pECW7 plasmid DNA, 1×PHUSION™ HF Buffer, 1 µl of a 10 mM blend of dATP, dTTP, dGTP, and dCTP, and 1 unit of PHUSION™ Hot Start II DNA Polymerase in a final volume of 50 µl. The PCR was performed in a thermocycler programmed for 1 cycle at 98° C. for 2 minutes; 34 cycles each at 98° C. for 15 seconds, 59° C. for 30 seconds, and 72° C. for 3 minutes, and 1 cycle at 72° C. for 10 minutes. The completed PCR was purified by 0.8% agarose gel electrophoresis in TAE buffer where a 0.25 kb DNA band was excised from the gel and extracted using a Nucleospin® Extract II Kit (Example 8).

A 5.3 kb PCR fragment containing the *Humicola insolens* endoglucanase V expression cassette and amdS marker was generated from plasmid pMJ05 (U.S. Pat. No. 8,735,549) using the forward and reverse primers shown below.

```
Forward primer:
                                     (SEQ ID NO: 250)
5'-ATCTCAATCAAGGTAAATGCTTTTCGACCGAATGTAGGATTGTTA-
3'

Reverse primer:
                                     (SEQ ID NO: 251)
5'-GTTAATTGTGTTGGCAATTATCAGTCTAGGATGCATTCTACGCCAG-
3'
```

Fifty picomoles of each of the primers were used in a PCR composed of 500 ng of pMJ05 plasmid DNA, 1×PHUSION™ HF Buffer, 1 μl of a 10 mM blend of dATP, dTTP, dGTP, and dCTP, and 1 unit of PHUSION™ Hot Start II DNA Polymerase in a final volume of 50 μl. The PCR was performed in a thermocycler programmed for 1 cycle at 98° C. for 2 minutes; 34 cycles each at 98° C. for 15 seconds, 59° C. for 30 seconds, and 72° C. for 3 minutes, and 1 cycle at 72° C. for 10 minutes. The completed PCR was purified by 0.8% agarose gel electrophoresis in TAE buffer where a 5.3 kb DNA band was excised from the gel and extracted using a Nucleospin® Extract II Kit (Example 8).

A 0.2 kb PCR fragment was generated from pECW7 using PHUSION™ Hot Start II DNA Polymerase and the forward and reverse primers shown below.

```
Forward primer:
                                     (SEQ ID NO: 252)
5'-CTGGCGTAGAATGCATCCTAGACTGATAATTGCCAACACAATTAAC-
3'

Reverse primer:
                                     (SEQ ID NO: 253)
5'-GCCATAATGCATAGGTAGGT-3'
```

Fifty picomoles of each of the primers were used in a PCR composed of 700 ng of pECW7 plasmid DNA, 1×PHUSION™ HF buffer, 1 μl of a 10 mM blend of dATP, dTTP, dGTP, and dCTP, and 1 unit of PHUSION™ Hot Start II DNA Polymerase in a final volume of 50 μl. The PCR was performed in a thermocycler programmed for 1 cycle at 98° C. for 2 minutes; 34 cycles each at 98° C. for 15 seconds, 59° C. for 30 seconds, and 72° C. for 3 minutes, and 1 cycle at 72° C. for 10 minutes. The completed PCR was purified by 0.8% agarose gel electrophoresis in TAE buffer. A 0.2 kb DNA band was excised from the gel, and extracted using a Nucleospin® Extract II Kit (Example 8).

The three purified PCR fragments described above were joined together using SOE PCR and the forward and reverse primers shown below.

```
Forward primer:
                                     (SEQ ID NO: 254)
5'-CTCAGAATTAACCCTCACTAA-3'

Reverse primer:
                                     (SEQ ID NO: 255)
5'-GTACTTAATTAACCAAGGGCG-3'
```

Fifty picomoles of each of the primers were used in a PCR composed of 24 ng of the 0.25 kb PCR fragment, 30 ng of the 5.3 kb PCR fragment, 26 ng of the 0.2 kb PCR fragment, 1×PHUSION™ HF buffer, 1 μl of a 10 mM blend of dATP, dTTP, dGTP, and dCTP, and 1 unit of PHUSION™ Hot Start II DNA Polymerase in a final volume of 50 μl. The PCRs were performed in triplicate. The primers were omitted until after cycle 6 as indicated below. The thermocycler was programmed for 1 cycle at 95° C. for 2 minutes; and 5 cycles each at: 95° C. for 30 seconds, 1 minute ramping down from 95° C. and decreasing by 1° C./second down to 35° C., and 72° C. for 4 minutes. The PCR samples were then cooled to 4° C. and held at 4° C. until the primers were added. After primer addition the program continued for 10 cycles at 95° C. for 30 seconds, 60° C. for 30 seconds, and 72° C. for 4 minutes. Then the program proceeded for 20 cycles at 95° C. for 30 seconds, 60° C. for 30 seconds, and 72° C. starting at 4 minutes with the addition of 20 seconds for each successive cycle. The three identical 50 μl reactions were combined and purified by 0.8% agarose gel electrophoresis in TAE buffer where an approximately 5.4 kb DNA band was excised from the gel and extracted using a Nucleospin® Extract II Kit (Example 8).

Approximately 25 μg of pECW7 DNA was digested with Sbf I and Mss I (also called Pme I). The digested DNA was separated by 0.8% agarose gel electrophoresis in TAE buffer where an approximately 7.1 kb fragment was excised from the gel and extracted using a Nucleospin® Extract II Kit (Example 8).

Figure 9:
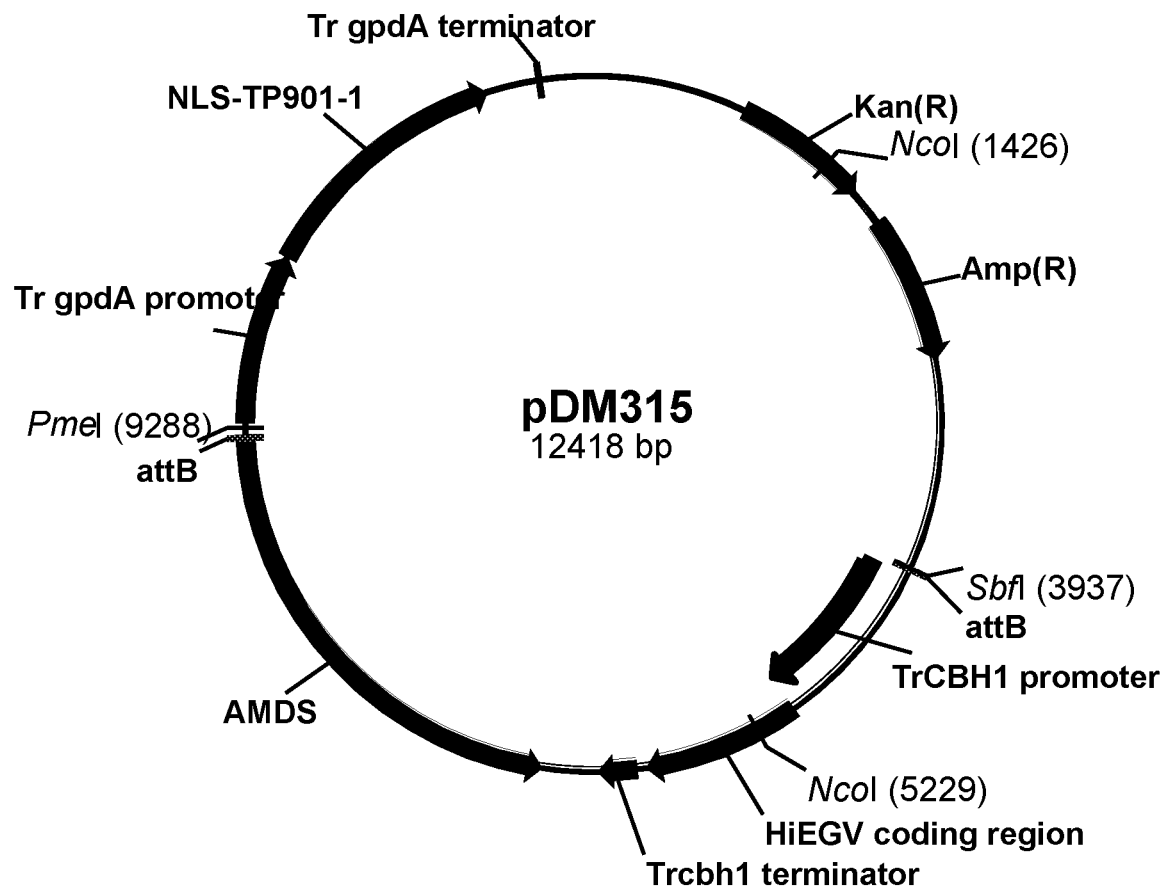
FIG. 9 shows a restriction map of plasmid pDM315.

The 5.4 kb SOE PCR fragment was inserted into Sbf I and Mss I digested pECW7 using an IN-FUSION® HD Cloning Kit. The reaction was composed of 50 ng of Sbf I and Mss I digested pECW7, 111 ng of the 5.4 kb SOE PCR product, and 4 μl of IN-FUSION® buffer plus Enzyme in a 20 μl reaction volume. The reaction was incubated for 15 minutes at 50° C. and then held on ice. A 2 μl aliquot was used to transform 50 μl of Stellar™ *E. coli* chemically competent cells by addition to a tube containing the competent cells and incubating the cells on ice for 30 minutes. The tube was incubated at 42° C. for 45 seconds after which 450 μl of SOC medium were added. The tube was then incubated at 37° C. with agitation at 200 rpm for 1 hour. The reaction was transferred to a microfuge tube and was centrifuged at 13,000 rpm for 10 seconds. Three hundred μl supernatant was discarded, the cells were resuspended in 200 μl supernatant and were transferred to two 150 mm 2XYT plus ampicillin plates. The plates were incubated overnight at 37° C. *E. coli* colonies were used to inoculate 3 ml of LB+Amp in a 14 ml Falcon round-bottom polypropylene tube and incubated 37° C. overnight with agitation at 200 rpm. Plasmid DNA was isolated using a QIAprep® Spin Miniprep Kit. The plasmid DNA from the transformants was screened by restriction digestion with Nco I HF for production 3.8 and 8.6 kb fragments. Sequencing of one of the plasmids verified that the construct contained the correct inserts with no PCR errors. The plasmid was designated pDM315 (FIG. 9).

Example 54: Multiple Site Specific Integrations at *Trichoderma reesei* cbh1 and cbh2 Loci Using TP901-1 Integrase and FLP/FRT Simultaneously In this Example *T. reesei* strain CKIe215 (Example 52) which has attP sites inserted at the cbh1 locus and FRT sites inserted at the cbh2 locus was transformed with plasmids pDM313 (Example 14) and pDM315 (Example 53) to achieve targeting of constructs to the attP sites and FRT sites at two different loci. Plasmid pDM313 has an *A. fumigatus* beta-glucosidase expression cassette and the hpt marker for hygromycin resistance flanked by FRT sites, and the *S. cerevisiae* flippase gene under the control of the *T. reesei* gpdA promoter. Plasmid pDM315 has a *Humicola insolens* endoglucanase V expression cassette and the amdS marker flanked by attB sites, and the TP901-1 recombinase gene under the control of the *T. reesei* gpdA promoter.

Protoplasts of CKIe215 were prepared as described in Example 1. Approximately 1.5 µg of pDM313 circular DNA and approximately 3.2 µg of pDM315 circular DNA were added to 100 µl of the protoplast solution and mixed gently. PEG buffer (250 µl) was added, and the reaction was mixed and incubated at 34° C. for 30 minutes. STC (3 ml) was then added and the reaction was mixed and then spread onto two COVE+2% glucose transformation plates. Ten transformation reactions were prepared and plated. After incubation at 28° C. for 16 hours, 20 ml of a COVE+2% glucose overlay supplemented with 35 µg of hygromycin B per ml were added to each plate.

The transformation plates were incubated at 28° C. for 9 days and at room temperature for 5 days. Twenty-eight transformants were transferred to COVE+2% glucose plates and incubated at 30° C. for 3-5 days. Spore PCR using a PHIRE® Plant Direct PCR Kit was utilized to identify transformants that had integrated the two different plasmids at the cbh1 and cbh2 loci. Briefly, spores from each transformant were collected with a sterile 1 µl inoculation loop and transferred to 15 µl of Kit-supplied dilution buffer in a 96-well plate and incubated for 5 minutes at room temperature. The spore suspension was centrifuged briefly in a plate spinner and 1 µl of supernatant was used in the spore PCR. The 20 µl spore PCR was composed of 1×PHIRE® Plant Direct PCR buffer (contains dNTPs and Mg), 10 pmol of the forward primers shown below, 10 pmol of the reverse primers shown below, 0.4 µl of PHIRE® II Hot Start DNA Polymerase, and 1 µl of supernatant from the spore suspension.

PCR Screen of 5' End of cbh1 Locus (Primer Set 1)

```
Forward primer (homology to 5' flanking
region of cbh1 upstream of attP site):
                                (SEQ ID NO: 256)
5'-GAGCTTGGACATAACTGTTCC-3'

Reverse primer (homology to H. insolens EGV gene):
                                (SEQ ID NO: 257)
5'-AAAAGACAGGCTGGTTCACG-3'
```

PCR Screen of 5' End of cbh2 Locus (Primer Set 2)

```
Forward primer (homology to 5' flanking
region of cbh2 upstream of FRT-F site):
                                (SEQ ID NO: 258)
5'-GTTGGTATAGAGCAGCGTTC-3'

Reverse primer (homology to 3' flanking
region of cbh2):
                                (SEQ ID NO: 259)
5'-CTAGGTAGGTAGGTAGTATA-3'

Reverse primer (homology to A. fumigatus
beta-glucosidase):
                                (SEQ ID NO: 260)
5'-TGGTGGAGAGAAAGCCAATT-3'
```

The PCRs were incubated in a thermocycler programmed for 1 cycle at 98° C. for 5 minutes; 40 cycles each at 98° C. for 10 seconds, 60° C. for 10 seconds, and 72° C. for 1 minute and 10 seconds; and 1 cycle at 72° C. for 1 minute and 10 seconds.

The completed PCRs were subjected to 0.8% agarose gel electrophoresis in TAE buffer. Transformants having the correct targeting of plasmid DNA to the cbh1 locus produced a 1.4 kb fragment with primer set 1. Transformants having the correct targeting of plasmid DNA to the cbh2 locus produced a 1.35 kb fragment with primer set 2. Transformants having the correct targeting to both the cbh1 and cbh2 loci produced the 1.4 kb fragment with primer set 1 and the 1.35 kb fragment with primer set 2.

Spore PCR using a PHIRE® Plant Direct PCR Kit, as described above, was utilized to verify correct integration at the 3' end of both the cbh1 and cbh2 loci. Transformants identified as having integration at both the cbh1 and cbh2 loci by the 5' end PCR screen described above were screened with the primers listed below.

PCR Screen of 3' End of cbh1 Locus

```
Forward primer (homology to amdS marker):
                                (SEQ ID NO: 261)
5' AATAACGCTGTCTTCCGCAG-3'

Reverse primer (homology to 3' flanking region of
cbh1, downstream of FRT-F3 site):
                                (SEQ ID NO: 262)
5' ATGGGTCATTACCAATTGGC-3'
```

PCR Screen of 3' End of cbh2 Locus

```
Forward primer (homology to hpt marker):
                                (SEQ ID NO: 263)
5' CGTGTTTCTTCCCATTCGCATGCGACCTCGTGGTCATTGAC-3'

Reverse primer (homology to 3' flanking region of
cbh2, past FRT-F3 site):
                                (SEQ ID NO: 264)
5' GCATTGCAACCGCGGCTTTC-3'
```

The PCRs were incubated in a thermocycler programmed for 1 cycle at 98° C. for 5 minutes; 40 cycles each at 98° C. for 10 seconds, 60° C. for 10 seconds, and 72° C. for 1 minute and 10 seconds; and 1 cycle at 72° C. for 1 minute and 10 seconds.

The completed PCRs were subjected to 0.8% agarose gel electrophoresis in TAE buffer. Transformants having the correct targeting of plasmid DNA to the cbh1 locus produced a 1.0 kb fragment. Transformants having the correct targeting of plasmid DNA to the cbh2 locus produced a 0.75 kb fragment. Transformants having the correct targeting to both the cbh1 and cbh2 loci produced the 1.0 kb fragment and the 0.75 kb fragment.

A transformant that produced the correct PCR fragments was chosen for spore isolation. Spores from a COVE+2% glucose plate culture were collected using a 1 µl inoculation loop and added to 2 ml of 0.01% TWEEN® 20. One µl of the spore suspension and 100 µl of 0.01% TWEEN® 20 were spread onto a 150 mm PDA plate. The plate was incubated at 30° C. for 2 days. Isolated colonies were picked with a sterile 10 µl inoculation loop and transferred to COVE2 plates and incubated at 30° C. for 5 days. Spore PCR using a PHIRE® Plant Direct PCR Kit and the primers and PCR conditions shown above for the PCR screen of the 5' end of both loci and the 3' end of the cbh1 locus was used to screen the spore isolates.

The completed PCRs were subjected to 0.8% agarose gel electrophoresis in TBE buffer. Spore isolates having the correct targeting of plasmid pDM315 to the cbh1 locus produced a 1.4 kb fragment from the 5' end of the locus and a 1.0 kb fragment from the 3' end of the locus. Transformants having the correct targeting of plasmid pDM313 to the cbh2 locus produced a 1.35 kb fragment from the 5' end of the locus. Two spore isolates having the correct targeting to both the cbh1 and cbh2 loci were chosen for further analysis. Genomic DNA from these two spore isolates was prepared as described in Example 15.

PCRs using the primers and PCR conditions shown below were used to generate PCR fragments from genomic DNA of the two spore isolates.

```
PCR fragment 1 (2.0 kb):
Forward primer (homology to 5' cbh1 flank,
upstream of attP site):
                                  (SEQ ID NO: 265)
5'-TTTGAGCTACAAGAACCTGTGGGG-3'

Reverse primer (homology to H. insolens EGV gene):
                                  (SEQ ID NO: 266)
5'-ATGTTGAGATCGAAGTGGTT-3'

PCR fragment 2 (1.3 kb):
Forward primer (homology to amdS marker):
                                  (SEQ ID NO: 267)
5'-AATAACGCTGTCTTCCGCAG-3'

Reverse primer (homology to 3' cbh1 flank,
downstream of attP site):
                                  (SEQ ID NO: 268)
5'-CGAAAAGGCCACCTGTTGAGAGGCT-3'
```

To amplify PCR fragments 1 and 2, twenty-five picomoles of each of the primers were used in a PCR composed of 100 ng of genomic DNA, 1×PHUSION™ HF buffer, 1 µl of a 10 mM blend of dATP, dTTP, dGTP, and dCTP, and 2 units of PHUSION™ Hot Start II DNA Polymerase in a final volume of 50 µl. The PCRs were performed in a thermocycler programmed for 1 cycle at 98° C. for 30 seconds; 30 cycles each at 98° C. for 7 seconds, 60° C. for 20 seconds, and 72° C. for 1 minute, and 1 cycle at 72° C. for 5 minutes. The PCR fragments were purified using a Nucleospin® Extract II Kit (Example 8).

Sequencing of PCR fragments 1 and 2 verified that the integration of pDM315 at the cbh1 locus had occurred by TP901-1 recombinase mediated recombination between the host attP sites and plasmid attB sites. The recombined attR site was present just upstream of the EGV expression cassette and the recombined attL site was present just downstream of the amdS marker.

```
PCR fragment 3 (1.35 kb):
Forward primer (homology to 5' cbh2 flank,
upstream of FRT-F site):
                                  (SEQ ID NO: 269)
5'-GTTGGTATAGAGCAGCGTTC-3'

Reverse primer (homology to A. fumigatus
beta-glucosidase gene):
                                  (SEQ ID NO: 270)
5'-TGGTGGAGAGAAAGCCAATT-3'

PCR fragment 4 (0.75 kb):
Forward primer (homology to hpt marker):
                                  (SEQ ID NO: 271)
5'-CGTGTTTCTTCCCATTCGCATGCGACCTCGTGGTCATTGAC-3'

Reverse primer (homology to 3' flanking region of
cbh2, downstream of FRT-F3 site):
                                  (SEQ ID NO: 272)
5'-GCATTGCAACCGCGGCTTTC-3'
```

To amplify PCR fragments 3 and 4, the 40 µl PCR contained 1×PHIRE® Plant Direct PCR buffer (contains dNTPs and Mg), 20 pmol each of the forward and reverse primers listed above, 0.8 µl of PHIRE® II Hot Start DNA Polymerase, and 100 ng of genomic DNA.

The PCRs were performed in a thermocycler programmed for 1 cycle at 98° C. for 5 minutes; 40 cycles each at 98° C. for 10 seconds, 60° C. for 10 seconds, and 72° C. for 1 minute 10 seconds, and 1 cycle at 72° C. for 1 minute 10 seconds. The PCR fragments were purified using a Nucleospin® Extract II Kit (Example 8).

Sequencing of PCR fragments 3 and 4 verified that integration of pDM313 at the cbh2 locus had occurred by flippase mediated recombination between the host FRT sites and plasmid FRT sites.

Genomic DNA from the final spore isolates was prepared and subjected to Southern blot analysis. *Trichoderma reesei* strains were grown in 25 ml of YP medium supplemented with 2% glucose (w/v) in a 125 ml baffled shake flask at 28° C. for 3 days with agitation at 200 rpm. Mycelia samples were harvested by filtering over Whatman 55 mm filter paper, rinsed with deionized water, and transferred to a pre-chilled mortar and pestle. Each mycelia preparation was ground into a fine powder and kept frozen with liquid nitrogen. A total of 0.2-0.3 g of powder was transferred to a 50 ml tube and genomic DNA was extracted using a DNEASY® Plant Maxi Kit.

For Southern blot analysis approximately 1 µg of genomic DNA was digested with of Sca I+Cla I+Hpa I (for cbh1 locus) and Nru I+Mlu I (for cbh2 locus) and subjected to 0.8% agarose electrophoresis in TBE buffer. The DNA in the gels was depurinated, denatured, neutralized, and transferred to NYTRAN® Supercharge membranes as described in Example 3. The DNA was UV cross-linked to the membranes using a CL-1000 UV Crosslinker and prehybridized for 1 hour at 42° C. in 20 ml of DIG Easy Hyb.

The probe for the 3' flank of cbh1 was produced as described in Example 10. Templates for probes hybridizing to the 3' flanks the cbh2 gene, as well as the *H. insolens* endoglucanase V (EGV) and *A. fumigatus* beta-glucosidase (BG) genes, were generated using PHUSION™ Hot Start II High Fidelity DNA Polymerase or PHUSION™ High-Fidelity Hot Start DNA Polymerase and gene-specific forward and reverse primers shown below.

3' cbh2 flank: Fifty picomoles of each of the primers were used in a PCR composed of 100 ng of *T. reesei* RutC30 genomic DNA, 1×PHUSION™ High-Fidelity Hot Start DNA Polymerase buffer, 1 µl of a 10 mM blend of dATP, dTTP, dGTP, and dCTP, and 1 unit of PHUSION™ High-Fidelity Hot Start DNA Polymerase in a final volume of 50 µl. The PCR was performed in a thermocycler programmed for 1 cycle at 98° C. for 2 minutes; 34 cycles each at 98° C. for 15 seconds, 60° C. for 30 seconds, and 72° C. for 1 minute 30 seconds, and 1 cycle at 72° C. for 10 minutes. The completed PCR was purified by 0.8% agarose gel electrophoresis in TAE buffer. A 0.46 kb DNA band was excised from the gel and the DNA was extracted using a Nucleospin® PCR Cleanup and Gel Extraction Kit.

A probe hybridizing to the 3' flanking region of the cbh2 gene was generated using a PCR DIG Probe Synthesis Kit with the forward and reverse primers indicated below. The 50 µl PCR was composed of 1×PCR DIG Probe Synthesis mix, 50 pmol of each primer, 1×PCR buffer with MgCl$_2$, 24 ng of purified probe template (described above), and 2.6 units of EXPAND® High Fidelity DNA polymerase. The PCR was incubated in a thermocycler programmed for 1 cycle at 95° C. for 2 minutes; 30 cycles each at 95° C. for 30 seconds, 59° C. for 30 seconds, and 72° C. for 45 seconds; and 1 cycle at 72° C. for 7 minutes.

```
Forward primer:
                                (SEQ ID NO: 273)
5'-TCTTGAGCCGCATCGCATAGA-3'

Reverse primer:
                                (SEQ ID NO: 274)
5'-TACGGTCAGCGCTCATGCGAA-3'
```

EGV and BG probes: To make probe templates, 25 picomoles of each of the primers listed below were used in a PCR composed of 5 ng of either pDM315 (EGV) or pDM313 (BG) DNA, 10 µl of 5×PHUSION™ HF buffer, 1 µl of a 10 mM blend of dATP, dTTP, dGTP, and dCTP, and 1 unit of PHUSION™ Hot Start II DNA Polymerase in a final volume of 50 µl. For EGV the PCR was performed in a thermocycler programmed for 1 cycle at 98° C. for 30 seconds; 35 cycles each at 98° C. for 7 seconds, 72° C. for 15 seconds; 1 cycle at 72° C. for 5 minutes and 1 cycle at 98° C. for 30 seconds. For BG the thermocycler was programmed for 1 cycle at 98° C. for 30 seconds; 35 cycles each at 98° C. for 7 seconds, 66° C. for 15 seconds, 72° C. for 15 seconds; and 1 cycle at 72° C. for 5 minutes. The completed PCRs were purified by 0.65% agarose gel electrophoresis in TBE buffer. A 0.54 kb DNA band (EGV) and 0.5 kb band (BG) were excised from the gels and the DNA was extracted using a Nucleospin® PCR Cleanup and Gel Extraction Kit.

Probes hybridizing to the EGV and BG genes were generated using a PCR DIG Probe Synthesis Kit with the forward and reverse primers indicated below. The 50 µl PCR contained 1×PCR DIG Probe Synthesis mix, 50 pmol of each primer, 1×PCR buffer with MgCl$_2$, 80-90 pg of purified probe template (described above), and 2.6 units of EXPAND® High Fidelity DNA polymerase. The PCRs were performed in a thermocycler programmed for 1 cycle at 95° C. for 2 minute; 30 cycles each at 95° C. for 30 seconds, 58° C. for 30 seconds, and 72° C. for 40 seconds; and 1 cycle at 72° C. for 7 minutes.

Primers for EGV Probe

```
Forward primer:
                                (SEQ ID NO: 275)
5'-TCCGGTCCTGTTGCTGGCAA-3'

Reverse primer:
                                (SEQ ID NO: 276)
5'-TTCGTGCAAGTGCTGCCAGC-3'
```

Primers for BG Probe

```
Forward primer:
                                (SEQ ID NO: 277)
5'-ATGAGATTCGGTTGGCTCGAG-3'

Reverse primer:
                                (SEQ ID NO: 278)
5'-AAAGACTCCGCGGGTATAGCTC-3'
```

Southern hybridization was performed as described in Example 3.

The Southern blot containing the Sca I/Cla I/Hpa I digested DNA was probed with both the 3' cbh1 flanking region and EGV probes. Southern blot analysis identified final spore isolates that produced 6 kb and 4.3 kb hybridizing fragments, verifying the correct integration of pDM315 DNA at the attP sites at the cbh1 locus. The parent *T. reesei* (CKIe215) cbh1 locus produced a 5.5 kb hybridizing fragment with these probes. The blot containing the Nru I/Mlu I digested DNA was probed with both the 3' cbh2 flanking region and BG probes. Southern blot analysis identified final spore isolates that produced 6.9 kb and 5.4 kb hybridizing fragments, verifying the correct integration of pDM313 DNA at the FRT sites of the cbh2 locus. The parent *T. reesei* (CKIe215) cbh2 locus produced a 6.4 kb hybridizing fragment with these probes. Combining the results of the two Southern blots indicates the final spore isolates had the correct simultaneous integration of pDM315 DNA at the attP sites of the cbh1 locus and pDM313 DNA at the FRT sites of the cbh2 locus.

Example 55: Construction of Plasmid pQM43 for Targeting a FRT-F Site Containing Non-Functional amdS Marker to *Trichoderma reesei* cbh1 Locus Plasmid pQM43 was constructed for targeting a non-functional amdS fragment (designated "non-functional amdS fragment 3") flanked at its 5' by a FRT-F site to the *T. reesei* cbh1 gene locus. In the construct, the FRT-F site (49 bp) was added within the first intron of an approximately 1 kb non-functional amdS fragment as described below. An approximately 400 bp fragment containing the *T. reesei* cbh1 5' flanking region and FRT-F fragment was amplified from *T. reesei* RutC30 genomic DNA using primers 1208187 and 1208194 shown below. The non-functional amdS fragment 3 flanked by a FRT-F site was amplified from pAllo1 (WO 04/111228) using primers 1208195 and 1208196 shown below.

```
Primer 1208187:
                                (SEQ ID NO: 279)
5'-GATTGAGTTGAAACTGCCTAAGATCTCG-3'

Primer 1208194:
                                (SEQ ID NO: 280)
5'-CTATACTTTCTAGAGAATAGGAACTCGGAATAGGAACTTCAAGGTGC
GCAGTCCGCGGTTGAC-3'

Primer 1208195:
                                (SEQ ID NO: 281)
5'-CTATTCCGAGTTCCTATTCTCTAGAAAGTATAGGAACTTCGGCGTTG
TTACATCTCCCTGAG-3'

Primer 1208196:
                                (SEQ ID NO: 282)
5'-GCGTCAGGCTTTCGCCACGTCTACGCCAGGACCGAGCAAG-3'
```

The first PCR was composed of 100 ng of *T. reesei* RutC30 genomic DNA, 1 µl of 10 mM dNTPs, 1 µM primers, 1×PHUSION® High-Fidelity Reaction Buffer, and 1 unit of PHUSION® Hot Start High-Fidelity DNA Polymerase in a final volume of 50 µl. The second PCR was composed of 100 ng of pAllo1, 1 µl of 10 mM dNTPs, 1 µM primers, 1×PHUSION® High-Fidelity Reaction Buffer, and 1 unit of PHUSION® Hot Start High-Fidelity DNA Polymerase in a final volume of 50 µl. Both reactions were performed in a thermocycler programmed for 1 cycle at 95° C. for 2 minutes; 35 cycles each at 95° C. for 15 seconds, 60° C. for 30 seconds, and 72° C. for 1 minute and 15 seconds; and 1 cycle at 72° C. for 10 minutes. The PCR products were separated by 0.7% agarose gel electrophoresis in TAE buffer where fragments of approximately 400 bp and 1 kb were excised from the gel and extracted using a Nucleospin® Extract II Kit (Example 8).

The third PCR was composed of 100 ng of each of the 400 bp and 1 kb purified PCR products, 1 µl of 10 mM dNTPs, 1×PHUSION® High-Fidelity Reaction Buffer, and 1 unit of PHUSION® Hot Start High-Fidelity DNA Polymerase in a final volume of 48 µl. The reaction was performed in a thermocycler programmed for 1 cycle at 95° C. for 2 minutes; and 5 cycles each at 95° C. for 15 seconds, 60° C. for 30 seconds, and 72° C. for 2 minutes. Primers 1208187 and 1208196 were then added at final concentrations of 1 µM and continued for 30 cycles each at 95° C. for 15 seconds, 60° C. for 30 seconds, and 72° C. for 2 minutes, and 1 cycle at 72° C. for 10 minutes. The PCR product was separated by 0.7% agarose gel electrophoresis in TAE buffer where a fragment of approximately 1.4 kb were excised from the gel and extracted using a Nucleospin® Extract II Kit (Example 8).

Figure 10:
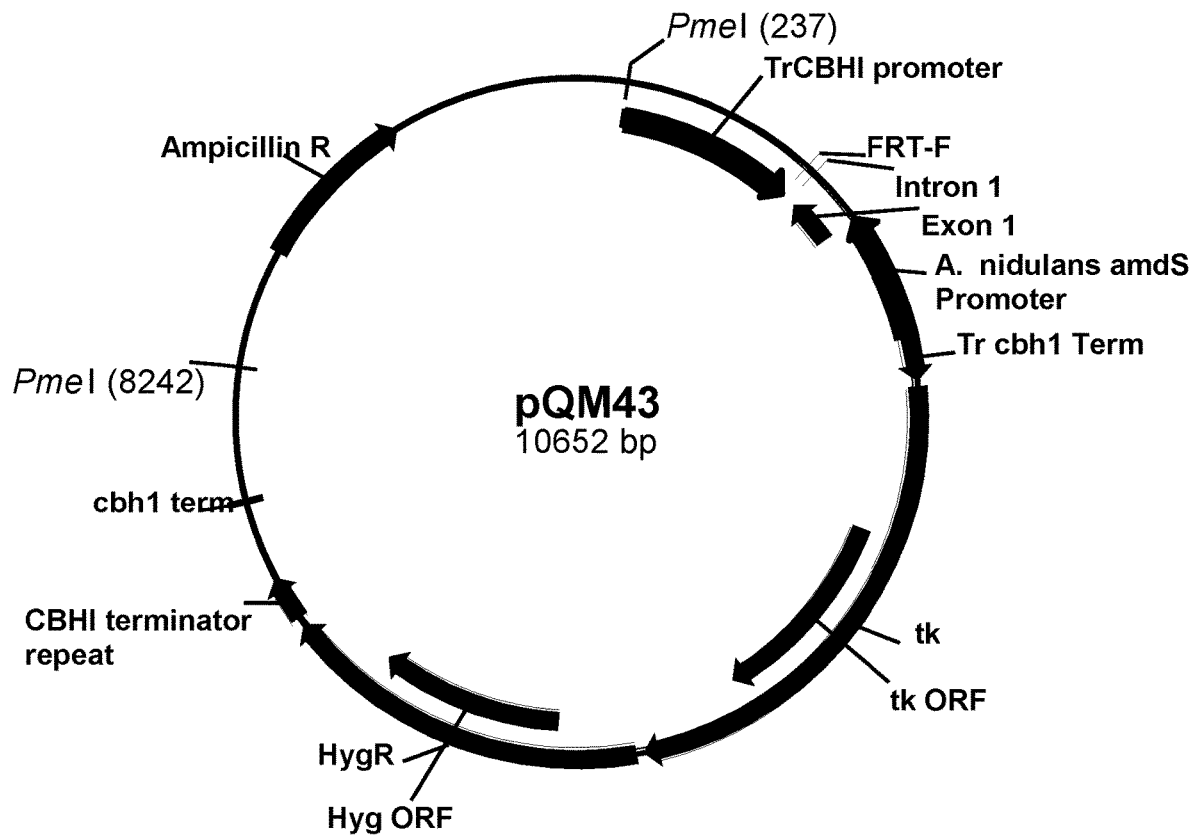
FIG. 10 shows a restriction map of plasmid pQM43.

The 1.4 kb PCR product was inserted into an approximately 9.3 kb Bgl II/Pac I digested pJfyS139 using an IN-FUSION™ HD Cloning Kit. The reaction was composed of 1× IN-FUSION™ HD Enzyme Premix, 200 ng of Bgl II/Pac I digested pJfyS139, and 61 ng of the 1.4 kb PCR product in a 10 µl reaction volume. The reaction was incubated at 50° C. for 15 minutes. After the incubation period, a 1 µl aliquot was transformed into ONE SHOT® TOP10 Chemically Competent cells according to Example 4. Plasmid DNA was isolated from the transformants according to Example 4. The insert was confirmed by DNA sequencing. One transformant was identified as containing the insert with no PCR errors and the plasmid was designated pQM43 (FIG. 10).

Example 56: Construction of *Trichoderma reesei* Strain QMJi057 for Targeting a Non-Functional amdS Fragment 3 Flanked by a FRT-F Site to the *Trichoderma reesei* cbh1 Locus

*Trichoderma reesei* AgJg115-118-1H (Example 9) was transformed with 1-5 µg of Pme I digested pQM43 to insert the non-functional amdS fragment 3 flanked at its 5' by a FRT-F site at the cbh1 gene locus. Twenty-six transformants were obtained and each one was picked and transferred to a PDA plate and incubated for 7 days at 30° C. The transformants were cultured in 2 ml of CIM and incubated at 30° C. for 3 days with agitation at 250 rpm. Supernatant from each culture was subjected to SDS-PAGE using a CRITERION® 8-16% TGX Stain-Free gel and PRECISION PLUS® Protein Unstained Standards. Since successful targeted integration of pQM43 at the cbh1 locus effectively disrupts the cbh1 gene, SDS-PAGE gels were visually analyzed for loss of the CBH1 protein from the proteome. *T. reesei* QMJi057-5 was identified as producing no CBHI protein and was selected for genomic DNA extraction and Southern blot analysis to confirm the integration of the FRT-F site containing the non-functional amdS fragment 3 at the *T. reesei* cbh1 gene locus. Genomic DNA was isolated from the transformants according to the procedure described in Example 2. Genomic DNA was digested with Nhe I for Southern blot analysis with a digoxigenin-labeled *T. reesei* cbh1 3' probe synthesized by PCR using a PCR DIG Probe Synthesis Kit and the primers shown below.

Primer 0610249:
(SEQ ID NO: 283)
5'-GAGAACACAGTGAGACCATAGC-3'

Primer 0610250:
(SEQ ID NO: 284)
5'-TCTCAACCCAATCAGCAACATG-3'

The DIG Probe Synthesis PCR was composed of approximately 100 µg of a PCR fragment containing the *T. reesei* cbh1 3' flanking region used to make pQM21 (WO 2013/028912) as template, 1 µM primers, 5 µl of PCR DIG Synthesis Mix, 1×PCR buffer with MgCl$_2$, and 0.75 µl of Enzyme Mix in a final volume of 50 µl. The reaction was performed in a thermocycler programmed for 1 cycle at 95° C. for 2 minutes; 10 cycles each at 95° C. for 30 seconds, 60° C. for 30 seconds, and 72° C. for 40 seconds; 20 cycles each at 95° C. for 30 seconds, 60° C. for 30 seconds, and 72° C. for 40 seconds plus an additional 20 seconds for each successive cycle; and 1 cycle at 72° C. for 7 minutes. The PCR product was separated by 1% agarose gel electrophoresis in TAE buffer where a 720 bp band was excised from the gel and extracted using a Nucleospin® Extract II Kit (Example 8).

Transformant QMJi057-5 was confirmed by Southern blot analysis to contain the non-functional amdS fragment 3 flanked at its 5' by a FRT-F site at the cbh1 locus, which resulted in a hybridized signal at approximately 7.1 kb recognized by the *T. reesei* cbh1 3' probe.

Example 57: Site Specific Integrations at *Trichoderma reesei* cbh1 Locus in Strain QMJi057-5

An approximately 3 kb DNA fragment containing the coding sequence of an *A. niger* mannosidase (SEQ ID NO: 285 for the DNA sequence and SEQ ID NO: 286 for the amino acid sequence) was amplified from *A. niger* Bo-1 derivative strain CKIe47 with primer 0614762 and 0614763 and cloned into Nco I and Pac I digested pMJ09 (U.S. Pat. No. 8,318,458 B2; approximately 7.2 kb), resulting in plasmid pQM27 (SEQ ID NO: 287). The *A. niger* mannosidase expression cassette in pQM27 is followed by a functional amdS marker.

An approximately 6.7 kb DNA fragment containing an *A. niger* mannosidase expression cassette, a non-functional amdS fragment 4, and the FRT-F site was amplified from pQM27 with primer 1201956 and 1201606. The PCR was composed of 100 ng of pQM27, 200 µM dNTPs, 0.4 µM primers, 1×PHUSION® Reaction Buffer (Thermo Fisher Scientific, Inc.), and 1 units of PHUSION® High Fidelity DNA polymerase (Thermo Fisher Scientific, Inc.) in a final volume of 50 µl. The reaction was performed in a thermocycler programmed for 1 cycle at 98° C. for 2 minutes; 35 cycles each at 98° C. for 15 seconds, 60° C. for 30 seconds, and 72° C. for 3.5 minutes; and 1 cycle at 72° C. for 10 minutes. The 6.7 kb PCR product was separated by 0.7% agarose gel electrophoresis in TAE, excised from the gel, and extracted using a Nucleospin® Extract II Kit (Example 8). The purified 6.7 kb PCR product was used as template to amplify a FRT-F site containing fragment using primers 1201956 and 1201957. The resulting FRT-F site containing PCR fragment was separated by 0.7% agarose gel electrophoresis in TAE and then excised from the gel and extracted using a Nucleospin® Extract II Kit (Example 8).

Primer 1210956:
(SEQ ID NO: 288)
5'-TGATTACGAATTGTTTAAACGGATCCGAATGTAGGATTGTTATCC G-3'

Primer 1201606:
(SEQ ID NO: 289)
5'-GAAGTTCCTATACTTTCTAGAGAATAGGAACTCGGAATAGGAACTTC AACCTTATGGGACTATCAAGCTGAC-3'

Primer 1210957:
(SEQ ID NO: 290)
5'-GTTACATTGACGTACTTATAAGAAGTTCCTATACTTTCTAGAGAA TAGGA-3'

Figure 11:
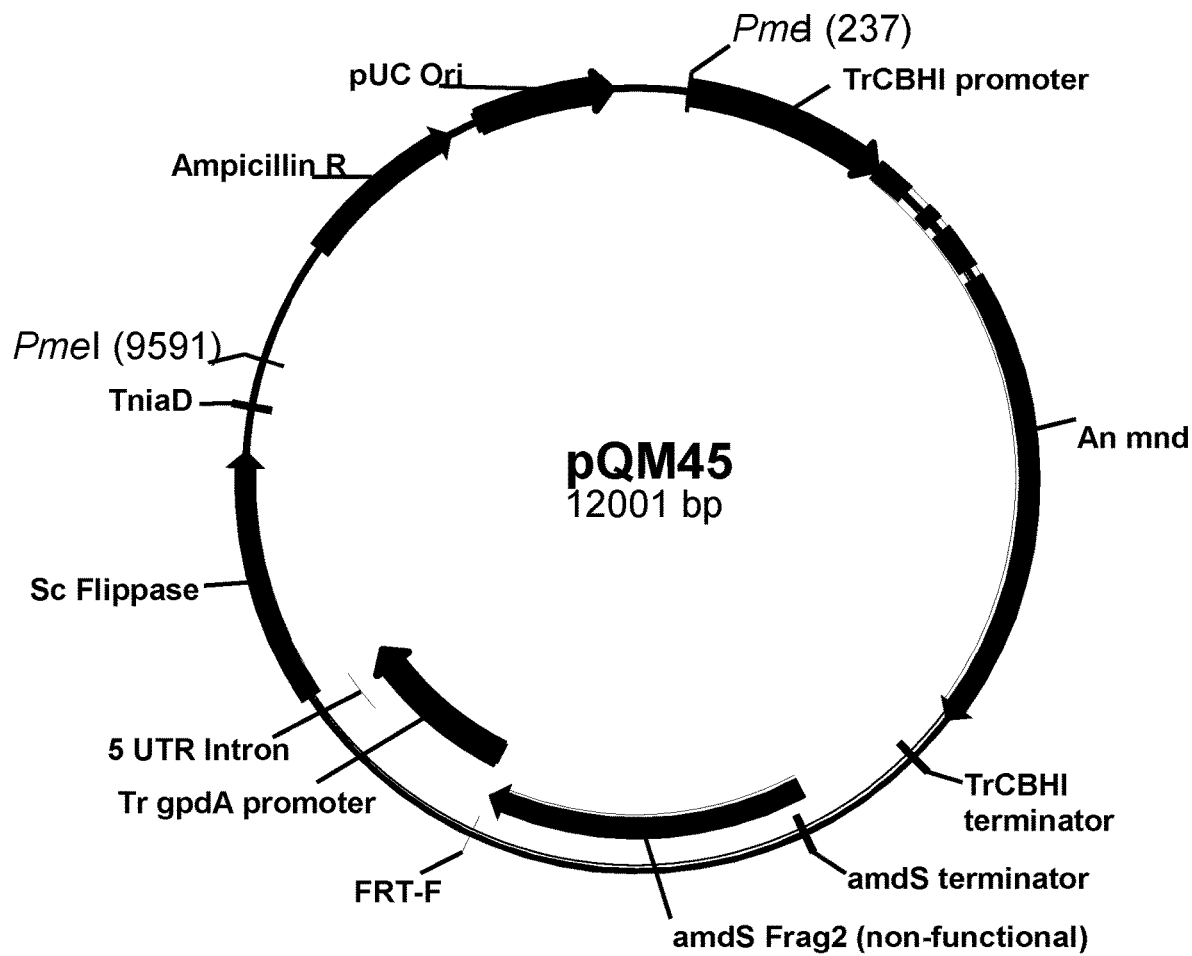
FIG. 11 shows a restriction map of plasmid pQM45.

The purified FRT-F site containing PCR fragment was inserted into Xba I and Psi I digested pDM313 (approximately 5.4 kb) using an 1N-FUSION™ HD Cloning Kit. The reaction was composed of 1× IN-FUSION™ HD Enzyme Premix, 323 ng of Xba I/Psi I digested pDM313, and 200 ng of the 6.7 kb FRT-F site containing the PCR product in a 15 µl reaction volume. The reaction was incubated at 50° C. for 15 minutes. After the incubation period, a 2 µl aliquot was transformed into 50 µl of Stellar™ E. coli chemically competent cells by addition to a tube containing the competent cells and incubating the cells on ice for 30 minutes. The tube was incubated at 42° C. for 45 seconds after which 450 µl of SOC medium were added. The tube was then incubated at 37° C. with agitation at 250 rpm for 1 hour. Volumes of 50 µl and 150 µl were transferred to two 150 mm 2XYT plus ampicillin plates. The plates were incubated overnight at 37° C. Plasmid DNA was isolated and sequenced as described in Example 4. One transformant was identified as containing the insert with no PCR errors and the plasmid was designated pQM45 (FIG. 11).

Plasmid pQM45 was digested with Pme I and used to test site specific integration at the *T. reesei* cbh1 locus in *T. reesei* strain QMJi057-5. The Pme I digested pQM45 was transformed into protoplasts of *T. reesei* strain QMJi057-5 as described in Example 1 and the transformation reactions were spread onto COVE plates and incubated at 30° C. for 7-10 days. All of the transformations resulted in visible transformants on COVE plates, suggesting that insertion of the FRT-F site into the first intron of the amdS gene allows recombination of a functional amdS marker and integration at the targeted site.

Genomic DNA was isolated from six transformants according to the procedure described in Example 2. Genomic DNA was digested with EcoR I for Southern blot analysis with a 358 bp digoxigenin-labeled *T. reesei* cbh1 5' probe (see below), which was synthesized by incorporation of digoxigenin-11-dUTP by PCR using a PCR DIG Probe Synthesis Kit.

Southern blot analysis of all six transformants resulted in a hybridized signal at approximately 4.2 kb recognized by the *T. reesei* cbh1 5' probe, indicating correct integration at the cbh1 locus.

```
T. reesei cbh1 5' probe sequence:
                                     (SEQ ID NO: 291)
5'-TAGGGTCGGCAACGGCAAAAAAGCACGTGGCTCACCGAAAAGCAAG

ATGTTTGCGATCTAACATCCAGGAACCTGGATACATCCATCATCACGCA

CGACCACTTTGATCTGCTGTAAACTCGTATTCGCCCTAAACCGAAGTGC

GTGGTAAATCTACACGTGGGCCCCTTTCGGTATACTGCGTGTGTCTTCTC

TAGGTGCCATTCTTTTCCCTTCCTCTAGTGTTGAATTGTTTGTGTTGGAG

TCCGAGCTGTAACTACCTCTGAATCTCTGGAGAATGGTGGACTAACGAC

ACCGTGCACCTGCATCATGTATATAATAGTGATCCTGAGAAGGGGGGTT

TGGAGCAATGTGGG-3'
```

Example 58: Construction of Plasmids pQM37, pQM38 and pQM39 (Functional amdS Marker with FRT-F3 Sites in amdS Introns)

Plasmids pQM37, pQM38 and pQM39 were constructed to test the impact on amdS function after inserting a FRT-F3 fragment into one of the three introns of the amdS gene. The primers shown below were designed to introduce a FRT-F3 fragment into each of the three introns in the amdS gene in plasmid pAllo1 using a QUICKCHANGE® II XL Site-Directed Mutagenesis Kit. Primers 1205503 and 1205504 were used to construct plasmid pQM37, where the FRT-F3 site was inserted into intron 1 of the amdS gene. Primers 1205505 and 1205506 were used to construct plasmid pQM38, where the FRT-F3 site was inserted into intron 2 of the amdS gene. Primers 1205507 and 1205508 were used to construct pQM39, where the FRT-F3 site was inserted into intron 3 of the amdS gene.

```
Primer 1205503:
                                     (SEQ ID NO: 292)
5'-GGGAGATGTAACAACGCCTTGAAGTTCCTATTCCGAGTTCCTATTC

TTCAAATAGTATAGGAACTTCAACCTTATGGGACTATCAAG-3'

Primer 1205504:
                                     (SEQ ID NO: 293)
5'-CTTGATAGTCCCATAAGGTTGAAGTTCCTATACTATTTGAAGAATAG

GAACTCGGAATAGGAACTTCAAGGCGTTGTTACATCTCCC-3'

Primer 1205505:
                                     (SEQ ID NO: 294)
5'-GCCCCTAAGTCGTTAGATGTTTGAAGTTCCTATTCCGAGTTCCTATT

CTTCAAATAGTATAGGAACTTCACCCTTTTTGTCAGC-3'

Primer 1205506:
                                     (SEQ ID NO: 295)
5'-GCTGACAAAAAGGGTGAAGTTCCTATACTATTTGAAGAATAGGAAC

TCGGAATAGGAACTTCAAACATCTAACGACTTAGGGGC-3'

Primer 1205507:
                                     (SEQ ID NO: 296)
5'-CTATACCAGGCCTCCACTTGAAGTTCCTATTCCGAGTTCCTATTCTT

CAAATAGTATAGGAACTTCATGTCCTCCTTTCTTGC-3'

Primer 1205508:
                                     (SEQ ID NO: 297)
5'-GCAAGAAAGGAGGACATGAAGTTCCTATACTATTTGAAGAATAGGA

ACTCGGAATAGGAACTTCAAGTGGAGGCCTGGTATAG-3'
```

The PCRs were composed of 10 ng of pAllo1, 1 µl of 10 mM dNTPs, 1× Reaction Buffer, 125 ng of each primer, 1 µl of QUIKSOLUTION® reagent, and 2.5 units of PfuUltra™ HF DNA Polymerase (Agilent Technologies) in a final volume of 50 µl. The reactions were performed in a thermocycler programmed for 1 cycle at 95° C. for 1 minutes; and 18 cycles each at 95° C. for 50 seconds, 60° C. for 50 seconds, and 68° C. for 7 minutes; and 1 cycle at 68° C. for 7 minutes. Ten units of Dpn I were added to each reaction and incubated at 37° C. for one hour. Two µl of each Dpn I treated reaction were transformed into XL10-Gold Ultracompetent E. coli cells. The transformation reactions were spread onto 2XYT plus ampicillin plates. About 4-6 colonies were picked for each transformation and cultured in 3 ml of LB plus ampicillin medium at 37° C. for 15-17 hours with agitation at 250 rpm. Plasmid DNA was extracted from each colony using a QIAprep® Spin Miniprep Kit and submitted for DNA sequencing. One transformant containing the FRT-F3 site inserted into intron 1 of the amdS gene was designated pQM37. One transformant containing the FRT-F3 site inserted into intron 2 of the amdS gene was designated pQM38. One transformant containing the FRT-F3 site inserted into intron 3 of the amdS gene was designated pQM39.

About 30-40 µg of each of pAllo1, pQM37, pQM38, and pQM39 were digested with Eco RI and Pac I. The digested DNAs were purified using a Nucleospin® Extract II Kit (Example 8). The purified linear DNA fragments of pAllo1, pQM37, pQM38, and pQM39 were each transformed into *T. reesei* RutC30 protoplasts according to Example 1. The transformation reactions were spread onto COVE plates and incubated at 28° C. for 7-10 days. All of the transformations resulted in visible transformants on COVE plates, indicating that amdS can be used as a functional selection marker with a FRT-F3 site inserted in any one of the three amdS introns.

Example 59: Construction of Plasmid pDM319

Plasmid pDM319 contains the FRT F13 and FRT F14 sites flanking an expression cassette which contains the *T. reesei* eg1 promoter, the *A. fumigatus* cellobiohydrolase II (cbh2) coding region, and the *T. reesei* eg1 terminator. Plasmid pDM319 also contains the *T. reesei* cbh2 promoter regulating the *S. cerevisiae* flippase gene.

A 1.1 kb fragment containing the FRT F13 site and the *T. reesei* eg1 promoter was amplified from *T. reesei* RutC30 genomic DNA using the primers shown below. In the forward primer sequence the FRT F13 site is underlined. The PCR was performed in a manner similar to that described in Example 14.

Forward primer:
(SEQ ID NO: 298)
5'-ACGCGGCCGCGAATTCGGCGCGCC<u>GAAGTTCCTATTCCGAAGTTCC</u>

<u>TATTCTCATATAAGTATAGGAACTTC</u>ATTTAAATTACCATCGTGCTCT

G-3'

Reverse primer:
(SEQ ID NO: 299)
5'-GGAAGATGCAAGGTGCTTCATTTTGGGACAACAAGAAGGAC-3'

A 1.8 kb PCR fragment containing the *A. fumigatus* cellobiohydrolase II coding region was amplified from plasmid pJfyS144 (WO 2013/028928A1) using the primers shown below. The PCRs were performed in a manner similar to that described in Example 14.

Forward primer:
(SEQ ID NO: 300)
5'-GTCCTTCTTGTTGTCCCAAAATGAAGCACCTTGCATCTTCC-3'

Reverse primer:
(SEQ ID NO: 301)
5'-ACCAGAGGCAAGTCAACGCTTAATTAAAAGGACGGGTTAGCGTT

GGT-3'

A 0.32 kb PCR fragment containing the *T. reesei* eg1 terminator region was amplified from *T. reesei* RutC30 genomic DNA using the primers shown below.

Forward primer:
(SEQ ID NO: 302)
5'-ACCAACGCTAACCCGTCCTTTTAATTAAGCGTTGACTTGCCTCTG

GT-3'

Reverse primer:
(SEQ ID NO: 303)
5'-CCTCGCATACCTAGCCTAGAATTCGCGATCGCGACGATAAGCTTGCC

CTGGTGGTGTCAACCCTG-3'

The PCRs were performed in a manner similar to that described in Example 14.

The three completed PCR fragments described above were gel purified by 0.8% agarose gel electrophoresis in TAE buffer. The fragments of 1.1 kb, 1.8 kb, and 0.32 kb were excised from the gel and extracted using a Nucleospin® Extract II Kit (Example 8).

The 1.8 kb and 0.32 kb PCR fragments were joined by SOE PCR using the primers shown below.

Forward primer:
(SEQ ID NO: 304)
5'-GTCCTTCTTGTTGTCCCAAAATGAAGCACCTTGCATCTTCC-3'

Reverse primer:
(SEQ ID NO: 305)
5'-CCTCGCATACCTAGCCTAGAATTCGCGATCGCGACGATAAGCTT

GCCCTGGTGGTGTCAACCCTG-3'

The PCR was composed of 50 picomoles of each of the primers, 12 ng of the 1.8 kb fragment, 12 ng of the 0.32 kb fragment, 1×PHUSION™ High-Fidelity Hot Start DNA Polymerase buffer, 1 μl of a 10 mM blend of dNTPs, and 1 unit of PHUSION™ High-Fidelity Hot Start DNA Polymerase in a final volume of 50 μl. The reaction was performed in a thermocycler programmed for 1 cycle at 98° C. for 2 minutes; 34 cycles each at 98° C. for 15 seconds, 59° C. for 30 seconds, and 72° C. for 1.5 minutes, and 1 cycle at 72° C. for 10 minutes. Two SOE PCRs were performed and the reactions were combined. The 2.1 kb SOE PCR fragment was gel purified by 0.8% agarose gel electrophoresis in TAE buffer. The 2.1 kb fragment was excised from the gel and extracted using a Nucleospin® Extract II Kit (Example 8).

Twenty-five μg of pJfyS156 DNA (Example 8) were digested with Eco RI and purified by 0.8% agarose gel electrophoresis in TAE buffer where an approximately 5.0 kb fragment was excised from the gel and extracted using a Nucleospin® Extract II Kit (Example 8).

The 2.1 kb SOE PCR fragment, containing the *A. fumigatus* cellobiohydrolase II coding region and the *T. reesei* eg1 terminator region, and the 1.1 kb PCR fragment containing the FRT F13 site and the *T. reesei* eg1 promoter, were inserted into Eco RI digested pJfyS156 using an IN-FUSION® HD Cloning Kit. The cloning and *E. coli* transformation were performed in a similar manner to that described in Example 14. Plasmid DNA was isolated from the transformants according to Example 4. Transformants were screened by restriction digestion with Asc I and Pac I which produced 2.8 and 5.3 kb fragments. DNA sequencing of one clone verified that the plasmid contained the correct inserts with no PCR errors. The plasmid was designated pDM319a.

A 2.8 kb fragment containing the amdS selectable marker was amplified from pMJ09 (U.S. Pat. No. 7,361,495) template DNA using the primers shown below. The PCR was performed in a manner similar to that described in Example 14.

Forward primer:
(SEQ ID NO: 306)
5'-GACACCACCAGGGCAAGCTTTGGAAACGCAACCCTGAAGG-3'

Reverse primer:
(SEQ ID NO: 307)
5'-ACCAGAGGCAAGTCAACGCTCGCCGGCGTCTACGCCAGGACCGA

GCAA-3'

A 0.36 kb fragment containing the *T. reesei* eg1 terminator and FRT F14 site was amplified from *T. reesei* RutC30 genomic DNA using the primers shown below. In the reverse primer sequence the FRT F14 site is underlined. The PCR was performed in a manner similar to that described in Example 14.

```
Forward primer:
                                        (SEQ ID NO: 308)
5'-TTGCTCGGTCCTGGCGTAGACGCCGGCGAGCGTTGACTTGCCTC

TGGT-3'

Reverse primer:
                                        (SEQ ID NO: 309)
5'-CCTAGCCTAGAATTCGCGATCGCGAAGTTCCTATACTTCTGATA

GAATAGGAACTTCGGAATAGGAACTTCCCTGCAGGCCCTGGTGGTGTCAA

C-3'
```

The PCR was performed in a manner similar to that described in Example 14.

The two completed PCR fragments described above were gel purified by 0.8% agarose gel electrophoresis in TAE buffer. The fragments of 2.8 kb and 0.36 kb were excised from the gel and extracted using a Nucleospin® Extract II Kit (Example 8).

Twenty-five μg of pDM319a DNA were digested with Hind III and Asi SI and purified by 0.8% agarose gel electrophoresis in TAE buffer where an approximately 8.0 kb fragment was excised from the gel and extracted using a Nucleospin® Extract II Kit (Example 8).

The 2.8 kb PCR fragment, containing the amdS selectable marker and the 0.36 kb PCR fragment containing the T. reesei eg1 terminator and FRT F14 site. were inserted into the Hind III and Asi SI pDM319a fragment using an IN-FUSION® HD Cloning Kit. The cloning and E. coli transformation were performed in a similar manner to that described in Example 14. Plasmid DNA was isolated from the transformants according to Example 4. Transformants were screened by restriction digestion with Bam HI and Spe I which produced 2.8 and 8.3 kb fragments. DNA sequencing of one clone verified that the plasmid contained the correct inserts with no PCR errors. The plasmid was designated pDM319.

Example 60: Construction of Plasmid pDM322

Plasmid pDM322 contains the FRT F13 and FRT F14 sites flanking an expression cassette which contains the T. reesei cbh2 promoter, the P. emersonii GH61A coding region, and the T. reesei cbh2 terminator. Plasmid pDM322 also contains the T. reesei cbh2 promoter regulating the S. cerevisiae flippase gene.

A 1.9 kb fragment containing the hpt marker was amplified using pDM313 template DNA (Example 14) and the primers shown below. PCR conditions were similar to those described in Example 14.

```
Forward primer:
                                        (SEQ ID NO: 310)
5'-GTATAACAACTCCGAGTTAATTAAGGGTTCGAATTCATTTAAAC

GG-3'

Reverse primer:
                                        (SEQ ID NO: 311)
5'-AACTTCGGAATAGGAACTTCCCTGCAGGTGGGAGCGCTCAATAT

TCATC-3'
```

The PCR fragment was purified using a Nucleospin® Extract II Kit. The DNA was eluted with 40 μl of NE buffer supplied with the Nucleospin® Extract II Kit. The eluted DNA was digested with Pac I and Sbf I and then gel purified by 0.8% agarose gel electrophoresis in TAE buffer. The 1.9 kb fragment was excised from the gel and extracted using a Nucleospin® Extract II Kit (Example 8).

Twenty μg of pDM319 DNA were digested with Pac I, Swa I, and Sbf I and purified by 0.8% agarose gel electrophoresis in TAE buffer where an approximately 5.1 kb Swa I/Sbf I fragment was excised from the gel and extracted using a Nucleospin® Extract II Kit (Example 8).

Twenty μg of pQM35 DNA (WO2013028928A1) were digested with Pme I and Pac I and purified by 0.8% agarose gel electrophoresis in TAE buffer where an approximately 1.8 kb fragment was excised from the gel and extracted using a Nucleospin® Extract II Kit (Example 8). The 1.8 kb fragment contains the T. reesei cbh2 promoter, the P. emersonii GH61A coding sequence, and T. reesei cbh2 terminator.

The 1.9 kb PCR fragment and 1.8 kb pQM35 fragment were ligated to the 5.1 kb pDM319 fragment using a QUICK LIGATION™ Kit. The ligation reaction was composed of 1× Quick Ligation buffer, 59 ng of the 5.1 kb Swa I/Sbf I pDM319 fragment, 64 ng of the 1.8 kb Pme I/Pac I pQM35 fragment, 57 ng of the 1.9 kb Pac I/Sbf I PCR fragment, and 1 μl of Quick Ligase in a 20 μl reaction volume. The reaction was incubated at room temperature for 5 minutes and 2 μl were used to transform ONE SHOT® TOP10 E. coli chemically competent cells according to Example 4. Plasmid DNA was isolated from the transformants according to Example 4. Transformants were screened by restriction digestion with Sbf I and Nco I which produced 3.0 and 5.8 kb fragments. DNA sequencing of one clone verified that the plasmid contained the correct inserts with no PCR errors. The plasmid was designated pDM322.

Example 61: Construction of Plasmid pDM325

Plasmid pDM325 contains the FRT F13 and FRT F10 sites flanking an expression cassette which contains the T. reesei cbh2 promoter, the P. emersonii GH61A coding sequence, and the T. reesei cbh2 terminator. Plasmid pDM325 also contains the T. reesei cbh2 promoter regulating the S. cerevisiae flippase gene.

Thirty μg of pDM322 DNA were digested with Nsi I and Eco RI and purified by 0.8% agarose gel electrophoresis in TAE buffer where an approximately 2.3 kb Nsi I/Eco RI fragment was excised from the gel and extracted using a Nucleospin® Extract II Kit (Example 8). This fragment was used as the template DNA for the 1.8 kb PCR fragment described below.

A 1.8 kb fragment containing the FRT F10 site, the T. reesei cbh2 promoter, and part of the S. cerevisiae flippase coding region was amplified using the primers shown below. In the forward primer sequence the FRT F10 site is underlined.

```
Forward primer:
                                        (SEQ ID NO: 312)
5'-GCGCTCCCACCTGCAGGGAAGTTCCTATTCCGAAGTTCCTATTC

ACTAGAATGTATAGGAACTTCATTTAAATGAATTCTAGGCTAGGTATGC-

3'

Reverse primer:
                                        (SEQ ID NO: 313)
5'-AGTAGCGGGAGACTAGTGCGAAGT-3'
```

Four PCRs were performed in a similar manner as described in Example 14. The four reactions were combined and the PCR fragment was purified using a Nucleospin® Extract II Kit (Example 8).

Thirty μg of pDM322 DNA were digested with Spe I and Sbf I and purified by 0.8% agarose gel electrophoresis in TAE buffer where an approximately 7.0 kb Spe I/Sbf I fragment was excised from the gel and extracted using a Nucleospin® Extract II Kit (Example 8).

Figure 12:
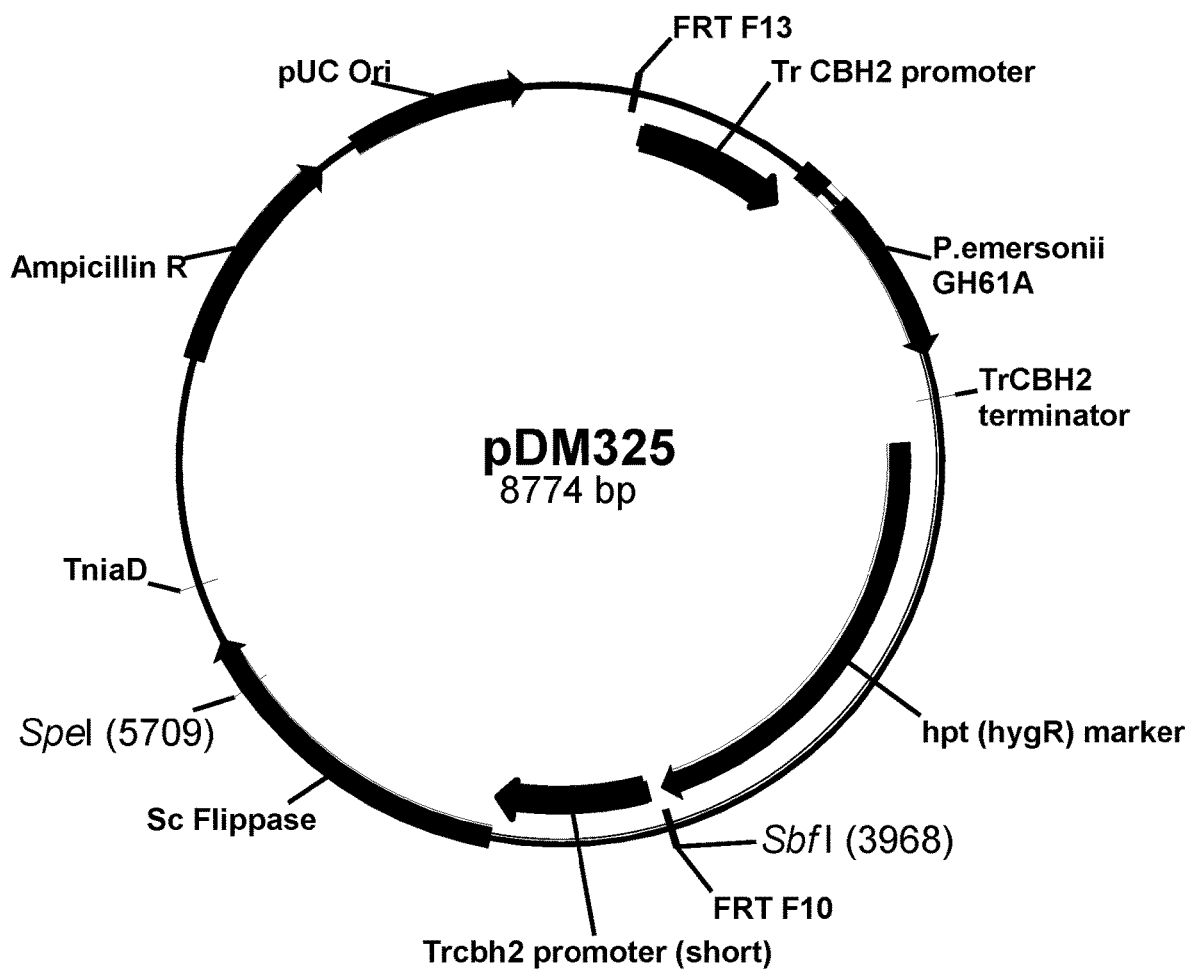
FIG. 12 shows a restriction map of plasmid pDM325.

The 1.8 kb PCR fragment was inserted into the 7.0 kb Spe I/Sbf I pDM322 vector using an IN-FUSION® HD Cloning Kit. The cloning and E. coli transformation were performed in a similar manner to that described in Example 14. Plasmid DNA was isolated from the transformants according to Example 4. DNA sequencing of one clone verified that the plasmid contained the correct insert with no PCR errors. The plasmid was designated pDM325 (FIG. 12).

Example 62: Construction of Plasmid pDM316

Plasmid pDM316 was constructed to introduce FRT F13 and FRT F14 sites at the *T. reesei* eg1 locus.

A 1.5 kb fragment containing the eg1 5' flanking sequence was amplified using the primers shown below.

```
Forward primer:
                                          (SEQ ID NO: 314)
5'-ACATGGTTTAAACGGCGCGCCGGAGCAGATGGCGACACCA-3'
Reverse primer:
                                          (SEQ ID NO: 315)
5'-GAATAGGAACTTCGCGGCCGCCATACCACTTCGTTGATACACTG-
3'
```

Two PCRs were performed in a similar manner as described in Example 14 using *T. reesei* RutC30 genomic DNA as the template. The two reactions were combined and gel purified by 0.8% agarose gel electrophoresis in TAE buffer. The 1.5 kb PCR fragment was excised from the gel and extracted using a Nucleospin® Extract II Kit (Example 8).

The following oligomers containing the FRT F13 site (underlined) were combined and annealed as described below.

```
                                          (SEQ ID NO: 316)
5'-CGGCCGCGAAGTTCCTATTCCGAAGTTCCTATTCTCATATAAGT

ATAGGAACTTCCGCGCCCGACAAAACAAGGC-3'

(SEQ ID NO: 317)
5'-GCCTTGTTTTGTCGGGCGCGGAAGTTCCTATACTTATATGAGAA

TAGGAACTTCGGAATAGGAACTTCGCGGCCG-3'
```

The oligomers were resuspended in sterile distilled water at a concentration of 100 pmoles/μl. Ten μl aliquots of each oligomer were combined along with 2.3 μl of 10× restriction buffer 3 (New England Biolabs). The combined oligomers were heated at 98° C. for 2 minutes and then cooled to room temperature. The annealed oligomers were diluted 1:200 using NE buffer from a Nucleospin® Extract II Kit.

Twenty-five μg of pJfyS1579-41-11 DNA (WO 2011/075677) were digested with Asc I and purified by 0.8% agarose gel electrophoresis in TAE buffer where an approximately 8.0 kb fragment was excised from the gel and extracted using a Nucleospin® Extract II Kit (Example 8).

The 1.5 kb 5' eg1 flanking PCR fragment and annealed oligomers were inserted into the 8.0 kb Asc I pJfyS1579-41-11 fragment using an IN-FUSION® HD Cloning Kit. The cloning and E. coli transformation were performed in a similar manner to that described in Example 14. Plasmid DNA was isolated from the transformants according to Example 4. Transformants were screened by restriction digestion with Pme I and Not I which produced 1.5 and 8.1 kb fragments. DNA sequencing of one clone verified that the plasmid contained the correct insert with no PCR errors. The plasmid was designated pDM316a.

A 1.5 kb fragment containing the eg1 3' flanking sequence was amplified using the primers shown below.

```
Forward primer:
                                          (SEQ ID NO: 318)
5'-TATAGGAACTTCTTAATTAAGATAATGGCCACTTTCATCTGA-3'

Reverse primer:
                                          (SEQ ID NO: 319)
5'-GGCCATATTTAAATCCTGCAGGGTCTGCCGTCACTGATGAGG-3'
```

Two PCRs were performed in a similar manner as described in Example 14 using *T. reesei* RutC30 genomic DNA as the template. The two reactions were combined and gel purified by 0.8% agarose gel electrophoresis in TAE buffer. The 1.5 kb PCR fragment was excised from the gel and extracted using a Nucleospin® Extract II Kit (Example 8).

The following oligomers containing the FRT F14 site (underlined) were combined and annealed as described above.

```
                                          (SEQ ID NO: 320)
5'-CTAGTTGGAGTATTCCTGCAGAAGTTCCTATTCCGAAGTTCCTA

TTCTATCAGAAGTATAGGAACTTCTTAATTAAG-3'

(SEQ ID NO: 321)
5'-CTTAATTAAGAAGTTCCTATACTTCTGATAGAATAGGAACTTCG

GAATAGGAACTTCTGCAGGAATACTCCAACTA-3'
```

Twenty μg of pDM316a were digested with Sbf I and purified by 0.8% agarose gel electrophoresis in TAE buffer where an approximately 9.6 kb fragment was excised from the gel and extracted using a Nucleospin® Extract II Kit (Example 8).

The 1.5 kb eg1 3' flanking PCR fragment and annealed oligomers were inserted into the 9.6 kb Sbf I pDM316a fragment using an IN-FUSION® HD Cloning Kit. The cloning and E. coli transformation were performed in a similar manner to that described in Example 14. Plasmid DNA was isolated from the transformants according to Example 4. DNA sequencing of one clone verified that the plasmid contained the correct insert with no PCR errors. The plasmid was designated pDM316.

Example 63: Construction of Plasmid pDM318

Plasmid pDM318 was constructed to introduce FRT F14 and FRT F15 sites at the *T. reesei* eg1 locus.

The 1.5 kb eg1 5' flanking sequence was PCR amplified as described in Example 62.

The following oligomers containing the FRT F14 site (underlined) were combined and annealed as described in Example 62.

```
                                                         (SEQ ID NO: 322)
5'-CGGCCGCGAAGTTCCTATTCCGAAGTTCCTATTCTATCAGAAGT

ATAGGAACTTCCGCGCCCGACAAAACAAGGC-3'

(SEQ ID NO: 323)
5'-GCCTTGTTTTGTCGGGCGCGGAAGTTCCTATACTTCTGATAGAA

TAGGAACTTCGGAATAGGAACTTCGCGGCCG-3'
```

Twenty-five µg of pJfyS1579-41-11 DNA (WO 2011/075677) were digested with Asc I and purified by 0.8% agarose gel electrophoresis in TAE buffer where an approximately 8.0 kb fragment was excised from the gel and extracted using a Nucleospin® Extract II Kit (Example 8).

The 1.5 kb 5' eg1 flanking PCR fragment and annealed oligomers were inserted into the 8.0 kb Asc I pJfyS1579-41-11 fragment using an IN-FUSION® HD Cloning Kit. The cloning and *E. coli* transformation were performed in a similar manner to that described in Example 14. Plasmid DNA was isolated from the transformants according to Example 4. Transformants were screened by restriction digestion with Pme I and Not I which produced 1.5 and 8.1 kb fragments. DNA sequencing of one clone verified that the plasmid contained the correct insert with no PCR errors. The plasmid was designated pDM318a.

A 1.5 kb 3' eg1 flanking PCR fragment was generated as described in Example 62.

The following oligomers containing the FRT F15 site (underlined) were combined and annealed as described above.

```
                                                         (SEQ ID NO: 324)
5'-CTAGTTGGAGTATTCCTGCAGAAGTTCCTATTCCGAAGTTCCTA

TTCTTATAGGAGTATAGGAACTTCTTAATTAAG-3'

(SEQ ID NO: 325)
5'-CTTAATTAAGAAGTTCCTATACTCCTATAAGAATAGGAACTTCG

GAATAGGAACTTCTGCAGGAATACTCCAACTAG-3'
```

Twenty µg of pDM318a were digested with Sbf I and purified by 0.8% agarose gel electrophoresis in TAE buffer where an approximately 9.6 kb fragment was excised from the gel and extracted using a Nucleospin® Extract II Kit (Example 8).

Figure 13:
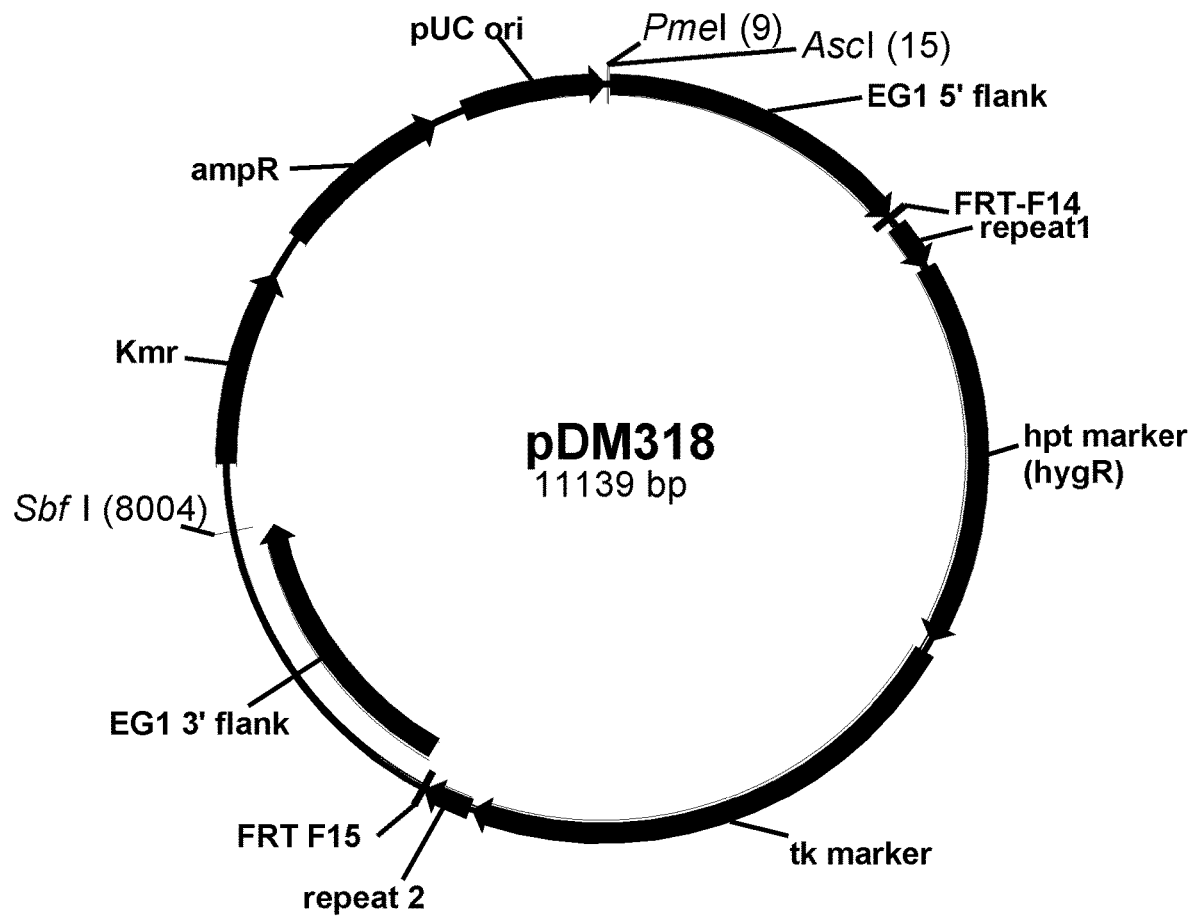
FIG. 13 shows a restriction map of plasmid pDM318.

The 1.5 kb eg1 3' flanking PCR fragment and annealed FRT F15 oligomers were inserted into the 9.6 kb Sbf I pDM316a fragment using an IN-FUSION® HD Cloning Kit. The cloning and *E. coli* transformation were performed in a similar manner to that described in Example 14. Plasmid DNA was isolated from the transformants according to Example 4. DNA sequencing of one clone verified that the plasmid contained the correct insert with no PCR errors. The plasmid was designated pDM318 (FIG. 13).

Example 64: Construction of Plasmid pDM320

Plasmid pDM320 contains FRT F14 and FRT F15 sites flanking an expression cassette which contains the *T. reesei* eg1 promoter, the *A. fumigatus* cellobiohydrolase II (cbh2) coding region, and the *T. reesei* eg1 terminator. Plasmid pDM325 also contains the *T. reesei* cbh2 promoter regulating the *S. cerevisiae* flippase gene.

Twenty-five µg of pDM319 (Example 59) were digested with Asc I and Swa I and purified by 0.8% agarose gel electrophoresis in TAE buffer where an approximately 11 kb fragment was excised from the gel and extracted using a Nucleospin® Extract II Kit (Example 8).

The following oligomers containing the FRT F14 site (underlined) were combined and annealed as described in Example 62.

```
                                                         (SEQ ID NO: 326)
5'-CGCGAATTCGGCGCGCCCTCGAGGAAGTTCCTATTCCGAAGTTC

CTATTCTATCAGAAGTATAGGAACTTCATTTAAATTACCATCGTGCTCT-
3'

(SEQ ID NO: 327)
5'-AGAGCACGATGGTAATTTAAATGAAGTTCCTATACTTCTGATAG

AATAGGAACTTCGGAATAGGAACTTCCTCGAGGGCGCGCCGAATTCGCG-
3'
```

The annealed oligomers containing the FRT F14 site were inserted into the 11 kb Asc I/Swa I pDM319 fragment using an IN-FUSION® HD Cloning Kit. The cloning and *E. coli* transformation were performed in a similar manner to that described in Example 14. Plasmid DNA was isolated from the transformants according to Example 4. DNA sequencing of one clone verified that the plasmid contained the correct insert with no PCR errors. The plasmid was designated pDM320a.

Twenty-five µg of pDM320a were digested with Sbf I and Asi SI and purified by 0.8% agarose gel electrophoresis in TAE buffer where an approximately 11 kb fragment was excised from the gel and extracted using a Nucleospin® Extract II Kit (Example 8).

The following oligomers containing the FRT F15 site (underlined) were combined and annealed as described in Example 62.

```
                                                         (SEQ ID NO: 328)
5'-GACACCACCAGGGCCTGCAGGGAAGTTCCTATTCCGAAGTTCCT

ATTCTTATAGGAGTATAGGAACTTCTACGTAGCGATCGCGAATTCTAGGC

T-3'

(SEQ ID NO: 329)
5'-AGCCTAGAATTCGCGATCGCTACGTAGAAGTTCCTATACTCCTA

TAAGAATAGGAACTTCGGAATAGGAACTTCCCTGCAGGCCCTGGTGGTGT

C
```

Figure 14:
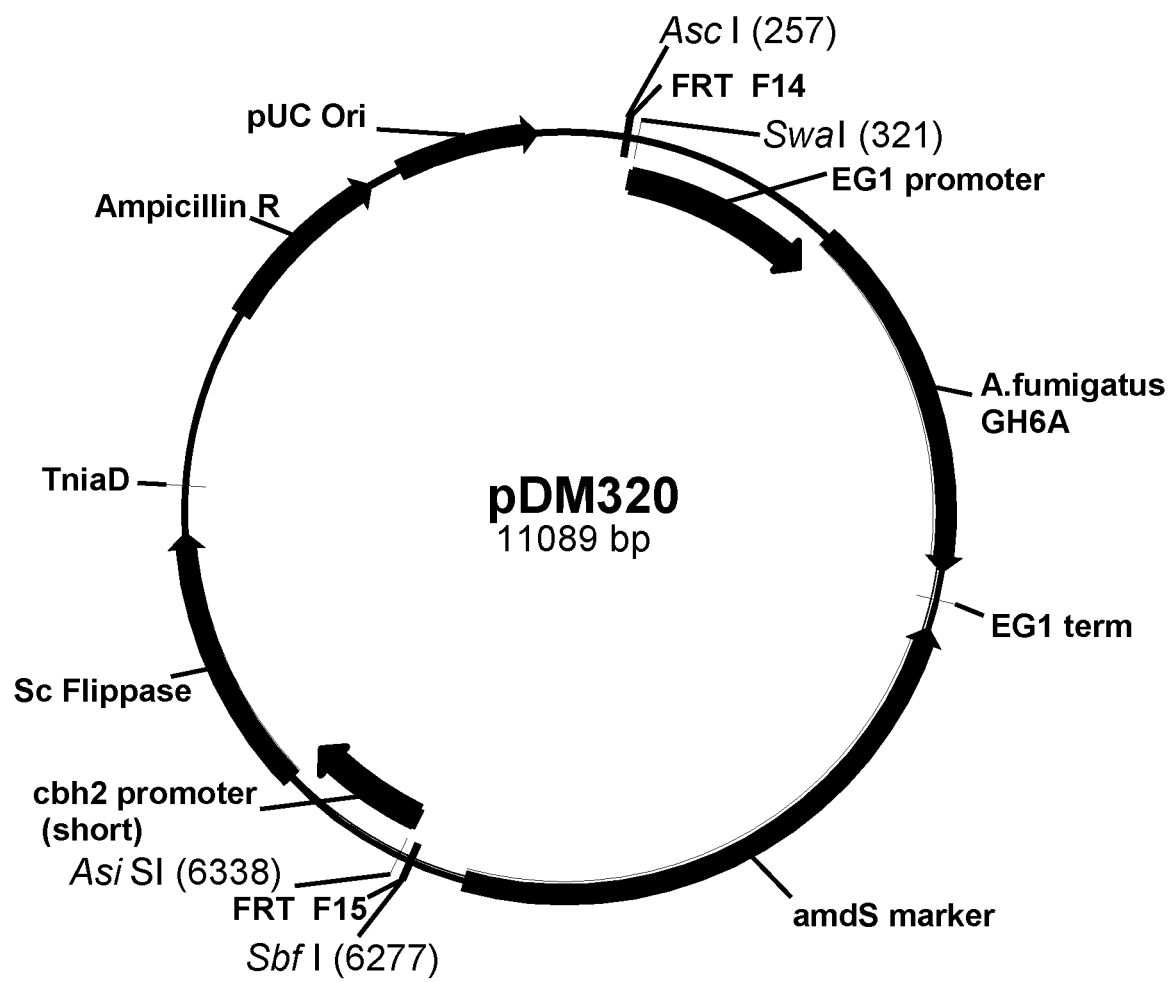
FIG. 14 shows a restriction map of plasmid pDM320.

The annealed oligomers containing the FRT F15 site were inserted into the 11 kb Sbf I/Asi SI pDM320a fragment using an IN-FUSION® HD Cloning Kit. The cloning and *E. coli* transformation were performed in a similar manner to that described in Example 14. Plasmid DNA was isolated from the transformants according to Example 4. DNA sequencing of one clone verified that the plasmid contained the correct insert with no PCR errors. The plasmid was designated pDM320 (FIG. 14).

Example 65: Transformation of Strain AgJg-FRT2-4B17 to Introduce FRT F14 and FRT F15 Sites at the eg1 Locus

*T. reesei* strain AgJg-FRT2-4B17 (Example 12) was transformed with pDM318 (Example 63) to introduce FRT F14 and FRT F15 sites at the eg1 locus and delete 1 kb of eg1 promoter sequence, the entire eg1 coding sequence, and 0.25 kb of the eg1 terminator sequence. Plasmid pDM318 contains 5' and 3' flanking regions from the eg1 locus, FRT F14 and FRT F15 sites, and the *E. coli* hygromycin phosphotransferase (hpt) gene and the *Herpes simplex* virus thymidine kinase (tk) gene flanked by direct repeats. The direct repeats were used to facilitate the curing out of the hpt and tk selectable markers.

A total of 125 μg of the transforming plasmid pDM318 was digested with Pme I and Sbf I. The digestion reaction was purified by 0.8% agarose gel electrophoresis in TAE buffer where an 8 kb DNA band was excised from the gel, and extracted using a Nucleospin® Extract II Kit (Example 8).

Protoplasts of *T. reesei* strain AgJg-FRT2-4B17 were prepared as described in Example 1. Approximately 3 μg of the purified DNA fragment were added to 100 μl of the protoplast solution for hygromycin selection transformation as described in Example 1. Transformants were sub-cultured onto PDA plates to generate spores. Transformants were screened using fungal spore PCR in a manner similar to that described in Example 16.

PCR Screen for Homologous Integration of pDM318: Checking 5' End of the eg1 Locus

```
Forward primer (homologous to 5' flanking
sequence of eg1 locus):
                                  (SEQ ID NO: 330)
5'-CCCGATGCCACCTCCCAGGATAAGA-3'

Reverse primer (homologous to hpt marker):
                                  (SEQ ID NO: 331)
5'-TTTGTGAGGCTGCTCAGGGACCCT-3'

Reverse primer (homologous to eg1 coding
sequence):
                                  (SEQ ID NO: 332)
5'-TTGTCAACTTGGGATGGACCTCGGGGGTGCTGGTACC-3'
```

The three primers above were combined in one PCR. Transformants that had the correct integration of the pDM318 fragment at the eg1 locus produced a 2.0 kb PCR fragment. Transformants that did not have pDM318 DNA correctly integrated produced a 2.8 kb PCR fragment.

PCR Screen for Homologous Integration of pDM318: Checking 3' End of the eg1 Locus

```
Forward primer (homologous to tk marker):
                                  (SEQ ID NO: 333)
5'-TACGGTGCGGTATCTGCAGT-3'

Forward primer (homologous to eg1 coding
sequence):
                                  (SEQ ID NO: 334)
5'-ACGGAGGAGCTCGACGACTT-3'

Reverse primer (homologous to 3' flanking
sequence of eg1 locus):
                                  (SEQ ID NO: 335)
5'-GCTCTCTCCGCCGATCCAAT-3'
```

The three primers were combined in one PCR. Transformants that had the correct integration of the pDM318 fragment at the eg1 locus produced a 3.0 kb PCR fragment. Transformants that did not have pDM318 DNA correctly integrated produced a 2.2 kb PCR fragment.

Transformants that produced PCR fragments indicating correct integration at the eg1 locus were chosen for spore isolation. Spore isolates were generated in a manner similar to that described in Example 15 and plated to PDA medium. The spore isolates were rescreened using the PCR primers and protocol described above. Spores from isolates that yielded the PCR fragments indicative of the correct integration were plated to *Trichoderma* Minimal medium plates containing 1 μM FdU (5-fluoro-2'-deoxyuridine) as described in Example 9. Isolates that lost the tk marker and looped out both the hpt and tk markers grow in the presence of FdU. Colonies from the FdU medium were transferred to PDA plates. Spores from the PDA plate cultures were used for screening by fungal spore PCR in a manner similar to that described in Example 16.

PCR Screen for Loopout of hpt and tk Markers

```
Forward primer (homologous to 5' flanking sequence
of eg1 locus):
                                  (SEQ ID NO: 336)
5'-TACCTCTTTGCGGTCAACTGTGTAAAA-3'

Reverse primer (homologous to 3' flanking sequence
of eg1 locus):
                                  (SEQ ID NO: 337)
5'-CTGTCCTTGATTCAGATGAAAGTGGCC-3'
```

Isolates that had the correct integration of the pDM318 fragment at the eg1 locus and the correct loop-out of the hpt and tk markers produced a 2.1 kb PCR fragment. One more round of spore isolation was performed on PDA plates and the resulting isolates were rescreened by fungal spore PCR using the primers listed above to determine those that produced the 2.1 kb PCR fragment. Genomic DNA from the final spore isolates was prepared in a manner similar to that described in Example 15. For Southern blot analysis approximately 1 μg of each genomic DNA was digested with Spe I and Bam HI. The digested DNA was subjected to 0.8% agarose gel electrophoresis in TAE buffer and transferred to a NYTRAN® SuperCharge membrane as described in Example 3.

A 1.0 kb probe hybridizing to the 5' flanking sequence of the eg1 locus was generated using a PCR DIG Probe Synthesis Kit with the primers shown below. The protocol was similar to that described in Example 15 and *T. reesei* RutC30 genomic DNA was used as the template.

```
Forward primer:
                                  (SEQ ID NO: 338)
5'-GGAGCAGATGGCGACACCATAGGCGGTGCGAATCGTCCAGAA-3'

Reverse primer:
                                  (SEQ ID NO: 339)
5'-TTCCATTTCCCTCCCAGGCCCTGA-3'
```

The Southern blot was hybridized, washed and processed as described in Example 3. Southern blot analysis yielded a 3.5 kb hybridizing fragment indicating the correct integration of plasmid pDM318 with the loop-out of the hpt/tk markers. The resulting *T. reesei* strain was designated *T. reesei* dlmFRT14FRT15.

Example 66: Construction of Plasmid pVCK218

Plasmid pVCK218 contains 5' and 3' flanking regions from the cbh1 locus, FRT F13 and FRT F14 sites, and the *E. coli* hygromycin phosphotransferase (hpt) gene and the *Herpes simplex* virus thymidine kinase (tk) gene flanked by direct repeats. The direct repeats were used to facilitate the curing out of the hpt and tk selectable markers.

A 1.5 kb fragment containing the 5' cbh1 region was amplified using the primers shown below and using plasmid pJfyS147 (Example 4) as the template DNA.

```
Forward primer:
                                        (SEQ ID NO: 340)
5'-ACATGGTTTAAACGGGGTGAAACACCGCCCCCTTCTTG-3'

Reverse primer:
                                        (SEQ ID NO: 341)
5'-AGGAACTTCGCGGCCTTCGAACAGCCCCAGTCGGTCAA-3'
```

Four PCRs were performed in a similar manner as described in Example 14. The four reactions were combined and the PCR fragment was purified by 0.8% agarose gel electrophoresis in TAE buffer where a 1.5 kb DNA band was excised from the gel, and extracted using a Nucleospin® Extract II Kit (Example 8).

Thirty µg of pDM316 (Example 62) DNA were digested with Asc I and Not I and purified by 0.8% agarose gel electrophoresis in TBE buffer where an approximately 9.6 kb Asc I/Not I fragment was excised from the gel and extracted using a Nucleospin® Extract II Kit (Example 8).

The 1.5 kb PCR fragment was inserted into the 9.6 kb Asc I/Not I pDM316 fragment using an IN-FUSION® HD Cloning Kit. The cloning and *E. coli* transformation were performed in a similar manner to that described in Example 14. Plasmid DNA was isolated from the transformants according to Example 4. DNA sequencing of one clone verified that the plasmid contained the correct insert with no PCR errors. The plasmid was designated pVCK218a.

A 1.5 kb fragment containing the 3' cbh1 region was amplified using the primers shown below and plasmid pJfyS147 (Example 4) as the template DNA.

```
Forward primer:
                                        (SEQ ID NO: 342)
5'-TAGGAACTTCTTAATGATAACGGAATAGAAGAAAGAGGAAATTAA

AA-3'

Reverse primer:
                                        (SEQ ID NO: 343)
5'-GCCATATTTAAATCCGTTTAAACAGTCAACACGTCTCCTATGTC

TG-3'
```

Four PCRs were performed in a similar manner as described in Example 14. The four reactions were combined and the PCR fragment was purified using a Nucleospin® Extract II Kit (Example 8).

Thirty µg of pVCK218a DNA were digested with Sbf I and Pac I and purified by 0.8% agarose gel electrophoresis in TBE buffer where an approximately 9.6 kb Sbf I/Pac I fragment was excised from the gel and extracted using a Nucleospin® Extract II Kit (Example 8).

The 1.5 kb 3'cbh1 PCR fragment was inserted into the 9.6 kb Sbf I/Pac I pVCK218a fragment using an IN-FUSION® HD Cloning Kit. The cloning and *E. coli* transformation were performed in a similar manner to that described in Example 14. Plasmid DNA was isolated from the transformants according to Example 4. DNA sequencing of one clone verified that the plasmid contained the correct insert with no PCR errors. The plasmid was designated pVCK218.

Example 67: Construction of Plasmid pDM324

Plasmid pDM324 was constructed to introduce FRT F13 and FRT F10 sites at the *T. reesei* cbh1 locus. The FRT F14 site in pVCK218 was changed to a FRT F10 site.

Thirty µg of pVCK218 (Example 66) were digested with Bgl II and purified by 0.8% agarose gel electrophoresis in TAE buffer where approximately 9.8 kb and 1.4 kb fragments were excised from the gel and extracted using a Nucleospin® Extract II Kit (Example 8).

A 0.33 kb PCR fragment was amplified using the 1.4 kb Bgl II pVCK218 fragment as template and the primers shown below. Three PCRs were performed in a similar manner as described in Example 14. The portion homologous to the FRT F10 site is underlined.

```
Forward primer (1215840):
                                        (SEQ ID NO: 344)
5'-TTCTTCCTTGAACTCTCAGATCTCCCTGCAGGGGGCGACAAAAC

AAGGCTAC-3'

Reverse primer:
                                        (SEQ ID NO: 345)
5'-TTATCATTAAGAAGTTCCTATACATTCTAGTGAATAGGAACTTCGG

AATAGGAAC-3'
```

The three PCRs were combined and purified by 0.8% agarose gel electrophoresis in TAE buffer where an approximately 0.33 kb fragment was excised from the gel and extracted using a Nucleospin® Extract II Kit (Example 8).

A 1.2 kb PCR fragment was amplified using the 1.4 kb Bgl II pVCK218 fragment as template and the primers shown below. Three PCRs were performed in a similar manner as described in Example 14. The portion homologous to the FRT F10 site is underlined.

```
Forward primer:
                                        (SEQ ID NO: 346)
5'-GTTCCTATTCCGAAGTTCCTATTCACTAGAATGTATAGGAACTTCT

TAATGATAA-3'

Reverse primer (1215843):
                                        (SEQ ID NO: 347)
5'-CCATGACTGTCACGATAGAGAGATCTCCACCATTTGCTGTCGA

ATT-3'
```

The three PCRs were combined and purified by 0.8% agarose gel electrophoresis in TAE buffer where an approximately 1.2 kb fragment was excised from the gel and extracted using a Nucleospin® Extract II Kit (Example 8).

The 0.33 kb and 1.2 kb PCR fragments were joined by SOE PCR using the primers 1215840 and 1215843 shown above.

The PCR was composed of 50 picomoles of each of the primers, 10 ng of the 0.33 kb fragment, 10 ng of the 1.2 kb fragment, 1×PHUSION™ High-Fidelity Hot Start DNA Polymerase buffer, 1 µl of a 10 mM blend of dNTPs, and 1 unit of PHUSION™ High-Fidelity Hot Start DNA Polymerase in a final volume of 50 µl. The reaction was performed in a thermocycler programmed for 1 cycle at 98° C. for 2 minutes; 34 cycles each at 98° C. for 15 seconds, 59° C. for 30 seconds, and 72° C. for 1 minute; and 1 cycle at 72° C. for 10 minutes. Two SOE PCRs were performed and the reactions were combined. The 1.5 kb SOE PCR fragment was gel purified by 0.8% agarose gel electrophoresis in TAE buffer where an approximately 1.5 kb fragment was excised from the gel and extracted using a Nucleospin® Extract II Kit (Example 8).

Figure 15:
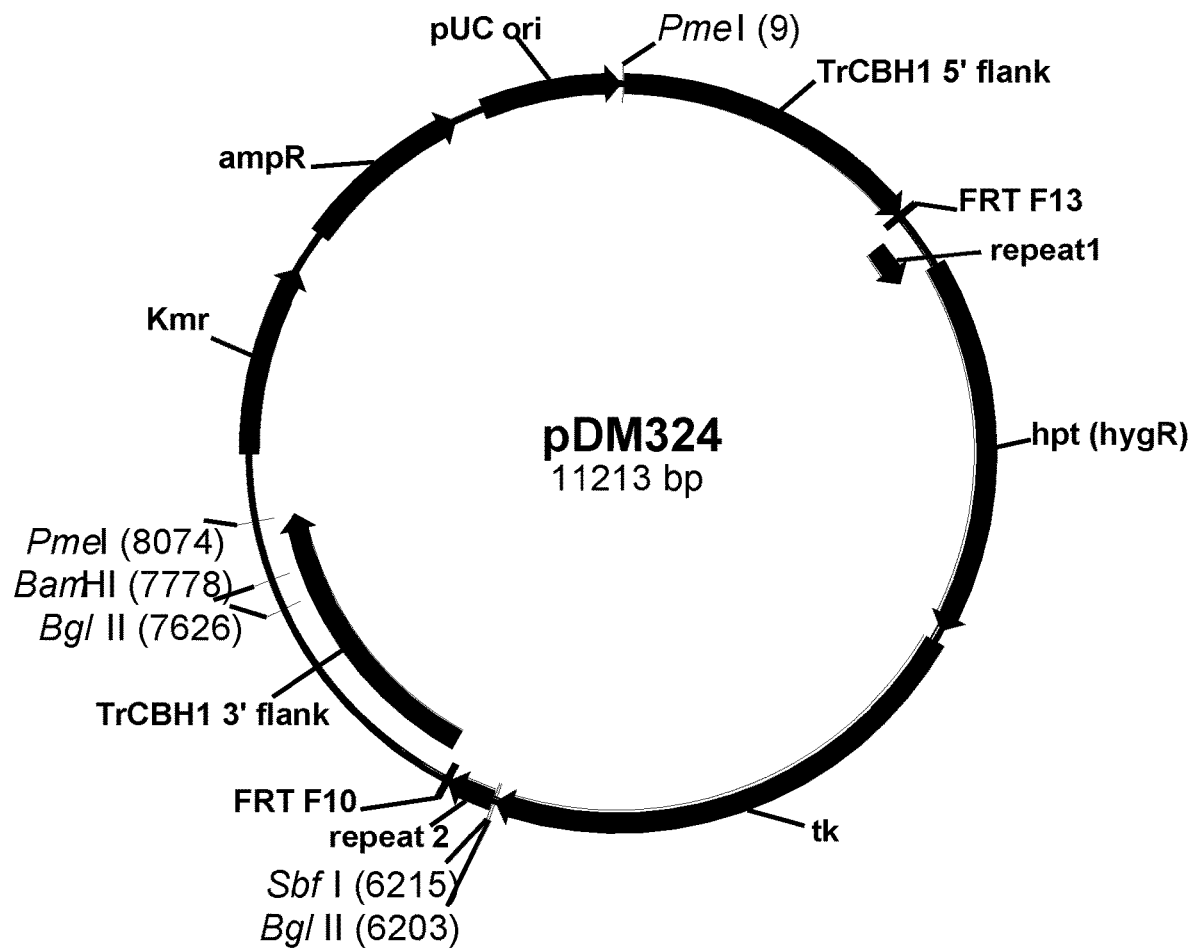
FIG. 15 shows a restriction map of plasmid pDM324.

The 1.5 kb SOE PCR fragment was inserted into the 9.8 kb Bgl II VCK218 fragment using an IN-FUSION® HD Cloning Kit. The cloning and *E. coli* transformation were performed in a similar manner to that described in Example 14. Plasmid DNA was isolated from the transformants according to Example 4. Transformants were screened by restriction digestion with Sbf I and Bam HI which produced 1.6 and 9.7 kb fragments. DNA sequencing of one clone verified that the plasmid contained the correct insert with no PCR errors. The plasmid was designated pDM324 (FIG. 15).

Example 68: Transformation of Strain dlmFRT14FRT15 to Introduce FRT F13 and FRT F10 Sites at the cbh1 Locus

*T. reesei* strain dlmFRT14FRT15 (Example 65) was transformed with pDM324 (Example 67) to introduce FRT F13 and FRT F10 sites at the cbh1 locus. Plasmid pDM324 contains 5' and 3' flanking regions from the cbh1 locus, FRT F13 and FRT F10 sites, and the *E. coli* hygromycin phosphotransferase (hpt) gene and the *Herpes simplex* virus thymidine kinase (tk) gene flanked by direct repeats. The direct repeats were used to facilitate the curing out of the hpt and tk selectable markers.

A total of 125 µg of the transforming plasmid pDM324 was digested with Pme I. The digestion reaction was purified by 0.8% agarose gel electrophoresis in TAE buffer where an 8.1 kb DNA band was excised from the gel, and extracted using a Nucleospin® Extract II Kit (Example 8).

Protoplasts of *T. reesei* strain dlmFRT14FRT15 were prepared as described in Example 1. Approximately 2 µg of the purified DNA fragment was added to 100 µl of the protoplast solution for hygromycin selection transformation as described in Example 1. Transformants were sub-cultured onto PDA plates to generate spores. Transformants were screened using fungal spore PCR in a manner similar to that described in Example 16.

PCR Screen for Homologous Integration of pDM324: Checking 5' End of the cbh1 Locus

```
Forward primer 1209484 (homologous to 5' flanking
sequence of cbh1 locus):
                                    (SEQ ID NO: 348)
5'-GAGATTCGGACCTCCCAACTG-3'

Reverse primer 1215169 (homologous to 3' flanking
sequence of cbh1 locus):
                                    (SEQ ID NO: 349)
5'-AAAAGGCCACCTGTTGAGAG-3'

Reverse primer 1215168 (homologous to 3' hpt
marker):
                                    (SEQ ID NO: 350)
5'-CCCGTGAAGCCGTTTAAATG-3'
```

These three primers were combined in one PCR. Transformants that had the correct integration of the pDM324 fragment at the cbh1 locus produced a 2.1 kb PCR fragment. Transformants that did not have pDM324 DNA correctly integrated produced a 2.7 kb PCR fragment.

PCR Screen for Homologous Integration of pDM324: Checking 3' End of the cbh1 Locus

```
Forward primer (homologous to tk marker):
                                    (SEQ ID NO: 351)
5'-TACGGTGCGGTATCTGCAGT-3'

Reverse primer (homologous to 3' flanking sequence
of cbh1 locus):
                                    (SEQ ID NO: 352)
5'-GCGTGCTAATATTCAGTAGAA-3'
```

Transformants that had the correct integration of the pDM324 fragment at the cbh1 locus produced a 2.9 kb PCR fragment. Transformants that produced PCR fragments indicating correct integration at the cbh1 locus were chosen for spore isolation. Spore isolates were generated in a manner similar to that described in Example 15. The spore isolates were rescreened using the PCR primers and protocol described above. Spores from isolates that yielded the PCR fragments indicative of the correct integration were plated to *Trichoderma* Minimal medium plates containing 1 µM FdU (5-fluoro-2'-deoxyuridine) as described in Example 9. Isolates that lost the tk marker and looped out both the hpt and tk markers could grow in the presence of FdU. Colonies from the FdU medium were transferred to PDA plates and incubated at 30° C. Spores from the PDA plates were transferred to PDA plates supplemented with 10 µg/ml hygromycin and incubated 5 days at 30° C. Isolates that grew on PDA but were unable to grow on PDA plus hygromycin were analyzed further.

Spores from the PDA plate cultures were screened using fungal spore PCR and primers 1215168, 1215169, and 1209484 as described above. Isolates that had pDM324 DNA correctly integrated and had lost the hpt and tk markers produced a 2.7 kb PCR fragment. Isolates that produced the correct PCR fragment were spore isolated one more time on PDA plates in a manner similar to that described in Example 15.

Genomic DNA was prepared from the final spore isolates in a manner similar to that described in Example 2. Approximately 2 µg of genomic DNA was digested with Eco RI and Nhe I. The digested DNA was subjected to 0.7% agarose gel electrophoresis in TAE buffer and transferred to a NYTRAN® SuperCharge membrane as described in Example 3. The DIG labeled probe homologous to the 3' end of the cbh1 locus was made in a manner similar to that described in Example 12 using the following primers.

```
Forward primer:
                                    (SEQ ID NO: 353)
5'-ACCAGTATCGAGGATTGACGGC-3'

Reverse primer:
                                    (SEQ ID NO: 354)
5'-AGCAACCATACGATCCAGGAGC-3'
```

The Southern blot was hybridized, washed and processed as described in Example 3. Southern blot analysis yielded a 2.9 kb hybridizing fragment indicating the correct integration of pDM324 with subsequent loop-out of the hpt/tk markers. The resulting *T. reesei* strain designated *T. reesei* TripleFRT1310-10C12 has FRT F13 and FRT F10 sites at the cbh1 locus, FRT F and FRT F3 sites at the cbh2 locus, and FRT F14 and FRT F15 sites at the eg1 locus.

Example 69: Transformation of *Trichoderma reesei* TripleFRT1310-10C12 to Simultaneously Target 3 Different Expression Cassettes to 3 Different Pairs of FRT Sites at 3 Loci

*T. reesei* TripleFRT1310-10C12 (Example 68) has FRT F13 and FRT F10 sites at the cbh1 locus, FRT F and FRT F3 sites at the cbh2 locus, and FRT F14 and FRT F15 sites at the eg1 locus.

Protoplasts of *T. reesei* strain TripleFRT1310-10C12 were prepared as described in Example 1 except that 2% beta-lactose (w/v) was added to the growth medium and protoplast solutions. Approximately 2.2 µg each of plasmids pDM325 (Example 61), pJfyS156 (Example 8) and pDM320 (Example 64) were added per 100 µl of the protoplast solution. The transformation was performed as described in Example 1 and transformation reactions were spread onto COVE plates.

| ILocus | FRT sites | Targeting plasmid | Marker | Expression cassette |
|---|---|---|---|---|
| ccbh1 | FRT F13, FRT F10 | pDM325 | hpt | cbh2 promoter/*P. emersonii* GH61A |
| ccbh2 | FRT F, FRT F3 | pJfyS156 | hpt | cbh1 promoter/*A. fumigatus* BG |
| eeg1 | FRT F14, FRT F15 | pDM320 | amdS | eg1 promoter/*A. fumigatus* cbh2 |

The plates were incubated overnight at 30° C. Then 20 ml COVE+2% beta-lactose overlay containing 2% dextrose and 35 µg/ml hygromycin B were added to each plate. The plates were incubated at 30° C. for 5 days. Colonies were transferred to COVE+2% glucose plates containing 10 µg/ml hygromycin B and were incubated at 30° C. for 4 days. Transformants that grew on the COVE+hygromycin medium were transferred to COVE+2% glucose plates to generate spores. Transformants were screened using fungal spore PCR in a manner similar to that described in Example 16.

PCR Screen for Targeted Integration of pDM325: Checking 5' End of the cbh1 Locus

```
Forward primer (homologous to 5' end of cbh1
locus):
                                 (SEQ ID NO: 355)
5'-GGCAACAAGAGGCCAGAGACAATCTATTC-3'

Reverse primer (homologous to P. emersonii GH61A
polypeptide coding sequence):
                                 (SEQ ID NO: 356)
5'-CAGGTAGGTGATGACGGGTCCGTG-3'
```

Transformants with pDM325 correctly targeted to the FRT F13 and FRT F10 sites at the cbh1 locus produced a 1.7 kb PCR fragment from the 5' end of the locus.

PCR Screen for Targeted Integration of pDM325: Checking 3' End of the cbh1 Locus

```
Forward primer (homologous to P. emersonii GH61A
polypeptide coding sequence):
                                 (SEQ ID NO: 357)
5'-GACGTATACCATTCCGGGGCCGCCTGAGCC-3'

Reverse primer (homologous to 3' end of cbh1
locus):
                                 (SEQ ID NO: 358)
5'-GTTGGCCTCGCAACGGACAAGTT-3'
```

Transformants with pDM325 correctly targeted to the FRT F13 and FRT F10 sites at the cbh1 locus produced a 2.6 kb PCR fragment from the 3' end of the locus.

PCR Screen for Targeted Integration of pJfyS156: Checking 5' End of the cbh2 Locus

```
Forward primer (homologous to 5' end of cbh2
locus):
                                 (SEQ ID NO: 359)
5'-AATGGTGAGGACTGAGATAAAAGAATTC-3'

Reverse primer (homologous to A. fumigatus
beta-glucosidase coding sequence):
                                 (SEQ ID NO: 360)
5'-CCATGACTATTGTCAACTATATCCGAAACAA-3'
```

Transformants with pJfyS156 correctly targeted to the FRT F and FRT F3 sites at the cbh2 locus produced a 1.4 kb PCR fragment from the 5' end of the locus.

PCR Screen for Targeted Integration of pJfyS156: Checking 3' End of the cbh2 Locus

```
Forward primer (homologous to hpt marker):
                                 (SEQ ID NO: 361)
5'-ACCTTCTGGCATGACCTTTTGATGATCG-3'

Reverse primer (homologous to 3' end of the cbh2
locus):
                                 (SEQ ID NO: 362)
5'-CCATCCAAAGAGCTCAACCCAAAGGAGG-3'
```

Transformants with pJfyS156 correctly targeted to the FRT F and FRT F3 sites at the cbh2 locus produced a 0.8 kb PCR fragment from the 3' end of the locus.

PCR Screen for Targeted Integration of pDM320: Checking 5' End of the eg1 Locus

```
Forward primer (homologous to 5' end of eg1
locus):
                                 (SEQ ID NO: 363)
5'-CCCGATGCCACCTCCCAGGATAAGA-3'

Reverse primer (homologous to A. fumigatus
cellobiohydrolase II coding region):
                                 (SEQ ID NO: 364)
5'-GCGATGGAAGATGCAAGGTGCTTCA-3'
```

Transformants with pDM320 correctly targeted to the FRT F14 and FRT F15 sites at the eg1 locus produced a 2.7 kb PCR fragment from the 5' end of the locus.

PCR Screen for Targeted Integration of pDM320: Checking 3' End of the eg1 Locus

```
Forward primer (homologous to amdS marker):
                                 (SEQ ID NO: 365)
5'-GTGCCAAGGAAATCTGCGTCGGTTC-3'

Reverse primer (homologous to 3' end of the eg1
locus):
                                 (SEQ ID NO: 366)
5'-CGCTCGACGATACGGACGACGATGA-3'
```

Transformants with pDM320 correctly targeted to the FRT F14 and FRT F15 sites at the eg1 locus produced a 1.9 kb PCR fragment from the 3' end of the locus.

Transformants showing correct targeting by the PCR screen were cultured in 25 ml of CIM supplemented with 2% beta-lactose in a 125 ml shake flask at 28° C. for 5 days with agitation at 200 rpm. Supernatant from each culture was subjected to SDS-PAGE using a CRITERION® 8-16% TGX Stain-Free gel and PRECISION PLUS® Protein Standards. Spore isolates were made from transformants that produced all three proteins (*P. emersonii* GH61A polypeptide, *A. fumigatus* beta-glucosidase, and *A. fumigatus* cellobiohydrolase II) as determined by SDS-PAGE. The spore isolates were grown in shake flasks and evaluated by SDS-PAGE. Genomic DNA was made from spore isolates using a method similar to that described in Example 2 and was used for Illumina next-generation sequencing. DNA sequence analysis of the cbh1, cbh2 and eg1 loci verified simultaneous correct targeting of three expression cassettes to three loci using FRT F and F3, FRT F13 and FRT F10, and FRT F14 and FRT F15 sites.

The present inventions are further described by the following numbered paragraphs:

[1] A method of introducing multiple expression constructs into two or more target loci of a eukaryotic cell, said method comprising. (a) transforming a population of the eukaryotic cell with one or more first constructs and one or more second constructs, wherein the eukaryotic cell comprises (1) one or more first target loci (e.g., 1, 2, 3, 4, 5, 6, 7, 8, etc.) each comprising a pair of a first recombination recognition site and a second recombination recognition site, and (2) one or more second target loci (e.g., 1, 2, 3, 4, 5, 6, 7, 8, etc.) each comprising a first fragment of a first selectable marker lacking a selectable function; wherein the one or more first constructs (e.g., 1, 2, 3, 4, 5, 6, 7, 8, etc.) each comprises one or more first expression cassettes each comprising a first polynucleotide encoding a first protein of interest, wherein in each of the first constructs the one or more first expression cassettes are flanked on one side by the first recombination recognition site and on the other side by the second recombination recognition site corresponding to the same recombination recognition sites of the first target loci; and wherein the one or more second constructs (e.g., 1, 2, 3, 4, 5, 6, 7, 8, etc.) each comprises one or more second expression cassettes each comprising a second polynucleotide encoding a second protein of interest, and wherein in each of the second constructs the one or more second expression cassettes are flanked on one side by a homologous region of the corresponding second target locus and on the other side by a second fragment of the first selectable marker that lacks the selectable function, wherein the second fragment comprises a sequence overlapping homologously the corresponding sequence of the first fragment of the first selectable marker of the second target loci; and (b) selecting a transformant using each of the first selectable markers wherein the first fragment and the second fragment of each of the first selectable markers undergo recombination (e.g., homologous recombination or recombinase-mediated recombination) to become functional and the homologous region of the second constructs undergo homologous recombination with the same corresponding region of the second target loci, wherein each of the second expression cassettes are integrated at the corresponding second target loci, and wherein the first and second recombination recognition sites of the first constructs undergo recombination at the corresponding first and second recombination recognition sites of the first target loci driven by at least one recombinase integrating each of the first expression cassettes at the corresponding first target loci.

[2] The method of paragraph 1, wherein the transforming of the population of the eukaryotic cell with the one or more first constructs and the one or more second constructs is performed sequentially in any order.

[3] The method of paragraph 1, wherein the transforming of the population of the eukaryotic cell with the one or more first constructs and the one or more second constructs is performed as a co-transformation.

[4] The method of any one of paragraphs 1-3, wherein the first and second recombination recognition sites at each of the first target loci are the same recombination recognition sites.

[5] The method of any one of paragraphs 1-3, wherein the first and second recombination recognition sites at each of the first target loci are different recombination recognition sites.

[6] The method of any one of paragraphs 1-3, wherein the first and second recombination recognition sites at each of the first target loci are a combination of the same and different recombination recognition sites.

[7] The method of any one of paragraphs 1-6, wherein the recombination recognition sites are selected from the group consisting of a B2 system from *Zygosaccharomyces bailii*, B3 system from *Zygosaccharomyces bisporus*, beta-recombinase-six system from a 25 *Bacillus subtilis* plasmid, Bxb1 from phage Bxb1, Cre-lox system of bacteriophase P1, Dre from Bacteriophage D6, FLP-FRT of *Saccharomyces cerevisiae*, Delta-gamma-es system from bacterial transposon Tn1000, Gin-gix system from bacteriophase Mu, HK022 from phage HK022, KD system from *Kluyveromyces drosophilarum*, Mx9 phage transformation system, *Streptomyces* phage IC31, R-RS system of *Zygosaccharomyces rouxii*, Tn3 from *E. coli*, Vika recombinase from *Vibrio coralliilyticus*, and Xis-att system of temperate lactococcal bacteriophage TP901-1; and combinations thereof.

[8] The method of paragraph 7, wherein the flippase recognition sites of the FLP-FRT system are selected from the group consisting F, F3, F10, F13, F14, F15, Fa, and F3a; and combinations thereof.

[9] The method of paragraph 7, wherein the TP901-1 sites of the Xis-att system are selected from the group consisting attB and attP, and combinations thereof.

[10] The method of paragraph 7, wherein the Lox sites of the Cre-lox system are selected from the group consisting of LoxP, Lox71, Lox66, 511, Lox 5171, Lox 2272, M2, M3, M7, and M11.

[11] The method of any one of paragraphs 1-10, wherein the eukaryotic cell comprises one or more recombinases, which are native, heterologous, or a combination of native and heterologous to the eukaryotic cell.

[12] The method of paragraph 11, wherein the one or more recombinases are selected from the group consisting of a Bxb1 recombinase, a Cre recombinase, a CinH recombinase, a Flp flippase, a HK022 integrase, a ParA recombinase, a Tn1721 recombinase, a Tn5053 recombinase, a TP901-1 integrase, an U153 recombinase, a λ integrase, and a φC31 recombinase.

[13] The method of any one of paragraphs 1-12, wherein each of the first polynucleotides is the same polynucleotide.

[14] The method of any one of paragraphs 1-12, wherein each of the first polynucleotides is a different polynucleotide.

[15] The method of any one of paragraphs 1-12, wherein each of the first polynucleotides is a combination of the same and different polynucleotides.

[16] The method of any one of paragraphs 1-15, wherein each of the second polynucleotides is the same polynucleotide.

[17] The method of any one of paragraphs 1-15, wherein each of the second polynucleotides is a different polynucleotide.

[18] The method of any one of paragraphs 1-15, wherein each of the second polynucleotides is a combination of the same and different polynucleotides.

[19] The method of any one of paragraphs 1-18, wherein the first selectable marker is the same at each of the second target loci.

[20] The method of any one of paragraphs 1-18, wherein the first selectable marker is different at each of the second target loci.

[21] The method of any one of paragraphs 1-18, wherein the first selectable marker at each of the second target loci is a combination of the same and different selectable markers.

[22] The method of any one of paragraphs 1-21, wherein the first and second fragments of the first selectable markers each further comprise a repeat sequence 5' of the first fragment and a repeat sequence 3' of the second fragment, and wherein the repeat sequences undergo homologous recombination to remove the selectable markers.

[23] The method of any one of paragraphs 1-22, wherein the first and second fragments of the first selectable markers each further comprise repeat sequences allowing removal of a portion of each of the selectable markers by homologous recombination resulting in selectable markers lacking a selectable function.

[24] The method of paragraph 23, wherein one of the repeat sequences is located within an intron of the first selectable markers and the other of the repeat sequences is located 5' or 3' of the first selectable markers, wherein the repeat sequences undergo homologous recombination to remove a portion of the first selectable markers.

[25] The method of paragraph 23, wherein one of the repeat sequences is located 5' or 3' of the first selectable markers and the other of the repeat sequences is a homologous region of the first selectable markers, wherein the repeat sequences undergo homologous recombination to remove a portion of the first selectable markers.

[26] The method of any one of paragraphs 1-25, wherein the one or more first target loci each further comprises a second selectable marker between the recombination recognition sites.

[27] The method of paragraph 26, wherein the second selectable marker at each of the first target loci is a counter selectable marker for negative selection.

[28] The method of paragraph 27, wherein the counter selectable marker for negative selection is selected from the group consisting of URA3, amdS, fcy1, pyrG, tk, and beta-tubulin.

[29] The method of any one of paragraphs 1-28, wherein the one or more second target loci each further comprises a third selectable marker before the non-functional first fragment of the first selectable marker.

[30] The method of paragraph 1-28, wherein the one or more second target loci each further comprises a third selectable marker after the non-functional first fragment of the first selectable marker.

[31] The method of paragraph 30, wherein the third selectable marker at each of the second target loci is a counter selectable marker for negative selection.

[32] The method of paragraph 31, wherein the counter selectable marker is selected from the group consisting of URA3, amdS, fcy1, pyrG, tk, and beta-tubulin.

[33] The method of any one of paragraphs 1-32, wherein the one or more first constructs each further comprises a fourth selectable marker between the recombination recognition sites.

[34] The method of paragraph 33, wherein each of the fourth selectable markers is the same selectable marker.

[35] The method of paragraph 33, wherein each of the fourth selectable markers is a different selectable marker.

[36] The method of paragraph 33, wherein each of the fourth selectable markers is a combination of the same and different selectable markers.

[37] The method of any one of paragraphs 33-36, wherein each of the fourth selectable markers is the same as the first selectable markers of the second constructs.

[38] The method of any one of paragraphs 33-36, wherein each of the fourth selectable markers is different from the first selectable markers of the second constructs.

[39] The method of any one of paragraphs 33-36, wherein each of the fourth selectable markers is a combination of the same and different selectable markers from the first selectable markers of the second constructs.

[40] The method of any one of paragraphs 33-39, wherein each of the fourth selectable markers of the one or more first constructs is a counter selectable marker for negative selection.

[41] The method of paragraph 40, wherein the counter selection selectable markers are selected from the group consisting of URA3, amdS, fcy1, pyrG, tk, and beta-tubulin.

[42] The method of any one of paragraphs 33-41, wherein each of the fourth selectable markers comprise a repeat sequence 5' and a repeat sequence 3' of each of the selectable markers.

[43] The method of paragraph 42, wherein the repeat sequences undergo homologous recombination to remove the selectable markers.

[44] The method of any one of paragraphs 1-43, wherein the selectable markers are selected from the group consisting of ADE2, ARO4-OFP, FLD1, HIS3, LEU2, LYS2, MET3, TRP1, URA3, adeA, adeB, amdS, argB, bar, bleR, bsd, fcy1, hpt, hpt-tk, nat1, niaD, ptr1, pyrG, sC, tk, Tn903kan$^r$, trpC, and beta-tubulin.

[45] The method of any one of paragraphs 1-44, wherein the eukaryotic cell is a yeast cell.

[46] The method of paragraph 45, wherein the yeast cell is selected from the group consisting of a *Candida, Hansenula, Kluyveromyces, Pichia, Saccharomyces, Schizosaccharomyces*, and *Yarrowia* cell.

[47] The method of paragraph 45, wherein the yeast cell is a *Kluyveromyces lactis, Saccharomyces carisbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

[48] The method of any one of paragraphs 1-47, wherein the eukaryotic cell is a filamentous fungal cell.

[49] The method of paragraph 48, wherein the filamentous fungal cell is selected from the group consisting of an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phiebia, Piromyces, Pleurotus, Schizophyllum, Talaromyces, Thermoascus, Thielavia, Tolypociadium, Trametes*, and *Trichoderma* cell.

[50] The method of paragraph 48, wherein the filamentous fungal cell is an *Aspergillus* cell.

[51] The method of paragraph 48, wherein the filamentous fungal cell is *Aspergillus nidulans*.

[52] The method of paragraph 48, wherein the filamentous fungal cell is *Aspergillus niger*.

[53] The method of paragraph 48, wherein the filamentous fungal cell is *Aspergillus oryzae*.

[54] The method of paragraph 48, wherein the filamentous fungal cell is a *Fusarium* cell.

[55] The method of paragraph 48, wherein the filamentous fungal cell is *Fusarium venenatum*.

[56] The method of paragraph 48, wherein the filamentous fungal cell is a *Myceliophthora* cell.

[57] The method of paragraph 48, wherein the filamentous fungal cell is *Myceliophthora thermophila*.
[58] The method of paragraph 48, wherein the filamentous fungal cell is a *Talaromyces* cell.
[59] The method of paragraph 48, wherein the filamentous fungal cell is *Talaromyces emersonii*.
[60] The method of paragraph 48, wherein the filamentous fungal cell is a *Trichoderma* cell.
[61] The method of paragraph 48, wherein the filamentous fungal cell is *Trichoderma reesei*.
[62] The method of any one of paragraphs 1-61, wherein the proteins of interest are selected from the group consisting of an antibody, an antigen, an antimicrobial peptide, an enzyme, a growth factor, a hormone, an immunodilator, a neurotransmitter, a receptor, a reporter protein, a structural protein, and a transcription factor.
[63] The method of paragraph 62, wherein the enzyme is selected from the group consisting of a hydrolase, isomerase, ligase, lyase, oxidoreductase, and transferase.
[64] The method of any one of paragraphs 1-63, wherein the eukaryotic cell is reusable by repeating steps (a) and (b) with one or more different first constructs, second constructs, or first and second constructs each comprising an expression cassette comprising a polynucleotide encoding a different protein of interest.
[65] A method of constructing a eukaryotic cell having multiple target loci for expressing multiple heterologous proteins of interest, comprising: (a) transforming a population of the eukaryotic cell with a first construct comprising (1) a 5' homologous region of a first target locus, (2) a first recombination recognition site, (3) a first selectable marker conferring a first selectable function, (4) a second recombination recognition site, and (5) a 3' homologous region of the first target locus; (b) selecting a first transformant having the first construct integrated at the first target locus using the first selectable marker for selection of the first transformant, wherein the 5' homologous region and the 3' homologous region of the first construct undergo homologous recombination with the corresponding regions of the first target locus integrating the first construct at the first target locus, and wherein the first recombination recognition site and the second recombination recognition site are integrated at the first target locus; (c) transforming a population of the first transformant with a second construct comprising (1) a 5' homologous region of a second target locus, (2) a first fragment of a second selectable marker that lacks a second selectable function, (3) a third selectable marker conferring a third selectable function, and (4) a 3' homologous region of the second target locus; (d) selecting a second transformant having the second construct integrated at the second target locus using the third selectable marker for selection of the second transformant, wherein the 5' homologous region and the 3' homologous region of the second construct undergo homologous recombination with the corresponding regions of the second target locus integrating the second construct at the second target locus, and wherein the first fragment of the second selectable marker that lacks a second selectable function is integrated at the second target locus; (e) co-transforming a population of the second transformant with (i) a third construct comprising (1) the first recombination recognition site, (2) one or more first expression cassettes each comprising a first polynucleotide encoding a first protein of interest, and (3) the second recombination recognition site, and (ii) a fourth construct comprising (1) the 5' homologous region of the second target locus, (2) one or more second expression cassettes each comprising a second polynucleotide encoding a second protein of interest, and (3) a second fragment of the second selectable marker that lacks the second selectable function wherein the second fragment comprises a sequence overlapping homologously the corresponding sequence of the first fragment of the first selectable marker; and (f) selecting a third transformant using the second selectable marker wherein the first integrated fragment and the second fragment of the second selectable marker become functional upon recombination (e.g., homologous recombination or recombinase-mediated recombination), wherein the 5' homologous region of the fourth construct undergoes homologous recombination with the same corresponding region of the second target locus, wherein the one or more second expression cassettes are integrated at the second target locus, and wherein the first recombination recognition site and the second recombination recognition site undergo recombination at the first target locus driven by at least one recombinase integrating the one or more first expression cassettes at the first target locus.
[66] The method of paragraph 65, wherein steps (a) and (b) are performed before steps (c) and (d).
[67] The method of paragraph 65, wherein steps (c) and (d) are performed before steps (a) and (b).
[68] The method of any one of paragraphs 65-67, wherein the recombination recognition sites are selected from the group consisting of B2 system from *Zygosaccharomyces bailii*, B3 system from *Zygosaccharomyces bisporus*, beta-recombinase-six system from a *Bacillus subtilis* plasmid, Bxb1 from phage Bxb1, Cre-lox system of bacteriophase P1, Dre from Bacteriophage D6, FLP-FRT of *Saccharomyces cerevisiae*, Delta-gamma-es system from bacterial transposon Tn1000, Gin-gix system from bacteriophase Mu, HK022 from phage HK022, KD system from *Kluyveromyces drosophilarum*, Mx9 phage transformation system, *Streptomyces* phage lC31, R-RS system of *Zygosaccharomyces rouxii*, Tn3 from *E. coli*, Vika recombinase from *Vibrio coralliilyticus*, and Xis-att system of temperate lactococcal bacteriophage TP901-1; and combinations thereof.
[69] The method of paragraph 68, wherein the flippase recognition (FRT) sites are selected from the group consisting F, F3, F10, F13, F14, F15, Fa, and F3a; and combinations thereof.
[70] The method of paragraph 68, wherein the TP901 sites are selected from the group consisting attB and attP, and combinations thereof.
[71] The method of paragraph 68, wherein the Lox sites of the Cre-lox system are selected from the group consisting of LoxP, Lox71, Lox66, 511, Lox 5171, Lox 2272, M2, M3, M7, and M11.
[72] The method of any one of paragraphs 65-71, wherein the eukaryotic cell comprises one or more recombinases.
[73] The method of paragraph 72, wherein the one or more recombinases are selected from the group consisting of a Bxb1 recombinase, a Cre recombinase, a CinH recombinase, a Flp flippase, a HK022 integrase, a ParA recombinase, a Tn1721 recombinase, a Tn5053 recombinase, a TP901-1 integrase, an U153 recombinase, a λ integrase, and a φC31 recombinase.
[74] The method of any one of paragraphs 65-73, wherein the first selectable marker further comprises a first repeat 5' of the first selectable marker and a second repeat 3' of the first selectable marker.
[75] The method of 74, wherein the first and second repeat sequences of the integrated first construct undergo homologous recombination to remove the first selectable marker.
[76] The method of any one of paragraphs 65-75, wherein the third selectable marker further comprises a third repeat 5' of the third selectable marker and a fourth repeat 3' of the third selectable marker.
[77] The method of paragraph 76, wherein the third and fourth repeat sequences of the second construct undergo homologous recombination to remove the third selectable marker.
[78] The method of any one of paragraphs 65-77, wherein the third selectable marker is the same as the first selectable marker.
[79] The method of any one of paragraphs 65-77, wherein the third selectable marker is different than the first selectable marker.
[80] The method of any one of paragraphs 65-77, wherein the second selectable marker is different than the first and third selectable markers.
[81] The method of any one of paragraphs 65-77, wherein the second selectable marker is the same as the first and third selectable markers.
[82] The method of any one of paragraphs 65-77, wherein the second selectable marker is the same as the first selectable marker.
[83] The method of any one of paragraphs 65-82, wherein the first and second non-functional fragments of the second selectable marker each further comprises a recombination recognition site in an intron of the second selectable marker.
[84] The method of paragraph 83, wherein each recombination recognition site in the first and second non-functional fragments is the same, which can undergo recombinase-mediated recombination.
[85] The method of paragraph 83, wherein each recombination recognition site in the first and second non-functional fragments are different but can undergo recombinase-mediated recombination.
[86] The method of any one of paragraphs 65-85, wherein the selectable markers are selected from the group consisting of ADE2, ARO4-OFP, FLD1, HIS3, LEU2, LYS2, MET3, TRP1, URA3, adeA, adeB, amdS, argB, bar, bleR, bsd, fcy1, hpt, hpt-tk, nat1, niaD, ptr1, pyrG, sC, tk, Tn903kan$^r$, trpC, and beta-tubulin.
[87] The method of any one of paragraphs 65-77, wherein the first selectable marker is a dual selectable marker system.
[88] The method of paragraph 87, wherein the dual selectable marker system is hpt-tk.
[89] The method of any one of paragraphs 65-77, wherein the first selectable marker is a counter selectable marker for negative selection.
[90] The method of any one of paragraphs 65-89, wherein the first construct further comprises a third counter selectable marker for negative selection between the first and the second recombination recognition sites.
[91] The method of any one of paragraphs 65-89, wherein the second construct further comprise a third counter selectable marker for negative selection before or after the non-functional first fragment of the second selectable marker.
[92] The method of any one of paragraphs 65-89, wherein the second transformant comprises the third counter selectable marker at both the first and the second target loci.
[93] The method of any one of paragraphs 65-89, wherein the third transformant comprising no counter selectable marker at both the first and second target loci is selected using the negative selection function of the counter selectable marker.
[94] The method of any one of paragraphs 89-93, wherein the counter selectable marker is selected from the group consisting of URA3, amdS, fcy1, pyrG, and beta-tubulin.
[95] The method of any one of paragraphs 65-94, wherein steps (a)-(f) are repeated at at least two additional target loci with different recombination recognition sites, different polynucleotides encoding proteins of interest, and the same or a different second selectable marker.
[96] The method of any one of paragraphs 65-94, wherein steps (a)-(b) or (c)-(d) are repeated at one additional target locus with different recombination recognition sites, different polynucleotides encoding proteins of interest, and the same or a different selectable marker.
[97] The method of any one of paragraphs 65-96, wherein the eukaryotic cell is a yeast cell.
[98] The method of paragraph 97, wherein the yeast cell is selected from the group consisting of a *Candida, Hansenula, Kluyveromyces, Pichia, Saccharomyces, Schizosaccharomyces,* and *Yarrowia* cell.
[99] The method of paragraph 97, wherein the yeast cell is *Saccharomyces cerevisiae.*
[100] The method of any one of paragraphs 65-96, wherein the eukaryotic cell is a filamentous fungal cell.
[101] The method of paragraph 100, wherein the filamentous fungal cell is selected from the group consisting of an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phiebia, Piromyces, Pleurotus, Schizophyllum, Talaromyces, Thermoascus, Thielavia, Tolypocladium, Trametes,* and *Trichoderma* cell.
[102] The method of paragraph 100, wherein the filamentous fungal cell is an *Aspergillus* cell.
[103] The method of paragraph 100, wherein the filamentous fungal cell is *Aspergillus nidulans.*
[104] The method of paragraph 100, wherein the filamentous fungal cell is *Aspergillus niger.*
[105] The method of paragraph 100, wherein the filamentous fungal cell is *Aspergillus oryzae.*
[106] The method of paragraph 100, wherein the filamentous fungal cell is a *Fusarium* cell.
[107] The method of paragraph 100, wherein the filamentous fungal cell is *Fusarium venenatum.*
[108] The method of paragraph 100, wherein the filamentous fungal cell is a *Myceliophthora* cell.
[109] The method of paragraph 100, wherein the filamentous fungal cell is *Myceliophthora thermophila.*
[110] The method of paragraph 100, wherein the filamentous fungal cell is a *Talaromyces* cell.
[111] The method of paragraph 100, wherein the filamentous fungal cell is *Talaromyces emersonii.*

[112] The method of paragraph 100, wherein the filamentous fungal cell is a *Trichoderma* cell.

[113] The method of paragraph 100, wherein the filamentous fungal cell is *Trichoderma reesei*.

[114] The method of any one of paragraphs 65-113, wherein the proteins of interest are selected from the group consisting of an antibody, an antigen, an antimicrobial peptide, an enzyme, a growth factor, a hormone, an immunodilator, a neurotransmitter, a receptor, a reporter protein, a structural protein, and a transcription factor.

[115] The method of paragraph 114, wherein the enzyme is selected from the group consisting of a hydrolase, isomerase, ligase, lyase, oxidoreductase, and transferase.

[116] A eukaryotic cell obtained according to the method of any one of paragraphs 1-64.

[117] A eukaryotic cell obtained according to the method of any one of paragraphs 65-115.

[118] A eukaryotic cell for expressing multiple heterologous proteins of interest, comprising: (a) one or more first target loci (e.g., 1, 2, 3, 4, 5, 6, 7, 8, etc.) each comprising a pair of a first recombination recognition site and a second recombination recognition site; and (b) one or more second target loci (e.g., 1, 2, 3, 4, 5, 6, 7, 8, etc.) each comprising a first fragment of a first selectable marker lacking a selectable function.

[119] The eukaryotic cell of paragraph 118, wherein the first and second recombination recognition sites are the same recombination recognition sites at each of the first target loci.

[120] The eukaryotic cell of paragraph 118, wherein the first and second recombination recognition sites are different recombination recognition sites at each of the first target loci.

[121] The eukaryotic cell of paragraph 118, wherein the first and second recombination recognition sites are a combination of the same and different recombination recognition sites at each of the first target loci.

[122] The eukaryotic cell of any one of paragraphs 118-121, wherein the recombination recognition sites are selected from the group consisting of a B2 system from *Zygesaccharomyces bailii*, B3 system from *Zygesaccharomyces bisporus*, beta-recombinase-six system from a 25 *Bacillus subtilis* plasmid, Bxb1 from phage Bxb1, Cre-lox system of bacteriophase P1, Dre from Bacteriophage D6, FLP-FRT of *Saccharomyces cerevisiae*, Delta-gamma-es system from bacterial transposon Tn1000, Gin-gix system from bacteriophase Mu, HK022 from phage HK022, KD system from *Kluyveromyces drosophilarum*, Mx9 phage transformation system, *Streptomyces* phage IC31, R-RS system of *Zygosaccharomyces rouxii*, Tn3 from *E. coli*, Vika recombinase from *Vibrio coralliilyticus*, and Xis-att system of temperate lactococcal bacteriophage TP901-1; and combinations thereof.

[123] The eukaryotic cell of paragraph 122, wherein the flippase recognition sites of the FLP-FRT system are selected from the group consisting F, F3, F10, F13, F14, F15, Fa, and F3a; and combinations thereof.

[124] The eukaryotic cell of paragraph 122, wherein the TP901-1 sites of the Xis-att system are selected from the group consisting attB and attP, and combinations thereof.

[125] The eukaryotic cell of paragraph 122, wherein the wherein the Lox sites of the Cre-lox system are selected from the group consisting of LoxP, Lox71, Lox66, 511, Lox 5171, Lox 2272, M2, M3, M7, and M11.

[126] The eukaryotic cell of any one of paragraphs 118-125, which comprises one or more recombinases.

[127] The eukaryotic cell of paragraph 126, wherein the one or more recombinases are selected from the group consisting of a Bxb1 recombinase, a Cre recombinase, a CinH recombinase, a Flp flippase, a HK022 integrase, a ParA recombinase, a Tn1721 recombinase, a Tn5053 recombinase, a TP901-1 integrase, an U153 recombinase, a λ integrase, and a ϕC31 recombinase.

[128] The eukaryotic cell of any one of paragraphs 118-127, further comprising one or more first expression cassettes each comprising a first polynucleotide encoding a first protein of interest at each of the first target loci, wherein each of the one or more first expression cassettes are flanked on one side by the first recombination recognition site and on the other side by the second recombination recognition site of the corresponding first target locus.

[129] The eukaryotic cell of paragraph 128, wherein each of the first polynucleotides is the same polynucleotide.

[130] The eukaryotic cell of paragraph 128, wherein each of the first polynucleotides is a different polynucleotide.

[131] The eukaryotic cell of paragraph 128, wherein each of the first polynucleotides is a combination of the same and different polynucleotides.

[132] The eukaryotic cell of any one of paragraphs 118-131, further comprising one or more second expression cassettes each comprising a second polynucleotide encoding a second protein of interest at each of the second target loci, wherein each of the one or more second expression cassettes are flanked on one side by the first fragment of the selectable marker lacking a selectable function.

[133] The eukaryotic cell of paragraph 132, wherein each of the second polynucleotides is the same polynucleotide.

[134] The eukaryotic cell of paragraph 132, wherein each of the second polynucleotides is a different polynucleotide.

[135] The eukaryotic cell of paragraph 132, wherein each of the second polynucleotides is a combination of the same and different polynucleotides.

[136] The eukaryotic cell of any one of paragraphs 118-135, wherein the one or more first target loci each further comprises a second selectable marker between the recombination recognition sites.

[137] The eukaryotic cell of paragraph 136, wherein the second selectable marker at each of the first target loci is a counter selectable marker for negative selection.

[138] The eukaryotic cell of paragraph 137, wherein the counter selectable marker for negative selection is selected from the group consisting of URA3, amdS, fcy1, pyrG, tk, and beta-tubulin.

[139] The eukaryotic cell of any one of paragraphs 118-138, wherein the one or more second target loci each further comprises a third selectable marker before the non-functional first fragment of the first selectable marker.

[140] The eukaryotic cell of paragraph 118-139, wherein the one or more second target loci each further comprises a third selectable marker after the non-functional first fragment of the first selectable marker.

[141] The eukaryotic cell of paragraph 140, wherein the third selectable marker at each of the second target loci is a counter selectable marker for negative selection.

[142] The eukaryotic cell of paragraph 141, wherein the counter selectable marker is selected from the group consisting of URA3, amdS, fcy1, pyrG, tk, and beta-tubulin.

[143] The eukaryotic cell of any one of paragraphs 118-142, wherein the first selectable marker is the same at each of the second target loci.

[144] The eukaryotic cell of any one of paragraphs 118-142, wherein the first selectable marker is different at each of the second target loci.

[145] The eukaryotic cell of any one of paragraphs 118-142, wherein the first selectable marker is a combination of the same and different selectable markers at each of the second target loci.

[146] The eukaryotic cell of any one of paragraphs 118-145, wherein the selectable marker is selected from the group consisting of ADE2, ARO4-OFP, FLD1, HIS3, LEU2, LYS2, MET3, TRP1, URA3, adeA, adeB, amdS, argB, bar, bleR, bsd, fcy1, hpt, hpt-tk, nat1, niaD, ptr1, pyrG, sC, tk, Tn903kan$^r$, trpC, and beta-tubulin.

[147] A eukaryotic cell comprising (1) one or more first target loci each comprising one or more first expression cassettes each comprising a first polynucleotide encoding a first protein of interest, wherein the one or more first expression cassettes are each flanked 5' by a first recombination recognition site and 3' by a second recombination recognition site, and (2) one or more second target loci each comprising one or more second expression cassettes each comprising a second polynucleotide encoding a second protein of interest, wherein each of the one or more second expression cassettes are flanked on one side by a region of the second target locus and on the other side by a first fragment of a first selectable marker that lacks selectable function, wherein each of the pairs of the first and second recombination recognition sites at the first loci are able to undergo recombination with a first construct comprising one or more third expression cassettes each comprising a third polynucleotide encoding a third protein of interest, wherein each of the one or more third expression cassettes are flanked on one side by the first recombination recognition site and on the other side by the second recombination recognition site of the corresponding first target locus, and wherein each of the target loci regions and the first fragment of the first selectable marker that lacks selectable function at the second loci are able to undergo recombination (e.g., homologous recombination or recombinase-mediated recombination) with a second construct comprising one or more fourth expression cassettes each comprising a fourth polynucleotide encoding a fourth protein of interest, wherein each of the one or more fourth expression cassettes are flanked on one side by a homologous region of the corresponding second target locus and on the other side by a second fragment of the first selectable marker that lacks the selectable function wherein the second fragment comprises a sequence overlapping homologously the corresponding sequence of the first fragment of the first selectable marker.

[148] The eukaryotic cell of paragraph 147, wherein the first and second recombination recognition sites at each of the first target loci are the same recombination recognition sites.

[149] The eukaryotic cell of paragraph 147, wherein the first and second recombination recognition sites at each of the first target loci are different recombination recognition sites.

[150] The eukaryotic cell of paragraph 147, wherein the first and second recombination recognition sites at each of the first target loci are a combination of the same and different recombination recognition sites.

[151] The eukaryotic cell of any one of paragraphs 147-150, wherein each of the first polynucleotides is the same polynucleotide.

[152] The eukaryotic cell of any one of paragraphs 147-150, wherein each of the first polynucleotides is a different polynucleotide.

[153] The eukaryotic cell of any one of paragraphs 147-150, wherein each of the first polynucleotides is a combination of the same and different polynucleotides.

[154] The eukaryotic cell of any one of paragraphs 147-153, wherein each of the second polynucleotides is the same polynucleotide.

[155] The eukaryotic cell of any one of paragraphs 147-153, wherein each of the second polynucleotides is a different polynucleotide.

[156] The eukaryotic cell of any one of paragraphs 147-153, wherein each of the second polynucleotides is a combination of the same and different polynucleotides.

[157] The eukaryotic cell of any one of paragraphs 147-156, wherein the first selectable marker is the same at each of the second target loci.

[158] The eukaryotic cell of any one of paragraphs 147-156, wherein the first selectable marker is different at each of the second target loci.

[159] The eukaryotic cell of any one of paragraphs 147-156, wherein the first selectable marker is a combination of the same and different selectable markers at each of the second target loci.

[160] The eukaryotic cell of any one of paragraphs 116-159, which is a yeast cell.

[161] The eukaryotic cell of paragraph 160, wherein the yeast cell is selected from the group consisting of a *Candida, Hansenula, Kluyveromyces, Pichia, Saccharomyces, Schizosaccharomyces*, and *Yarrowia* cell.

[162] The eukaryotic cell of paragraph 160, wherein the yeast cell is *Saccharomyces cerevisiae*.

[163] The eukaryotic cell of any one of paragraphs 116-159, which is a filamentous fungal cell.

[164] The eukaryotic cell of paragraph 163, wherein the filamentous fungal cell is selected from the group consisting of an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phiebia, Piromyces, Pleurotus, Schizophyllum, Talaromyces, Thermoascus, Thielavia, Tolypocladium, Trametes*, or *Trichoderma* cell.

[165] The eukaryotic cell of paragraph 163, wherein the filamentous fungal cell is an *Aspergillus* cell.

[166] The eukaryotic cell of paragraph 163, wherein the filamentous fungal cell is *Aspergillus nidulans*.

[167] The eukaryotic cell of paragraph 163, wherein the filamentous fungal cell is *Aspergillus niger*.

[168] The eukaryotic cell of paragraph 163, wherein the filamentous fungal cell is *Aspergillus oryzae*.

[169] The eukaryotic cell of paragraph 163, wherein the filamentous fungal cell is a *Fusarium* cell.

[170] The eukaryotic cell of paragraph 163, wherein the filamentous fungal cell is *Fusarium venenatum*.

[171] The eukaryotic cell of paragraph 163, wherein the filamentous fungal cell is a *Myceliophthora* cell.

[172] The eukaryotic cell of paragraph 163, wherein the filamentous fungal cell is *Myceliophthora thermophila*.

[173] The eukaryotic cell of paragraph 163, wherein the filamentous fungal cell is a *Talaromyces* cell.

[174] The eukaryotic cell of paragraph 163, wherein the filamentous fungal cell is *Talaromyces emersonii*.

[175] The eukaryotic cell of paragraph 163, wherein the filamentous fungal cell is a *Trichoderma* cell.

[176] The eukaryotic cell of paragraph 163, wherein the filamentous fungal cell is *Trichoderma reesei*.

[177] The eukaryotic cell of any one of paragraphs 147-176, wherein the selectable markers are selected from the group consisting of ADE2, ARO4-OFP, FLD1, HIS3, LEU2, LYS2, MET3, TRP1, URA3, adeA, adeB, amdS, argB, bar, bleR, bsd, fcy1, hpt, hpt-tk, nat1, niaD, ptr1, pyrG, sC, tk, Tn903kan$^r$, trpC, and beta-tubulin.

[178] A method for producing proteins of interest, comprising cultivating the eukaryotic cell of any one of paragraphs 116-177 under conditions conducive for production of the proteins.

[179] The method of paragraph 178, further comprising recovering the proteins.

[180] A nucleic acid construct selected from the group consisting of: (a) a first nucleic acid construct comprising (i) a 5' homologous region of a first target locus of a eukaryotic cell, (ii) a first recombination recognition site, (iii) a first repeat sequence, (iv) a first selectable marker conferring a first selectable function, (v) a second repeat sequence, (vi) a second recombination recognition site, and (vii) a 3' homologous region of the first target locus of the eukaryotic cell; (b) a second nucleic acid construct comprising: (1) a 5' homologous region of a second target locus of a eukaryotic cell, (2) a first fragment of a second selectable marker that lacks a second selectable function, (3) a third repeat sequence, (4) a third selectable marker conferring a third selectable function, (5) a fourth repeat sequence, and (6) a 3' homologous region of the second target locus of the eukaryotic cell; (c) a third nucleic acid construct comprising: (1) a first recombination recognition site, (2) one or more first expression cassettes each comprising a first polynucleotide encoding a first protein of interest, and (3) a second recombination recognition site; and (d) a fourth nucleic acid construct comprising: (1) a 5' homologous region of the second target locus, (2) one or more second expression cassettes each comprising a second polynucleotide encoding a second protein of interest, and (3) a second fragment of a second selectable marker that lacks a second selectable function.

[181] A eukaryotic cell comprising one or more of the nucleic acid constructs of paragraph 180.

[182] A method of introducing multiple expression constructs into a eukaryotic cell, said method comprising. (a) transforming a population of the eukaryotic cell with one or more first constructs and one or more second constructs, wherein the eukaryotic cell comprises (1) one or more first target loci (e.g., 1, 2, 3, 4, 5, 6, 7, 8, etc.) each comprising a pair of a first recombination recognition site and a second recombination recognition site, wherein the first recombination recognition site and a second recombination recognition site are TP901-1 sites of the Xis-att system, and (2) one or more second target loci (e.g., 1, 2, 3, 4, 5, 6, 7, 8, etc.) each comprising a pair of a third recombination recognition site and a fourth recombination recognition site, wherein the third recombination recognition site and a fourth recombination recognition site are flippase recognition sites of the FLP-FRT system; wherein the one or more first constructs (e.g., 1, 2, 3, 4, 5, 6, 7, 8, etc.) each comprises one or more first expression cassettes each comprising a first polynucleotide encoding a first protein of interest, wherein in each of the first constructs the one or more first expression cassettes are flanked on one side by the first recombination recognition site and on the other side by the second recombination recognition site corresponding to the same recombination recognition sites of the first target loci; wherein the one or more second constructs (e.g., 1, 2, 3, 4, 5, 6, 7, 8, etc.) each comprises one or more second expression cassettes each comprising a second polynucleotide encoding a second protein of interest, and wherein in each of the second constructs the one or more second expression cassettes are flanked on one side by the third recombination recognition site and on the other side by the fourth recombination recognition site corresponding to the same recombination recognition sites of the second target loci; and wherein one or more of the first constructs and second constructs comprise one or more first selectable markers; (b) selecting a transformant using the one or more first selectable markers, wherein each of the second expression cassettes are integrated at the corresponding second target loci, and wherein the first and second recombination recognition sites of the first constructs undergo recombination at the corresponding first and second recombination recognition sites of the first target loci driven by at least one recombinase integrating each of the first expression cassettes at the corresponding first target loci.

[183] The method of paragraph 182, wherein the TP901-1 sites of the Xis-att system are selected from the group consisting of attB and attP, and combinations thereof.

[184] The method of paragraph 182, wherein the flippase recognition sites of the FLP-FRT system are selected from the group consisting F, F3, F10, F13, F14, F15, Fa, and F3a; and combinations thereof.

[185] The method of any one of paragraphs 182-184, wherein the one or more first selectable markers are the same selectable markers.

[186] The method of any one of paragraphs 182-184, wherein the one or more first selectable markers are different selectable markers.

[187] The method of any one of paragraphs 182-186, wherein the one or more first target loci each further comprises a second selectable marker between the recombination recognition sites.

[188] The method of any one of paragraphs 182-187, wherein the selectable markers are selected from the group consisting of ADE2, ARO4-OFP, FLD1, HIS3, LEU2, LYS2, MET3, TRP1, URA3, adeA, adeB, amdS, argB, bar, bleR, bsd, fcy1, hpt, hpt-tk, nat1, niaD, ptr1, pyrG, sC, tk, Tn903kan$^r$, trpC, and beta-tubulin.

[189] The method of paragraph 187, wherein the second selectable marker at each of the first target loci is a counter selectable marker for negative selection.

[190] The method of paragraph 189, wherein the counter selectable marker for negative selection is selected from the group consisting of URA3, amdS, fcy1, pyrG, tk, and beta-tubulin.

[191] The method of any one of paragraphs 182-190, wherein the one or more second target loci each further comprises a third selectable marker between the recombination recognition sites.

[192] The method of paragraph 191, wherein the third selectable marker at each of the second target loci is a counter selectable marker for negative selection.

[193] The method of paragraph 192, wherein the counter selectable marker is selected from the group consisting of URA3, amdS, fcy1, pyrG, tk, and beta-tubulin.

[194] The method of any one of paragraphs 182-193, wherein the one or more first constructs, the one or more second constructs, or the one or more first constructs and the one or more second constructs each further comprises a fourth selectable marker between the recombination recognition sites.

[195] The method of paragraph 194, wherein each of the fourth selectable markers is the same selectable marker.

[196] The method of paragraph 194, wherein each of the fourth selectable markers is a different selectable marker.

[197] The method of paragraph 194, wherein each of the fourth selectable markers is a combination of the same and different selectable markers.

[198] The method of paragraph 194, wherein each of the fourth selectable markers is the same as the first selectable markers of the second constructs, different from the first selectable markers of the second constructs, or a combination of the same and different selectable markers from the first selectable markers of the second constructs.

[199] The method of any one of paragraphs 194-198, wherein each of the fourth selectable markers of the one or more first constructs, the one or more second constructs, and the one or more first constructs and the one or more second constructs is a counter selectable marker for negative selection.

[199] The method of paragraph 199, wherein the counter selection selectable markers are selected from the group consisting of URA3, amdS, fcy1, pyrG, tk, and beta-tubulin.

[200] A eukaryotic cell obtained according to the method of any one of paragraphs 182-199.

[201] A eukaryotic cell for expressing multiple heterologous proteins of interest, comprising: (1) one or more first target loci each comprising a pair of a first recombination recognition site and a second recombination recognition site, wherein the first recombination recognition site and a second recombination recognition site are TP901-1 sites of the Xis-att system, and (2) one or more second target loci each comprising a pair of a third recombination recognition site and a fourth recombination recognition site, wherein the third recombination recognition site and a fourth recombination recognition site are flippase recognition sites of the FLP-FRT system.

What is claimed is:

1. A eukaryotic cell for expressing multiple heterologous proteins of interest, comprising:
   (a) one or more first target loci each comprising a pair of a first recombination recognition site and a second recombination recognition site;
   (b) one or more second target loci each comprising a first fragment of a first selectable marker lacking a selectable function;
   (c) one or more first constructs, wherein the one or more first constructs each comprises one or more first expression cassettes each comprising a first polynucleotide encoding a first protein of interest, wherein in each of the first constructs the one or more first expression cassettes are flanked on one side by the first recombination recognition site and on the other side by the second recombination recognition site, wherein the first and second recombination recognition sites flanking the first expression cassettes are the same as the first and second recombination recognition sites of the first target loci; and
   (d) one or more second constructs, wherein the one or more second constructs each comprises one or more second expression cassettes each comprising a second polynucleotide encoding a second protein of interest, wherein in each of the second constructs the one or more second expression cassettes are flanked on one side by a homologous region of the second target locus and on the other side by a second fragment of the first selectable marker that lacks the selectable function, wherein the second fragment comprises a sequence overlapping homologously a sequence of the first fragment of the first selectable marker of the second target loci.

2. The eukaryotic cell of claim 1, wherein the first and second fragments of the first selectable marker each further comprise a repeat sequence 5' of the first fragment and a repeat sequence 3' of the second fragment.

3. The eukaryotic cell of claim 1, wherein the first and second recombination recognition sites are the same recombination recognition sites at each of the first target loci, different recombination recognition sites at each of the first target loci, or a combination of the same and different recombination recognition sites at each of the first target loci.

4. The eukaryotic cell of claim 1, wherein the recombination recognition sites are selected from the group consisting of a B2 system from *Zygosaccharomyces bailii*, B3 system from *Zygosaccharomyces bisporus*, beta-recombinase-six system from a 25 *Bacillus subtilis* plasmid, Bxb1 from phage Bxb1, Cre-lox system of bacteriophase P1, Dre from Bacteriophage D6, FLP-FRT of *Saccharomyces cerevisiae*, Delta-gamma-es system from bacterial transposon Tn1000, Gin-gix system from bacteriophase Mu, HK022 from phage HK022, KD system from *Kluyveromyces drosophilarum*, Mx9 phage transformation system, *Streptomyces* phage 1C31, R-RS system of *Zygosaccharomyces rouxii*, Tn3 from *E. coli*, Vika recombinase from *Vibrio coralliilyticus*, Xis-att system of temperate lactococcal bacteriophage TP901-1; and combinations thereof.

5. The eukaryotic cell of claim 1, wherein each of the first polynucleotides is the same polynucleotide, different polynucleotides, or a combination of the same and different polynucleotides, and each of the second polynucleotides is the same polynucleotide, different polynucleotides, or a combination of the same and different polynucleotides.

6. The eukaryotic cell of claim 1, wherein the one or more first target loci each further comprises a second selectable marker between the recombination recognition sites.

7. The eukaryotic cell of claim 1, wherein the one or more second target loci each further comprises a third selectable marker before the non-functional first fragment of the first selectable marker.

8. The eukaryotic cell of claim 1, wherein the one or more second target loci each further comprises a third selectable marker after the non-functional first fragment of the first selectable marker.

9. The eukaryotic cell of claim 1, wherein the first selectable marker is the same at each of the second target loci, different at each of the second target loci, or a combination of the same and different selectable markers at each of the second target loci.

10. The eukaryotic cell of claim 1, wherein the selectable markers are selected from the group consisting of ADE2, ARO4-OFP, FLD1, HIS3, LEU2, LYS2, MET3, TRP1, URA3, adeA, adeB, amdS, argB, bar, bleR, bsd, fcy1, hpt, hpt-tk, nat1, niaD, ptr1, pyrG, sC, tk, Tn903kan$^r$, trpC, and beta-tubulin.

11. A eukaryotic cell, comprising:
    (a) one or more first target loci each comprising one or more first expression cassettes each comprising a first polynucleotide encoding a first protein of interest, wherein the one or more first expression cassettes are each flanked 5' by a first recombination recognition site and 3' by a second recombination recognition site, and
    (b) one or more second target loci each comprising one or more second expression cassettes each comprising a second polynucleotide encoding a second protein of interest, wherein each of the one or more second expression cassettes are flanked on one side by a region of the second target locus and on the other side by a first fragment of a first selectable marker that lacks selectable function.

12. The eukaryotic cell of claim 11, wherein the first fragment of the first selectable marker further comprises a repeat sequence 5' of the first fragment.

13. The eukaryotic cell of claim 11, wherein the first and second recombination recognition sites are the same recombination recognition sites at each of the first target loci, different recombination recognition sites at each of the first target loci, or a combination of the same and different recombination recognition sites at each of the first target loci.

14. The eukaryotic cell of claim 11, wherein the recombination recognition sites are selected from the group consisting of a B2 system from *Zygosaccharomyces bailii*, B3 system from *Zygosaccharomyces bisporus*, beta-recombinase-six system from a 25 *Bacillus subtilis* plasmid, Bxb1 from phage Bxb1, Cre-lox system of bacteriophase P1, Dre from Bacteriophage D6, FLP-FRT of *Saccharomyces cerevisiae*, Delta-gamma-es system from bacterial transposon Tn1000, Gin-gix system from bacteriophase Mu, HK022 from phage HK022, KD system from *Kluyveromyces drosophilarum*, Mx9 phage transformation system, *Streptomyces* phage 1C31, R-RS system of *Zygosaccharomyces rouxii*, Tn3 from *E. coli*, Vika recombinase from *Vibrio coralliilyticus*, Xis-att system of temperate lactococcal bacteriophage TP901-1; and combinations thereof.

15. The eukaryotic cell of claim 11, wherein each of the first polynucleotides is the same polynucleotide, a different polynucleotide, or a combination of the same and different polynucleotides, and each of the second polynucleotides is the same polynucleotide, a different polynucleotide, or a combination of the same and different polynucleotides.

16. The eukaryotic cell of claim 11, wherein the first selectable marker is the same at each of the second target loci, different at each of the second target loci, or a combination of the same and different selectable markers at each of the second target loci.

17. The eukaryotic cell of claim 11, wherein the selectable markers are selected from the group consisting of ADE2, ARO4-OFP, FLD1, HIS3, LEU2, LYS2, MET3, TRP1, URA3, adeA, adeB, amdS, argB, bar, bleR, bsd, fcy1, hpt, hpt-tk, nat1, niaD, ptr1, pyrG, sC, tk, Tn903kan$^r$, trpC, and beta-tubulin.

* * * * *

SEQUENCE LISTING

<160> NUMBER OF SEQ ID NOS: 366

<210> SEQ ID NO 1
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 1
gaagttccta ttccgagttc ctattctcta gaaagtatag gaacttc        47

<210> SEQ ID NO 2
<211> LENGTH: 43
<212> TYPE: DNA
<213> ORGANISM: Artificial Sequence
<220> FEATURE:
<223> OTHER INFORMATION: Artificial DNA Primer

<400> SEQUENCE: 2
tcacatggtt taaacggcgc gccggtgaaa caccgccccc ttc           43

<210> SEQ ID NO 3
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 3
ttcgaacagc cccagtcggt                                      20

<210> SEQ ID NO 4
<211> LENGTH: 40

```
<212> TYPE: DNA
<213> ORGANISM: Artificial Sequence
<220> FEATURE:
<223> OTHER INFORMATION: Artificial DNA Primer

<400> SEQUENCE: 4
accgactggg gctgttcgaa cggccgcgaa ttcatcttga                             40

<210> SEQ ID NO 5
<211> LENGTH: 43
<212> TYPE: DNA
<213> ORGANISM: Artificial Sequence
<220> FEATURE:
<223> OTHER INFORMATION: Artificial DNA Primer

<400> SEQUENCE: 5
agccttgttt tgtcgggcgc gccgctgctc tcggctagcg aag                         43

<210> SEQ ID NO 6
<211> LENGTH: 43
<212> TYPE: DNA
<213> ORGANISM: Artificial Sequence
<220> FEATURE:
<223> OTHER INFORMATION: Artificial DNA Primer

<400> SEQUENCE: 6
tcacatggtt taaacggcgc gccggtgaaa caccgccccc ttc                         43

<210> SEQ ID NO 7
<211> LENGTH: 43
<212> TYPE: DNA
<213> ORGANISM: Artificial Sequence
<220> FEATURE:
<223> OTHER INFORMATION: Artificial DNA Primer

<400> SEQUENCE: 7
agccttgttt tgtcgggcgc gccgctgctc tcggctagcg aag                         43

<210> SEQ ID NO 8
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 8
gaagttccta ttccgagttc ctattcttca aatagtatag gaacttca                    48

<210> SEQ ID NO 9
<211> LENGTH: 22
<212> TYPE: DNA
<213> ORGANISM: Artificial Sequence
<220> FEATURE:
<223> OTHER INFORMATION: Artificial DNA Primer

<400> SEQUENCE: 9
gataacggaa tagaagaaag ag                                                22

<210> SEQ ID NO 10
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 10
```

```
gccatattta aatccgttta aacagtcaac acgtctccta tgtct            45
```

<210> SEQ ID NO 11
<211> LENGTH: 63
<212> TYPE: DNA
<213> ORGANISM: Artificial Sequence
<220> FEATURE:
<223> OTHER INFORMATION: Artificial DNA Primer

<400> SEQUENCE: 11

```
cctagttgga gtattcctgc aggtcaactc tctcctctag gttgaagttc ctattccgag    60
ttc                                                                  63
```

<210> SEQ ID NO 12
<211> LENGTH: 52
<212> TYPE: DNA
<213> ORGANISM: Artificial Sequence
<220> FEATURE:
<223> OTHER INFORMATION: Artificial DNA Primer

<400> SEQUENCE: 12

```
ctctttcttc tattccgtta tcgcatgcac tagctagttg aagttcctat ac           52
```

<210> SEQ ID NO 13
<211> LENGTH: 63
<212> TYPE: DNA
<213> ORGANISM: Artificial Sequence
<220> FEATURE:
<223> OTHER INFORMATION: Artificial DNA Primer

<400> SEQUENCE: 13

```
cctagttgga gtattcctgc aggtcaactc tctcctctag gttgaagttc ctattccgag    60
ttc                                                                  63
```

<210> SEQ ID NO 14
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 14

```
gccatattta aatccgttta aacagtcaac acgtctccta tgtct            45
```

<210> SEQ ID NO 15
<211> LENGTH: 25
<212> TYPE: DNA
<213> ORGANISM: Artificial Sequence
<220> FEATURE:
<223> OTHER INFORMATION: Artificial DNA Primer

<400> SEQUENCE: 15

```
aaaaaacaaa catcccgttc ataac                                  25
```

<210> SEQ ID NO 16
<211> LENGTH: 25
<212> TYPE: DNA
<213> ORGANISM: Artificial Sequence
<220> FEATURE:
<223> OTHER INFORMATION: Artificial DNA Primer

<400> SEQUENCE: 16

```
aacaaggttt accggtttcg aaaag                                  25
```

```
<210> SEQ ID NO 17
<211> LENGTH: 80
<212> TYPE: DNA
<213> ORGANISM: Artificial Sequence
<220> FEATURE:
<223> OTHER INFORMATION: Artificial DNA Primer

<400> SEQUENCE: 17
cgaattctgc attgaagttc ctattccgag ttcctattct tcaaatagta taggaacttc    60
agatatccat cacactggcg                                                 80

<210> SEQ ID NO 18
<211> LENGTH: 80
<212> TYPE: DNA
<213> ORGANISM: Artificial Sequence
<220> FEATURE:
<223> OTHER INFORMATION: Artificial DNA Primer

<400> SEQUENCE: 18
gccagtgtga tggatatctg aagttcctat actatttgaa gataggaac tcggaatagg    60 aacttcaatg cagaattcgc                                                 80

<210> SEQ ID NO 19
<211> LENGTH: 63
<212> TYPE: DNA
<213> ORGANISM: Artificial Sequence
<220> FEATURE:
<223> OTHER INFORMATION: Artificial DNA Primer

<400> SEQUENCE: 19
atatccatca cactggcggc cgctcaactc tctcctctag gttgaagttc ctattccgag    60
ttc                                                                   63

<210> SEQ ID NO 20
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 20
aggatgcatg ctcgagcatg cactagctag ttgaagttcc tatac                     45

<210> SEQ ID NO 21
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 21
atctacgcgt actagttaat taaggctttc gtgaccgggc ttcaaaca                  48

<210> SEQ ID NO 22
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 22
gcggccgtta ctagtggatc cactcggagt tgttatacgc tactcg                    46

<210> SEQ ID NO 23
```

```
<211> LENGTH: 39
<212> TYPE: DNA
<213> ORGANISM: Artificial Sequence
<220> FEATURE:
<223> OTHER INFORMATION: Artificial DNA Primer

<400> SEQUENCE: 23
accgcggact gcgcaccatg agattcggtt ggctcgagg                                  39

<210> SEQ ID NO 24
<211> LENGTH: 38
<212> TYPE: DNA
<213> ORGANISM: Artificial Sequence
<220> FEATURE:
<223> OTHER INFORMATION: Artificial DNA Primer

<400> SEQUENCE: 24
ttcgccacgg agcttactag tagacacggg gcagaggc                                   38

<210> SEQ ID NO 25
<211> LENGTH: 22
<212> TYPE: DNA
<213> ORGANISM: Artificial Sequence
<220> FEATURE:
<223> OTHER INFORMATION: Artificial DNA Primer

<400> SEQUENCE: 25
ttcccttcct ctagtgttga at                                                    22

<210> SEQ ID NO 26
<211> LENGTH: 22
<212> TYPE: DNA
<213> ORGANISM: Artificial Sequence
<220> FEATURE:
<223> OTHER INFORMATION: Artificial DNA Primer

<400> SEQUENCE: 26
tcgtcgaata ctaacatctt gc                                                    22

<210> SEQ ID NO 27
<211> LENGTH: 22
<212> TYPE: DNA
<213> ORGANISM: Artificial Sequence
<220> FEATURE:
<223> OTHER INFORMATION: Artificial DNA Primer

<400> SEQUENCE: 27
cacggacctc gaacctttat at                                                    22

<210> SEQ ID NO 28
<211> LENGTH: 25
<212> TYPE: DNA
<213> ORGANISM: Artificial Sequence
<220> FEATURE:
<223> OTHER INFORMATION: Artificial DNA Primer

<400> SEQUENCE: 28
cagcgagagc ctgacctatt gcatc                                                 25

<210> SEQ ID NO 29
<211> LENGTH: 25
<212> TYPE: DNA
<213> ORGANISM: Artificial Sequence
<220> FEATURE:
<223> OTHER INFORMATION: Artificial DNA Primer

<400> SEQUENCE: 29
```

```
aacaaggttt accggtttcg aaaag                                           25

<210> SEQ ID NO 30
<211> LENGTH: 24
<212> TYPE: DNA
<213> ORGANISM: Artificial Sequence
<220> FEATURE:
<223> OTHER INFORMATION: Artificial DNA Primer

<400> SEQUENCE: 30
gtggctgccg aggtgtgtat acca                                            24

<210> SEQ ID NO 31
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 31
caccctctgt gtattgcacc atgccccagt tcgatatcct ctgca                     45

<210> SEQ ID NO 32
<211> LENGTH: 43
<212> TYPE: DNA
<213> ORGANISM: Artificial Sequence
<220> FEATURE:
<223> OTHER INFORMATION: Artificial DNA Primer

<400> SEQUENCE: 32
aaactctagg atgcatgcaa gtgaggctat tgcctatcag ctc                       43

<210> SEQ ID NO 33
<211> LENGTH: 38
<212> TYPE: DNA
<213> ORGANISM: Artificial Sequence
<220> FEATURE:
<223> OTHER INFORMATION: Artificial DNA Primer

<400> SEQUENCE: 33
catcacactg gcggccgcga attctaggct aggtatgc                             38

<210> SEQ ID NO 34
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 34
ggtgcaatac acagagggtg                                                 20

<210> SEQ ID NO 35
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 35
cgcaatctat cgaatagcag                                                 20

<210> SEQ ID NO 36
<211> LENGTH: 25
<212> TYPE: DNA
```

```
<213> ORGANISM: Artificial Sequence
<220> FEATURE:
<223> OTHER INFORMATION: Artificial DNA Primer

<400> SEQUENCE: 36
ctacatcgaa gctgaaagca cgaga                                          25

<210> SEQ ID NO 37
<211> LENGTH: 31
<212> TYPE: DNA
<213> ORGANISM: Artificial Sequence
<220> FEATURE:
<223> OTHER INFORMATION: Artificial DNA Primer

<400> SEQUENCE: 37
cttctatctt gggatgcttc acgatacgtg a                                   31

<210> SEQ ID NO 38
<211> LENGTH: 25
<212> TYPE: DNA
<213> ORGANISM: Artificial Sequence
<220> FEATURE:
<223> OTHER INFORMATION: Artificial DNA Primer

<400> SEQUENCE: 38
cgcgcccttg aatatcggag aaggt                                          25

<210> SEQ ID NO 39
<211> LENGTH: 25
<212> TYPE: DNA
<213> ORGANISM: Artificial Sequence
<220> FEATURE:
<223> OTHER INFORMATION: Artificial DNA Primer

<400> SEQUENCE: 39
actgagtcag gccgcccttg tctga                                          25

<210> SEQ ID NO 40
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 40
gtacaaacaa ctacctggtg                                                20

<210> SEQ ID NO 41
<211> LENGTH: 22
<212> TYPE: DNA
<213> ORGANISM: Artificial Sequence
<220> FEATURE:
<223> OTHER INFORMATION: Artificial DNA Primer

<400> SEQUENCE: 41
gtttcaggca ggtcttgcaa cg                                             22

<210> SEQ ID NO 42
<211> LENGTH: 500
<212> TYPE: DNA
<213> ORGANISM: Trichoderma reesei

<400> SEQUENCE: 42
accagtatcg aggattgacg gcagaatagc agtggctctc caggatttga ctggacaaaa    60
tcttccagta ttcccaggtc acagtgtctg gcagaagtcc cttctcgcgt gcgagtcgaa   120
```

```
agtcgctata gtgcgcaatg agagcacagt aggagaatag gaacccgcga gcacattgtt    180
caatctccac atgaattgga tgactgctgg gcagaatgtg ctgcctccaa aatcctgcgt    240
ccaacagata ctctggcagg ggcttcagat gaatgcctct gggcccccag ataagatgca    300
gctctggatt ctcggttacg atgatatcgc gagagagcac gagttggtga tggaggggac    360
gaggaggcat aggtcggccg caggcccata accagtcttg cacagcattg atcttcctca    420
cgaggagctc ctgatgcaga aactcctcca tgttgctgat tgggttgaga atttcatcgc    480
tcctggatcg tatggttgct                                                500

<210> SEQ ID NO 43
<211> LENGTH: 43
<212> TYPE: DNA
<213> ORGANISM: Artificial Sequence
<220> FEATURE:
<223> OTHER INFORMATION: Artificial DNA Primer

<400> SEQUENCE: 43
tcacatggtt taaacggcgc gccacactta ctcttctaca cag                       43

<210> SEQ ID NO 44
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 44
ttcgaacagc cccagtcggt                                                 20

<210> SEQ ID NO 45
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 45
ggaaatacag gatagacact cggccgcgaa ttcatcttga                           40

<210> SEQ ID NO 46
<211> LENGTH: 43
<212> TYPE: DNA
<213> ORGANISM: Artificial Sequence
<220> FEATURE:
<223> OTHER INFORMATION: Artificial DNA Primer

<400> SEQUENCE: 46
agccttgttt tgtcgggcgc gccgctgctc tcggctagcg aag                       43

<210> SEQ ID NO 47
<211> LENGTH: 43
<212> TYPE: DNA
<213> ORGANISM: Artificial Sequence
<220> FEATURE:
<223> OTHER INFORMATION: Artificial DNA Primer

<400> SEQUENCE: 47
tcacatggtt taaacggcgc gccacactta ctcttctaca cag                       43

<210> SEQ ID NO 48
<211> LENGTH: 43
<212> TYPE: DNA
```

```
<213> ORGANISM: Artificial Sequence
<220> FEATURE:
<223> OTHER INFORMATION: Artificial DNA Primer

<400> SEQUENCE: 48
agccttgttt tgtcgggcgc gccgctgctc tcggctagcg aag                43

<210> SEQ ID NO 49
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 49
cacaatgtcg agtgtctatt                                          20

<210> SEQ ID NO 50
<211> LENGTH: 43
<212> TYPE: DNA
<213> ORGANISM: Artificial Sequence
<220> FEATURE:
<223> OTHER INFORMATION: Artificial DNA Primer

<400> SEQUENCE: 50
gccatattta atccgtttta aacgtttata aaatgttcct gcc                43

<210> SEQ ID NO 51
<211> LENGTH: 63
<212> TYPE: DNA
<213> ORGANISM: Artificial Sequence
<220> FEATURE:
<223> OTHER INFORMATION: Artificial DNA Primer

<400> SEQUENCE: 51
cctagttgga gtattcctgc aggtcaactc tctcctctag gttgaagttc ctattccgag    60
ttc                                                            63

<210> SEQ ID NO 52
<211> LENGTH: 50
<212> TYPE: DNA
<213> ORGANISM: Artificial Sequence
<220> FEATURE:
<223> OTHER INFORMATION: Artificial DNA Primer

<400> SEQUENCE: 52
aatagacact cgacattgtg gcatgcacta gctagttgaa gttcctatac         50

<210> SEQ ID NO 53
<211> LENGTH: 63
<212> TYPE: DNA
<213> ORGANISM: Artificial Sequence
<220> FEATURE:
<223> OTHER INFORMATION: Artificial DNA Primer

<400> SEQUENCE: 53
cctagttgga gtattcctgc aggtcaactc tctcctctag gttgaagttc ctattccgag    60
ttc                                                            63

<210> SEQ ID NO 54
<211> LENGTH: 43
<212> TYPE: DNA
<213> ORGANISM: Artificial Sequence
<220> FEATURE:
<223> OTHER INFORMATION: Artificial DNA Primer
```

-continued

<400> SEQUENCE: 54
gccatattta aatccgttta aacgtttata aaatgttcct gcc                                    43

<210> SEQ ID NO 55
<211> LENGTH: 22
<212> TYPE: DNA
<213> ORGANISM: Artificial Sequence
<220> FEATURE:
<223> OTHER INFORMATION: Artificial DNA Primer

<400> SEQUENCE: 55
gtttcaggca ggtcttgcaa cg                                                            22

<210> SEQ ID NO 56
<211> LENGTH: 22
<212> TYPE: DNA
<213> ORGANISM: Artificial Sequence
<220> FEATURE:
<223> OTHER INFORMATION: Artificial DNA Primer

<400> SEQUENCE: 56
gctgatcgag aagattagca tg                                                            22

<210> SEQ ID NO 57
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 57
gatcagtgat gaagaaggcg                                                               20

<210> SEQ ID NO 58
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 58
ctcaggccat cgtaggaaat                                                               20

<210> SEQ ID NO 59
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 59
ctaggtaggt aggtagtata                                                               20

<210> SEQ ID NO 60
<211> LENGTH: 22
<212> TYPE: DNA
<213> ORGANISM: Artificial Sequence
<220> FEATURE:
<223> OTHER INFORMATION: Artificial DNA Primer

<400> SEQUENCE: 60
ccagtaacaa ctttgcttgg cc                                                            22

<210> SEQ ID NO 61

```
<211> LENGTH: 26
<212> TYPE: DNA
<213> ORGANISM: Artificial Sequence
<220> FEATURE:
<223> OTHER INFORMATION: Artificial DNA Primer

<400> SEQUENCE: 61
caccatgtta ctttcaccca aataca                                          26

<210> SEQ ID NO 62
<211> LENGTH: 37
<212> TYPE: DNA
<213> ORGANISM: Artificial Sequence
<220> FEATURE:
<223> OTHER INFORMATION: Artificial DNA Primer

<400> SEQUENCE: 62
cttggtaccg agctctggaa acgcaaccct gaaggga                              37

<210> SEQ ID NO 63
<211> LENGTH: 37
<212> TYPE: DNA
<213> ORGANISM: Artificial Sequence
<220> FEATURE:
<223> OTHER INFORMATION: Artificial DNA Primer

<400> SEQUENCE: 63
cagaattcgc ccttgtctac gccaggaccg agcaagc                              37

<210> SEQ ID NO 64
<211> LENGTH: 38
<212> TYPE: DNA
<213> ORGANISM: Artificial Sequence
<220> FEATURE:
<223> OTHER INFORMATION: Artificial DNA Primer

<400> SEQUENCE: 64
catcacactg gcggccgcga attctaggct aggtatgc                             38

<210> SEQ ID NO 65
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 65
ggtgcaatac acagagggtg                                                 20

<210> SEQ ID NO 66
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 66
caccctctgt gtattgcacc atgccccagt tcgatatcct ctgca                     45

<210> SEQ ID NO 67
<211> LENGTH: 43
<212> TYPE: DNA
<213> ORGANISM: Artificial Sequence
<220> FEATURE:
<223> OTHER INFORMATION: Artificial DNA Primer

<400> SEQUENCE: 67
```
aaactctagg atgcatgcaa gtgaggctat tgcctatcag ctc    43

<210> SEQ ID NO 68
<211> LENGTH: 36
<212> TYPE: DNA
<213> ORGANISM: Artificial Sequence
<220> FEATURE:
<223> OTHER INFORMATION: Artificial DNA Primer

<400> SEQUENCE: 68
cgcggactgc gcaccatgag attcggttgg ctcgag    36

<210> SEQ ID NO 69
<211> LENGTH: 38
<212> TYPE: DNA
<213> ORGANISM: Artificial Sequence
<220> FEATURE:
<223> OTHER INFORMATION: Artificial DNA Primer

<400> SEQUENCE: 69
tcgccacgga gcttactagt agacacgggg cagaggcg    38

<210> SEQ ID NO 70
<211> LENGTH: 41
<212> TYPE: DNA
<213> ORGANISM: Artificial Sequence
<220> FEATURE:
<223> OTHER INFORMATION: Artificial DNA Primer

<400> SEQUENCE: 70
cgtgtttctt cccattcgca tgcgacctcg tggtcattga c    41

<210> SEQ ID NO 71
<211> LENGTH: 49
<212> TYPE: DNA
<213> ORGANISM: Artificial Sequence
<220> FEATURE:
<223> OTHER INFORMATION: Artificial DNA Primer

<400> SEQUENCE: 71
gctttgacgt tacattgacg tacttataag cggccgccag tgtgatgga    49

<210> SEQ ID NO 72
<211> LENGTH: 49
<212> TYPE: DNA
<213> ORGANISM: Artificial Sequence
<220> FEATURE:
<223> OTHER INFORMATION: Artificial DNA Primer

<400> SEQUENCE: 72
tccatcacac tggcggccgc ttataagtac gtcaatgtaa cgtcaaagc    49

<210> SEQ ID NO 73
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 73
tgcagaggat atcgaactgg ggcattttgt atctgcgaat tgagcttg    48

<210> SEQ ID NO 74
<211> LENGTH: 48
<212> TYPE: DNA

```
<213> ORGANISM: Artificial Sequence
<220> FEATURE:
<223> OTHER INFORMATION: Artificial DNA Primer

<400> SEQUENCE: 74
caagctcaat tcgcagatac aaaatgcccc agttcgatat cctctgca          48

<210> SEQ ID NO 75
<211> LENGTH: 41
<212> TYPE: DNA
<213> ORGANISM: Artificial Sequence
<220> FEATURE:
<223> OTHER INFORMATION: Artificial DNA Primer

<400> SEQUENCE: 75
gctgtttaaa ctctaggatg catgcaagtg aggctattgc c                 41

<210> SEQ ID NO 76
<211> LENGTH: 41
<212> TYPE: DNA
<213> ORGANISM: Artificial Sequence
<220> FEATURE:
<223> OTHER INFORMATION: Artificial DNA Primer

<400> SEQUENCE: 76
cgtgtttctt cccattcgca tgcgacctcg tggtcattga c                 41

<210> SEQ ID NO 77
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 77
tgcagaggat atcgaactgg ggcattttgt atctgcgaat tgagcttg          48

<210> SEQ ID NO 78
<211> LENGTH: 22
<212> TYPE: DNA
<213> ORGANISM: Artificial Sequence
<220> FEATURE:
<223> OTHER INFORMATION: Artificial DNA Primer

<400> SEQUENCE: 78
ttcccttcct ctagtgttga at                                      22

<210> SEQ ID NO 79
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 79
gttggtatag agcagcgttc                                         20

<210> SEQ ID NO 80
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 80
ctatatccga aacaatgacg                                         20
```

<210> SEQ ID NO 81
<211> LENGTH: 41
<212> TYPE: DNA
<213> ORGANISM: Artificial Sequence
<220> FEATURE:
<223> OTHER INFORMATION: Artificial DNA Primer

<400> SEQUENCE: 81
cgtgtttctt cccattcgca tgcgacctcg tggtcattga c             41

<210> SEQ ID NO 82
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 82
aaagacaggc cagcgacgaa g             21

<210> SEQ ID NO 83
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 83
gcattgcaac cgcggctttc             20

<210> SEQ ID NO 84
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 84
atgagattcg gttggctcga g             21

<210> SEQ ID NO 85
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 85
ccgtgatgtt gtaaccatat             20

<210> SEQ ID NO 86
<211> LENGTH: 22
<212> TYPE: DNA
<213> ORGANISM: Artificial Sequence
<220> FEATURE:
<223> OTHER INFORMATION: Artificial DNA Primer

<400> SEQUENCE: 86
ttcccttcct ctagtgttga at             22

<210> SEQ ID NO 87
<211> LENGTH: 20
<212> TYPE: DNA
<213> ORGANISM: Artificial Sequence
<220> FEATURE:

<223> OTHER INFORMATION: Artificial DNA Primer

<400> SEQUENCE: 87
gttggtatag agcagcgttc                                               20

<210> SEQ ID NO 88
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 88
ctatatccga aacaatgacg                                               20

<210> SEQ ID NO 89
<211> LENGTH: 41
<212> TYPE: DNA
<213> ORGANISM: Artificial Sequence
<220> FEATURE:
<223> OTHER INFORMATION: Artificial DNA Primer

<400> SEQUENCE: 89
cgtgtttctt cccattcgca tgcgacctcg tggtcattga c                       41

<210> SEQ ID NO 90
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 90
aaagacaggc cagcgacgaa g                                             21

<210> SEQ ID NO 91
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 91
gcattgcaac cgcggctttc                                               20

<210> SEQ ID NO 92
<211> LENGTH: 24
<212> TYPE: DNA
<213> ORGANISM: Artificial Sequence
<220> FEATURE:
<223> OTHER INFORMATION: Artificial DNA Primer

<400> SEQUENCE: 92
aatagaaaga gaagcttagc caag                                          24

<210> SEQ ID NO 93
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 93
gccgtttaaa tgaattcgaa cccttaatta actagtacgc gtagatc                 47

-continued

<210> SEQ ID NO 94
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 94
gatctacgcg tactagttaa ttaagggttc gaattcattt aaacggc        47

<210> SEQ ID NO 95
<211> LENGTH: 23
<212> TYPE: DNA
<213> ORGANISM: Artificial Sequence
<220> FEATURE:
<223> OTHER INFORMATION: Artificial DNA Primer

<400> SEQUENCE: 95
gaccgattcc ttgcggtccg aat                                  23

<210> SEQ ID NO 96
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 96
ccgcggactg cgcaccatgg atgcatctgg aaacgcaacc                40

<210> SEQ ID NO 97
<211> LENGTH: 50
<212> TYPE: DNA
<213> ORGANISM: Artificial Sequence
<220> FEATURE:
<223> OTHER INFORMATION: Artificial DNA Primer

<400> SEQUENCE: 97
ggtgcgtcag gctttcgcca catttaaatc atgcattcta cgccaggacc     50

<210> SEQ ID NO 98
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 98
tggcgtagaa tgcatgattt aaatgtggcg aaagcctgac gcacc          45

<210> SEQ ID NO 99
<211> LENGTH: 29
<212> TYPE: DNA
<213> ORGANISM: Artificial Sequence
<220> FEATURE:
<223> OTHER INFORMATION: Artificial DNA Primer

<400> SEQUENCE: 99
atgcatgctc gagcggccgc acggcacgg                            29

<210> SEQ ID NO 100
<211> LENGTH: 22
<212> TYPE: DNA
<213> ORGANISM: Artificial Sequence
<220> FEATURE:
<223> OTHER INFORMATION: Artificial DNA Primer

```
<400> SEQUENCE: 100
ttcccttcct ctagtgttga at                                              22

<210> SEQ ID NO 101
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 101
gttggtatag agcagcgttc                                                 20

<210> SEQ ID NO 102
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 102
ctatatccga aacaatgacg                                                 20

<210> SEQ ID NO 103
<211> LENGTH: 41
<212> TYPE: DNA
<213> ORGANISM: Artificial Sequence
<220> FEATURE:
<223> OTHER INFORMATION: Artificial DNA Primer

<400> SEQUENCE: 103
cgtgtttctt cccattcgca tgcgacctcg tggtcattga c                         41

<210> SEQ ID NO 104
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 104
aaagacaggc cagcgacgaa g                                               21

<210> SEQ ID NO 105
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 105
gcattgcaac cgcggctttc                                                 20

<210> SEQ ID NO 106
<211> LENGTH: 29
<212> TYPE: DNA
<213> ORGANISM: Artificial Sequence
<220> FEATURE:
<223> OTHER INFORMATION: Artificial DNA Primer

<400> SEQUENCE: 106
acctgccgtg tcagcctcta cggttgtta                                       29

<210> SEQ ID NO 107
<211> LENGTH: 21
```

```
<212> TYPE: DNA
<213> ORGANISM: Artificial Sequence
<220> FEATURE:
<223> OTHER INFORMATION: Artificial DNA Primer

<400> SEQUENCE: 107
aaagacaggc cagcgacgaa g                                              21

<210> SEQ ID NO 108
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 108
gcattgcaac cgcggctttc                                                20

<210> SEQ ID NO 109
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 109
atgaaaaagc ctgaactcac c                                              21

<210> SEQ ID NO 110
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 110
tccatcacag tttgccagtg a                                              21

<210> SEQ ID NO 111
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 111
acattgccgt cgaagttgta                                                20

<210> SEQ ID NO 112
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 112
aagacctctg tcccgcagac                                                20

<210> SEQ ID NO 113
<211> LENGTH: 42
<212> TYPE: DNA
<213> ORGANISM: Artificial Sequence
<220> FEATURE:
<223> OTHER INFORMATION: Artificial DNA Primer

<400> SEQUENCE: 113
```
atcaccctct gtgtattgca ccagggcatg gggatgacct tg    42

<210> SEQ ID NO 114
<211> LENGTH: 44
<212> TYPE: DNA
<213> ORGANISM: Artificial Sequence
<220> FEATURE:
<223> OTHER INFORMATION: Artificial DNA Primer

<400> SEQUENCE: 114
ccggtcacga aagccttaat taatctacgc caggaccgag caag    44

<210> SEQ ID NO 115
<211> LENGTH: 25
<212> TYPE: DNA
<213> ORGANISM: Artificial Sequence
<220> FEATURE:
<223> OTHER INFORMATION: Artificial DNA Primer

<400> SEQUENCE: 115
caaccaaaat ttctgtttat agatc    25

<210> SEQ ID NO 116
<211> LENGTH: 25
<212> TYPE: DNA
<213> ORGANISM: Artificial Sequence
<220> FEATURE:
<223> OTHER INFORMATION: Artificial DNA Primer

<400> SEQUENCE: 116
gatgatataa tggagcaaat aaggg    25

<210> SEQ ID NO 117
<211> LENGTH: 52
<212> TYPE: DNA
<213> ORGANISM: Artificial Sequence
<220> FEATURE:
<223> OTHER INFORMATION: Artificial DNA Primer

<400> SEQUENCE: 117
ataacaactc cgagtggatc ctggaaacgc aaccctgaag ggattcttcc tt    52

<210> SEQ ID NO 118
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 118
tgtttaaact ctaggatgca ttctacgcca ggaccgagca agccca    46

<210> SEQ ID NO 119
<211> LENGTH: 41
<212> TYPE: DNA
<213> ORGANISM: Artificial Sequence
<220> FEATURE:
<223> OTHER INFORMATION: Artificial DNA Primer

<400> SEQUENCE: 119
ctctgtgtat tgcaccatga agcaccttgc atcttccatc g    41

<210> SEQ ID NO 120
<211> LENGTH: 41
<212> TYPE: DNA
<213> ORGANISM: Artificial Sequence

```
<220> FEATURE:
<223> OTHER INFORMATION: Artificial DNA Primer

<400> SEQUENCE: 120
ctctgtgtat tgcaccatga agcaccttgc atcttccatc g                41

<210> SEQ ID NO 121
<211> LENGTH: 54
<212> TYPE: DNA
<213> ORGANISM: Artificial Sequence
<220> FEATURE:
<223> OTHER INFORMATION: Artificial DNA Primer

<400> SEQUENCE: 121
acgaattgtt taaacgtcga cccaagtatc cagaggtgta tggaaatatc agat    54

<210> SEQ ID NO 122
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 122
gtgcgtcagg ctttcgccac ggatcctttc agaggccgaa ctgaag            46

<210> SEQ ID NO 123
<211> LENGTH: 36
<212> TYPE: DNA
<213> ORGANISM: Artificial Sequence
<220> FEATURE:
<223> OTHER INFORMATION: Artificial DNA Primer

<400> SEQUENCE: 123
aaaaaacctg caggggagt cttgatctga cgctgc                        36

<210> SEQ ID NO 124
<211> LENGTH: 41
<212> TYPE: DNA
<213> ORGANISM: Artificial Sequence
<220> FEATURE:
<223> OTHER INFORMATION: Artificial DNA Primer

<400> SEQUENCE: 124
aaaaaacctg caggcggccg catatcgaac ggtagtgact g                 41

<210> SEQ ID NO 125
<211> LENGTH: 42
<212> TYPE: DNA
<213> ORGANISM: Artificial Sequence
<220> FEATURE:
<223> OTHER INFORMATION: Artificial DNA Primer

<400> SEQUENCE: 125
aaaaaagttt aaacgcggcc gcgagaatgc ttcctaatgc ta                42

<210> SEQ ID NO 126
<211> LENGTH: 34
<212> TYPE: DNA
<213> ORGANISM: Artificial Sequence
<220> FEATURE:
<223> OTHER INFORMATION: Artificial DNA Primer

<400> SEQUENCE: 126
aaaaaagttt aaaccttgaa cgtcgagaga gagc                         34
```

<210> SEQ ID NO 127
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 127
ccacactaca gatgctgtcg                                         20

<210> SEQ ID NO 128
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 128
tccatgactc gcaagatacg                                         20

<210> SEQ ID NO 129
<211> LENGTH: 29
<212> TYPE: DNA
<213> ORGANISM: Artificial Sequence
<220> FEATURE:
<223> OTHER INFORMATION: Artificial DNA Primer

<400> SEQUENCE: 129
ccaatgcata gtctgaacag cgataacaa                               29

<210> SEQ ID NO 130
<211> LENGTH: 29
<212> TYPE: DNA
<213> ORGANISM: Artificial Sequence
<220> FEATURE:
<223> OTHER INFORMATION: Artificial DNA Primer

<400> SEQUENCE: 130
ccaatgcata ggcattaagt gggttgtat                               29

<210> SEQ ID NO 131
<211> LENGTH: 42
<212> TYPE: DNA
<213> ORGANISM: Artificial Sequence
<220> FEATURE:
<223> OTHER INFORMATION: Artificial DNA Primer

<400> SEQUENCE: 131
tatagcgtac ctgcaggtgt catgcccgcg gctttgcctt ga                42

<210> SEQ ID NO 132
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 132
atgctgtacc tgcaggcggc cgccgctccc gatcatcatc cctccgag          48

<210> SEQ ID NO 133
<211> LENGTH: 56
<212> TYPE: DNA
<213> ORGANISM: Artificial Sequence
<220> FEATURE:
<223> OTHER INFORMATION: Artificial DNA Primer

<400> SEQUENCE: 133
catggtttaa acggcggcgc gccgcggccg caattcagag catcacggtt gaggga   56

<210> SEQ ID NO 134
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 134
ccttgttttg tcgggcgcgc cacatggcct tggattgacg caggac   46

<210> SEQ ID NO 135
<211> LENGTH: 35
<212> TYPE: DNA
<213> ORGANISM: Artificial Sequence
<220> FEATURE:
<223> OTHER INFORMATION: Artificial DNA Primer

<400> SEQUENCE: 135
gacgcataca atacaagcat atgctgttgg tgtct   35

<210> SEQ ID NO 136
<211> LENGTH: 25
<212> TYPE: DNA
<213> ORGANISM: Artificial Sequence
<220> FEATURE:
<223> OTHER INFORMATION: Artificial DNA Primer

<400> SEQUENCE: 136
aaggcgtctg gaaacagaag ctgct   25

<210> SEQ ID NO 137
<211> LENGTH: 43
<212> TYPE: DNA
<213> ORGANISM: Artificial Sequence
<220> FEATURE:
<223> OTHER INFORMATION: Artificial DNA Primer

<400> SEQUENCE: 137
cgattcctta gtagccatgc actttaagat aacggaatag aag   43

<210> SEQ ID NO 138
<211> LENGTH: 43
<212> TYPE: DNA
<213> ORGANISM: Artificial Sequence
<220> FEATURE:
<223> OTHER INFORMATION: Artificial DNA Primer

<400> SEQUENCE: 138
cttctattcc gttatcttaa agtgcatggc tactaaggaa tcg   43

<210> SEQ ID NO 139
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 139
tatcactgtc attcaatgca ttctttgtgt gtgtgtcagc attgta   46

<210> SEQ ID NO 140

```
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 140
tatcactgtc attcaatgca ttctttgtgt gtgtgtcagc attgta          46

<210> SEQ ID NO 141
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 141
tctgccccgt gtctacgtgg cgaaagcctg acgcaccggt agatt            45

<210> SEQ ID NO 142
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 142
cacggagctt actagacggc acggttaagc agggtcttgc                  40

<210> SEQ ID NO 143
<211> LENGTH: 30
<212> TYPE: DNA
<213> ORGANISM: Artificial Sequence
<220> FEATURE:
<223> OTHER INFORMATION: Artificial DNA Primer

<400> SEQUENCE: 143
caagcaaagc gttccgtcgc agtagcaggc                             30

<210> SEQ ID NO 144
<211> LENGTH: 30
<212> TYPE: DNA
<213> ORGANISM: Artificial Sequence
<220> FEATURE:
<223> OTHER INFORMATION: Artificial DNA Primer

<400> SEQUENCE: 144
gcatcacaaa cctgggcatt ggctacagaa                             30

<210> SEQ ID NO 145
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 145
atgagattcg gttggctcga g                                      21

<210> SEQ ID NO 146
<211> LENGTH: 22
<212> TYPE: DNA
<213> ORGANISM: Artificial Sequence
<220> FEATURE:
<223> OTHER INFORMATION: Artificial DNA Primer

<400> SEQUENCE: 146
```
aaagactccg cgggtatagc tc                                           22

<210> SEQ ID NO 147
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 147
cgaattgttt aaacgggctc ctatgttcaa tcatggcaca                        40

<210> SEQ ID NO 148
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 148
cctacattcg gtcgacttga cgattcagtg tcttctcttg                        40

<210> SEQ ID NO 149
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 149
aaacgattcc ttaataaaac aatgcttgga ctccgaaagt                        40

<210> SEQ ID NO 150
<211> LENGTH: 41
<212> TYPE: DNA
<213> ORGANISM: Artificial Sequence
<220> FEATURE:
<223> OTHER INFORMATION: Artificial DNA Primer

<400> SEQUENCE: 150
cagtcacctc tagttatgca attaaacaaa tgcccaccta g                      41

<210> SEQ ID NO 151
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 151
ctaagatctc gggccctcgg gccttcggcc tttgggtgta catgt                  45

<210> SEQ ID NO 152
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 152
gctactagta cgcgtctagt agacacgggg cagaggcgct                        40

<210> SEQ ID NO 153
<211> LENGTH: 25
<212> TYPE: DNA

```
<213> ORGANISM: Artificial Sequence
<220> FEATURE:
<223> OTHER INFORMATION: Artificial DNA Primer

<400> SEQUENCE: 153
ctgaggaaag gcagtcttca cattc                                          25

<210> SEQ ID NO 154
<211> LENGTH: 30
<212> TYPE: DNA
<213> ORGANISM: Artificial Sequence
<220> FEATURE:
<223> OTHER INFORMATION: Artificial DNA Primer

<400> SEQUENCE: 154
gcatcacaaa cctgggcatt ggctacagaa                                     30

<210> SEQ ID NO 155
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 155
cgaattgttt aaacgaagtc tgcttccttg caattatgca                          40

<210> SEQ ID NO 156
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 156
cctacattcg gtcgaaacga gaagttctca actaagggct                          40

<210> SEQ ID NO 157
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 157
aaacgattcc ttaatgttat ctgtacgctc tgatgagaag                          40

<210> SEQ ID NO 158
<211> LENGTH: 51
<212> TYPE: DNA
<213> ORGANISM: Artificial Sequence
<220> FEATURE:
<223> OTHER INFORMATION: Artificial DNA Primer

<400> SEQUENCE: 158
cagtcacctc tagttaggac agctggccta gagcgctcag cagactcctt t             51

<210> SEQ ID NO 159
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 159
ctaagatctc gggccctcgg gccttcggcc tttgggtgta catgt                    45
```

<210> SEQ ID NO 160
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 160
gctactagta cgcgtctagt agacacgggg cagaggcgct                        40

<210> SEQ ID NO 161
<211> LENGTH: 25
<212> TYPE: DNA
<213> ORGANISM: Artificial Sequence
<220> FEATURE:
<223> OTHER INFORMATION: Artificial DNA Primer

<400> SEQUENCE: 161
atctcatccc acgagaaggt tatgc                                        25

<210> SEQ ID NO 162
<211> LENGTH: 30
<212> TYPE: DNA
<213> ORGANISM: Artificial Sequence
<220> FEATURE:
<223> OTHER INFORMATION: Artificial DNA Primer

<400> SEQUENCE: 162
gcatcacaaa cctgggcatt ggctacagaa                                   30

<210> SEQ ID NO 163
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 163
gtttaaacgt cgacgcatgg aagtggtatg taccatcgtg ctctgt                 46

<210> SEQ ID NO 164
<211> LENGTH: 68
<212> TYPE: DNA
<213> ORGANISM: Artificial Sequence
<220> FEATURE:
<223> OTHER INFORMATION: Artificial DNA Primer

<400> SEQUENCE: 164
ctttcgccac ggagcttaat taatagtacg cgtagatctg cggactagtt tgggacaaca  60
agaaggac                                                           68

<210> SEQ ID NO 165
<211> LENGTH: 500
<212> TYPE: DNA
<213> ORGANISM: Artificial Sequence
<220> FEATURE:
<223> OTHER INFORMATION: Artificial DNA Sequence

<400> SEQUENCE: 165
tgtaagatca ccctctgtgt attgcaccat gcggtctctt ctcgcccttg cacctactct  60
actcgcgccc gttgtgcagg cccagcagac catgtggggc caatgtggcg gccaaggctg 120
gaccggcccg acgatctgtg ttgccggcgc aacatgtagc acacagaatc cctggtacgc 180

-continued

| | |
|---|---|
| tcagtgtacc ccggcaccta ccgcgccgac gactttgcaa acgacgacga cgacgagctc | 240 |
| gaaatcgtcc acgaccacca gctcgaagtc gtccactacc acaggtggaa gtggcggtgg | 300 |
| tactactaca tccacgtcag ccaccatcac cgcggcacca tccggtaacc cttacagcgg | 360 |
| ctaccagctg tatgtgaacc aggaatactc ctccgaggtc tacgcgtctg ccattccttc | 420 |
| tctgaccggc actctggtcg cgaaggctag tgctgcggct gaagtgccct cattcctgtg | 480 |
| gctggacact gcctccaagg | 500 |

<210> SEQ ID NO 166
<211> LENGTH: 500
<212> TYPE: DNA
<213> ORGANISM: Artificial Sequence
<220> FEATURE:
<223> OTHER INFORMATION: Artificial DNA Sequence

<400> SEQUENCE: 166

| | |
|---|---|
| gaagtgccct cattcctgtg gctggacact gcctccaagg tgcccctgat gggaacctac | 60 |
| ctgcaggaca tccaggccaa gaacgctgcc ggcgccaacc ctccttacgc tggtcaattc | 120 |
| gtggtctacg acttgccgga ccgtgactgc gccgctctgg ccagtaatgg cgagtactca | 180 |
| attgccaaca acggtgtggc caactacaag gcgtacattg actccatccg tgctcttctg | 240 |
| gtgcaatact ctaacgttca cgtcatcctc gtcatcgaac ccgacagctt ggccaacctg | 300 |
| gtgaccaacc tcaacgtcca gaaatgcgcc aacgcccaga gcgcctacct ggagtgtatc | 360 |
| aactatgctc tgactcagct caacctgaag aacgtcgcca tgtacatcga cgcaggccat | 420 |
| gcgggctggc tcggatggcc cgccaacttg agcccgccg cacaactctt cgcctccgtc | 480 |
| taccagaatg ccagttcccc | 500 |

<210> SEQ ID NO 167
<211> LENGTH: 500
<212> TYPE: DNA
<213> ORGANISM: Artificial Sequence
<220> FEATURE:
<223> OTHER INFORMATION: Artificial DNA Sequence

<400> SEQUENCE: 167

| | |
|---|---|
| cgcctccgtc taccagaatg ccagttcccc cgcggctgtt cgtggcctgg ccaccaacgt | 60 |
| cgccaactac aacgcctggt cgatcgccac ctgcccctcc tacacccagg gagaccccaa | 120 |
| ctgcgacgag cagaagtaca tcaacgccct ggcccctctt ctccagcaac agggctggtc | 180 |
| atcagttcac ttcatcaccg ataccggccg gaatggcgtc cagcccacga agcaaaacgc | 240 |
| ctggggtgac tggtgcaacg tcatcggcac cggcttcggt gttcgcccca ccacgaacac | 300 |
| cggcgatccg ctcgaggatg cctttgtgtg ggtcaagccc ggtggagaga gtgatggcac | 360 |
| gtccaactcg acttcccctc ggtatgacgc ccactgcgga tatagtgatg ctctgcagcc | 420 |
| tgctcctgag gcaggtactt ggttcgaggc ctactttgag cagcttctga ccaacgctaa | 480 |
| cccgtccttt taatagttaa | 500 |

<210> SEQ ID NO 168
<211> LENGTH: 50
<212> TYPE: DNA
<213> ORGANISM: Artificial Sequence
<220> FEATURE:
<223> OTHER INFORMATION: Artificial DNA Primer

<400> SEQUENCE: 168

| | |
|---|---|
| gcagctcacc tgaagaggct tgtaagatca ccctctgtgt attgcaccat | 50 |

<210> SEQ ID NO 169
<211> LENGTH: 49
<212> TYPE: DNA
<213> ORGANISM: Artificial Sequence
<220> FEATURE:
<223> OTHER INFORMATION: Artificial DNA Primer

<400> SEQUENCE: 169
ccggtcacga aagccttaat taactattaa aaggacgggt tagcgttgg            49

<210> SEQ ID NO 170
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 170
cggtttaaac gggagagcaa caacaatcat tctgctgtcg                      40

<210> SEQ ID NO 171
<211> LENGTH: 70
<212> TYPE: DNA
<213> ORGANISM: Artificial Sequence
<220> FEATURE:
<223> OTHER INFORMATION: Artificial DNA Primer

<400> SEQUENCE: 171
ttattaatta actagtacgc gtagatctgc ggccatgggc ttcgaacagc cccagtcggt    60
caagcaggca                                                          70

<210> SEQ ID NO 172
<211> LENGTH: 70
<212> TYPE: DNA
<213> ORGANISM: Artificial Sequence
<220> FEATURE:
<223> OTHER INFORMATION: Artificial DNA Primer

<400> SEQUENCE: 172
gcccatggcc gcagatctac gcgtactagt taattaataa agctccgtgg cgaaagcctg    60
acgcaccggt                                                          70

<210> SEQ ID NO 173
<211> LENGTH: 39
<212> TYPE: DNA
<213> ORGANISM: Artificial Sequence
<220> FEATURE:
<223> OTHER INFORMATION: Artificial DNA Primer

<400> SEQUENCE: 173
cggtttaaac ggacttcggt ggaggtgtcg agtacgagt                       39

<210> SEQ ID NO 174
<211> LENGTH: 34
<212> TYPE: DNA
<213> ORGANISM: Artificial Sequence
<220> FEATURE:
<223> OTHER INFORMATION: Artificial DNA Primer

<400> SEQUENCE: 174
cggactgcgc accatgcgta ccttctcgtc tctt                            34

<210> SEQ ID NO 175

```
<211> LENGTH: 35
<212> TYPE: DNA
<213> ORGANISM: Artificial Sequence
<220> FEATURE:
<223> OTHER INFORMATION: Artificial DNA Primer

<400> SEQUENCE: 175
tcgccacgga gcttatcaag ccgcaagagc agacg                             35

<210> SEQ ID NO 176
<211> LENGTH: 56
<212> TYPE: DNA
<213> ORGANISM: Artificial Sequence
<220> FEATURE:
<223> OTHER INFORMATION: Artificial DNA Primer

<400> SEQUENCE: 176
tccaactcgc ttaattgcga gttttttattt cgtttatttc aattaaggta actaaa    56

<210> SEQ ID NO 177
<211> LENGTH: 60
<212> TYPE: DNA
<213> ORGANISM: Artificial Sequence
<220> FEATURE:
<223> OTHER INFORMATION: Artificial DNA Primer

<400> SEQUENCE: 177
cgtttatttc aattaaggta actaaattct acgccaggac cgagcaagcc cagatgagaa 60

<210> SEQ ID NO 178
<211> LENGTH: 60
<212> TYPE: DNA
<213> ORGANISM: Artificial Sequence
<220> FEATURE:
<223> OTHER INFORMATION: Artificial DNA Primer

<400> SEQUENCE: 178
ataaaaactc gcaattaagc gagttggaat gcatctggaa acgcaaccct gaagggattc 60

<210> SEQ ID NO 179
<211> LENGTH: 75
<212> TYPE: DNA
<213> ORGANISM: Artificial Sequence
<220> FEATURE:
<223> OTHER INFORMATION: Artificial DNA Primer

<400> SEQUENCE: 179
gcccatggtc caactcgctt aattgcgagt ttttatttcg tttatttcaa ttaaggtaac 60
taaattctac gccag                                                  75

<210> SEQ ID NO 180
<211> LENGTH: 75
<212> TYPE: DNA
<213> ORGANISM: Artificial Sequence
<220> FEATURE:
<223> OTHER INFORMATION: Artificial DNA Primer

<400> SEQUENCE: 180
cgttaattaa tttagttacc ttaattgaaa taaacgaaat aaaaactcgc aattaagcga 60
gttggaatgc atctg                                                  75

<210> SEQ ID NO 181
<211> LENGTH: 24
<212> TYPE: DNA
<213> ORGANISM: Artificial Sequence
```

```
<220> FEATURE:
<223> OTHER INFORMATION: Artificial DNA Primer

<400> SEQUENCE: 181
acagcactct ctcgcccaat gatg                                          24

<210> SEQ ID NO 182
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 182
gggcgaactt gactgtcgtc                                               20

<210> SEQ ID NO 183
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 183
ttccatctct caaaggaaga                                               20

<210> SEQ ID NO 184
<211> LENGTH: 22
<212> TYPE: DNA
<213> ORGANISM: Artificial Sequence
<220> FEATURE:
<223> OTHER INFORMATION: Artificial DNA Primer

<400> SEQUENCE: 184
cagtttcagc cctagaagcg cc                                            22

<210> SEQ ID NO 185
<211> LENGTH: 30
<212> TYPE: DNA
<213> ORGANISM: Artificial Sequence
<220> FEATURE:
<223> OTHER INFORMATION: Artificial DNA Primer

<400> SEQUENCE: 185
aatgacccat agggagacaa acagcataat                                    30

<210> SEQ ID NO 186
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 186
tgttggacgc aggattttgg a                                             21

<210> SEQ ID NO 187
<211> LENGTH: 54
<212> TYPE: DNA
<213> ORGANISM: Artificial Sequence
<220> FEATURE:
<223> OTHER INFORMATION: Artificial DNA Primer

<400> SEQUENCE: 187
tcgggtctcc gttctcgtgc ggaccccaag aagaagcgca aggtcgaccg tcct          54
```

<210> SEQ ID NO 188
<211> LENGTH: 1458
<212> TYPE: DNA
<213> ORGANISM: Trichoderma reesei

<400> SEQUENCE: 188

| | | | | | |
|---|---|---|---|---|---|
| atgactaaga | aagtagcaat | ctatacacga | gtatccacta | ctaaccaagc | agaggaaggg | 60 |
| ttctcaattg | atgagcaaat | tgaccgttta | acaaaatatg | ctgaagcaat | ggggtggcaa | 120 |
| gtatctgata | cttatactga | tgctggtttt | tcaggggcca | aacttgaacg | cccagcaatg | 180 |
| caaagattaa | tcaacgatat | cgagaataaa | gcttttgata | cagttcttgt | atataagcta | 240 |
| gaccgccttt | cacgtagtgt | aagagatact | ctttatcttg | ttaaggatgt | gttcacaaaa | 300 |
| aataaaatag | actttatctc | gcttaatgaa | agtattgata | cttcttctgc | tatgggtagc | 360 |
| ttgtttctca | ctattctttc | tgcaattaat | gagtttgaaa | gagagaatat | aaaagaacgc | 420 |
| atgactatgg | gtaaactagg | gcgagcgaaa | tctggtaagt | ctatgatgtg | gactaagaca | 480 |
| gcttttgggt | attccacaa | cagaaagaca | ggtatattag | aaattgttcc | tttacaagct | 540 |
| acaatagttg | aacaaatatt | cactgattat | ttatcaggaa | tatcacttac | aaaattaaga | 600 |
| gataaactca | atgaatctgg | acacatcggt | aaagatatac | cgtggtctta | tcgtacccta | 660 |
| agacaaacac | ttgataatcc | agtttactgt | ggttatatca | aatttaagga | cagcctattt | 720 |
| gaaggtatgc | acaaaccaat | tatcccttat | gagacttatt | taaagttca | aaagagcta | 780 |
| gaagaaagac | aacagcagac | ttatgaaaga | aataacaacc | ctagaccttt | ccaagctaaa | 840 |
| tatatgctgt | cagggatggc | aaggtgcggt | tactgtggag | cacctttaaa | aattgttctt | 900 |
| ggccacaaaa | gaaagatgg | aagccgcact | atgaaatatc | actgtgcaaa | tagatttcct | 960 |
| cgaaaaacaa | aaggaattac | agtatataat | gacaataaaa | agtgtgattc | aggaacttat | 1020 |
| gatttaagta | atttagaaaa | tactgttatt | gacaacctga | ttggatttca | agaaaataat | 1080 |
| gactccttat | tgaaaattat | caatggcaac | aaccaaccta | ttcttgatac | ttcgtcattt | 1140 |
| aaaaagcaaa | tttcacagat | cgataaaaaa | atacaaaaga | actctgattt | gtacctaaat | 1200 |
| gattttatca | ctatggatga | gttgaaagat | cgtactgatt | cccttcaggc | tgagaaaaag | 1260 |
| ctgcttaaag | ctaagattag | cgaaaataaa | tttaatgact | ctactgatgt | ttttgagtta | 1320 |
| gttaaaactc | agttgggctc | aattccgatt | aatgaactat | catatgataa | taaaaagaaa | 1380 |
| atcgtcaaca | accttgtatc | aaaggttgat | gttactgctg | ataatgtaga | tatcatattt | 1440 |
| aaattccaac | tcgcttaa | | | | | 1458 |

<210> SEQ ID NO 189
<211> LENGTH: 1458
<212> TYPE: DNA
<213> ORGANISM: Trichoderma reesei

<400> SEQUENCE: 189

| | | | | | |
|---|---|---|---|---|---|
| atgaccaaga | aggtcgccat | ctatactaga | gtctcgacga | ccaaccaggc | cgaggagggc | 60 |
| ttcagcatcg | acgagcagat | cgatcgcctc | accaagtatg | ccgaggcgat | gggttggcag | 120 |
| gtcagcgaca | cttacaccga | tgctggcttc | tccggtgcta | agctcgaacg | tcccgctatg | 180 |
| cagcgcctca | tcaacgatat | cgagaataag | gcgttcgata | ctgtgcttgt | ctacaagctg | 240 |
| gaccgcctct | ccagatcggt | ccgggatacg | ctgtacttgg | tcaaggatgt | cttcacgaag | 300 |
| aacaagatcg | atttcatctc | gttgaacgag | tccatcgaca | cgtcttccgc | tatgggctct | 360 |
| ctgttcttga | ccatcctttc | cgccattaac | gagttcgagc | gcgagaacat | taaggagcgc | 420 |

```
atgacgatgg gcaagctcgg tcgagctaag tctggcaaga gcatgatgtg gactaagacc    480
gcgttcggtt actaccataa ccgcaagact ggcatcctcg agatcgtccc tctccaagcc    540
actatcgtcg agcagatctt caccgattac ctctccggca tttctctcac gaagctgcgt    600
gacaagctga acgagtctgg ccacattggc aaggacatcc cttggtccta ccgcaccctc    660
cgtcaaaccc ttgataaccc agtttactgt ggctacatca gttcaagga ctcgttgttc    720 gagggcatgc acaagccgat cattccctac gagacgtatc ttaaggtcca aaggaattg    780 gaagagcgcc agcagcagac ctatgaacgc aataacaatc ctcgcccttt ccaggccaag    840
tacatgctgt cgggaatggc tcggtgtggc tactgtggcg ctccactgaa gattgtcctc    900
ggccacaagc gaaaggacgg ttcgcggacg atgaagtacc actgcgccaa ccgtttccca    960
cgcaagacca aggaatcac cgtgtacaat gacaataaga agtgcgactc gggaacttac   1020
gacctgagca acctcgagaa cactgtcatc gataatctca ttggcttcca ggaaaacaac   1080
gactcgctcc tcaagattat caacggcaac aatcagccca ttctcgacac ctccagcttc   1140
aagaagcaga tctcgcagat cgataagaag atccaaaaga cagcgaccct ctaccttaat   1200
gatttcatca cgatggatga gctgaaggac cgcaccgaca gcctccaggc cgaaaagaag   1260
ttgttgaagg ccaagatctc ggagaacaag ttcaatgact ccaccgatgt cttcgagctg   1320
gtgaagaccc agttgggcag catcccatc aatgaactct cctacgacaa taagaagaag   1380
atcgttaaca acctcgtcag caaggtggac gtgactgccg acaacgtcga cattatcttc   1440
aagtttcagc tcgcttaa                                                 1458

<210> SEQ ID NO 190
<211> LENGTH: 485
<212> TYPE: PRT
<213> ORGANISM: Trichoderma reesei

<400> SEQUENCE: 190

Met Thr Lys Lys Val Ala Ile Tyr Thr Arg Val Ser Thr Thr Asn Gln
1               5                   10                  15

Ala Glu Glu Gly Phe Ser Ile Asp Glu Gln Ile Asp Arg Leu Thr Lys
            20                  25                  30

Tyr Ala Glu Ala Met Gly Trp Gln Val Ser Asp Thr Tyr Thr Asp Ala
        35                  40                  45

Gly Phe Ser Gly Ala Lys Leu Glu Arg Pro Ala Met Gln Arg Leu Ile
    50                  55                  60

Asn Asp Ile Glu Asn Lys Ala Phe Asp Thr Val Leu Val Tyr Lys Leu
65                  70                  75                  80

Asp Arg Leu Ser Arg Ser Val Arg Asp Thr Leu Tyr Leu Val Lys Asp
                85                  90                  95

Val Phe Thr Lys Asn Lys Ile Asp Phe Ile Ser Leu Asn Glu Ser Ile
            100                 105                 110

Asp Thr Ser Ser Ala Met Gly Ser Leu Phe Leu Thr Ile Leu Ser Ala
        115                 120                 125

Ile Asn Glu Phe Glu Arg Glu Asn Ile Lys Glu Arg Met Thr Met Gly
    130                 135                 140

Lys Leu Gly Arg Ala Lys Ser Gly Lys Ser Met Met Trp Thr Lys Thr
145                 150                 155                 160

Ala Phe Gly Tyr Tyr His Asn Arg Lys Thr Gly Ile Leu Glu Ile Val
                165                 170                 175

Pro Leu Gln Ala Thr Ile Val Glu Gln Ile Phe Thr Asp Tyr Leu Ser
```

```
            180                 185                 190
Gly Ile Ser Leu Thr Lys Leu Arg Asp Lys Leu Asn Glu Ser Gly His
        195                 200                 205
Ile Gly Lys Asp Ile Pro Trp Ser Tyr Arg Thr Leu Arg Gln Thr Leu
    210                 215                 220
Asp Asn Pro Val Tyr Cys Gly Tyr Ile Lys Phe Lys Asp Ser Leu Phe
225                 230                 235                 240
Glu Gly Met His Lys Pro Ile Ile Pro Tyr Glu Thr Tyr Leu Lys Val
                245                 250                 255
Gln Lys Glu Leu Glu Glu Arg Gln Gln Thr Tyr Glu Arg Asn Asn
            260                 265                 270
Asn Pro Arg Pro Phe Gln Ala Lys Tyr Met Leu Ser Gly Met Ala Arg
        275                 280                 285
Cys Gly Tyr Cys Gly Ala Pro Leu Lys Ile Val Leu Gly His Lys Arg
    290                 295                 300
Lys Asp Gly Ser Arg Thr Met Lys Tyr His Cys Ala Asn Arg Phe Pro
305                 310                 315                 320
Arg Lys Thr Lys Gly Ile Thr Val Tyr Asn Asp Asn Lys Lys Cys Asp
                325                 330                 335
Ser Gly Thr Tyr Asp Leu Ser Asn Leu Glu Asn Thr Val Ile Asp Asn
            340                 345                 350
Leu Ile Gly Phe Gln Glu Asn Asn Asp Ser Leu Leu Lys Ile Asn
        355                 360                 365
Gly Asn Asn Gln Pro Ile Leu Asp Thr Ser Ser Phe Lys Lys Gln Ile
    370                 375                 380
Ser Gln Ile Asp Lys Lys Ile Gln Lys Asn Ser Asp Leu Tyr Leu Asn
385                 390                 395                 400
Asp Phe Ile Thr Met Asp Glu Leu Lys Asp Arg Thr Asp Ser Leu Gln
                405                 410                 415
Ala Glu Lys Lys Leu Leu Lys Ala Lys Ile Ser Glu Asn Lys Phe Asn
            420                 425                 430
Asp Ser Thr Asp Val Phe Glu Leu Val Lys Thr Gln Leu Gly Ser Ile
        435                 440                 445
Pro Ile Asn Glu Leu Ser Tyr Asp Asn Lys Lys Ile Val Asn Asn
    450                 455                 460
Leu Val Ser Lys Val Asp Val Thr Ala Asp Asn Val Asp Ile Ile Phe
465                 470                 475                 480
Lys Phe Gln Leu Ala
            485

<210> SEQ ID NO 191
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 191
ggttaattaa gtacgtcaat gtaacgtcaa agccgccctc                           40

<210> SEQ ID NO 192
<211> LENGTH: 35
<212> TYPE: DNA
<213> ORGANISM: Artificial Sequence
<220> FEATURE:
<223> OTHER INFORMATION: Artificial DNA Primer
```

```
<400> SEQUENCE: 192
cattttgtat ctgcgaattg agcttgcgtg agtcg                                35

<210> SEQ ID NO 193
<211> LENGTH: 39
<212> TYPE: DNA
<213> ORGANISM: Artificial Sequence
<220> FEATURE:
<223> OTHER INFORMATION: Artificial DNA Primer

<400> SEQUENCE: 193
taataagtgc tgtgttcctc agaatgggcc ccagaaggg                            39

<210> SEQ ID NO 194
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 194
cgcttaatta acggcctctt gagatcattc ttcttctgct ccttttc                   47

<210> SEQ ID NO 195
<211> LENGTH: 85
<212> TYPE: DNA
<213> ORGANISM: Artificial Sequence
<220> FEATURE:
<223> OTHER INFORMATION: Artificial DNA Primer

<400> SEQUENCE: 195
gctcacgact cacgcaagct caattcgcag atacaaaatg tcgggtctcc gttctcgtgc     60
ggaccccaag aagaagcgca aggtc                                          85

<210> SEQ ID NO 196
<211> LENGTH: 85
<212> TYPE: DNA
<213> ORGANISM: Artificial Sequence
<220> FEATURE:
<223> OTHER INFORMATION: Artificial DNA Primer

<400> SEQUENCE: 196
cccttctggg gcccattctg aggaacacag cacttattaa gcgagctgaa acttgaagat     60
aatgtcgacg ttgtcggcag tcacg                                          85

<210> SEQ ID NO 197
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 197
ctgataattg ccaacacaat taacatctca atcaaggtaa atgcttt                   47

<210> SEQ ID NO 198
<211> LENGTH: 71
<212> TYPE: DNA
<213> ORGANISM: Artificial Sequence
<220> FEATURE:
<223> OTHER INFORMATION: Artificial DNA Primer

<400> SEQUENCE: 198
taacatctca atcaaggtaa atgctttgag ctgaacccgt actactacca gtgtttgtga     60
```

```
ttacattaag c                                                           71

<210> SEQ ID NO 199
<211> LENGTH: 41
<212> TYPE: DNA
<213> ORGANISM: Artificial Sequence
<220> FEATURE:
<223> OTHER INFORMATION: Artificial DNA Primer

<400> SEQUENCE: 199
ggccatggtg cccgtgaagc cgtttaaatg aattcgaacc c                          41

<210> SEQ ID NO 200
<211> LENGTH: 66
<212> TYPE: DNA
<213> ORGANISM: Artificial Sequence
<220> FEATURE:
<223> OTHER INFORMATION: Artificial DNA Primer

<400> SEQUENCE: 200
cggtttaaac ctgataattg ccaacacaat taacatctca atcaaggtaa atgctttgag      60
ctgaac                                                                 66

<210> SEQ ID NO 201
<211> LENGTH: 41
<212> TYPE: DNA
<213> ORGANISM: Artificial Sequence
<220> FEATURE:
<223> OTHER INFORMATION: Artificial DNA Primer

<400> SEQUENCE: 201
ggccatggtg cccgtgaagc cgtttaaatg aattcgaacc c                          41

<210> SEQ ID NO 202
<211> LENGTH: 39
<212> TYPE: DNA
<213> ORGANISM: Artificial Sequence
<220> FEATURE:
<223> OTHER INFORMATION: Artificial DNA Primer

<400> SEQUENCE: 202
gcccatgggt tcgaattcat ttaaacggct tcacgggca                             39

<210> SEQ ID NO 203
<211> LENGTH: 77
<212> TYPE: DNA
<213> ORGANISM: Artificial Sequence
<220> FEATURE:
<223> OTHER INFORMATION: Artificial DNA Primer

<400> SEQUENCE: 203
cggtttaaac ttaattaaag catttacctt gattgagatg ttaattgtgt tggcaattat      60
caggccgtgg tactggg                                                     77

<210> SEQ ID NO 204
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 204
cacctcttct caacctttgg                                                  20
```

<210> SEQ ID NO 205
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 205
acggggcaaa gctgcctacc                                               20

<210> SEQ ID NO 206
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 206
gcagggtcga tgcgacgcaa                                               20

<210> SEQ ID NO 207
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 207
taccatgact gtcacgatag                                               20

<210> SEQ ID NO 208
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 208
atgaaaaagc ctgaactcac c                                             21

<210> SEQ ID NO 209
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 209
tccatcacag tttgccagtg a                                             21

<210> SEQ ID NO 210
<211> LENGTH: 54
<212> TYPE: DNA
<213> ORGANISM: Artificial Sequence
<220> FEATURE:
<223> OTHER INFORMATION: Artificial DNA Primer

<400> SEQUENCE: 210
tccaactcgc ttaattgcga gttttttattt cgtttatttc aatcaaggta aatg        54

<210> SEQ ID NO 211
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 211
ctgataattg ccaacacaat taacatctca attaaggtaa ctaaa					45

<210> SEQ ID NO 212
<211> LENGTH: 44
<212> TYPE: DNA
<213> ORGANISM: Artificial Sequence
<220> FEATURE:
<223> OTHER INFORMATION: Artificial DNA Primer

<400> SEQUENCE: 212
agcatgaatg tcgctcatcc gatgccgcat caccgttgtg tcag					44

<210> SEQ ID NO 213
<211> LENGTH: 69
<212> TYPE: DNA
<213> ORGANISM: Artificial Sequence
<220> FEATURE:
<223> OTHER INFORMATION: Artificial DNA Primer

<400> SEQUENCE: 213
tagtatagat ggcgaccttc ttggtcattt tgtatctgcg aattgagctt gcgtgagtcg					60 tgagcttcc					69

<210> SEQ ID NO 214
<211> LENGTH: 62
<212> TYPE: DNA
<213> ORGANISM: Artificial Sequence
<220> FEATURE:
<223> OTHER INFORMATION: Artificial DNA Primer

<400> SEQUENCE: 214
ttcgcagata caaaatgacc aagaaggtcg ccatctatac tagagtctcg acgaccaacc					60 ag					62

<210> SEQ ID NO 215
<211> LENGTH: 43
<212> TYPE: DNA
<213> ORGANISM: Artificial Sequence
<220> FEATURE:
<223> OTHER INFORMATION: Artificial DNA Primer

<400> SEQUENCE: 215
ctgctgctgg cgctcttcca attccttttg gaccttaaga tac					43

<210> SEQ ID NO 216
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 216
gtaatttgcc tgcttgaccg					20

<210> SEQ ID NO 217
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 217
caccagcctt tccacttcgg                                               20

<210> SEQ ID NO 218
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 218
ccttctggca tgaccttttg                                               20

<210> SEQ ID NO 219
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 219
taccatgact gtcacgatag                                               20

<210> SEQ ID NO 220
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 220
ctgatcgaga agattagcat g                                             21

<210> SEQ ID NO 221
<211> LENGTH: 22
<212> TYPE: DNA
<213> ORGANISM: Artificial Sequence
<220> FEATURE:
<223> OTHER INFORMATION: Artificial DNA Primer

<400> SEQUENCE: 221
gtttcaggca ggtcttgcaa cg                                            22

<210> SEQ ID NO 222
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 222
gatcagtgat gaagaaggcg                                               20

<210> SEQ ID NO 223
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 223
ctcaggccat cgtaggaaat                                               20

<210> SEQ ID NO 224
<211> LENGTH: 20
<212> TYPE: DNA
<213> ORGANISM: Artificial Sequence

```
<220> FEATURE:
<223> OTHER INFORMATION: Artificial DNA Primer

<400> SEQUENCE: 224
ctaggtaggt aggtagtata                                            20

<210> SEQ ID NO 225
<211> LENGTH: 41
<212> TYPE: DNA
<213> ORGANISM: Artificial Sequence
<220> FEATURE:
<223> OTHER INFORMATION: Artificial DNA Primer

<400> SEQUENCE: 225
cgtgtttctt cccattcgca tgcgacctcg tggtcattga c                    41

<210> SEQ ID NO 226
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 226
ctcctgtcac gacgtgcttt t                                          21

<210> SEQ ID NO 227
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 227
tcttgagccg catcgcatag a                                          21

<210> SEQ ID NO 228
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 228
tacggtcagc gctcatgcga a                                          21

<210> SEQ ID NO 229
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 229
catggtttaa acggcgcgcc ggtgaaacac cgcccccttc                      40

<210> SEQ ID NO 230
<211> LENGTH: 82
<212> TYPE: DNA
<213> ORGANISM: Artificial Sequence
<220> FEATURE:
<223> OTHER INFORMATION: Artificial DNA Primer

<400> SEQUENCE: 230
ccttgttttg tcgtttagtt accttaattg aaataaacga aataaaaact cgcaattaag  60
```
cgagttggat tcgaacagcc cc                                              82

<210> SEQ ID NO 231
<211> LENGTH: 82
<212> TYPE: DNA
<213> ORGANISM: Artificial Sequence
<220> FEATURE:
<223> OTHER INFORMATION: Artificial DNA Primer

<400> SEQUENCE: 231
gtattcctgc aggtccaact cgcttaattg cgagttttta tttcgtttat ttcaattaag    60
gtaactaaag ataacggaat ag                                              82

<210> SEQ ID NO 232
<211> LENGTH: 37
<212> TYPE: DNA
<213> ORGANISM: Artificial Sequence
<220> FEATURE:
<223> OTHER INFORMATION: Artificial DNA Primer

<400> SEQUENCE: 232
tggccatatt taaatagtca acacgtctcc tatgtct                              37

<210> SEQ ID NO 233
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 233
tacctccggg atggtccaga                                                 20

<210> SEQ ID NO 234
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 234
ttccatctct caaaggaaga                                                 20

<210> SEQ ID NO 235
<211> LENGTH: 22
<212> TYPE: DNA
<213> ORGANISM: Artificial Sequence
<220> FEATURE:
<223> OTHER INFORMATION: Artificial DNA Primer

<400> SEQUENCE: 235
ttgctcttat tgagaccatg cg                                              22

<210> SEQ ID NO 236
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 236
gtacaaacaa ctacctggtg                                                 20

<210> SEQ ID NO 237
<211> LENGTH: 20

```
<212> TYPE: DNA
<213> ORGANISM: Artificial Sequence
<220> FEATURE:
<223> OTHER INFORMATION: Artificial DNA Primer

<400> SEQUENCE: 237
gtcagcttca ttttccgtgt                                            20

<210> SEQ ID NO 238
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 238
ctcgaatcga gccaccgata                                            20

<210> SEQ ID NO 239
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 239
tacctccggg atggtccaga                                            20

<210> SEQ ID NO 240
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 240
atgggtcatt accaattggc                                            20

<210> SEQ ID NO 241
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 241
gtaatttgcc tgcttgaccg                                            20

<210> SEQ ID NO 242
<211> LENGTH: 24
<212> TYPE: DNA
<213> ORGANISM: Artificial Sequence
<220> FEATURE:
<223> OTHER INFORMATION: Artificial DNA Primer

<400> SEQUENCE: 242
tttgagctac aagaacctgt gggg                                       24

<210> SEQ ID NO 243
<211> LENGTH: 25
<212> TYPE: DNA
<213> ORGANISM: Artificial Sequence
<220> FEATURE:
<223> OTHER INFORMATION: Artificial DNA Primer

<400> SEQUENCE: 243
```
cgaaaaggcc acctgttgag aggct                                          25

<210> SEQ ID NO 244
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 244
tagggtcggc aacggcaaaa                                                20

<210> SEQ ID NO 245
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 245
cccacattgc tccaaacccc                                                20

<210> SEQ ID NO 246
<211> LENGTH: 30
<212> TYPE: DNA
<213> ORGANISM: Artificial Sequence
<220> FEATURE:
<223> OTHER INFORMATION: Artificial DNA Primer

<400> SEQUENCE: 246
aatgacccat agggagacaa acagcataat                                     30

<210> SEQ ID NO 247
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 247
tgttggacgc aggattttgg a                                              21

<210> SEQ ID NO 248
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 248
gcaattaatg tgagttagct                                                20

<210> SEQ ID NO 249
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 249
taacaatcct acattcggtc gaaaagcatt taccttgatt gagat                    45

<210> SEQ ID NO 250
<211> LENGTH: 45
<212> TYPE: DNA
<213> ORGANISM: Artificial Sequence

```
<220> FEATURE:
<223> OTHER INFORMATION: Artificial DNA Primer

<400> SEQUENCE: 250
atctcaatca aggtaaatgc ttttcgaccg aatgtaggat tgtta          45

<210> SEQ ID NO 251
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 251
gttaattgtg ttggcaatta tcagtctagg atgcattcta cgccag          46

<210> SEQ ID NO 252
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 252
ctggcgtaga atgcatccta gactgataat tgccaacaca attaac          46

<210> SEQ ID NO 253
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 253
gccataatgc ataggtaggt          20

<210> SEQ ID NO 254
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 254
ctcagaatta accctcacta a          21

<210> SEQ ID NO 255
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 255
gtacttaatt aaccaagggc g          21

<210> SEQ ID NO 256
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 256
gagcttggac ataactgttc c          21
```

```
<210> SEQ ID NO 257
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 257
aaaagacagg ctggttcacg                                               20

<210> SEQ ID NO 258
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 258
gttggtatag agcagcgttc                                               20

<210> SEQ ID NO 259
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 259
ctaggtaggt aggtagtata                                               20

<210> SEQ ID NO 260
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 260
tggtggagag aaagccaatt                                               20

<210> SEQ ID NO 261
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 261
aataacgctg tcttccgcag                                               20

<210> SEQ ID NO 262
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 262
atgggtcatt accaattggc                                               20

<210> SEQ ID NO 263
<211> LENGTH: 41
<212> TYPE: DNA
<213> ORGANISM: Artificial Sequence
<220> FEATURE:
<223> OTHER INFORMATION: Artificial DNA Primer
```

<400> SEQUENCE: 263
cgtgtttctt cccattcgca tgcgacctcg tggtcattga c                41

<210> SEQ ID NO 264
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 264
gcattgcaac cgcggctttc                                        20

<210> SEQ ID NO 265
<211> LENGTH: 24
<212> TYPE: DNA
<213> ORGANISM: Artificial Sequence
<220> FEATURE:
<223> OTHER INFORMATION: Artificial DNA Primer

<400> SEQUENCE: 265
tttgagctac aagaacctgt gggg                                   24

<210> SEQ ID NO 266
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 266
atgttgagat cgaagtggtt                                        20

<210> SEQ ID NO 267
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 267
aataacgctg tcttccgcag                                        20

<210> SEQ ID NO 268
<211> LENGTH: 25
<212> TYPE: DNA
<213> ORGANISM: Artificial Sequence
<220> FEATURE:
<223> OTHER INFORMATION: Artificial DNA Primer

<400> SEQUENCE: 268
cgaaaaggcc acctgttgag aggct                                  25

<210> SEQ ID NO 269
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 269
gttggtatag agcagcgttc                                        20

<210> SEQ ID NO 270

```
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 270
tggtggagag aaagccaatt                                               20

<210> SEQ ID NO 271
<211> LENGTH: 41
<212> TYPE: DNA
<213> ORGANISM: Artificial Sequence
<220> FEATURE:
<223> OTHER INFORMATION: Artificial DNA Primer

<400> SEQUENCE: 271
cgtgtttctt cccattcgca tgcgacctcg tggtcattga c                       41

<210> SEQ ID NO 272
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 272
gcattgcaac cgcggctttc                                               20

<210> SEQ ID NO 273
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 273
tcttgagccg catcgcatag a                                             21

<210> SEQ ID NO 274
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 274
tacggtcagc gctcatgcga a                                             21

<210> SEQ ID NO 275
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 275
tccggtcctg ttgctggcaa                                               20

<210> SEQ ID NO 276
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 276
```

```
ttcgtgcaag tgctgccagc                                              20

<210> SEQ ID NO 277
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 277
atgagattcg gttggctcga g                                            21

<210> SEQ ID NO 278
<211> LENGTH: 22
<212> TYPE: DNA
<213> ORGANISM: Artificial Sequence
<220> FEATURE:
<223> OTHER INFORMATION: Artificial DNA Primer

<400> SEQUENCE: 278
aaagactccg cgggtatagc tc                                           22

<210> SEQ ID NO 279
<211> LENGTH: 28
<212> TYPE: DNA
<213> ORGANISM: Artificial Sequence
<220> FEATURE:
<223> OTHER INFORMATION: ARTIFICIAL DNA PRIMER

<400> SEQUENCE: 279
gattgagttg aaactgccta agatctcg                                     28

<210> SEQ ID NO 280
<211> LENGTH: 63
<212> TYPE: DNA
<213> ORGANISM: Artificial Sequence
<220> FEATURE:
<223> OTHER INFORMATION: ARTIFICIAL DNA PRIMER

<400> SEQUENCE: 280
ctatactttc tagagaatag gaactcggaa taggaacttc aaggtgcgca gtccgcggtt  60
gac                                                                63

<210> SEQ ID NO 281
<211> LENGTH: 62
<212> TYPE: DNA
<213> ORGANISM: Artificial Sequence
<220> FEATURE:
<223> OTHER INFORMATION: ARTIFICIAL DNA PRIMER

<400> SEQUENCE: 281
ctattccgag ttcctattct ctagaaagta taggaacttc ggcgttgtta catctccctg  60
ag                                                                 62

<210> SEQ ID NO 282
<211> LENGTH: 40
<212> TYPE: DNA
<213> ORGANISM: Artificial Sequence
<220> FEATURE:
<223> OTHER INFORMATION: ARTIFICIAL DNA PRIMER

<400> SEQUENCE: 282
gcgtcaggct ttcgccacgt ctacgccagg accgagcaag                        40
```

```
<210> SEQ ID NO 283
<211> LENGTH: 22
<212> TYPE: DNA
<213> ORGANISM: Artificial Sequence
<220> FEATURE:
<223> OTHER INFORMATION: ARTIFICIAL DNA PRIMER

<400> SEQUENCE: 283
gagaacacag tgagaccata gc                                              22

<210> SEQ ID NO 284
<211> LENGTH: 22
<212> TYPE: DNA
<213> ORGANISM: Artificial Sequence
<220> FEATURE:
<223> OTHER INFORMATION: ARTIFICIAL DNA PRIMER

<400> SEQUENCE: 284
tctcaaccca atcagcaaca tg                                              22

<210> SEQ ID NO 285
<211> LENGTH: 3021
<212> TYPE: DNA
<213> ORGANISM: Aspergillus niger

<400> SEQUENCE: 285
atgcgccaca gcatcggatt ggcagcggcc ctactggcac caaccctacc tgtagcgttg       60
ggtcaatata ttcgagactt aagcaccgag aaatggactc tcagtagtcg agccttgaat      120
cggacagtac ctgctcaatt tccatcgcag gttcacttag atctactaag ggccggagtg      180
attggtgagt actatttgga agtcaagtcc tgtgagtata caaccgctaa cagcctcaat      240
agatgatccg taagtgactt catctgccat ggatgagaat tgaatcgcac taaatattgc      300
tggagatacc atggtttgaa cgatttcaat cttcgctgga tcgctgctgc caactggact      360
tataccagtc aacccatcaa aggcctgtga gtcgctgtga agtttgtgca atgtcgttcg      420
acaatactaa gaaccaatag cctggacaat tacgactcaa cttggctcgt gtttgacgga      480
ctggacactt tcgcaacaat ctcattctgt gggcagcaaa tcgcatccac ggacaatcag      540
tttcgccagt atgcgttcga tgtatccacc gcactagggt cctgcaaagg agatcctgtt      600
ctgagcatca acttttggaag cgcaccgaat attgttgatg ctatcgcaca ggactctaat      660
tcgcaaagta agtttcagag gtgggggact gccgaagttg ttacatgcta attgtatata      720
gaatggcccg atgacgtcca actcacctac gagtacccaa atcggtggtt tatgcgcaaa      780
gaacaatcgg acttcggatg ggattggggt ccagcatttg cccctgcagg tccatggaag      840
cctgcatata ttgttcagct agacaagaaa gaaagtgtct atgtcctgaa cacggatttg      900
gatatatacc gaaagggcca aattaactac cttccgccag accagagcca accttgggtc      960
gtcaacgcta gcattgacat tttgggtcca ctacctacca aaccaaccat gtcgattgaa     1020
gtgcgcgata ctcattctgg cacgattctt acttcgcgga ctctgaacaa tgtcagtgtg     1080
gctggtaatg ccataactgg tgtcaccgtt ctcgacgggc tgaccccgaa actgtggtgg     1140
ccgcaaggcc tcggtgatca gaacctctac aatgtttcta tcactgtcca agtagagga      1200 aaccagaccg tggccagtgt gaacaaacgg acgggcttcc gcaccatttt tctcaaccag     1260
cgcaacatta ctgaagcaca gcgtgcgcaa ggaatcgccc tggagcaaa ctggcacttt      1320 gaagtcaacg gtcatgagtt ctacgcaaaa ggatcgaacc ttatcccacc agacagtttc     1380
tggacccgtg ttacagaaga gaagatgtca cggctattcg atgcagtggt cgttggaaac     1440
```

-continued

```
cagaatatgc tccgtgtctg gtcctccggc gcgtacctgc atgactacat ctatgatctg  1500
gccgatgaaa agggcattct cttatggagc gagttcgagt tcagtgacgc tttatatccc  1560
tccgacgacg ctttcctcga gaacgttgct gctgagatag tatacaatgt tcgacgagtg  1620
aaccaccatc cctccttggc tctatgggct ggcggaaatg aaatcgaatc cttgatgctc  1680
ccacgtgtca agatgcagc cccatcttca tattcctact atgtgggcga gtatgagaag  1740
atgtacatta gcctcttctt gcctctggtc tacgagaaca cgcgttccat ctcatactcc  1800
cccagcagca caaccgaagg ctacctgtac attgaccttt ctgcccctgt cccaatggct  1860
gaacgttacg acaacactac ctccggctca tactacggcg atacagacca ctacgactac  1920
gacactagcg tggcgtttga ctacggttcc tatccggtag gccgctttgc caacgaattc  1980
ggcttccaca gcatgcccag cctccagaca tggcaacaag ctgtcgacac tgaggatctt  2040
tacttcaaca gcagcgtcgt catgctgcgc aaccaccacg atcccgcagg tggtctcatg  2100
acggacaact acgcgaactc ggccactggc atgggcgaaa tgaccatggg cgtggtaagc  2160
tactatccga taccgagtaa atccgaccac atctccaact tcagcgcctg gtgccatgcc  2220
acccagctct ttcaggcaga catgtacaaa agtcagatcc agttctaccg tcgtggaagt  2280
ggcatgcccg agcgccagct tggctccttg tattggcagc tcgaagatat ctggcaagcg  2340
ccatcatggg caggcattga gtacggtggt agatggaagg tccttcacca cgttatgaga  2400
gatatctatc agcctgttat tgtttcacct ttttggaact atactaccgg ctcgttggat  2460
gtctatgtta cttccgatct gtggagccct gcagcaggta ctgtcgactt gacctggttg  2520
gacctgtccg gccgccctat tgcgggtaac gcgggcacgc caaaatctgt tccctttacc  2580
gtgggaggtc tcaacagcac tcgcatctat gggacgaatg tttcttctct gggcttgccg  2640
gatactaaag atgctgttct gatcctctcg ctctcggctc acggccgtct tccgaactca  2700
gaccggacca ccaacttgac tcatgagaat tacgctacgc tttcttggcc caaggatttg  2760
aagattgttg acccgggact taagatagga cacagctcaa agaagacaac cgttacggtg  2820
gaagctacat ccggtgtttc attgtacacc tggctcgact acccagaggg tgtggtggga  2880
tactttgaag agaatgcctt cgtccttagc accaggcgaga agaaagagat tagtttttact  2940 gttctagagg acactactga cggggcttgg gtccgtaaca tcaccgtcca gagtctctgg  3000
gaccaaaagg ttcgcggttg a                                             3021
```

<210> SEQ ID NO 286
<211> LENGTH: 931
<212> TYPE: PRT
<213> ORGANISM: Aspergillus niger

<400> SEQUENCE: 286

```
Met Arg His Ser Ile Gly Leu Ala Ala Ala Leu Leu Ala Pro Thr Leu
1               5                   10                  15

Pro Val Ala Leu Gly Gln Tyr Ile Arg Asp Leu Ser Thr Glu Lys Trp
            20                  25                  30

Thr Leu Ser Ser Arg Ala Leu Asn Arg Thr Val Pro Ala Gln Phe Pro
        35                  40                  45

Ser Gln Val His Leu Asp Leu Leu Arg Ala Gly Val Ile Gly Glu Tyr
    50                  55                  60

His Gly Leu Asn Asp Phe Asn Leu Arg Trp Ile Ala Ala Ala Asn Trp
65                  70                  75                  80

Thr Tyr Thr Ser Gln Pro Ile Lys Gly Leu Leu Asp Asn Tyr Asp Ser
```

```
                    85                  90                  95
Thr Trp Leu Val Phe Asp Gly Leu Asp Thr Phe Ala Thr Ile Ser Phe
                100                 105                 110

Cys Gly Gln Gln Ile Ala Ser Thr Asp Asn Gln Phe Arg Gln Tyr Ala
                115                 120                 125

Phe Asp Val Ser Thr Ala Leu Gly Ser Cys Lys Gly Asp Pro Val Leu
            130                 135                 140

Ser Ile Asn Phe Gly Ser Ala Pro Asn Ile Val Asp Ala Ile Ala Gln
145                 150                 155                 160

Asp Ser Asn Ser Gln Lys Trp Pro Asp Val Gln Leu Thr Tyr Glu
                165                 170                 175

Tyr Pro Asn Arg Trp Phe Met Arg Lys Glu Gln Ser Asp Phe Gly Trp
                180                 185                 190

Asp Trp Gly Pro Ala Phe Ala Pro Ala Gly Pro Trp Lys Pro Ala Tyr
            195                 200                 205

Ile Val Gln Leu Asp Lys Lys Glu Ser Val Tyr Val Leu Asn Thr Asp
        210                 215                 220

Leu Asp Ile Tyr Arg Lys Gly Gln Ile Asn Tyr Leu Pro Pro Asp Gln
225                 230                 235                 240

Ser Gln Pro Trp Val Val Asn Ala Ser Ile Asp Ile Leu Gly Pro Leu
                245                 250                 255

Pro Thr Lys Pro Thr Met Ser Ile Glu Val Arg Asp Thr His Ser Gly
                260                 265                 270

Thr Ile Leu Thr Ser Arg Thr Leu Asn Asn Val Ser Val Ala Gly Asn
            275                 280                 285

Ala Ile Thr Gly Val Thr Val Leu Asp Gly Leu Thr Pro Lys Leu Trp
        290                 295                 300

Trp Pro Gln Gly Leu Gly Asp Gln Asn Leu Tyr Asn Val Ser Ile Thr
305                 310                 315                 320

Val Gln Ser Arg Gly Asn Gln Thr Val Ala Ser Val Asn Lys Arg Thr
                325                 330                 335

Gly Phe Arg Thr Ile Phe Leu Asn Gln Arg Asn Ile Thr Glu Ala Gln
                340                 345                 350

Arg Ala Gln Gly Ile Ala Pro Gly Ala Asn Trp His Phe Glu Val Asn
            355                 360                 365

Gly His Glu Phe Tyr Ala Lys Gly Ser Asn Leu Ile Pro Pro Asp Ser
        370                 375                 380

Phe Trp Thr Arg Val Thr Glu Glu Lys Met Ser Arg Leu Phe Asp Ala
385                 390                 395                 400

Val Val Val Gly Asn Gln Asn Met Leu Arg Val Trp Ser Ser Gly Ala
                405                 410                 415

Tyr Leu His Asp Tyr Ile Tyr Asp Leu Ala Asp Glu Lys Gly Ile Leu
                420                 425                 430

Leu Trp Ser Glu Phe Glu Phe Ser Asp Ala Leu Tyr Pro Ser Asp Asp
            435                 440                 445

Ala Phe Leu Glu Asn Val Ala Ala Glu Ile Val Tyr Asn Val Arg Arg
        450                 455                 460

Val Asn His His Pro Ser Leu Ala Leu Trp Ala Gly Gly Asn Glu Ile
465                 470                 475                 480

Glu Ser Leu Met Leu Pro Arg Val Lys Asp Ala Ala Pro Ser Ser Tyr
                485                 490                 495

Ser Tyr Tyr Val Gly Glu Tyr Glu Lys Met Tyr Ile Ser Leu Phe Leu
                500                 505                 510
```

```
Pro Leu Val Tyr Glu Asn Thr Arg Ser Ile Ser Tyr Ser Pro Ser Ser
        515                 520                 525

Thr Thr Glu Gly Tyr Leu Tyr Ile Asp Leu Ser Ala Pro Val Pro Met
530                 535                 540

Ala Glu Arg Tyr Asp Asn Thr Thr Ser Gly Ser Tyr Tyr Gly Asp Thr
545                 550                 555                 560

Asp His Tyr Asp Tyr Asp Thr Ser Val Ala Phe Asp Tyr Gly Ser Tyr
                565                 570                 575

Pro Val Gly Arg Phe Ala Asn Glu Phe Gly Phe His Ser Met Pro Ser
                580                 585                 590

Leu Gln Thr Trp Gln Gln Ala Val Asp Thr Glu Asp Leu Tyr Phe Asn
        595                 600                 605

Ser Ser Val Val Met Leu Arg Asn His His Asp Pro Ala Gly Gly Leu
        610                 615                 620

Met Thr Asp Asn Tyr Ala Asn Ser Ala Thr Gly Met Gly Glu Met Thr
625                 630                 635                 640

Met Gly Val Val Ser Tyr Tyr Pro Ile Pro Ser Lys Ser Asp His Ile
                645                 650                 655

Ser Asn Phe Ser Ala Trp Cys His Ala Thr Gln Leu Phe Gln Ala Asp
                660                 665                 670

Met Tyr Lys Ser Gln Ile Gln Phe Tyr Arg Arg Gly Ser Gly Met Pro
        675                 680                 685

Glu Arg Gln Leu Gly Ser Leu Tyr Trp Gln Leu Glu Asp Ile Trp Gln
690                 695                 700

Ala Pro Ser Trp Ala Gly Ile Glu Tyr Gly Gly Arg Trp Lys Val Leu
705                 710                 715                 720

His His Val Met Arg Asp Ile Tyr Gln Pro Val Ile Val Ser Pro Phe
                725                 730                 735

Trp Asn Tyr Thr Thr Gly Ser Leu Asp Val Tyr Val Thr Ser Asp Leu
                740                 745                 750

Trp Ser Pro Ala Ala Gly Thr Val Asp Leu Thr Trp Leu Asp Leu Ser
        755                 760                 765

Gly Arg Pro Ile Ala Gly Asn Ala Gly Thr Pro Lys Ser Val Pro Phe
        770                 775                 780

Thr Val Gly Gly Leu Asn Ser Thr Arg Ile Tyr Gly Thr Asn Val Ser
785                 790                 795                 800

Ser Leu Gly Leu Pro Asp Thr Lys Asp Ala Val Leu Ile Leu Ser Leu
                805                 810                 815

Ser Ala His Gly Arg Leu Pro Asn Ser Asp Arg Thr Thr Asn Leu Thr
                820                 825                 830

His Glu Asn Tyr Ala Thr Leu Ser Trp Pro Lys Asp Leu Lys Ile Val
        835                 840                 845

Asp Pro Gly Leu Lys Ile Gly His Ser Lys Lys Thr Thr Val Thr
850                 855                 860

Val Glu Ala Thr Ser Gly Val Ser Leu Tyr Thr Trp Leu Asp Tyr Pro
865                 870                 875                 880

Glu Gly Val Val Gly Tyr Phe Glu Glu Asn Ala Phe Val Leu Ala Pro
                885                 890                 895

Gly Glu Lys Lys Glu Ile Ser Phe Thr Val Leu Glu Asp Thr Thr Asp
        900                 905                 910

Gly Ala Trp Val Arg Asn Ile Thr Val Gln Ser Leu Trp Asp Gln Lys
        915                 920                 925
```

Val Arg Gly
    930

<210> SEQ ID NO 287
<211> LENGTH: 10207
<212> TYPE: DNA
<213> ORGANISM: Artificial Sequence
<220> FEATURE:
<223> OTHER INFORMATION: ARTIFICIAL PLASMID

<400> SEQUENCE: 287

```
gcccaatacg caaaccgcct ctccccgcgc gttggccgat tcattaatgc agctggcacg      60
acaggtttcc cgactggaaa gcgggcagtg agcgcaacgc aattaatgtg agttagctca     120
ctcattaggc accccaggct ttacacttta tgcttccggc tcgtatgttg tgtggaattg     180
tgagcggata caatttcac acaggaaaca gctatgacca tgattacgaa ttgtttaaac     240
gtcgaccgaa tgtaggattg ttatccgaac tctgctcgta gaggcatgtt gtgaatctgt     300
gtcgggcagg acacgcctcg aaggttcacg gcaagggaaa ccaccgatag cagtgtctag     360
tagcaacctg taaagccgca atgcagcatc actggaaaat acaaaccaat ggctaaaagt     420
acataagtta atgcctaaag aagtcatata ccagcggcta ataattgtac aatcaagtgg     480
ctaaacgtac cgtaatttgc aacggcttg tggggttgca gaagcaacgg caaagcccca     540
cttccccacg tttgtttctt cactcagtcc aatctcagct ggtgatcccc caattgggtc     600
gcttgtttgt tccggtgaag tgaaagaaga cagaggtaag aatgtctgac tcggagcgtt     660
ttgcatacaa ccaagggcag tgatggaaga cagtgaaatg ttgacattca aggagtattt     720
agccagggat gcttgagtgt atcgtgtaag gaggtttgtc tgccgatacg acgaatactg     780
tatagtcact tctgatgaag tggtccatat tgaaatgtaa gtcggcactg aacaggcaaa     840
agattgagtt gaaactgcct aagatctcgg ccctcgggc cttcggcctt tgggtgtaca     900
tgtttgtgct ccgggcaaat gcaaagtgtg gtaggatcga acacactgct gcctttacca     960
agcagctgag ggtatgtgat aggcaaatgt tcaggggcca ctgcatggtt tcgaatagaa    1020
agagaagctt agccaagaac aatagccgat aaagatagcc tcattaaacg gaatgagcta    1080
gtaggcaaag tcagcgaatg tgtatatata aaggttcgag gtccgtgcct ccctcatgct    1140
ctccccatct actcatcaac tcagatcctc caggagactt gtacaccatc ttttgaggca    1200
cagaaaccca atagtcaacc gcggactgcg caccatgcgc cacagcatcg gattggcagc    1260
ggccctactg gcaccaaccc tacctgtagc gttgggtcaa tatattcgag acttaagcac    1320
cgagaaatgg actctcagta gtcgagcctt gaatcggaca gtacctgctc aatttccatc    1380
gcaggttcac ttagatctac taagggccgg agtgattggt gagtactatt tggaagtcaa    1440
gtcctgtgag tatacaaccg ctaacagcct caatagatga tccgtaagtg acttcatctg    1500
ccatggatga gaattgaatc gcactaaata ttgctggaga taccatggtt tgaacgattt    1560
caatcttcgc tggatcgctg ctgccaactg gacttatacc agtcaaccca tcaaaggcct    1620
gtgagtcgct gtgaagtttg tgcaatgtcg ttcgacaata ctaagaacca atagcctgga    1680
caattacgac tcaacttggc tcgtgtttga cggactggac actttcgcaa caatctcatt    1740
ctgtgggcag caaatcgcat ccacggacaa tcagtttcgc cagtatgcgt tcgatgtatc    1800
caccgcacta gggtcctgca aaggagatcc tgttctgagc atcaactttg gaagcgcacc    1860
gaatattgtt gatgctatcg cacaggactc taattcgcaa agtaagtttc agaggtgggg    1920
gactgccgaa gttgttacat gctaattgta tatagaatgg cccgatgacg tccaactcac    1980
```

```
ctacgagtac ccaaatcggt ggtttatgcg caaagaacaa tcggacttcg gatgggattg    2040
gggtccagca tttgcccctg caggtccatg gaagcctgca tatattgttc agctagacaa    2100
gaaagaaagt gtctatgtcc tgaacacgga tttggatata taccgaaagg gccaaattaa    2160
ctaccttccg ccagaccaga gccaaccttg ggtcgtcaac gctagcattg acattttggg    2220
tccactacct accaaaccaa ccatgtcgat tgaagtgcgc gatactcatt ctggcacgat    2280
tcttacttcg cggactctga acaatgtcag tgtggctggt aatgccataa ctggtgtcac    2340
cgttctcgac gggctgaccc cgaaactgtg gtggccgcaa ggcctcggtg atcagaacct    2400
ctacaatgtt tctatcactg tccaaagtag aggaaaccag accgtggcca gtgtgaacaa    2460
acggacgggc ttccgcacca tttttctcaa ccagcgcaac attactgaag cacagcgtgc    2520
gcaaggaatc gcccctggag caaactggca ctttgaagtc aacggtcatg agttctacgc    2580
aaaaggatcg aaccttatcc caccagacag tttctggacc cgtgttacag aagagaagat    2640
gtcacggcta ttcgatgcag tggtcgttgg aaaccagaat atgctccgtg tctggtcctc    2700
cggcgcgtac ctgcatgact acatctatga tctggccgat gaaaagggca ttctcttatg    2760
gagcgagttc gagttcagtg acgctttata tccctccgac gacgctttcc tcgagaacgt    2820
tgctgctgag atagtataca atgttcgacg agtgaaccac catccctcct ggctctatg    2880 ggctggcgga aatgaaatcg aatccttgat gctcccacgt gtcaaagatg cagccccatc    2940
ttcatattcc tactatgtgg gcgagtatga aagatgtac attagcctct tcttgcctct    3000
ggtctacgag aacacgcgtt ccatctcata ctcccccagc agcacaaccg aaggctacct    3060
gtacattgac ctttctgccc ctgtcccaat ggctgaacgt tacgcaacaa ctacctccgg    3120
ctcatactac ggcgatacag accactacga ctacgacact agcgtggcgt ttgactacgg    3180
ttcctatccg gtaggccgct ttgccaacga attcggcttc cacagcatgc ccagcctcca    3240
gacatggcaa caagctgtcg acactgagga tctttacttc aacagcagcg tcgtcatgct    3300
gcgcaaccac cacgatcccg caggtggtct catgacggac aactacgcga actcggccac    3360
tggcatgggc gaaatgacca tgggcgtggt aagctactat ccgataccga gtaaatccga    3420
ccacatctcc aacttcagcg cctggtgcca tgccacccag ctctttcagg cagacatgta    3480
caaaagtcag atccagttct accgtcgtgg aagtggcatg cccgagcgcc agcttggctc    3540
cttgtattgg cagctcgaag atatctggca agcgccatca tgggcaggca ttgagtacgg    3600
tggtagatgg aaggtccttc accacgttat gagagatatc tatcagcctg ttattgtttc    3660 accttttttgg aactatacta ccggctcgtt ggatgtctat gttacttccg atctgtggag    3720
ccctgcagca ggtactgtcg acttgacctg gttggacctg tccggccgcc ctattgcggg    3780
taacgcgggc acgccaaaat ctgttccctt taccgtggga ggtctcaaca gcactcgcat    3840
ctatgggacg aatgtttctt ctctgggctt gccggatact aaagatgctg ttctgatcct    3900
ctcgctctcg gctcacggcc gtcttccgaa ctcagaccgg accaccaact tgactcatga    3960
gaattacgct acgctttctt ggcccaagga tttgaagatt gttgacccgg gacttaagat    4020
aggacacagc tcaaagaaga caaccgttac ggtggaagct acatccggtg tttcattgta    4080
cacctggctc gactacccag agggtgtggt gggatacttt gaagagaatg ccttcgtctt    4140
agcaccaggc gagaagaaag agattagttt tactgttcta gaggacacta ctgacggggc    4200
ttgggtccgt aacatcaccg tccagagtct ctgggaccaa aaggttcgcg ttgattaat    4260 taagctccgt ggcgaaagcc tgacgcaccg gtagattctt ggtgagcccg tatcatgacg    4320
gcggcgggag ctacatggcc ccgggtgatt tattttttt gtatctactt ctgacccttt    4380
```

```
tcaaatatac ggtcaactca tctttcactg gagatgcggc ctgcttggta ttgcgatgtt    4440
gtcagcttgg caaattgtgg ctttcgaaaa cacaaaacga ttccttagta gccatgcatt    4500
ttaagataac ggaatagaag aaagaggaaa ttaaaaaaaa aaaaaaaaca aacatcccgt    4560
tcataacccg tagaatcgcc gctcttcgtg tatcccagta ccacggcaaa ggtatttcat    4620
gatcgttcaa tgttgatatt gttcccgcca gtatggctcc accccatctc cgcgaatct    4680 cctcttctcg aacgcggtag tggcgcgcca attggtaatg acccataggg agacgaatta    4740
actagaggtg actgacacct ggcggtagac aatcaatcca tttcgctata gttaaaggat    4800
ggggatgagg gcaattggtt atatgatcat gtatgtagtg ggtgtgcata atagtagtga    4860
aatggaagcc aagtcatgtg attgtaatcg accgacggaa ttgaggatat ccggaaatac    4920
agacaccgtg aaagccatgc tctttccttc gtgtagaaga ccagacagac agtccctgat    4980
ttacccttgc acaaagcact agaaaattag cattccatcc ttctctgctt gctctgctga    5040
tatcactgtc attcaatgca tctggaaacg caaccctgaa gggattcttc ctttgagaga    5100
tggaagcgtg tcatatctct tcggttctac ggcaggtttt tttctgctct ttcgtagcat    5160
ggcatggtca cttcagcgct tatttacagt tgctggtatt gatttcttgt gcaaattgct    5220
atctgacact tattagctat ggagtcacca catttcccag caacttcccc acttcctctg    5280
caatcgccaa cgtcctctct tcactgagtc tccgtccgat aacctgcact gcaaccggtg    5340
ccccatgata cgcctccgga tcatactctt cctgcacgag ggcatcaagc tcactaaccg    5400
ccttgaaact ctcattcttc ttatcgatgt tcttatccgc aaaggtaacc ggaacaacca    5460
cgctcgtgaa atccagcagg ttgatcacag aggcataccc atagtaccgg aactggtcat    5520
gccgtaccgc agcggtaggc gtaatcgcg cgatgatggc gtccagttcc ttcccggcct    5580
tttcttcagc ctcccgccat ttctcaaggt actccatctg gtaattccac ttctggagat    5640
gcgtgtccca gagctcgttc atgttaacag ctttgatgtt cgggttcagt aggtctttga    5700
tatttggagt cgccggctcg ccggatgcac tgatatcgcg cattacgtcg gcgctgccgt    5760
cagccgcgta gatatgggag atgagatcgt ggccgaaatc gtgcttgtat ggcgtccacg    5820
gggtcacggt gtgaccggct ttggcgagtg cggcgacggg gtttccacg ccgcgcagga    5880 taggagggtg tggaaggaca ttgccgtcga agttgtagta gccgatattg agcccgccgt    5940
tcttgatctt ggaggcaata atgtccgact cggactggcg ccaggcatg gggatgacct    6000 tggagtcgta tttccaaggc tcctgaccga ggacggattt ggtgaagagg cggaggtcta    6060
acatacttca tcagtgactg ccggtctcgt atatagtata aaaagcaaga aaggaggaca    6120
gtggaggcct ggtatagagc aggaaaagaa ggaagaggcg aaggactcac cctcaacaga    6180
gtgcgtaatc ggcccgacaa cgctgtgcac cgtctcctga ccctccatgc tgttcgccat    6240
ctttgcatac ggcagccgcc catgactcgg ccttagaccg tacaggaagt tgaacgcggc    6300
cggcactcga atcgagccac cgatatccgt tcctacaccg atgacgccac cacgaatccc    6360
aacgatcgca ccctcaccac cagaactgcc gccgcacgac cagttcttgt tgcgtgggtt    6420
gacggtgcgc ccgatgatgt tgttgactgt ctcgcagacc atcagggtct gcggacaga    6480 ggtcttgacg tagaagacgg caccggcttt gcggagcatg gttgtcagaa ccgagtcccc    6540
ttcgtcgtac ttgtttagcc atgagatgta gcccattgat gtttcgtagc cctggtggca    6600
tatgttagct gacaaaaagg gacatctaac gacttagggg caacggtgta ccttgactcg    6660
aagctggtct tgagagaga tggggaggcc atgaagtgga ccaacgggtc tcttgtgctt    6720
```

```
tgcgtagtat tcatcgagtt cccttgcctg cgcgagagcg gcgtcaggga agaactcgtg      6780
ggcgcagttt gtctgcacag aagccagcgt cagcttgata gtcccataag gtggcgttgt      6840
tacatctccc tgagaggtag aggggaccct actaactgct gggcgattgc tgcccgttta      6900
cagaatgcta gcgtaacttc caccgaggtc aactctccgg ccgccagctt ggacacaaga      6960
tctgcagcgg aggcctctgt gatcttcagt tcggcctctg aaaggatccc cgatttcttt      7020
gggaaatcaa taacgctgtc ttccgcaggc agcgtctgga cttcccattc atcagggatg      7080 gttttgcga ggcgggcgcg cttatcagcg gccagttctt cccaggattg aggcattctg      7140
tgttagctta tagtcaggat gttggctcga cgagtgtaaa ctgggagttg gcatgagggt      7200
tatgtaggct tctttagccc cgcatccccc tcattctcct cattgatccc ggggagcgg      7260 atggtgttga taagagacta attataggt ttagctggtg cctagctggt gattggctgg      7320
cttcgccgaa ttttacgggc caaggaaagc tgcagaaccg cggcactggt aaacggtaat      7380
taagctatca gccccatgct aacgagttta aattacgtgt attgctgata aacaccaaca      7440
gagctttact gaaagatggg agtcacggtg tggcttcccc actgcgatta ttgcacaagc      7500
agcgagggcg aacttgactg tcgtcgctga gcagcctgca gtcaaacata catatatatc      7560
aaccgcgaag acgtctggcc ttgtagaaca cgacgctccc tagcaacacc tgccgtgtca      7620
gcctctacgg ttgttacttg cattcaggat gctctccagc gggcgagcta ttcaaaatat      7680
tcaaagcagg tatctcgtat tgccaggatt cagctgaagc aacaggtgcc aaggaaatct      7740
gcgtcggttc tcatctgggc ttgctcggtc ctggcgtaga atgcatccta gagtttaaac      7800
agcttggcac tggccgtcgt tttacaacgt cgtgactggg aaaaccctgg cgttacccaa      7860
cttaatcgcc ttgcagcaca tccccctttc gccagctggc gtaatagcga agaggcccgc      7920
accgatcgcc cttcccaaca gttgcgcagc ctgaacggcg aatggcgcct gatgcggtat      7980
tttctcctta cgcatctgtg cggtatttca caccgcatat ggtgcactct cagtacaatc      8040
tgctctgatg ccgcatagtt aagccagccc cgacacccgc caacacccgc tgacgcgccc      8100
tgacgggctt gtctgctccc ggcatccgct tacagacaag ctgtgaccgt ctccgggagc      8160
tgcatgtgtc agaggttttc accgtcatca ccgaaacgcg cgagacgaaa gggcctcgtg      8220
atacgcctat ttttataggt taatgtcatg ataataatgg tttcttagac gtcaggtggc      8280
acttttcggg gaaatgtgcg cggaacccct atttgtttat ttttctaaat acattcaaat      8340
atgtatccgc tcatgagaca ataaccctga taaatgcttc aataatattg aaaaaggaag      8400
agtatgagta ttcaacattt ccgtgtcgcc cttattccct tttttgcggc attttgcctt      8460 cctgttttg ctcacccaga aacgctggtg aaagtaaaag atgctgaaga tcagttgggt      8520
gcacgagtgg gttacatcga actggatctc aacagcggta agatccttga gtttttcgc      8580 cccgaagaac gttttccaat gatgagcact tttaaagttc tgctatgtgg cgcggtatta      8640
tcccgtattg acgccgggca agagcaactc ggtcgccgca tacactattc tcagaatgac      8700
ttggttgagt actcaccagt cacagaaaag catcttacgg atggcatgac agtaagagaa      8760
ttatgcagtg ctgccataac catgagtgat aacactgcgg ccaacttact tctgacaacg      8820
atcggaggac cgaaggagct aaccgctttt ttgcacaaca tgggggatca tgtaactcgc      8880
cttgatcgtt gggaaccgga gctgaatgaa gccataccaa acgacgagcg tgacaccacg      8940
atgcctgtag caatggcaac aacgttgcgc aaactattaa ctggcgaact acttactcta      9000
gcttcccggc aacaattaat agactggatg gaggcggata aagttgcagg accacttctg      9060
cgctcggccc ttccggctgg ctggtttatt gctgataaat ctggagccgg tgagcgtggg      9120
```

```
tctcgcggta tcattgcagc actggggcca gatggtaagc cctcccgtat cgtagttatc    9180
tacacgacgg ggagtcaggc aactatggat gaacgaaata gacagatcgc tgagataggt    9240
gcctcactga ttaagcattg gtaactgtca gaccaagttt actcatatat actttagatt    9300
gatttaaaac ttcattttta atttaaaagg atctaggtga agatccttt tgataatctc    9360 atgaccaaaa tcccttaacg tgagttttcg ttccactgag cgtcagaccc cgtagaaaag    9420
atcaaaggat cttcttgaga tcctttttt ctgcgcgtaa tctgctgctt gcaaacaaaa    9480
aaaccaccgc taccagcggt ggtttgtttg ccggatcaag agctaccaac tcttttccg    9540 aaggtaactg gcttcagcag agcgcagata ccaaatactg ttcttctagt gtagccgtag    9600
ttaggccacc acttcaagaa ctctgtagca ccgcctacat acctcgctct gctaatcctg    9660
ttaccagtgg ctgctgccag tggcgataag tcgtgtctta ccgggttgga ctcaagacga    9720
tagttaccgg ataaggcgca gcggtcgggc tgaacggggg gttcgtgcac acagcccagc    9780
ttggagcgaa cgacctacac cgaactgaga tacctacagc gtgagctatg agaaagcgcc    9840
acgcttcccg aagggagaaa ggcggacagg tatccggtaa gcggcagggt cggaacagga    9900
gagcgcacga gggagcttcc agggggaaac gcctggtatc tttatagtcc tgtcgggttt    9960
cgccacctct gacttgagcg tcgatttttg tgatgctcgt caggggggcg gagcctatgg   10020
aaaaacgcca gcaacgcggc cttttacgg ttcctggcct tttgctgcc ttttgctcac   10080 atgttctttc ctgcgttatc ccctgattct gtggataacc gtattaccgc ctttgagtga   10140
gctgataccg ctcgccgcag ccgaacgacc gagcgcagcg agtcagtgag cgaggaagcg   10200
gaagagc                                                             10207

<210> SEQ ID NO 288
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 288
tgattacgaa ttgtttaaac ggatccgaat gtaggattgt tatccg                      46

<210> SEQ ID NO 289
<211> LENGTH: 72
<212> TYPE: DNA
<213> ORGANISM: Artificial Sequence
<220> FEATURE:
<223> OTHER INFORMATION: Artificial DNA Primer

<400> SEQUENCE: 289
gaagttccta tactttctag agaataggaa ctcggaatag gaacttcaac cttatgggac        60
tatcaagctg ac                                                           72

<210> SEQ ID NO 290
<211> LENGTH: 50
<212> TYPE: DNA
<213> ORGANISM: Artificial Sequence
<220> FEATURE:
<223> OTHER INFORMATION: Artificial DNA Primer

<400> SEQUENCE: 290
gttacattga cgtacttata agaagttcct atactttcta gagaatagga                  50

<210> SEQ ID NO 291
```

<211> LENGTH: 357
<212> TYPE: DNA
<213> ORGANISM: Artificial Sequence
<220> FEATURE:
<223> OTHER INFORMATION: Artificial DNA Primer

<400> SEQUENCE: 291
tagggtcggc aacggcaaaa agcacgtggg ctcaccgaaa agcaagatgt ttgcgatcta    60
acatccagga acctggatac atccatcatc acgcacgacc actttgatct gctgtaaact   120
cgtattcgcc ctaaaccgaa gtgcgtggta aatctacacg tgggccccct tcggtatact   180
gcgtgtgtct tctctaggtg ccattctttt cccttcctct agtgttgaat tgtttgtgtt   240
ggagtccgag ctgtaactac ctctgaatct ctggagaatg gtggactaac gactaccgtg   300
cacctgcatc atgtatataa tagtgatcct gagaaggggg gtttggagca atgtggg     357

<210> SEQ ID NO 292
<211> LENGTH: 87
<212> TYPE: DNA
<213> ORGANISM: Artificial Sequence
<220> FEATURE:
<223> OTHER INFORMATION: Artificial DNA Primer

<400> SEQUENCE: 292
gggagatgta acaacgcctt gaagttccta ttccgagttc ctattcttca aatagtatag    60
gaacttcaac cttatgggac tatcaag                                        87

<210> SEQ ID NO 293
<211> LENGTH: 87
<212> TYPE: DNA
<213> ORGANISM: Artificial Sequence
<220> FEATURE:
<223> OTHER INFORMATION: Artificial DNA Primer

<400> SEQUENCE: 293
cttgatagtc ccataaggtt gaagttccta tactatttga agaataggaa ctcggaatag    60
gaacttcaag gcgttgttac atctccc                                        87

<210> SEQ ID NO 294
<211> LENGTH: 84
<212> TYPE: DNA
<213> ORGANISM: Artificial Sequence
<220> FEATURE:
<223> OTHER INFORMATION: Artificial DNA Primer

<400> SEQUENCE: 294
gcccctaagt cgttagatgt ttgaagttcc tattccgagt tcctattctt caaatagtat    60
aggaacttca ccctttttgt cagc                                           84

<210> SEQ ID NO 295
<211> LENGTH: 84
<212> TYPE: DNA
<213> ORGANISM: Artificial Sequence
<220> FEATURE:
<223> OTHER INFORMATION: Artificial DNA Primer

<400> SEQUENCE: 295
gctgacaaaa agggtgaagt tcctatacta tttgaagaat aggaactcgg aataggaact   60
tcaaacatct aacgacttag gggc                                           84

<210> SEQ ID NO 296
<211> LENGTH: 83

```
<212> TYPE: DNA
<213> ORGANISM: Artificial Sequence
<220> FEATURE:
<223> OTHER INFORMATION: Artificial DNA Primer

<400> SEQUENCE: 296
ctataccagg cctccacttg aagttcctat tccgagttcc tattcttcaa atagtatagg    60
aacttcatgt cctcctttct tgc                                           83

<210> SEQ ID NO 297
<211> LENGTH: 83
<212> TYPE: DNA
<213> ORGANISM: Artificial Sequence
<220> FEATURE:
<223> OTHER INFORMATION: Artificial DNA Primer

<400> SEQUENCE: 297
gcaagaaagg aggacatgaa gttcctatac tatttgaaga ataggaactc ggaataggaa    60
cttcaagtgg aggcctggta tag                                           83

<210> SEQ ID NO 298
<211> LENGTH: 95
<212> TYPE: DNA
<213> ORGANISM: Artificial Sequence
<220> FEATURE:
<223> OTHER INFORMATION: Artificial DNA Primer

<400> SEQUENCE: 298
acgcggccgc gaattcggcg cgccgaagtt cctattccga agttcctatt ctcatataag    60
tataggaact tcatttaaat taccatcgtg ctctg                              95

<210> SEQ ID NO 299
<211> LENGTH: 41
<212> TYPE: DNA
<213> ORGANISM: Artificial Sequence
<220> FEATURE:
<223> OTHER INFORMATION: Artificial DNA Primer

<400> SEQUENCE: 299
ggaagatgca aggtgcttca ttttgggaca acaagaagga c                       41

<210> SEQ ID NO 300
<211> LENGTH: 41
<212> TYPE: DNA
<213> ORGANISM: Artificial Sequence
<220> FEATURE:
<223> OTHER INFORMATION: Artificial DNA Primer

<400> SEQUENCE: 300
gtccttcttg ttgtcccaaa atgaagcacc ttgcatcttc c                       41

<210> SEQ ID NO 301
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 301
accagaggca agtcaacgct taattaaaag gacgggttag cgttggt                 47

<210> SEQ ID NO 302
<211> LENGTH: 47
<212> TYPE: DNA
```

<213> ORGANISM: Artificial Sequence
<220> FEATURE:
<223> OTHER INFORMATION: Artificial DNA Primer

<400> SEQUENCE: 302
accaacgcta acccgtcctt ttaattaagc gttgacttgc ctctggt    47

<210> SEQ ID NO 303
<211> LENGTH: 65
<212> TYPE: DNA
<213> ORGANISM: Artificial Sequence
<220> FEATURE:
<223> OTHER INFORMATION: Artificial DNA Primer

<400> SEQUENCE: 303
cctcgcatac ctagcctaga attcgcgatc gcgacgataa gcttgccctg gtggtgtcaa    60
ccctg    65

<210> SEQ ID NO 304
<211> LENGTH: 41
<212> TYPE: DNA
<213> ORGANISM: Artificial Sequence
<220> FEATURE:
<223> OTHER INFORMATION: Artificial DNA Primer

<400> SEQUENCE: 304
gtccttcttg ttgtcccaaa atgaagcacc ttgcatcttc c    41

<210> SEQ ID NO 305
<211> LENGTH: 65
<212> TYPE: DNA
<213> ORGANISM: Artificial Sequence
<220> FEATURE:
<223> OTHER INFORMATION: Artificial DNA Primer

<400> SEQUENCE: 305
cctcgcatac ctagcctaga attcgcgatc gcgacgataa gcttgccctg gtggtgtcaa    60
ccctg    65

<210> SEQ ID NO 306
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 306
gacaccacca gggcaagctt tggaaacgca accctgaagg    40

<210> SEQ ID NO 307
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 307
accagaggca agtcaacgct cgccggcgtc tacgccagga ccgagcaa    48

<210> SEQ ID NO 308
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 308
ttgctcggtc ctggcgtaga cgccggcgag cgttgacttg cctctggt         48

<210> SEQ ID NO 309
<211> LENGTH: 95
<212> TYPE: DNA
<213> ORGANISM: Artificial Sequence
<220> FEATURE:
<223> OTHER INFORMATION: Artificial DNA Primer

<400> SEQUENCE: 309
cctagcctag aattcgcgat cgcgaagttc ctatacttct gatagaatag gaacttcgga    60
ataggaactt ccctgcaggc cctggtggtg tcaac                              95

<210> SEQ ID NO 310
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 310
gtataacaac tccgagttaa ttaagggttc gaattcattt aaacgg                  46

<210> SEQ ID NO 311
<211> LENGTH: 49
<212> TYPE: DNA
<213> ORGANISM: Artificial Sequence
<220> FEATURE:
<223> OTHER INFORMATION: Artificial DNA Primer

<400> SEQUENCE: 311
aacttcggaa taggaacttc cctgcaggtg ggagcgctca atattcatc               49

<210> SEQ ID NO 312
<211> LENGTH: 93
<212> TYPE: DNA
<213> ORGANISM: Artificial Sequence
<220> FEATURE:
<223> OTHER INFORMATION: Artificial DNA Primer

<400> SEQUENCE: 312
gcgctcccac ctgcagggaa gttcctattc cgaagttcct attcactaga atgtatagga   60
acttcattta aatgaattct aggctaggta tgc                                93

<210> SEQ ID NO 313
<211> LENGTH: 24
<212> TYPE: DNA
<213> ORGANISM: Artificial Sequence
<220> FEATURE:
<223> OTHER INFORMATION: Artificial DNA Primer

<400> SEQUENCE: 313
agtagcggga gactagtgcg aagt                                          24

<210> SEQ ID NO 314
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 314

```
acatggttta aacggcgcgc cggagcagat ggcgacacca                    40
```

<210> SEQ ID NO 315
<211> LENGTH: 44
<212> TYPE: DNA
<213> ORGANISM: Artificial Sequence
<220> FEATURE:
<223> OTHER INFORMATION: Artificial DNA Primer

<400> SEQUENCE: 315

```
gaataggaac ttcgcggccg ccataccact tcgttgatac actg               44
```

<210> SEQ ID NO 316
<211> LENGTH: 75
<212> TYPE: DNA
<213> ORGANISM: Artificial Sequence
<220> FEATURE:
<223> OTHER INFORMATION: Artificial DNA Primer

<400> SEQUENCE: 316

```
cggccgcgaa gttcctattc cgaagttcct attctcatat aagtatagga acttccgcgc    60
ccgacaaaac aaggc                                              75
```

<210> SEQ ID NO 317
<211> LENGTH: 75
<212> TYPE: DNA
<213> ORGANISM: Artificial Sequence
<220> FEATURE:
<223> OTHER INFORMATION: Artificial DNA Primer

<400> SEQUENCE: 317

```
gccttgtttt gtcgggcgcg gaagttccta tacttatatg agaataggaa cttcggaata    60
ggaacttcgc ggccg                                              75
```

<210> SEQ ID NO 318
<211> LENGTH: 42
<212> TYPE: DNA
<213> ORGANISM: Artificial Sequence
<220> FEATURE:
<223> OTHER INFORMATION: Artificial DNA Primer

<400> SEQUENCE: 318

```
tataggaact tcttaattaa gataatggcc actttcatct ga                 42
```

<210> SEQ ID NO 319
<211> LENGTH: 42
<212> TYPE: DNA
<213> ORGANISM: Artificial Sequence
<220> FEATURE:
<223> OTHER INFORMATION: Artificial DNA Primer

<400> SEQUENCE: 319

```
ggccatattt aaatcctgca gggtctgccg tcactgatga gg                 42
```

<210> SEQ ID NO 320
<211> LENGTH: 77
<212> TYPE: DNA
<213> ORGANISM: Artificial Sequence
<220> FEATURE:
<223> OTHER INFORMATION: Artificial DNA Primer

<400> SEQUENCE: 320

```
ctagttggag tattcctgca gaagttccta ttccgaagtt cctattctat cagaagtata    60
ggaacttctt aattaag                                            77
```

<210> SEQ ID NO 321
<211> LENGTH: 76
<212> TYPE: DNA
<213> ORGANISM: Artificial Sequence
<220> FEATURE:
<223> OTHER INFORMATION: Artificial DNA Primer

<400> SEQUENCE: 321
cttaattaag aagttcctat acttctgata gaataggaac ttcggaatag gaacttctgc    60
aggaatactc caacta                                                   76

<210> SEQ ID NO 322
<211> LENGTH: 75
<212> TYPE: DNA
<213> ORGANISM: Artificial Sequence
<220> FEATURE:
<223> OTHER INFORMATION: Artificial DNA Primer

<400> SEQUENCE: 322
cggccgcgaa gttcctattc cgaagttcct attctatcag aagtatagga acttccgcgc    60
ccgacaaaac aaggc                                                    75

<210> SEQ ID NO 323
<211> LENGTH: 75
<212> TYPE: DNA
<213> ORGANISM: Artificial Sequence
<220> FEATURE:
<223> OTHER INFORMATION: Artificial DNA Primer

<400> SEQUENCE: 323
gccttgtttt gtcgggcgcg gaagttccta tacttctgat agaataggaa cttcggaata    60
ggaacttcgc ggccg                                                    75

<210> SEQ ID NO 324
<211> LENGTH: 77
<212> TYPE: DNA
<213> ORGANISM: Artificial Sequence
<220> FEATURE:
<223> OTHER INFORMATION: Artificial DNA Primer

<400> SEQUENCE: 324
ctagttggag tattcctgca gaagttccta ttccgaagtt cctattctta taggagtata    60
ggaacttctt aattaag                                                  77

<210> SEQ ID NO 325
<211> LENGTH: 77
<212> TYPE: DNA
<213> ORGANISM: Artificial Sequence
<220> FEATURE:
<223> OTHER INFORMATION: Artificial DNA Primer

<400> SEQUENCE: 325
cttaattaag aagttcctat actcctataa gaataggaac ttcggaatag gaacttctgc    60
aggaatactc caactag                                                  77

<210> SEQ ID NO 326
<211> LENGTH: 93
<212> TYPE: DNA
<213> ORGANISM: Artificial Sequence
<220> FEATURE:
<223> OTHER INFORMATION: Artificial DNA Primer

```
<400> SEQUENCE: 326
cgcgaattcg gcgcgccctc gaggaagttc ctattccgaa gttcctattc tatcagaagt    60
ataggaactt catttaaatt accatcgtgc tct                                 93

<210> SEQ ID NO 327
<211> LENGTH: 93
<212> TYPE: DNA
<213> ORGANISM: Artificial Sequence
<220> FEATURE:
<223> OTHER INFORMATION: Artificial DNA Primer

<400> SEQUENCE: 327
agagcacgat ggtaatttaa atgaagttcc tatacttctg atagaatagg aacttcggaa    60
taggaacttc ctcgagggcg cgccgaattc gcg                                 93

<210> SEQ ID NO 328
<211> LENGTH: 95
<212> TYPE: DNA
<213> ORGANISM: Artificial Sequence
<220> FEATURE:
<223> OTHER INFORMATION: Artificial DNA Primer

<400> SEQUENCE: 328
gacaccacca gggcctgcag ggaagttcct attccgaagt tcctattctt ataggagtat    60
aggaacttct acgtagcgat cgcgaattct aggct                               95

<210> SEQ ID NO 329
<211> LENGTH: 95
<212> TYPE: DNA
<213> ORGANISM: Artificial Sequence
<220> FEATURE:
<223> OTHER INFORMATION: Artificial DNA Primer

<400> SEQUENCE: 329
agcctagaat tcgcgatcgc tacgtagaag ttcctatact cctataagaa taggaacttc    60
ggaataggaa cttccctgca ggccctggtg gtgtc                               95

<210> SEQ ID NO 330
<211> LENGTH: 25
<212> TYPE: DNA
<213> ORGANISM: Artificial Sequence
<220> FEATURE:
<223> OTHER INFORMATION: Artificial DNA Primer

<400> SEQUENCE: 330
cccgatgcca cctcccagga taaga                                          25

<210> SEQ ID NO 331
<211> LENGTH: 24
<212> TYPE: DNA
<213> ORGANISM: Artificial Sequence
<220> FEATURE:
<223> OTHER INFORMATION: Artificial DNA Primer

<400> SEQUENCE: 331
tttgtgaggc tgctcaggga ccct                                           24

<210> SEQ ID NO 332
<211> LENGTH: 37
<212> TYPE: DNA
<213> ORGANISM: Artificial Sequence
<220> FEATURE:
<223> OTHER INFORMATION: Artificial DNA Primer
```

```
<400> SEQUENCE: 332
ttgtcaactt gggatggacc tcggggtgc tggtacc                              37

<210> SEQ ID NO 333
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 333
tacggtgcgg tatctgcagt                                                20

<210> SEQ ID NO 334
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 334
acggaggagc tcgacgactt                                                20

<210> SEQ ID NO 335
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 335
gctctctccg ccgatccaat                                                20

<210> SEQ ID NO 336
<211> LENGTH: 27
<212> TYPE: DNA
<213> ORGANISM: Artificial Sequence
<220> FEATURE:
<223> OTHER INFORMATION: Artificial DNA Primer

<400> SEQUENCE: 336
tacctctttg cggtcaactg tgtaaaa                                        27

<210> SEQ ID NO 337
<211> LENGTH: 27
<212> TYPE: DNA
<213> ORGANISM: Artificial Sequence
<220> FEATURE:
<223> OTHER INFORMATION: Artificial DNA Primer

<400> SEQUENCE: 337
ctgtccttga ttcagatgaa agtggcc                                        27

<210> SEQ ID NO 338
<211> LENGTH: 42
<212> TYPE: DNA
<213> ORGANISM: Artificial Sequence
<220> FEATURE:
<223> OTHER INFORMATION: Artificial DNA Primer

<400> SEQUENCE: 338
ggagcagatg gcgacaccat aggcggtgcg aatcgtccag aa                       42

<210> SEQ ID NO 339
```

```
<211> LENGTH: 24
<212> TYPE: DNA
<213> ORGANISM: Artificial Sequence
<220> FEATURE:
<223> OTHER INFORMATION: Artificial DNA Primer

<400> SEQUENCE: 339
ttccatttcc ctcccaggcc ctga                                              24

<210> SEQ ID NO 340
<211> LENGTH: 38
<212> TYPE: DNA
<213> ORGANISM: Artificial Sequence
<220> FEATURE:
<223> OTHER INFORMATION: Artificial DNA Primer

<400> SEQUENCE: 340
acatggttta acggggtga aacaccgccc ccttcttg                                38

<210> SEQ ID NO 341
<211> LENGTH: 38
<212> TYPE: DNA
<213> ORGANISM: Artificial Sequence
<220> FEATURE:
<223> OTHER INFORMATION: Artificial DNA Primer

<400> SEQUENCE: 341
aggaacttcg cggccttcga acagccccag tcggtcaa                               38

<210> SEQ ID NO 342
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 342
taggaacttc ttaatgataa cggaatagaa gaaagaggaa attaaaa                     47

<210> SEQ ID NO 343
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 343
gccatattta atccgttta aacagtcaac acgtctccta tgtctg                       46

<210> SEQ ID NO 344
<211> LENGTH: 52
<212> TYPE: DNA
<213> ORGANISM: Artificial Sequence
<220> FEATURE:
<223> OTHER INFORMATION: Artificial DNA Primer

<400> SEQUENCE: 344
ttcttccttg aactctcaga tctccctgca gggggcgaca aaacaaggct ac               52

<210> SEQ ID NO 345
<211> LENGTH: 55
<212> TYPE: DNA
<213> ORGANISM: Artificial Sequence
<220> FEATURE:
<223> OTHER INFORMATION: Artificial DNA Primer

<400> SEQUENCE: 345
```
ttatcattaa gaagttccta tacattctag tgaataggaa cttcggaata ggaac         55

<210> SEQ ID NO 346
<211> LENGTH: 55
<212> TYPE: DNA
<213> ORGANISM: Artificial Sequence
<220> FEATURE:
<223> OTHER INFORMATION: Artificial DNA Primer

<400> SEQUENCE: 346
gttcctattc cgaagttcct attcactaga atgtatagga acttcttaat gataa         55

<210> SEQ ID NO 347
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 347
ccatgactgt cacgatagag agatctccac catttgctgt cgaatt                   46

<210> SEQ ID NO 348
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 348
gagattcgga cctcccaact g                                              21

<210> SEQ ID NO 349
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 349
aaaaggccac ctgttgagag                                                20

<210> SEQ ID NO 350
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 350
cccgtgaagc cgtttaaatg                                                20

<210> SEQ ID NO 351
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 351
tacggtgcgg tatctgcagt                                                20

<210> SEQ ID NO 352
<211> LENGTH: 21
<212> TYPE: DNA

```
<213> ORGANISM: Artificial Sequence
<220> FEATURE:
<223> OTHER INFORMATION: Artificial DNA Primer

<400> SEQUENCE: 352
gcgtgctaat attcagtaga a                                       21

<210> SEQ ID NO 353
<211> LENGTH: 22
<212> TYPE: DNA
<213> ORGANISM: Artificial Sequence
<220> FEATURE:
<223> OTHER INFORMATION: Artificial DNA Primer

<400> SEQUENCE: 353
accagtatcg aggattgacg gc                                      22

<210> SEQ ID NO 354
<211> LENGTH: 22
<212> TYPE: DNA
<213> ORGANISM: Artificial Sequence
<220> FEATURE:
<223> OTHER INFORMATION: Artificial DNA Primer

<400> SEQUENCE: 354
agcaaccata cgatccagga gc                                      22

<210> SEQ ID NO 355
<211> LENGTH: 29
<212> TYPE: DNA
<213> ORGANISM: Artificial Sequence
<220> FEATURE:
<223> OTHER INFORMATION: Artificial DNA Primer

<400> SEQUENCE: 355
ggcaacaaga ggccagagac aatctattc                               29

<210> SEQ ID NO 356
<211> LENGTH: 24
<212> TYPE: DNA
<213> ORGANISM: Artificial Sequence
<220> FEATURE:
<223> OTHER INFORMATION: Artificial DNA Primer

<400> SEQUENCE: 356
caggtaggtg atgacgggtc cgtg                                    24

<210> SEQ ID NO 357
<211> LENGTH: 30
<212> TYPE: DNA
<213> ORGANISM: Artificial Sequence
<220> FEATURE:
<223> OTHER INFORMATION: Artificial DNA Primer

<400> SEQUENCE: 357
gacgtatacc attccggggc cgcctgagcc                              30

<210> SEQ ID NO 358
<211> LENGTH: 23
<212> TYPE: DNA
<213> ORGANISM: Artificial Sequence
<220> FEATURE:
<223> OTHER INFORMATION: Artificial DNA Primer

<400> SEQUENCE: 358
gttggcctcg caacggacaa gtt                                     23
```

```
<210> SEQ ID NO 359
<211> LENGTH: 28
<212> TYPE: DNA
<213> ORGANISM: Artificial Sequence
<220> FEATURE:
<223> OTHER INFORMATION: Artificial DNA Primer

<400> SEQUENCE: 359
aatggtgagg actgagataa aagaattc                                        28

<210> SEQ ID NO 360
<211> LENGTH: 31
<212> TYPE: DNA
<213> ORGANISM: Artificial Sequence
<220> FEATURE:
<223> OTHER INFORMATION: Artificial DNA Primer

<400> SEQUENCE: 360
ccatgactat tgtcaactat atccgaaaca a                                    31

<210> SEQ ID NO 361
<211> LENGTH: 28
<212> TYPE: DNA
<213> ORGANISM: Artificial Sequence
<220> FEATURE:
<223> OTHER INFORMATION: Artificial DNA Primer

<400> SEQUENCE: 361
accttctggc atgaccttlt gatgatcg                                        28

<210> SEQ ID NO 362
<211> LENGTH: 28
<212> TYPE: DNA
<213> ORGANISM: Artificial Sequence
<220> FEATURE:
<223> OTHER INFORMATION: Artificial DNA Primer

<400> SEQUENCE: 362
ccatccaaag agctcaaccc aaaggagg                                        28

<210> SEQ ID NO 363
<211> LENGTH: 25
<212> TYPE: DNA
<213> ORGANISM: Artificial Sequence
<220> FEATURE:
<223> OTHER INFORMATION: Artificial DNA Primer

<400> SEQUENCE: 363
cccgatgcca cctcccagga taaga                                           25

<210> SEQ ID NO 364
<211> LENGTH: 25
<212> TYPE: DNA
<213> ORGANISM: Artificial Sequence
<220> FEATURE:
<223> OTHER INFORMATION: Artificial DNA Primer

<400> SEQUENCE: 364
gcgatggaag atgcaaggtg cttca                                           25

<210> SEQ ID NO 365
<211> LENGTH: 25
<212> TYPE: DNA
<213> ORGANISM: Artificial Sequence
<220> FEATURE:
```

```
-continued

<223> OTHER INFORMATION: Artificial DNA Primer

<400> SEQUENCE: 365
gtgccaagga aatctgcgtc ggttc                                           25

<210> SEQ ID NO 366
<211> LENGTH: 25
<212> TYPE: DNA
<213> ORGANISM: Artificial Sequence
<220> FEATURE:
<223> OTHER INFORMATION: Artificial DNA Primer

<400> SEQUENCE: 366
cgctcgacga tacggacgac gatga                                           25
```